United States Patent
Igawa et al.

(10) Patent No.: US 11,124,576 B2
(45) Date of Patent: Sep. 21, 2021

(54) METHOD FOR PRODUCING POLYPEPTIDE HETEROMULTIMER

(71) Applicant: CHUGAI SEIYAKU KABUSHIKI KAISHA, Tokyo (JP)

(72) Inventors: Tomoyuki Igawa, Shizuoka (JP); Hitoshi Katada, Shizuoka (JP); Futa Mimoto, Shizuoka (JP)

(73) Assignee: Chungai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/024,063

(22) PCT Filed: Sep. 26, 2014

(86) PCT No.: PCT/JP2014/075728
§ 371 (c)(1),
(2) Date: Mar. 23, 2016

(87) PCT Pub. No.: WO2015/046467
PCT Pub. Date: Apr. 2, 2015

(65) Prior Publication Data
US 2016/0229915 A1 Aug. 11, 2016

(30) Foreign Application Priority Data

Sep. 27, 2013 (JP) .............................. JP2013-200845

(51) Int. Cl.
| | | |
|---|---|---|
| *C07K 16/28* | (2006.01) | |
| *C07K 16/00* | (2006.01) | |
| *C07K 16/46* | (2006.01) | |
| *C07K 16/30* | (2006.01) | |
| *C07K 16/24* | (2006.01) | |
| *A61K 39/00* | (2006.01) | |

(52) U.S. Cl.
CPC .......... *C07K 16/2866* (2013.01); *C07K 16/00* (2013.01); *C07K 16/248* (2013.01); *C07K 16/2809* (2013.01); *C07K 16/303* (2013.01); *C07K 16/46* (2013.01); *A61K 2039/505* (2013.01); *A61K 2039/507* (2013.01); *C07K 2317/10* (2013.01); *C07K 2317/14* (2013.01); *C07K 2317/20* (2013.01); *C07K 2317/31* (2013.01); *C07K 2317/51* (2013.01); *C07K 2317/515* (2013.01); *C07K 2317/52* (2013.01); *C07K 2317/526* (2013.01); *C07K 2317/53* (2013.01); *C07K 2317/55* (2013.01); *C07K 2317/73* (2013.01); *C07K 2317/94* (2013.01)

(58) Field of Classification Search
CPC .............. C07K 16/2866; C07K 16/303; C07K 16/2809; C07K 16/248; C07K 16/46; C07K 16/00; C07K 2317/52; C07K 2317/10; C07K 2317/73; C07K 2317/14; C07K 2317/20; C07K 2317/51; C07K 2317/515; C07K 2317/526; C07K 2317/53; C07K 2317/55; C07K 2317/31; C07K 2317/94; A61K 2039/505; A61K 2039/507; A61P 35/02; A61P 35/00

See application file for complete search history.

(56) References Cited

U.S. PATENT DOCUMENTS

| | | |
|---|---|---|
| 4,208,479 A | 6/1980 | Zuk et al. |
| 4,444,878 A | 4/1984 | Paulus |
| 4,474,893 A | 10/1984 | Reading |
| 5,126,250 A | 6/1992 | McDonough et al. |
| 5,322,678 A | 6/1994 | Morgan et al. |
| 5,496,549 A | 3/1996 | Yamazaki et al. |
| 5,591,828 A | 1/1997 | Bosslet et al. |
| 5,639,641 A | 6/1997 | Pedersen et al. |
| 5,670,373 A | 9/1997 | Kishimoto |
| 5,744,446 A | 4/1998 | Lollar et al. |
| 5,795,965 A | 8/1998 | Tsuchiya et al. |
| 5,837,821 A | 11/1998 | Wu |
| 5,859,205 A | 1/1999 | Adair et al. |
| 5,877,291 A | 3/1999 | Mezes et al. |
| 5,945,311 A | 8/1999 | Lindhofer et al. |
| 5,990,286 A | 11/1999 | Khawli et al. |
| 6,005,091 A | 12/1999 | Blackburn et al. |
| 6,010,902 A | 1/2000 | Ledbetter et al. |
| 6,126,980 A | 10/2000 | Smith et al. |
| 6,129,914 A | 10/2000 | Weiner |
| 6,132,992 A | 10/2000 | Ledbetter et al. |

(Continued)

FOREIGN PATENT DOCUMENTS

| | | |
|---|---|---|
| AU | 755822 | 3/1999 |
| AU | 2009290162 | 4/2010 |

(Continued)

OTHER PUBLICATIONS

Stancovski et al., PNAS, 88: 8691-8695, 1991.*

(Continued)

*Primary Examiner* — Phuong Huynh
(74) *Attorney, Agent, or Firm* — Fish & Richardson P.C.

(57) ABSTRACT

It is intended to provide a method for efficiently and stably producing a heteromultimer by incubating, under a reducing condition, homo variants of plural types of polypeptides in which the alteration of amino acids that form the interface between Fc regions and/or the alteration to destabilize the stability of a heavy chain CH3 region has been introduced in the heavy chain CH3 regions so at to achieve the promotion of the dissociation of the Fc regions and/or the control of the association thereof through the use of charge repulsion.

38 Claims, 7 Drawing Sheets

Specification includes a Sequence Listing.

(56) References Cited

U.S. PATENT DOCUMENTS

| | | |
|---|---|---|
| 6,183,744 B1 | 2/2001 | Goldenberg |
| 6,323,000 B2 | 11/2001 | Briggs et al. |
| 6,329,511 B1 | 12/2001 | Vasquez et al. |
| 6,342,220 B1 | 1/2002 | Adams et al. |
| 6,368,596 B1 | 4/2002 | Ghetie et al. |
| 6,485,943 B2 | 11/2002 | Stevens et al. |
| 6,677,436 B1 | 1/2004 | Sato et al. |
| 6,683,157 B2 | 1/2004 | Briggs et al. |
| 6,699,686 B1 | 3/2004 | Brocard et al. |
| 6,723,319 B1 | 4/2004 | Ito et al. |
| 6,884,879 B1 | 4/2005 | Baca et al. |
| 6,913,747 B1 | 7/2005 | Co et al. |
| 7,018,632 B2 | 3/2006 | Lindhofer et al. |
| 7,033,590 B1 | 4/2006 | Scheiflinger et al. |
| 7,052,873 B2 | 5/2006 | Tsuchiya |
| 7,122,637 B2 | 10/2006 | Presta |
| 7,217,797 B2 | 5/2007 | Hinton et al. |
| 7,276,585 B2 | 10/2007 | Lazar et al. |
| 7,538,196 B2 | 5/2009 | Jung |
| 7,732,149 B2 | 6/2010 | Kojima et al. |
| 7,951,917 B1 | 5/2011 | Arathoon et al. |
| 8,062,635 B2 | 11/2011 | Hattori et al. |
| 8,217,147 B2 | 7/2012 | Stavenhagen |
| 8,524,867 B2 | 9/2013 | Bernett et al. |
| 8,592,562 B2 | 11/2013 | Kannan et al. |
| 8,597,911 B2 | 12/2013 | Miyazaki et al. |
| 9,096,651 B2 | 8/2015 | Igawa et al. |
| 9,150,663 B2 | 10/2015 | Labrijn et al. |
| 9,200,060 B2 | 12/2015 | Kannan et al. |
| 9,228,017 B2 | 1/2016 | Igawa et al. |
| 9,334,331 B2 | 5/2016 | Igawa et al. |
| 9,527,926 B2 | 12/2016 | Ho et al. |
| 9,556,279 B2 | 1/2017 | Niwa et al. |
| 9,637,557 B2 | 5/2017 | Scheer et al. |
| 10,011,858 B2 | 7/2018 | Igawa et al. |
| 10,066,018 B2 | 9/2018 | Igawa et al. |
| 10,150,808 B2 | 12/2018 | Kuramochi et al. |
| 10,253,091 B2 | 4/2019 | Igawa et al. |
| 10,435,458 B2 | 10/2019 | Kuramochi et al. |
| 10,450,381 B2 | 10/2019 | Igawa et al. |
| 2001/0001663 A1 | 5/2001 | Kishimoto et al. |
| 2001/0006796 A1 | 7/2001 | Briggs et al. |
| 2002/0028178 A1 | 3/2002 | Hanna et al. |
| 2002/0062010 A1 | 5/2002 | Arathoon et al. |
| 2002/0142374 A1 | 10/2002 | Gallo et al. |
| 2002/0147326 A1 | 10/2002 | Chaiklin et al. |
| 2002/0155537 A1 | 10/2002 | Carter et al. |
| 2002/0164339 A1 | 11/2002 | Do et al. |
| 2002/0164668 A1 | 11/2002 | Durham et al. |
| 2002/0187150 A1 | 12/2002 | Mihara et al. |
| 2002/0193571 A1 | 12/2002 | Carter et al. |
| 2002/0197706 A1 | 12/2002 | Nadkarni et al. |
| 2003/0073161 A1 | 4/2003 | Briggs et al. |
| 2003/0082612 A1 | 5/2003 | Snodgrass et al. |
| 2003/0148409 A1 | 8/2003 | Rossi et al. |
| 2003/0187225 A1 | 10/2003 | Penichet et al. |
| 2003/0190311 A1 | 10/2003 | Dall'Acqua et al. |
| 2003/0207346 A1 | 11/2003 | Arathoon et al. |
| 2003/0219441 A1 | 11/2003 | Thorpe et al. |
| 2003/0224397 A1 | 12/2003 | Lowman et al. |
| 2004/0071706 A1 | 4/2004 | Ito et al. |
| 2004/0081651 A1 | 4/2004 | Karpusas et al. |
| 2004/0091475 A1 | 5/2004 | Tsuchiya et al. |
| 2004/0219643 A1 | 11/2004 | Winter et al. |
| 2004/0236080 A1 | 11/2004 | Aburatani et al. |
| 2004/0242847 A1 | 12/2004 | Fukushima et al. |
| 2005/0095243 A1 | 5/2005 | Chan et al. |
| 2005/0130224 A1 | 6/2005 | Saito et al. |
| 2005/0142133 A1 | 6/2005 | Lazar et al. |
| 2005/0142635 A1 | 6/2005 | Tsuchiya et al. |
| 2005/0164352 A1 | 7/2005 | Scott |
| 2005/0191293 A1 | 9/2005 | Deshpande et al. |
| 2005/0244403 A1 | 11/2005 | Lazar et al. |
| 2005/0261229 A1 | 11/2005 | Gillies |
| 2005/0266425 A1 | 12/2005 | Zauderer et al. |
| 2006/0019342 A1 | 1/2006 | Dall Acqua et al. |
| 2006/0024298 A1 | 2/2006 | Lazar et al. |
| 2006/0057149 A1 | 3/2006 | Johnson et al. |
| 2006/0058511 A1 | 3/2006 | Tanikawa et al. |
| 2006/0063228 A1 | 3/2006 | Kasaian et al. |
| 2006/0074225 A1* | 4/2006 | Chamberlain ......... C07K 16/00 530/387.1 |
| 2006/0134105 A1 | 6/2006 | Lazar |
| 2006/0134709 A1 | 6/2006 | Stavenhagen et al. |
| 2006/0134805 A1 | 6/2006 | Berg et al. |
| 2006/0141456 A1 | 6/2006 | Edwards et al. |
| 2006/0159673 A1 | 7/2006 | Kojima |
| 2006/0160184 A1 | 7/2006 | Hoogenboom et al. |
| 2006/0189794 A1 | 8/2006 | Tsuchiya et al. |
| 2006/0194280 A1 | 8/2006 | Dillon et al. |
| 2006/0204493 A1 | 9/2006 | Huang et al. |
| 2006/0222643 A1 | 10/2006 | Tsunoda et al. |
| 2006/0269989 A1 | 11/2006 | Miyazaki et al. |
| 2006/0275282 A1 | 12/2006 | Moore et al. |
| 2006/0275301 A1 | 12/2006 | Ozaki et al. |
| 2006/0292147 A1 | 12/2006 | Yoshizaki et al. |
| 2007/0003556 A1 | 1/2007 | Tsuchiya et al. |
| 2007/0036785 A1 | 2/2007 | Kishimoto et al. |
| 2007/0041978 A1 | 2/2007 | Hattori et al. |
| 2007/0054354 A1 | 3/2007 | Humphreys et al. |
| 2007/0059312 A1 | 3/2007 | Baca et al. |
| 2007/0087381 A1 | 4/2007 | Kojima |
| 2007/0110757 A1 | 5/2007 | Wei et al. |
| 2007/0134234 A1 | 6/2007 | Smith et al. |
| 2007/0148163 A1 | 6/2007 | Takahashi et al. |
| 2007/0148164 A1 | 6/2007 | Farrington et al. |
| 2007/0212357 A1 | 9/2007 | Pons et al. |
| 2007/0281327 A1 | 12/2007 | Nakano et al. |
| 2007/0287170 A1 | 12/2007 | Davis et al. |
| 2008/0009038 A1 | 1/2008 | Ohtomo et al. |
| 2008/0063635 A1 | 3/2008 | Takahashi et al. |
| 2008/0075712 A1 | 3/2008 | Hattori et al. |
| 2008/0166756 A1 | 7/2008 | Tsuchiya et al. |
| 2008/0206229 A1 | 8/2008 | Ono et al. |
| 2009/0028854 A1 | 1/2009 | Igawa et al. |
| 2009/0117097 A1 | 5/2009 | Igawa et al. |
| 2009/0208416 A1 | 8/2009 | Moretta et al. |
| 2009/0214535 A1 | 8/2009 | Igawa et al. |
| 2009/0221803 A1 | 9/2009 | Dall'Acqua et al. |
| 2009/0263392 A1 | 10/2009 | Igawa et al. |
| 2009/0297501 A1 | 12/2009 | Igawa et al. |
| 2009/0324589 A1 | 12/2009 | Igawa et al. |
| 2010/0003254 A1 | 1/2010 | Hattori et al. |
| 2010/0004429 A1 | 1/2010 | Kai et al. |
| 2010/0008907 A1 | 1/2010 | Nishimoto et al. |
| 2010/0015133 A1* | 1/2010 | Igawa ..................... C12P 21/02 424/133.1 |
| 2010/0055092 A1 | 3/2010 | Hasegawa et al. |
| 2010/0105874 A1 | 4/2010 | Schuurman et al. |
| 2010/0239577 A1 | 9/2010 | Igawa et al. |
| 2010/0286374 A1 | 11/2010 | Kannan et al. |
| 2010/0291072 A1 | 11/2010 | Lowman et al. |
| 2010/0298542 A1 | 11/2010 | Igawa et al. |
| 2010/0331527 A1 | 12/2010 | Davis et al. |
| 2011/0021755 A1 | 1/2011 | Lazar et al. |
| 2011/0076275 A1 | 3/2011 | Igawa et al. |
| 2011/0111406 A1 | 5/2011 | Igawa et al. |
| 2011/0123532 A1 | 5/2011 | Gurney et al. |
| 2011/0129459 A1 | 6/2011 | Kuramochi et al. |
| 2011/0236374 A1 | 9/2011 | Shitara et al. |
| 2011/0245473 A1 | 10/2011 | Igawa et al. |
| 2012/0009188 A1* | 1/2012 | Behrens ................. C07K 16/00 424/133.1 |
| 2012/0028304 A1 | 2/2012 | Dahiyat et al. |
| 2012/0065379 A1 | 3/2012 | Igawa et al. |
| 2012/0071634 A1 | 3/2012 | Igawa et al. |
| 2012/0149876 A1* | 6/2012 | Von Kreudenstein ...................... C07K 16/00 530/387.3 |
| 2012/0237517 A1 | 9/2012 | Hattori et al. |
| 2012/0238729 A1 | 9/2012 | Kuramochi et al. |
| 2013/0011866 A1 | 1/2013 | Igawa et al. |
| 2013/0018174 A1 | 1/2013 | Igawa et al. |
| 2013/0030156 A1 | 1/2013 | Apostolou et al. |

(56) References Cited

U.S. PATENT DOCUMENTS

| | | | |
|---|---|---|---|
| 2013/0039913 A1* | 2/2013 | Labrijn | C07K 16/1063 424/136.1 |
| 2013/0052196 A1 | 2/2013 | Apostolou et al. | |
| 2013/0085199 A1 | 4/2013 | Tamori et al. | |
| 2013/0101581 A1 | 4/2013 | Kuramochi et al. | |
| 2013/0115208 A1 | 5/2013 | Ho et al. | |
| 2013/0195849 A1 | 8/2013 | Spreter et al. | |
| 2013/0330345 A1 | 12/2013 | Igawa et al. | |
| 2014/0037632 A1 | 2/2014 | Igawa et al. | |
| 2014/0051833 A1 | 2/2014 | Fischer et al. | |
| 2014/0112883 A1 | 4/2014 | Ponath et al. | |
| 2014/0112914 A1 | 4/2014 | Nezu et al. | |
| 2014/0303356 A1 | 10/2014 | Gramer et al. | |
| 2014/0370018 A1 | 12/2014 | Igawa et al. | |
| 2014/0370020 A1 | 12/2014 | Kuramochi et al. | |
| 2014/0377253 A1 | 12/2014 | Harding et al. | |
| 2015/0118184 A1 | 4/2015 | Kawai | |
| 2015/0166636 A1 | 6/2015 | Igawa et al. | |
| 2015/0274809 A1 | 10/2015 | Igawa et al. | |
| 2015/0284465 A1 | 10/2015 | Igawa et al. | |
| 2015/0315278 A1 | 11/2015 | Igawa et al. | |
| 2015/0344570 A1 | 12/2015 | Igawa et al. | |
| 2016/0159915 A1 | 6/2016 | Igawa et al. | |
| 2016/0168259 A1 | 6/2016 | Igawa et al. | |
| 2016/0222129 A1 | 8/2016 | Igawa et al. | |
| 2016/0229915 A1 | 8/2016 | Igawa et al. | |
| 2016/0344570 A1 | 11/2016 | Ong et al. | |
| 2017/0022287 A1 | 1/2017 | Igawa et al. | |
| 2017/0022293 A1 | 1/2017 | Igawa et al. | |
| 2017/0267783 A1 | 9/2017 | Nezu et al. | |
| 2017/0275332 A1 | 9/2017 | Igawa et al. | |
| 2018/0051307 A1 | 2/2018 | Igawa et al. | |
| 2018/0057607 A1 | 3/2018 | Igawa et al. | |
| 2018/0142027 A1 | 5/2018 | Igawa et al. | |
| 2018/0162902 A1 | 6/2018 | Igawa et al. | |
| 2018/0244800 A1 | 8/2018 | Hattori et al. | |
| 2019/0062368 A1 | 2/2019 | Igawa et al. | |
| 2019/0112390 A1 | 4/2019 | Hattori et al. | |
| 2019/0211081 A1 | 7/2019 | Igawa et al. | |
| 2019/0315884 A1 | 10/2019 | Igawa et al. | |
| 2019/0330268 A1 | 10/2019 | Tanaka et al. | |
| 2019/0352334 A1 | 11/2019 | Igawa et al. | |
| 2019/0359728 A1 | 11/2019 | Hattori et al. | |
| 2020/0087380 A1 | 3/2020 | Kuramochi et al. | |
| 2020/0207805 A1 | 7/2020 | Igawa et al. | |
| 2020/0179010 A1 | 9/2020 | Hattori et al. | |
| 2020/0277402 A1 | 9/2020 | Hattori et al. | |

FOREIGN PATENT DOCUMENTS

| | | |
|---|---|---|
| CA | 2 203 182 | 5/1996 |
| CA | 2 331 641 | 11/1999 |
| CA | 2 019 559 | 1/2002 |
| CA | 2 443 294 | 10/2002 |
| CA | 2 523 577 | 11/2004 |
| CA | 2 531 482 | 1/2005 |
| CA | 2 549 467 | 7/2005 |
| CA | 2 560 953 | 9/2005 |
| CA | 2 603 264 | 10/2006 |
| CA | 2 625 773 | 4/2007 |
| CA | 2 626 688 | 4/2007 |
| CA | 2 647 846 | 10/2007 |
| CA | 2 700 986 | 4/2009 |
| CA | 2 819 530 | 6/2012 |
| CN | 101198698 | 6/2008 |
| CN | 101874042 | 10/2010 |
| CN | 102471378 | 5/2012 |
| CN | 102782131 | 11/2012 |
| CN | 102946906 | 2/2013 |
| CN | 103429737 | 12/2013 |
| CN | 103833852 | 6/2014 |
| DE | 198 19 846 | 11/1999 |
| EP | 0 369 566 | 5/1990 |
| EP | 437 622 | 7/1991 |
| EP | 0 329 185 | 4/1994 |
| EP | 0 637 593 | 2/1995 |
| EP | 0 404 097 | 9/1996 |
| EP | 0 774 511 | 5/1997 |
| EP | 0 783 893 | 7/1997 |
| EP | 0 811 691 | 12/1997 |
| EP | 1 069 185 | 1/2001 |
| EP | 1 220 923 | 7/2002 |
| EP | 1 327 681 | 7/2003 |
| EP | 1 510 943 | 3/2005 |
| EP | 0 979 281 | 7/2005 |
| EP | 1 605 058 | 12/2005 |
| EP | 1 693 448 | 8/2006 |
| EP | 1 701 979 | 9/2006 |
| EP | 1 773 391 | 4/2007 |
| EP | 1 847 602 | 10/2007 |
| EP | 1 870 458 | 12/2007 |
| EP | 1 870 459 | 12/2007 |
| EP | 1 876 236 | 1/2008 |
| EP | 1 900 814 | 3/2008 |
| EP | 2 006 381 | 12/2008 |
| EP | 2 009 101 | 12/2008 |
| EP | 2 031 064 | 3/2009 |
| EP | 1 505 148 | 4/2009 |
| EP | 2 107 115 | 10/2009 |
| EP | 2 194 066 | 6/2010 |
| EP | 2 196 541 | 6/2010 |
| EP | 2 202 245 | 6/2010 |
| EP | 2 206 775 | 7/2010 |
| EP | 2 236 604 | 10/2010 |
| EP | 2 275 443 | 1/2011 |
| EP | 1 688 488 | 8/2011 |
| EP | 2 409 991 | 1/2012 |
| EP | 2 238 985 | 8/2012 |
| EP | 2 522 724 | 11/2012 |
| EP | 2 526 963 | 11/2012 |
| EP | 2 543 727 | 1/2013 |
| EP | 2 644 698 | 10/2013 |
| EP | 2 647 707 | 10/2013 |
| EP | 2 905 290 | 8/2015 |
| EP | 2 914 634 | 9/2015 |
| EP | 3 199 628 | 8/2017 |
| JP | S63-52890 | 3/1988 |
| JP | 2-028200 | 1/1990 |
| JP | H02-145187 | 6/1990 |
| JP | H03-500644 | 2/1991 |
| JP | H05-184383 | 7/1993 |
| JP | H05-199894 | 8/1993 |
| JP | H05-203652 | 8/1993 |
| JP | H05-213775 | 8/1993 |
| JP | H05-304992 | 11/1993 |
| JP | 07-67688 | 3/1995 |
| JP | 7-503622 | 4/1995 |
| JP | 8-500979 | 2/1996 |
| JP | 8-510555 | 11/1996 |
| JP | 09-506001 | 6/1997 |
| JP | 10-505231 | 5/1998 |
| JP | 10-165184 | 6/1998 |
| JP | 10-511085 | 10/1998 |
| JP | 11-500915 | 1/1999 |
| JP | 11-500916 | 1/1999 |
| JP | 11-71288 | 3/1999 |
| JP | 11-506310 | 6/1999 |
| JP | 3032287 | 4/2000 |
| JP | 2001-506135 | 5/2001 |
| JP | 2001-513999 | 9/2001 |
| JP | 2001-518930 | 10/2001 |
| JP | 2001-523971 | 11/2001 |
| JP | 2002-514406 | 5/2002 |
| JP | 2002-518041 | 6/2002 |
| JP | 2002-543822 | 12/2002 |
| JP | 2002-544173 | 12/2002 |
| JP | 2003-055398 | 2/2003 |
| JP | 2003-509049 | 3/2003 |
| JP | 2003-515323 | 5/2003 |
| JP | 2004-086682 | 3/2004 |
| JP | 2004-086862 | 3/2004 |
| JP | 2004-511426 | 4/2004 |
| JP | 2005-501514 | 1/2005 |

(56) References Cited

FOREIGN PATENT DOCUMENTS

| | | |
|---|---|---|
| JP | 2005-101105 | 3/2005 |
| JP | 2005-535341 | 11/2005 |
| JP | 2005-378266 | 12/2005 |
| JP | 2005-537009 | 12/2005 |
| JP | 2008-512995 | 5/2008 |
| JP | 2008-523140 | 7/2008 |
| JP | 2008-538920 | 11/2008 |
| JP | 2009-500458 | 1/2009 |
| JP | 2010-522701 | 7/2010 |
| JP | 2011-508604 | 3/2011 |
| JP | 2012-504970 | 3/2012 |
| JP | 2012-510281 | 5/2012 |
| JP | 2012-522527 | 9/2012 |
| JP | 2012-531439 | 12/2012 |
| JP | 5144499 | 2/2013 |
| JP | 2013-515509 | 5/2013 |
| JP | 2013-529084 | 7/2013 |
| JP | 2013-529190 | 7/2013 |
| JP | 2013-165716 | 8/2013 |
| JP | 5334319 | 11/2013 |
| JP | 5484060 | 5/2014 |
| JP | 5681482 | 3/2015 |
| JP | 2015-510764 | 4/2015 |
| JP | 5717624 | 5/2015 |
| JP | 2015-130883 | 7/2015 |
| JP | 5787446 | 9/2015 |
| JP | 5912436 | 4/2016 |
| JP | 2016-69329 | 5/2016 |
| JP | 6175590 | 8/2017 |
| JP | 6534615 | 6/2019 |
| KR | 2009/0107091 | 10/2009 |
| KR | 2010/0056467 | 5/2010 |
| KR | 2010/0074221 | 7/2010 |
| KR | 2012/0123055 | 11/2012 |
| KR | 2013/0102113 | 9/2013 |
| KR | 2013/0102640 | 9/2013 |
| KR | 2013/0130765 | 12/2013 |
| MX | 9905856 A | 7/2000 |
| NO | 20062087 | 7/2006 |
| RU | 94028282 | 7/1996 |
| RU | 2232773 | 7/2004 |
| RU | 2266298 | 12/2005 |
| RU | 2339696 | 11/2008 |
| RU | 2009/149451 | 7/2011 |
| RU | 2427588 | 8/2011 |
| RU | 2012/112067 | 10/2013 |
| SG | 11201701119 R | 3/2017 |
| TW | 2007/14313 | 4/2007 |
| TW | 2007/22517 | 6/2007 |
| TW | 2012/49872 | 12/2012 |
| TW | I452135 | 9/2014 |
| TW | I452136 | 9/2014 |
| TW | 2016/19193 | 6/2016 |
| WO | WO 89/01343 | 2/1989 |
| WO | WO 91/01335 | 2/1991 |
| WO | WO 91/08770 | 6/1991 |
| WO | WO 92/19759 | 11/1992 |
| WO | WO 93/11161 | 6/1993 |
| WO | WO 94/05690 | 3/1994 |
| WO | WO 94/13804 | 6/1994 |
| WO | WO 95/01571 | 1/1995 |
| WO | WO 95/014710 | 6/1995 |
| WO | WO 95/33844 | 12/1995 |
| WO | WO 96/01653 | 1/1996 |
| WO | WO 96/04925 | 2/1996 |
| WO | WO 96/07754 | 3/1996 |
| WO | WO 96/11020 | 4/1996 |
| WO | WO 96/12503 | 5/1996 |
| WO | WO 96/16673 | 6/1996 |
| WO | WO 96/26964 | 9/1996 |
| WO | WO 96/27011 | 9/1996 |
| WO | WO 96/34892 | 11/1996 |
| WO | WO 97/09351 | 3/1997 |
| WO | WO 97/10354 | 3/1997 |
| WO | WO 97/31108 | 8/1997 |
| WO | WO 98/03546 | 1/1998 |
| WO | WO 98/28331 | 7/1998 |
| WO | WO 98/41641 | 9/1998 |
| WO | WO 98/42378 | 10/1998 |
| WO | WO 98/50431 | 11/1998 |
| WO | WO 99/02567 | 1/1999 |
| WO | WO 99/03495 | 1/1999 |
| WO | WO 99/10494 | 3/1999 |
| WO | WO 99/18212 | 4/1999 |
| WO | WO 99/51743 | 10/1999 |
| WO | WO 99/58572 | 11/1999 |
| WO | WO 99/67359 | 12/1999 |
| WO | WO 00/44788 | 8/2000 |
| WO | WO 00/67795 | 11/2000 |
| WO | WO 00/69462 | 11/2000 |
| WO | WO 01/19992 | 3/2001 |
| WO | WO 01/30854 | 5/2001 |
| WO | WO 01/36486 | 5/2001 |
| WO | WO 01/44282 | 6/2001 |
| WO | WO 01/64713 | 9/2001 |
| WO | WO 01/66737 | 9/2001 |
| WO | WO 01/70775 | 9/2001 |
| WO | WO 01/74388 | 10/2001 |
| WO | WO 01/79494 | 10/2001 |
| WO | WO 01/82899 | 11/2001 |
| WO | WO 01/90192 | 11/2001 |
| WO | WO 01/97858 | 12/2001 |
| WO | WO 02/04021 | 1/2002 |
| WO | WO 02/06838 | 1/2002 |
| WO | WO 02/22212 | 3/2002 |
| WO | WO 02/30463 | 4/2002 |
| WO | WO 02/33072 | 4/2002 |
| WO | WO 02/33073 | 4/2002 |
| WO | WO 02/060919 | 8/2002 |
| WO | WO 02/072605 | 9/2002 |
| WO | WO 02/078612 | 10/2002 |
| WO | WO 03/000883 | 1/2003 |
| WO | WO 03/012069 | 2/2003 |
| WO | WO 03/020949 | 3/2003 |
| WO | WO 03/033654 | 4/2003 |
| WO | WO 03/035835 | 5/2003 |
| WO | WO 03/042231 | 5/2003 |
| WO | WO 03/074679 | 9/2003 |
| WO | WO 03/087163 | 10/2003 |
| WO | WO 03/091424 | 11/2003 |
| WO | WO 03/104425 | 12/2003 |
| WO | WO 03/105757 | 12/2003 |
| WO | WO 2004/009618 | 1/2004 |
| WO | WO 2004/016740 | 2/2004 |
| WO | WO 2004/019966 | 3/2004 |
| WO | WO 2004/020579 | 3/2004 |
| WO | WO 2004/033499 | 4/2004 |
| WO | WO 2004/060919 | 7/2004 |
| WO | WO 2004/065611 | 8/2004 |
| WO | WO 2004/068931 | 8/2004 |
| WO | WO 2004/081048 | 9/2004 |
| WO | WO 2004/087763 | 10/2004 |
| WO | WO 2004/096273 | 11/2004 |
| WO | WO 2004/097041 | 11/2004 |
| WO | WO 2004/111233 | 12/2004 |
| WO | WO 2004/113387 | 12/2004 |
| WO | WO 2005/000900 | 1/2005 |
| WO | WO 2005/005604 | 1/2005 |
| WO | WO 2005/025615 | 3/2005 |
| WO | WO 2005/035753 | 4/2005 |
| WO | WO 2005/035754 | 4/2005 |
| WO | WO 2005/035756 | 4/2005 |
| WO | WO 2005/047327 | 5/2005 |
| WO | WO 2005/056604 | 6/2005 |
| WO | WO 2005/056606 | 6/2005 |
| WO | WO 2005/059106 | 6/2005 |
| WO | WO 2005/062916 | 7/2005 |
| WO | WO 2005/067620 | 7/2005 |
| WO | WO 2005/092925 | 10/2005 |
| WO | WO 2005/107784 | 11/2005 |
| WO | WO 2005/112564 | 12/2005 |
| WO | WO 2005/121180 | 12/2005 |
| WO | WO 2005/123126 | 12/2005 |
| WO | WO 2006/004663 | 1/2006 |

(56) References Cited

FOREIGN PATENT DOCUMENTS

| | | |
|---|---|---|
| WO | WO 2006/019447 | 2/2006 |
| WO | WO 2006/029879 | 3/2006 |
| WO | WO 2006/030200 | 3/2006 |
| WO | WO 2006/030220 | 3/2006 |
| WO | WO 2006/033386 | 3/2006 |
| WO | WO 2006/047340 | 5/2006 |
| WO | WO 2006/047350 | 5/2006 |
| WO | WO 2006/050491 | 5/2006 |
| WO | WO 2006/065208 | 6/2006 |
| WO | WO 2006/067913 | 6/2006 |
| WO | WO 2006/071877 | 7/2006 |
| WO | WO 2006/075668 | 7/2006 |
| WO | WO 2006/106903 | 10/2006 |
| WO | WO 2006/106905 | 10/2006 |
| WO | WO 2006/109592 | 10/2006 |
| WO | WO 2006/113767 | 10/2006 |
| WO | WO 2006/116260 | 11/2006 |
| WO | WO 2006/121852 | 11/2006 |
| WO | WO 2007/009065 | 1/2007 |
| WO | WO 2007/024535 | 3/2007 |
| WO | WO 2007/060411 | 5/2007 |
| WO | WO 2007/108559 | 9/2007 |
| WO | WO 2007/110205 | 10/2007 |
| WO | WO 2007/114319 | 10/2007 |
| WO | WO 2007/114325 | 10/2007 |
| WO | WO 2007/142325 | 12/2007 |
| WO | WO 2007/147901 | 12/2007 |
| WO | WO 2008/043822 | 4/2008 |
| WO | WO 2008/090960 | 7/2008 |
| WO | WO 2008/092117 | 7/2008 |
| WO | WO 2008/118970 | 10/2008 |
| WO | WO 2008/119353 | 10/2008 |
| WO | WO 2008/145141 | 12/2008 |
| WO | WO 2008/145142 | 12/2008 |
| WO | WO 2009/012394 | 1/2009 |
| WO | WO 2009/036209 | 3/2009 |
| WO | WO 2009/041062 | 4/2009 |
| WO | WO 2009/041613 | 4/2009 |
| WO | WO 2009/041621 | 4/2009 |
| WO | WO 2009/041643 | 4/2009 |
| WO | WO 2009/041734 | 4/2009 |
| WO | WO 2009/052439 | 4/2009 |
| WO | WO 2009/053368 | 4/2009 |
| WO | WO 2009/072604 | 6/2009 |
| WO | WO 2009/079649 | 6/2009 |
| WO | WO 2009/084659 | 7/2009 |
| WO | WO 2009/089004 | 7/2009 |
| WO | WO 2009/100309 | 8/2009 |
| WO | WO 2009/125825 | 10/2009 |
| WO | WO 2009/139822 | 11/2009 |
| WO | WO2012020096 * | 1/2010 |
| WO | WO 2010/035769 | 4/2010 |
| WO | WO 2010/042904 | 4/2010 |
| WO | WO 2010/063746 | 6/2010 |
| WO | WO 2010/064090 | 6/2010 |
| WO | WO 2010/106180 | 9/2010 |
| WO | WO 2010/107109 | 9/2010 |
| WO | WO 2010/107110 | 9/2010 |
| WO | WO 2010/115589 | 10/2010 |
| WO | WO 2010/129304 | 11/2010 |
| WO | WO 2010/151792 | 12/2010 |
| WO | WO 2011/090088 | 2/2011 |
| WO | WO 2011/025964 | 3/2011 |
| WO | WO 2011/037158 | 3/2011 |
| WO | WO 2011/078332 | 6/2011 |
| WO | WO 2011/090754 | 7/2011 |
| WO | WO 2011/090762 | 7/2011 |
| WO | WO 2011/091177 | 7/2011 |
| WO | WO 2011/091181 | 7/2011 |
| WO | WO 2011/108502 | 9/2011 |
| WO | WO 2011/108714 | 9/2011 |
| WO | WO 2011/111007 | 9/2011 |
| WO | WO 2011/125674 | 10/2011 |
| WO | WO 2011/131746 | 10/2011 |
| WO | WO 2011/133886 | 10/2011 |
| WO | WO 2011/143545 | 11/2011 |
| WO | WO 2012/067176 | 5/2012 |
| WO | WO 2012/073985 | 6/2012 |
| WO | WO 2012/131555 | 10/2012 |
| WO | WO 2012/145238 | 10/2012 |
| WO | WO 2013/060867 | 5/2013 |
| WO | WO 2013/065708 | 5/2013 |
| WO | WO 2013/124450 | 8/2013 |
| WO | WO 2013/131866 | 9/2013 |
| WO | WO 2013/136186 | 9/2013 |
| WO | WO 2013/157954 | 10/2013 |
| WO | WO 2013/158856 | 10/2013 |
| WO | WO 2013/181543 | 12/2013 |
| WO | WO 2014/028354 | 2/2014 |
| WO | WO 2014/051433 | 4/2014 |
| WO | WO 2014/054804 | 4/2014 |
| WO | WO 2014/067011 | 5/2014 |
| WO | WO 2015/046467 | 4/2015 |
| WO | WO 2015/046554 | 4/2015 |
| WO | WO 2015/063339 | 5/2015 |
| WO | WO 2015/156268 | 10/2015 |
| WO | WO 2015/174439 | 11/2015 |
| WO | WO 2015/194233 | 12/2015 |
| WO | WO 2016/047722 | 3/2016 |
| WO | WO 2016/159213 | 10/2016 |
| WO | WO 2016/166014 | 10/2016 |
| WO | WO 2016/171202 | 10/2016 |
| WO | WO 2017/115773 | 7/2017 |
| WO | WO 2017/129585 | 8/2017 |
| WO | WO 2017/159287 | 9/2017 |
| WO | WO 2017/188356 | 11/2017 |
| WO | WO 2018/181870 | 10/2018 |

OTHER PUBLICATIONS

Bowie et al., Science. 247 (4948): 1306-1310, Mar. 16, 1990.*
Labrijn et al., J Immunol 187:3238-3246 (Year: 2011).*
U.S. Appl. No. 14/921,590, Hattori et al., filed Oct. 23, 2015.
U.S. Appl. No. 15/172,727, Hattori et al., filed Apr. 3, 2016.
U.S. Appl. No. 15/701,630, Hattori et al., filed Sep. 12, 2017.
"Hemophilia and von Willebrand's disease: 2. Management. Association of Hemophilia Clinic Directors of Canada," CMAJ., 153(2):147-157, Jul. 15, 1995.
Buque et al., "Trial Watch: Immunomodulatory monoclonal antibodies for oncological indications," Oncoimmunology, Mar. 2015 2:4(4):e1008814. eCollection 2015.
Chugai Seiyaku Kabushiki Kaisha's letter dated Jun. 12, 2013, regarding oral proceedings scheduled on Jun. 26, 2013, in App. Ser. No. EP 06730769.4 (Annex A submitted with patentee's letter dated Jun. 12, 2013).
Gunawardane et al., "Agonistic Human Antibodies Binding to Lecithin-Cholesterol Acyltransferase Modulate High Density Lipoprotein Metabolism," J Biol Chem. Feb. 5, 2016;291(6):2799-811. doi: 10.1074/jbc.M115.672790. Epub Dec. 7, 2015.
Hattori, Introduction of ART-Ig and application to hemophilia A treatment, Chugai Seiyaku ni Okeru Dokuji no Kakushinteki Kotai Gijutsu. Dec. 2012; 18: 42-57 (with English translation).
Iwai et al., "Therapeutic Agents for Gastric Cancer," Igan Chiryoyaku, Yakkyoku, Jan. 5, 2016:67(1)138-41 (with English translation).
Kabat et al., Sequences of Proteins of Immunological Interest, National Institute of Health, Publ'n No. 91-3242, vol. 1 p. 647-660 (5th ed. 1991).
Kitazawa et al., "A bispecific antibody to factors IXa and X restores factor VIII hemostatic activity in a hemophilia A model," Nat. Med., Oct. 2012;18(10):1570-4. doi:10.1038/nm.2942. Epub Sep. 30, 2012.
Klinger et al., "Harnessing T cells to fight cancer with BiTE((R)) antibody constructs—past developments and future directions," Immunol. Rev., Mar. 2016:270(1):193-208. doi:10.1111/imr.12393.
Labrijn et al., "Controlled Fab-arm exchange for the generation of stable bispecific IgG1," Nat Protoc. Oct. 2014; 9(10): 2450-63. doi: 10.1038/nprot.2014.169. Epub Sep. 25, 2014.
Larkin et al., "Combined Nivoluniab and Ipilimumab or Monotherapy in Untreated Melanoma," N. Engl. J. Med., Jul. 2, 2015:373(1):23-34. doi:10.1056/NEJMoa1504030. Epub May 31, 2015.

(56) References Cited

OTHER PUBLICATIONS

Narhi et al., "Asn to Lys mutations at three sites which are N-glycosylated in the mammalian protein decrease the aggregation of *Escherichia coli*-derived erythropoietin," Protein Eng., Feb. 2001;14(2) :135-40.
Peters et al., "Engineering an improved IgG4 molecule with reduced disulfide bond heterogeneity and increased Fab domain thermal stability," J Biol Chem. Jul. 13, 2012; 287(29): 24525-33. doi: 10.1074/jbc.M112.369744. Epub May 18, 2012.
Petkova et al., Enhanced half-life of genetically engineered human IgG1 antibodies in a humanized FcRn mouse model: potential application in Immorally mediated autoimmune disease, Int. Immunol. Dec. 2006;18(12):1759-69. Epub 2006.
Ruggeri et al., "von Willebrand factor and von Willebrand disease," Blood. Oct. 1987;70(4):895-904.
Vaccaro et al., "Divergent activities of an engineered antibody in murine and human systems have implications for therapeutic antibodies," Proc Natl Acad Sci U S A. Dec. 5, 2006;103(49):18709-14. Epub Nov. 20, 2006.
Xiang et al., "Production of murine V-human Crl chimeric anti-TAG72 antibody using V region cDNA amplified by PCR," Mol Immunol., Aug. 1990;27(8):809-817.
Yasukawa et al., "Structure and expression of human B cell stimulatory factor-2 (BSF-2/IL-6) gene," EMBO J., Oct. 1987;6(10):2939-45.
USPTO Notice of Allowance in U.S. Appl. No. 14/127,576 dated Oct. 19, 2017, 7 pages.
USPTO Notice of Allowance in U.S. Appl. No. 14/127,576, dated Dec. 15, 2017, 8 pages.
Abe et al., "Surrogate thrombopoietin," *Immunology Letters*, 61:73-78 (1998).
Abe et al., "Purification of monoclonal antibodies with light-chain heterogeneity produced by mouse hybridomas raised with NS-1 myeloma: application of hydrophobic interaction high-performance liquid chromatography," *J. Biochem. Biophys. Methods*, 27:215-227 (1993).
Adams et al., "Humanization of a recombinant monoclonal antibody to produce a therapeutic HER dimerization inhibitor, pertuzumab," Cancer Immunol. Immunother., 55:717-727 (2006).
Algonomics—Tripole® applications [online] [retrieved on Feb. 29, 2012]. Retrieved from the Internet: http://web.archive.org/web20090221052902/http://www.algonomics.com/proteinengineering/tripole_applications.php, 2 pages (Feb. 21, 2009).
Allard et al., "Antigen binding properties of highly purified bispecific antibodies," Mol Immunol., Oct. 1992;29(10):1219-27.
Allen et al., "Interchain disulfide bonding in human IgG2 antibodies probed by site-directed mutagenesis," Biochemistry, 48(17):3755-66 (2009).
Almagro et al., "Humanization of antibodies," Front Biosci., 13:1619-33 (2008).
Amersham Biosciences, "Protein Purification Handbook," Edition AC, 98 pages (2001).
Amersham Biosciences, "Affinity Chromatography: Principles and Methods," Edition AD, pp. 16-18, 137 (2002).
Andris-Widhopf et al., "Methods for the generation of chicken monoclonal antibody fragments by phage display," Journal of Immunological Methods, 242:159-181 (2000).
Angal et al., "A single amino acid substitution abolishes the heterogeneity of chimeric mouse/human (IgG4) antibody," Mol. Immunol., 30:105-108 (1993).
Arndt et al., "Factors influencing the dimer to monomer transition of an antibody single-chain Fv fragment" Biochemistry, 37(37):12918-26 (1998).
Arndt et al., "Generation of a highly stable, internalizing anti-DC22 single-chain Fv fragment for targeting non-Hodgkin's lymphoma," Int. J. Cancer, 107(5):822-829 (2003).
Arndt et al., "Helix-stabilized Fv (hsFv) antibody fragments: substituting the constant domains of a Fab fragment for a heterodimeric coiled-coil domain," J. Mol. Biol., 312:221-228 (2001).

Armour et al., "Recombinant human IgG molecules lacking Fcgamma receptor I binding and monocyte triggering activities," Eur. J. Immunol., 29(8):2613-24 (1999).
Aslan et al., "Engineering a novel, stable dimeric streptavidin with lower isoelectric point," J. Biotechnol., 128(2):213-25 (2007).
Atwell et al., "Stable heterodimers from remodeling the domain interface of a homodimer using a phage display library," J. Mol. Biol., 270:26-35 (1997).
Baerga-Ortiz et al., "Two different proteins that compete for binding to thrombin have opposite kinetic and thermodynamic profiles," Protein Sci., 13(1):166-76 (2004).
Baker et al., "Conversion of a T cell antagonist into an agonist by repairing a defect in the TCR/peptide/MHC interface: implications for TCR signaling," Immunity, 13:475-484 (2000).
Ballmaier et al., "c-mpl mutations are the cause of congenital amegakaryocytic thrombocytopenia," Blood, 97:139-146 (2001).
Bartelds et al., "Clinical response to adalimumab: relationship to anti-adalimumab antibodies and serum adalimumab concentrations in rheumatoid arthritis," Ann Rheum. Dis., 66:921-926 (2007).
Batra et al., "Pharmacokinetics and biodistribution of genetically engineered antibodies," Curr Opin Biotechnol., Dec. 2002;13(6):603-8.
Bayry et al., "Immuno affinity purification of foot and mouth disease virus type specific antibodies using recombinant protein adsorbed to polystyrene wells," J. Virol. Methods, 81:21-30 (1999).
Bender et al., "Immunogenicity, efficacy and adverse events of adalimumab in RA patients," Rheumatol. Int., 27:269-274 (2007).
Binz et al., "Engineering novel binding proteins from nonimmunoglobulin domains," Nat. Biotechnol., 23:1257-68 (2005).
Blazar, "Infusion of Anti-B7.1 (CD80) and Anti-B7.2 (CD86) Monoclonal Antibodies Inhibits Murine Graft-Versus-Host Disease Lethality in Part Via Direct Effects on CD4+ and CD8+ T Cells," J. Immunol., 157:3250-59 (1996).
Borrebaeck et al., "Antibody evolution beyond Nature," Nat Biotechnol., Dec. 2002;20(12):1189-90.
Bowen, Haemophilia A and haemophilia B: molecular insights, Mol Pathol., Feb. 2002;55(1):1-18.
Bowie et al., "Deciphering the Message in Protein Sequences: Tolerance to Amino Acid Substitutions," Science, 247:1306-1310 (1990).
Branden and Tooze, "Recognition of Foreign Molecules by the Immune System," Introduction to Protein Structure, 2d Ed., Garland Publishing, pp. 299-323 (1999).
Brandstetter et al., "X-ray structure of clotting factor IXa: active site and module structure related to Xase activity and hemophilia B," Proc Natl Acad Sci U S A, Oct. 10, 1995;92(21):9796-800.
Brinkmann et al., "FTY720: targeting G-protein-coupled receptors for sphingosine 1-phosphate in transplantation and autoimmunity," Curr. Opin. Immunol., 14:569-575 (2002).
Brown et al., "Tolerance of single, but not multiple, amino acid replacements in antibody $V_H$ CDR2: a means of minimizing B cell wastage from somatic hypermutation?," J. Immunol., 156(9):3285-91 (1996).
Bruenke et al., "A recombinant bispecific single-chain Fv antibody against HLA class II and FcγRIII (CD16) triggers effective lysis of lymphoma cells," Br. J. Haematol., 125:167-179 (2004).
Burges et al., "Effective relief of malignant ascites in patients with advanced ovarian cancer by a trifunctional anti-EpCAM x anti-CD3 antibody: a phase I/II study," Clin. Cancer Res., 13(13):3899-905 (2007).
Burgess, "Possible dissociation of the heparin-binding and mitogenic activities of heparin-binding (acidic fibroblast) growth factor-1 from its receptor-binding activities by site-directed mutagenesis of a single lysine residue," J. Cell. Biol., 111:2129-2138 (1990).
Calbiochem® Buffers, "A guide for the preparation and use of buffers in biological systems," by Chandra Mohan, Ph.D., Copyright © 2003 EMD Biosciences, Inc., an Affiliate of Merck KGaA, Darmstadt, Germany, 37 pages.
Carter, "Bispecific human IgG by design," J. Immunol. Methods, 248:7-15 (2001).
Casset et al., "A peptide mimetic of an anti-CD4 monoclonal antibody by rational design," Biochemical and Biophysical Research Communications, 307:198-205 (2003).

(56) References Cited

OTHER PUBLICATIONS

Cekaite et al., "Protein Arrays: A versatile toolbox for target identification and monitoring of patient immune responses," Methods Mol. Biol., 360:335-348 (2007).

Chamow et al., "A humanized, bispecific immunoadhesin-antibody that retargets CD3+ effectors to kill HIV-1-infected cells," J. Immunol., 153(9):4268-80 (1994).

Chau et al., "HuM291(Nuvion), a humanized Fc receptor-nonbinding antibody against CD3, anergizes peripheral blood T cells as partial agonist of the T cell receptor," Transplantation., 71(7):941-50 (2001).

Chappel et al., "Identification of a secondary Fc gamma RI binding site within a genetically engineered human IgG antibody," J Biol Chem., Nov. 25, 1993;268(33):25124-31.

Chappel et al., "Identification of the Fc gamma receptor class I binding site in human IgG through the use of recombinant IgG1/IgG2 hybrid and point-mutated antibodies," Proc Natl Acad Sci U S A., Oct. 15, 1991;88(20):9036-40.

Chatellier et al., "Functional mapping of conserved residues located at the VL and VH domain interface of a Fab," J. Mol. Biol., 264(1):1-6 (1996).

Chen et al., "Selection and analysis of an optimized anti-VEGF antibody: crystal structure of an affinity-matured Fab in complex with antigen," Journal of Molecular Biology, 293:865-881 (1999).

Chen et al., "Generation and analysis of random point mutations in an antibody CDR2 sequence: many mutated antibodies lose their ability to bind antigen," J. Exp. Med., 176(3):855-66 (1992).

Chen et al., "Defective secretion of an immunoglobulin caused by mutations in the heavy chain complementarity determining region 2," J. Exp. Med., 180(2):577-86 (1994).

Chirino et al., "Minimizing the immunogenicity of protein therapeutics," Drug Discov. Today., 9:82-90 (2004).

Chowdhury et al., "Engineering scFvs for improved stability," Methods Mol. Biol., 207:237-54 (2003).

Chu et al., "Accumulation of succinimide in a recombinant monoclonal antibody in mildly acidic buffers under elevated temperatures," Pharm. Res., 24(6):1145-56 (2007).

Clackson et al., "Making antibody fragments using phage display libraries," Nature, 352:624-628 (1991).

Clark, "CD22, a B Cell-Specific Receptor, Mediates Adhesion and Signal Transduction," J. Immunol., 150:4715-4718 (1993).

Co et al., "A Humanized Antibody Specific for the Platelet Integrin gpIIb/IIIa," J. Immunol., 152:2968-2976 (1994).

Cochlovius et al., "Treatment of human B cell lymphoma xenografts with a CD3xCD19 diabody and T cells," The Journal of Immunology, 165:888-895 (2000).

Cole et al., "Human IgG2 variants of chimeric anti-CD3 are nonmitogenic to T cells," J. Immunol., 159(7):3613-21 (1997).

Comper et al., "Charge selectivity in kidney ultrafiltration," Kidney Int., 47:1242-51 (1995).

Cordoba et al., "Non-enzymatic hinge region fragmentation of antibodies in solution," J. Chromatogr. B. Analyt. Technol. Biomed. Life Sci., 818(2):115-21 (2005).

Couto et al., "Anti-BA46 Monoclonal Antibody Mc3: Humanization Using a Novel Positional Consensus and in Vivo and in Vitro Characterization," Cancer Research, 55:1717-1722 (1995).

Creighton, "Protein folding," Biochem. J., 270(1):1-16 (1990).

Dahlback, "Blood coagulation," Lancet, 355(9215):1627-32 (2000).

Dall'Acqua et al., "Antibody humanization by framework shuffling," Methods, 36(1):43-60 (2005).

Dall'Acqua et al., "Modulation of the effector functions of a human IgG1 through engineering of its hinge region," J. Immunol., 177(2):1129-38 (2006).

Damschroder et al., "Framework shuffling of antibodies to reduce immunogenicity and manipulate functional and biophysical properties," Mol. Immunol., 44(11):3049-60 (2007).

Daniel et al., "Induction of Apoptosis in Human Lymphocytes by Human Anti-HLA Class I Antibodies," Transplantation, 75:1380-1386 (2003).

Datta-Mannan et al., "Monoclonal antibody clearance. Impact of modulating the interaction of IgG with the neonatal Fc receptor," J Biol Chem., 282(3):1709-17 (2007).

Davies et al., "Antibody VH domains as small recognition units," Biotechnology (N.Y.), 13(5):475-9 (1995).

Deen et al., "Structural determinants of glomerular permeability," Am. J. Physiol. Renal. Physiol., 281:F579-F596 (2001).

De Felice et al., "Differential regulatory role of monomorphic and polymorphic determinants of histocompatibility leukocyte antigen class I antigens in monoclonal antibody OKT3-induced T cell proliferation," J. Immunol., 139:2683-2689 (1987).

De Groot et al., "De-immunization of therapeutic proteins by T-cell epitope modification," Dev. Biol. (Basel), 122:171-94 (2005).

De Jonge et al., "Production and Characterization of Bispecific Single-Chain Antibody Fragments," Mol. Immunol., 32:1405-1412 (1995).

Dejonge et al., "In vivo retargeting of T cell effector function by recombinant bispecific single chain Fv (anti-DC3 × anti-idiottype) induces long term survival of the murine BCL1 lymphoma model," J. Immunol., 161(3):1454-1461 (1998).

Del Rio et al., "An Engineered Penicillin Acylase with Altered Surface Charge Is More Stable in Alkaline pH," Ann NY Acad. Sci., 799:61-64 (1996).

Denardo et al., "Anti-HLA-DR/anti-DOTA Diabody Construction in a Modular Gene Design Platform: Bispecific Antibodies for Pretargeted Radioimmunotherapy," Cancer Biother. Radiopharm., 16:525-535 (2001).

Deng et al., "An Agonist Murine Monoclonal Antibody to the Human c-Mpl Receptor Stimulates Megakaryocytopoiesis," Blood, 92:1981-1988 (1998).

Depascalis et al., "Grafting of "abbreviated" complementarity-determining regions containing specificity-determining residues essential for ligand contact to engineer a less immunogenic humanized monoclonal antibody," J Immunol, Sep. 15, 2002;169(6):3076-84.

Desplancq et al., "Multimerization behaviour of single chain Fv variants for the tumour-binding antibody B72.3," Protein Engineering, 7(8):1027-1033 (1994).

Dillon et al., "Structural and functional characterization of disulfide isoforms of the human IgG2 subclass," J. Biol. Chem., 283(23):16206-15 (2008).

Dumont et al., "Monomeric Fc fusions: impact on pharmacokinetic and biological activity of protein therapeutics," BioDrugs., 20(3):151-60 (2006).

Ebert et al., "Expression of Metallothionein II in Intestinal Metaplasia, Dysplasia, and Gastric Cancer," Cancer Res., 60:1995-2001 (2000).

Edelman et al., "The covalent structure of an entire gammaG immunoglobulin molecule," Proc Natl Acad Sci U S A., May 1969;63(1):78-85.

Eijsink et al., "Rational engineering of enzyme stability," Journal of Biotechnology, 113:105-120 (2004).

Elliott et al., "Activation of the Erythropoietin (EPO) Receptor by Bivalent Anti-EPO Receptor Antibodies," J. Biol. Chem., 271:24691-24697 (1996).

Ewert et al., "Biophysical properties of human antibody variable domains," J. Mol. Biol., 325:531-553 (2003).

Ewert et al., "Stability improvement of antibodies for extracellular and intracellular applications: CDR grafting to stable frameworks and structure-based framework engineering," Methods, 34:184-199 (2004).

Ewert et al., "Structure-based improvement of the biophysical properties of immunoglobulin $V_H$ domains with a generalizable approach," Biochemistry, 42:1517-1528 (2003).

Fay, "Activation of factor VIII and mechanisms of cofactor action," Blood Rev., Mar. 2004;18(1):1-15.

Fay et al., "The size of human factor VIII heterodimers and the effects produced by thrombin," Biochim Biophys Acta., 871(3):268-78 (1986).

Fay et al., "Chapter 2B Nonenzymatic cofactors: factor VIII," Comprehensive Biochemistry, 13:35-37 (1986).

Fayen et al., "Negative signaling by anti-HLA class I antibodies is dependent upon two triggering events," Int. Immunol., 10:1347-1358 (1998).

(56) References Cited

OTHER PUBLICATIONS

Figini et al., "In vitro assembly of repertoires of antibody chains on the surface of phage by renaturation," J Mol Biol., May 27, 1994;239(1):68-78.
Fujii, "Antibody affinity maturation by random mutagenesis," Methods Mol. Biol., 248:345-59 (2004).
Funaro et al., "Monoclonal antibodies and therapy of human cancers," Biotechnol. Adv., 18:385-401 (2000).
Gelderman et al., "The inhibitory effect of CD46, CD55, and CD59 on complement activation after immunotherapeutic treatment of cervical carcinoma cells with monoclonal antibodies or bispecific monoclonal antibodies," Lab Invest., 82(4):483-93 (2002).
Genestier et al., "Caspase-dependent Ceramide Production in Fas- and HLA Class I-mediated Peripheral T Cell Apoptosis," J. Biol. Chem., 273:5060-5066 (1998).
Genestier et al., "Antibodies to HLA Class 1 α1 Domain Trigger Apoptosis of CD40-Activated Human B Lymphocytes," Blood, 90:726-735 (1997).
Genestier et al., "Fas-Independent Apoptosis of Activated T Cells Induced by Antibodies to the HLA Class I α1 Domain," Blood, 90:3629-3639 (1997).
Genestier et al., "T cell sensitivity to HLA class I-mediated apoptosis is dependent on interleukin-2 and interleukin-4," Eur. J. Immunol., 27:495-499 (1997).
Gerstner et al., "Sequence plasticity in the antigen-binding site of a therapeutic anti-HER2 antibody," J. Mol. Biol., 321(5):851-62 (2002).
Gessner et al., "The IgG Fc receptor family," Ann. Hematol., 76:231-248 (1998).
Ghetie et al., "FcRn: the MHC class I-related receptor that is more than an IgG transporter," Immunol. Today, 18:592-598 (1997).
Ghetie et al., "Homodimerization of tumor-reactive monoclonal antibodies markedly increases their ability to induce growth arrest or apoptosis of tumor cells," Proc. Natl. Acad. Sci. USA, 94:7509-7514 (1997).
Ghetie et al., "Increasing the serum persistence of an IgG fragment by random mutagenesis," Nature Biotechnology, 15:637-640 (1997).
Ghetie et al., "Multiple roles for the major histocompatibility complex class I—related receptor FcRn," Annu. Rev. Immunol., 18:739-766 (2000).
Gobburu et al., "Pharmacokinetics/dynamics of 5c8, a monoclonal antibody to CD154 (CD40 ligand) suppression of an immune response in monkeys," J. Pharmacol. Exp. Ther., 286:925-930 (1998).
Goding, "Monoclonal Antibodies: Principles and Practice," Academic Press, second Ed., 125:129 (1986).
Goel et al., "$^{99m}$Tc-Labeled Divalent and Tetravalent CC49 Single-Chain Fv's: Novel Imaging Agents for Rapid In Vivo Localization of Human Colon Carcinoma," J. Nucl. Med., 42:1519-1527 (2001).
Goel et al., "Genetically Engineered Tetravalent Single-Chain Fv of the Pancarcinoma Monoclonal Antibody CC49: Improved Biodistribution and Potential for Therapeutic Application," Cancer Res., 60:6964-6971 (2000).
Goldstein et al., "Cytolytic and Cytostatic Properties of an Anti-Human FcγRI (CD64) × Epidermal Growth Factor Bispecific Fusion Protein," J. Immunol., 158:872-879 (1997).
Gonzales et al., "Minimizing the immunogenicity of antibodies for clinical application," Tumour Biol., Jan.-Feb. 2005;26(1):31-43.
Goode et al., "The glomerular basement membrane charge-selectivity barrier: an oversimplified concept?," Nephrol. Dial. Transplant., 11:1714-16 (1996).
Goto et al., "A Novel Membrane Antigen Selectively Expressed on Terminally Differentiated Human B Cells," Blood, 84:1922-1930 (1994).
Gramer et al., "Production of stable bispecific IgG1 by controlled Fab-arm exchange: scalability from bench to large-scale manufacturing by application of standard approaches," MAbs., Nov.-Dec. 2013;5(6):962-73. doi: 10.4161/mabs.26233. Epub Aug. 22, 2013.

Graves et al., "Molecular modeling and preclinical evaluation of the humanized NR-LU-13 antibody," Clin. Cancer Res., 5:899-908 (1999).
Greenwood et al., "Structural motifs involved in human IgG antibody effector functions," Eur J Immunol., May 1993;23(5):1098-104.
Griffin et al., "Analysis of heavy and light chain sequences of conventional camelid antibodies from *Camelus dromedarius* and *Camelus bactrianus* species," J Immunol Methods, Mar. 2014;405:35-46. doi: 10.1016/j.jim.2014.01.003. Epub Jan. 18, 2014.
Gruber et al., "Efficient tumor cell lysis mediated by a bispecific single chain antibody expressed in *Escherichia coli*," Journal of Immunology, 152:5368-5374 (1994).
Gunasekaran et al., "Enhancing antibody Fc heterodimer formation through electrostatic steering effects: applications to bispecific molecules and monovalent IgG," J. Biol. Chem., Jun. 18, 2010;285(25):19637-46. doi: 10.1074/jbc.M110.117382. Epub Apr. 16, 2010.
Gupta et al., "Affinity chromatography and co-chromatography of bispecific monoclonal antibody immunoconjugates," J. Biochem. Biophys. Methods, 51:203-216 (2002).
Guyre et al., "Increased potency of Fc-receptor-targeted antigens," Cancer Immunol. Immunother., 45(3-4):146-8 (1997).
Haagen et al., "Unprimed CD4+ and CD8+ T cells can be rapidly activated by a CD3×CD19 bispecific antibody to proliferate and become cytotoxic," Cancer Immunol Immunother., Dec. 1994;39(6):391-6.
Hamers-Casterman et al., "Naturally occurring antibodies devoid of light chains," Nature, Jun. 3, 1993;363(6428):446-8.
Hanson et al., "Catalytic antibodies and their applications," Curr. Opin. Biotechnol., 16:631-636 (2005).
He et al., "Humanization and pharmacokinetics of a monoclonal antibody with specificity for both E- and P-selectin," J. Immunol., 160:1029-35 (1998).
Helfrich et al., "A rapid and versatile method for harnessing scFv antibody fragments with various biological effector functions," J. Immunol. Methods, 237(1-2):131-45 (2000).
Hinton et al., "An engineered human IgG1 antibody with longer serum half-life," J. Immunol., Jan. 1, 2006;176:346-56.
Hinton et al., "Engineered human IgG antibodies with longer serum half-lives in primates," J Biol Chem., Feb. 20, 2004;279(8):6213-6. Epub Dec. 29, 2003.
Holliger et al., "'Diabodies': Small bivalent and bispecific antibody fragments," Proc. Natl. Acad. Sci. USA, 90:6444-6448 (1993).
Hombach et al., "A CD16/CD30 bispecific monoclonal antibody induces lysis of Hodgkin's cells by unstimulated natural killer cells in vitro and in vivo," Int J Cancer, 55:830-6 (1993).
Hoogenboom et al., "Multi-subunit proteins on the surface of filamentous phage: methodologies for displaying antibody (Fab) heavy and light chains," Nucleic Acids Res., 19:4133-4137 (1991).
Hover, L.W., "The factor VIII complex: structure and function," Blood, 58(1):1-13 (1981).
Hozumi et al., "Evidence for somatic rearrangement of immunoglobulin genes coding for variable and constant regions," Proc. Natl. Acad. Sci. USA, 73(10):3628-3632 (1976).
Hu et al., "Minibody: A Novel Engineered Anti-Carcinoembryonic Antigen Antibody Fragment (Single-Chain Fv-$C_H3$) Which Exhibits Rapid, High-Level Targeting of Xenografts," Cancer Res., 56:3055-3061 (1996).
Hu et al., "Development and characterization of a novel fusion protein composed of a human IgG1 heavy chain constant region and a single-chain fragment variable antibody against Venezuelan equine encephalitis virus," J Biochem., 133(1):59-66 (2003).
Hudson et al., "High avidity scFv multimers; diabodies and triabodies," J. Immunol. Methods, 231:177-189 (1999).
Hwang et al., "Use of human germline genes in a CDR homology-based approach to antibody humanization," Methods, 36:35-42 (2005).
Igawa et al., "Engineering the variable region of therapeutic IgG antibodies," MAbs, 3(3):243-52 (2011).
Igawa et al., "Reduced elimination of IgG antibodies by engineering the variable region," Protein Eng. Des. Sel., 23(5):385-92 (2010).

(56) References Cited

OTHER PUBLICATIONS

Igawa et al., "Antibody recycling by engineered pH-dependent antigen binding improves the duration of antigen neutralization," Nat. Biotechnol., 28(11):1203-7 (2010).

Igawa et al., "VH/VL interface engineering to promote selective expression and inhibit conformational isomerization of thrombopoietin receptor agonist single-chain diabody," Protein Eng Des Sel., Aug. 2010;23(8):667-77. doi: 10.1093/protein/gzq034. Epub Jun. 24, 2010.

IMGT Scientific charts depicting the correspondence between Eu and Kabat numberings for the human IgG constant region, created May 17, 2001 and last updated Aug. 13, 2014.

Ito et al., "The His-probe method: effects of histidine residues introduced into the complementarity-determining regions of antibodies on antigen-antibody interactions at different pH values," FEBS Lett., 309:85-88 (1992).

Iwahashi et al., "CDR substitutions of a humanized monoclonal antibody (CC49): contributions of individual CDRs to antigen binding and immunogenicity," Mol Immunol., Oct.-Nov. 1999;36(15-16):1079-91.

Jackman et al., "Development of a two-part strategy to identify a therapeutic human bispecific antibody that inhibits IgE receptor signaling," J Biol Chem., Jul. 2, 2010;285(27): 20850-9. doi: 10.1074/jbc.M110.113910. Epub May 5, 2010.

Jäger et al., "Folding and assembly of an antibody Fv fragment, a heterodimer stabilized by antigen," Journal of Molecular Biology, 285:2005-2019 (1999).

Jain et al., "Engineering antibodies for clinical applications," Trends Biotechnol., 25(7):307-16 (2007).

Janeway et al., "Structure of the Antibody Molecule and Immunoglobulin Genes," Immunobiology, 3$^{rd}$ Edition, Garland Press, 3:1-3:11 (1997).

Jefferis et al., "Recognition sites on human IgG for Fc gamma receptors: the role of glycosylation," Immunol. Lett., 44(2-3):111-7 (1995).

Jendeberg et al., "Engineering of Fc(1) and Fc(3) from human immunoglobulin G to analyse subclass specificity for staphylococcal protein A," J. Immunol. Methods., 201(1):25-34 (1997).

Jirholt et al., "Exploiting sequence space: shuffling in vivo formed complementarity determining regions into a master framework," Gene., Jul. 30, 1998;215(2):471-6.

Johnson et al., "Cation exchange-HPLC and mass spectrometry reveal C-terminal amidation of an IgG1 heavy chain," Anal. Biochem., 360:75-83 (2007).

Johnson et al., "Kabat database and its applications: 30 years after the first variability plot," Nucleic Acids Res., Jan. 1, 2000;28(1):214-8.

Jones et al., "Identification and removal of a promiscuous CD4+ T cell epitope from the C1 domain of factor VIII," Thromb. Haemost., 3:991-1000 (2005).

Ju et al., "Conversion of the interleukin 1 receptor antagonist into an agonist by site-specific mutagenesis," Proc. Natl. Acad. Sci. U.S.A., 88:2658-2662 (1991).

Jung et al., "The importance of framework residues H6, H7 and H10 in antibody heavy chains: experimental evidence for a new structural subclassification of antibody V(H) domains," J. Mol. Biol., Jun. 8, 2001;309(3):701-16.

Kabat et al., Sequence of Proteins of Immunological Interest, 5$^{th}$ Edition 1991, p. 690 and p. 693.

Kai et al., "Switching constant domains enhances agonist activities of antibodies to a thrombopoietin receptor," Nat. Biotechnol., 26(2):209-11 (2008).

Kashmiri et al., "Generation, characterization, and in vivo studies of humanized anticarcinoma antibody CC49," Hybridoma, 14:461-473 (1995).

Katayose et al., "MUC1-specific targeting immunotherapy with bispecific antibodies: inhibition of xenografted human bile duct carcinoma growth," Cancer Res., 56(18):4205-12 (1996).

Kenanova et al., "Tailoring the pharmacokinetics and positron emission tomography imaging properties of anti-carcinoembryonic antigen single-chain Fv-Fc antibody fragments," Cancer Res., Jan. 15, 2005;65(2):622-31.

Kerschbaumer et al., "An antibody specific for coagulation factor IX enhances the activity of the intrinsic factor X-activating complex," J. Biol. Chem., 279(39):40445-50 (2004).

Khalifa et al., "Effects on interaction kinetics of mutations at the VH-VL interface of Fabs depend on the structural context," J. Mol. Recognit., May-Jun. 2000;13(3):127-39.

Khawli et al., "Improved tumor localization and radioimaging with chemically modified monoclonal antibodies," Cancer Biother. Radiopharm., 11:203-215 (1996).

Kikuchi et al., "A bivalent single-chain Fv fragment against CD47 induces apoptosis for leukemic cells," Biochem. Biophys. Res. Commun., 315:912-918 (2004).

Kim et al., "Antibody Engineering for the Development of Therapeutic Antibodies," Mol. Cells, 20:17-29 (2005).

Kim et al., "Chemical modification to reduce renal uptake of disulfide-bonded variable region fragment of anti-tac monoclonal antibody labeled with 99mTc," Bioconjugate Chem., 10:447-453 (1999).

Kim et al., "Lowering of pI by acylation improves the renal uptake of 99mTc-labeled anti-Tac dsFv: effect of different acylating reagents," Nucl. Med. Biol., 29:795-801 (2002).

Kim et al., "Mapping the site on human IgG for binding of the MHC class I-related receptor, FcRn," Eur. J. Immunol., Sep. 1999;29(9):2819-25.

Kimura et al., "2D7 diabody bound to the α2 domain of HLA class I efficiently induces caspase-independent cell death against malignant and activated lymphoid cells," Biochem. Biophys. Res. Commun., 325:1201-1209 (2004).

Kipriyanov and Little, "Generation of Recombinant Antibodies," Molecular Biotechnology, 12:173-201 (1999).

Kipriyanov et al., "Bispecific CD3×CD19 diabody for T cell-mediated lysis of malignant human B cells," in. J. Cancer, 77:763-772 (1998).

Kipriyanov et al., "Bispecific tandem diabody for tumor therapy with imprived antigen binding and pharmacokinetics," J Mol Biol., Oct. 15, 1999;293(1):41-56.

Kipriyanov et al., "Effect of Domain Order on the Activity of Bacterially Produced Bispecific Single-chain Fv Antibodies," J. Mol. Biol., Jun. 27, 2003;330(1):99-111.

Klein et al., "Progress in overcoming the chain association issue in bispecific heterodimeric IgG antibodies," MAbs., Nov.-Dec. 2012;4(6):653-63. doi: 10.4161/mabs.21379. Epub Aug. 27, 2012.

Kobayashi et al., "The pharmacokinetic characteristics of glycolated humanized anti-Tac Fabs are determined by their isoelectric points," Cancer Res., 59:422-430 (1999).

Kobayashi et al., "A monoclonal antibody specific for a distinct region of hen egg-white lysozyme," Mol. Immunol., 19:619-30 (1982).

Komissarov et al., "Site-specific mutagenesis of a recombinant anti-single-stranded DNA Fab. Role of heavy chain complementarity-determining region 3 residues in antigen interaction," J. Biol. Chem., 272(43):26864-70 (1997).

Kong et al., "A Single Residue, Aspartic Acid 95, in the δ Opioid Receptor Specifies Selective High Affinity Agonist Binding," The Journal of Biological Chemistry, 268(31):23056-23058 (1993).

Kontermann, R., "Recombinant bispecific antibodies for cancer therapy," Acta Pharmacol Sin., Jan. 2005;26(1):1-9.

Korn et al., "Recombinant bispecific antibodies for the targeting of adenoviruses to CEA-expressing tumour cells: a comparative analysis of bacterially expressed single-chain diabody and tandem scFv," J Gene Med., Jun. 2004;6(6):642-651.

Kortt et al., "Dimeric and trimeric antibodies: high avidity scFvs for cancer targeting," Biomol. Eng., 18:95-108 (2001).

Kranenborg et al., "Development and characterization of anti-renal cell carcinoma x antichelate bispecific monoclonal antibodies for two-phase targeting of renal cell carcinoma," Cancer Res., 55:5864s-5867s (1995).

(56) References Cited

OTHER PUBLICATIONS

Krebber et al., "Reliable cloning of functional antibody variable domains from hybridomas and spleen cell repertoires employing a reengineered phage display system," J. Immunol. Methods, 201:35-55 (1997).
Kreitman et al., "Cytotoxic Activity of Disulfide-stabilized Recombinant Immunotoxin RFB4(dsFv)-PE38 (BL22) toward Fresh Malignant Cells from Patients with B-Cell Leukemias," Clin. Cancer Res., 6:1476-1487 (2000).
Kreutz et al., "Efficient bispecific monoclonal antibody purification using gradient thiophilic affinity chromatography," J. Chromatogr. B, 714:161-170 (1998).
Kriangkum et al., "Bispecific and bifunctional single chain recombinant antibodies," Biomol. Eng., 18(2):31-40 (2001).
Kufer et al., "A revival of bispecific antibodies," Trends Biotechnol., 22(5):238-44 (2004).
Kulkarni et al., "Construction of a Single-Chain Antibody Derived From 5H7, A Monoclonal Antibody Specific for a Death Signaling Domain of Human Class I Major Histocompatibility Complex," Transplant. Proc., 30:1081 (1998).
Kulkarni et al., "Programmed Cell Death Signaling Via Cell-Surface Expression of a Single-Chain Antibody Transgene," Transplantation, 69:1209-1217 (2000).
Kumar et al., "Molecular cloning and expression of the fabs of human autoantibodies in *Escherichia coli*," The Journal of Biological Chemistry, 275(41):35129-35136 (2000).
Kumar et al., "The second PDZ domain of INAD is a type I domain involved in binding to eye protein kinase C. Mutational analysis and naturally occuring variants," J Biol Chem., Jul. 6, 2001;276(27):24971-7.
Kurfis et al., "Role of Arg182 in the second extracellular loop of angiotensin II receptor AT2 in ligand binding," Biochem Biophys Res Commun., Oct. 5, 1999;263:816-9.
Kurucz et al., "Retargeting of CTL by an efficiently refolded bispecific single-chain Fv dimer produced in bacteria," The Journal of Immunology, 154:4576-4582 (1995).
Labrijn et al., "Species-specific determinants in the IgG CH3 domain enable Fab-arm exchange by affecting the noncovalent CH3-CH3 interaction strength," J Immunol., Sep. 15, 2011;187(6):3238-46. doi: 10.4049/jimmunol.1003336. Epub Aug. 12, 2011.
Labrijn et al., "Efficient generation of stable bispecific IgG1 by controlled Fab-arm exchange," Pro Natl Acad Sci U S A., Mar. 26, 2013;110(13):5145-50. doi: 10.1073/pnas.1220145110. Epub Mar. 11, 2013.
Lansdorp et al., "Purification and analysis of bispecific tetrameric antibody complexes," IMol. Immunol., 27:659-666 (1990).
Lazar et al., "Transforming growth factor alpha: mutation of aspartic acid 47 and leucine 48 results in different biological activities," Mol. Cell Biol., 8:1247-1252 (1988).
Le Gall et al., "Effect of linker sequences between the antibody variable domains on the formation, stability and biological activity of a bispecific tandem diabody," Protein Eng Des Sel., Apr. 2004;17(4):357-66. Epub May 4, 2004.
Lebégue et al., "Production and characterization of hybrid monoclonal antibodies with IgG1/IgG3 double isotype," C R Acad Sci III., 1990;310(9):377-82.
Lebrun et al., "Antibodies to the Extracellular Receptor Domain Restore the Hormone-insensitive Kinase and Conformation of the Mutant Insulin Receptor Valine 382," J. Biol. Chem., 268:11272-11277 (1993).
Ledbetter et al., "Agonistic Activity of a CD4O-Specific Single-Chain Fv Constructed from the Variable Regions of mAb G28-5," Critical Reviews in Immunology, 17:427-435 (1997).
Leong et al., "Adapting pharmacokinetic properties of a humanized anti-interleukin-8 antibody for therapeutic applications using site-specific pegylation," Cytokine, 16(3):106-19 (2001).
Li et al., "The Epitope Specificity and Tissue Reactivity of Four Murine Monoclonal Anti-CD22 Antibodies," Cell. Immunol., 118:85-99 (1989).
Life Technologies (Invitrogen: "ecdysone analogue" and pIND plasmid), Aug. 10, 2012, 2 pages.
Lin et al., "Preclinical pharmacokinetics, interspecies scaling, and tissue distribution of a humanized monoclonal antibody against vascular endothelial growth factor," J Pharmacol Exp Ther., 288(1):371-8 (1999).
Lindhofer et al., "Preferential Species-Restricted Heavy/Light Chain Pairing in Rat/Mouse Quadromas," J. Immunol., 155:219-225 (1995).
Lindsay, "Chapter 4: Determination of the Kinetics and Mechanism of tg-FIX Activation by Factor XIa," 49-75 (2004).
Little et al., "Of mice and men: hybridoma and recombinant antibodies," Immunol. Today, 21:364-370 (2000).
Liu et al., "Functional interactions between arginine-133 and aspartate-88 in the human reduced folate carrier: evidence for a charge-pair association," Biochem J.,Sep. 1, 2001;358(Pt 2):511-6.
Liu et al., "Heterogeneity of monoclonal antibodies," J. Pharm. Sci., 97(7):2426-47 (2008).
Lloyd et al., "The production of a bispecific anti-CEA, anti-hapten (4-amino-phthalate) hybrid-hybridoma," J Natl Med Assoc., Oct. 1991;83(10):901-4.
Lobo et al., "Antibody pharmacokinetics and pharmacodynamics," J. Pharm. Sci., 93:2645-68 (2004).
Lund et al., "Expression and characterization of truncated forms of humanized L243 IgG1. Architectural features can influence synthesis of its oligosaccharide chains and affect superoxide production triggered through human Fcgamma receptor I," Eur. J. Biochem., 267(24):7246-57 (2000).
MacCallum et al., "Antibody-antigen interactions: contact analysis and binding site topography," J. Mol. Biol., 262:732-45 (1996).
Mack et al., "A small bispecific antibody construct expressed as a functional single-chain molecule with high tumor cell cytotoxicity," Proc. Natl. Acad. Sci. USA, 92(15):7021-7025 (1995).
Maeda et al., "pH-dependent receptor/ligand dissociation as a determining factor for intracellular sorting of ligands for epidermal growth factor receptors in rat hepatocytes," J. Control Release, 82(1):71-82 (2002).
Maini et al., "Double-blind randomized controlled clinical trial of the interleukin-6 receptor antagonist, tocilizumab, in European patients with rheumatoid arthritis who had an incomplete response to methotrexate," Arthritis Rheum., 54:2817-29 (2006).
Malty et al., "Equilibrium unfolding of dimeric and engineered monomeric forms of Cro (F58W) repressor and the effect of added salts: evidence for the formation of folded monomer induced by sodium perchlorate," Arch Biochem Biophys., Feb. 1, 2005;434(1):93-107.
Male et al., "Antibodies" Immunology, 7th Edition (2006), published by Elsevier Ltd., pp. 59-86.
Mallender et al., "Construction, expression and activity of a bivalent bispecific single-chain antibody," J. Biol. Chem., 269(1):199-206 (1994).
Manz et al., Bioanalytical Chemistry, World Scientific Publishing Co. (2003).
Manzke et al., "Single-step purification of bispecific monoclonal antibodies for immunotherapeutic use by hydrophobic interaction chromatography," J. Immunol. Methods, 1997;208:65-73.
Marti et al., "Inverse electrostatic effect: electrostatic repulsion in the unfolded state stabilizes a leucine zipper," Biochemistry, 43(39):12436-47 (2004).
Martin et al., "Crystal structure at 2.8 A of an FcRn/heterodimeric Fc complex: mechanism of pH-dependent binding," Mol. Cell, 7:867-877 (2001).
Martinez et al., "Disulfide connectivity of human immunoglobulin G2 structural isoforms," Jul. 15, 2008;47(28):7496-508. doi: 10.1021/bi800576c. Epub Jun. 13, 2008.
Marvin et al., "Recombinant approaches to IgG-like bispecific antibodies," Acta Pharmacol Sin., Jun. 2005;26:649-58.
Marvin et al., "Redesigning an antibody fragment for faster association with its antigen," Biochemistry, 42:7077-83 (2003).
Matsuoka et al., "A Monoclonal Antibody to the α2 Domain of Murine Major Histocompatibility Complex Class I that Specifically Kills Activated Lymphocytes and Blocks Liver Damage in the Concanavalin A Hepatitis Model," J. Exp. Med., 198:497-503 (2003).

(56) References Cited

OTHER PUBLICATIONS

Matsuoka et al., "A Novel Type of Cell Death of Lymphocytes Induced by a Monoclonal Antibody without Participation of Complement," J. Exp. Med., 181:2007-2015 (1995).
Maxfield et al., "Endocytic recycling," Nat. Rev. Mol. Cell Biol., 5(2):121-32 (2004).
McGuinness et al., "Phage diabody repertoires for selection of large No. Of bispecific antibody fragments," Nature Biotechnology, 14(9):1149-1154 (1996).
Medesan et al., "Delineation of the amino acid residues involved in transcytosis and catabolism of mouse IgG1," J Immunol., Mar. 1, 1997;158(5):2211-7.
Medline Plus Drug Information: Dexamethasone Oral www.nlm.nih.gov/medlineplus/druginfo/meddmaster/a682792.html, downloaded Jul. 19, 2007; last revised Apr. 1, 2003 (see p. 3) (4 pages).
Meng et al., "The evaluation of recombinant, chimeric, tetravalent antihuman CD22 antibodies," Clinical Cancer Research, 10:1274-1281 (2004).
Merchant et al., "An efficient route to human bispecific IgG," Nat Biotechnol., Jul. 1998;16(7):677-81.
Michaelsen et al., "A mutant human IgG molecule with only one C1q binding site can activate complement and induce lysis of target cells," Eur J Immunol., Jan. 2006;36(1):129-38.
Miyazaki et al., "Generation of bispecific IgG, which mimics the cofactor function of blood coagulation factor VIII," Seikagaku, Poster sessions (2P-B-161) (2006).
Moore et al., "Kinetics and thermodynamics of dimer formation and dissociation for a recombinant humanized monoclonal antibody to vascular endothelial growth factor," Biochemistry, 38:13960-13967 (1999).
Morell et al., "Metabolic properties of IgG subclasses in man," J. Clin. Invest., 49(4):673-80 (1970).
Morimoto et al., "Single-step purification of F(ab')2 fragments of mouse monoclonal antibodies (immunoglobulins G1) by hydrophobic interaction high performance liquid chromatography using TSKgel Phenyl-5PW," J. Biochem. Biophys. Methods, 24:107-117 (1992).
Murtaugh et al., "A combinatorial histidine scanning library approach to engineer highly pH-dependent protein switches," Protein Sci., 20(9):1619-31 doi:10.1002/pro 696 (2011).
Nesterova et al., "Glypican-3 as a novel target for an antibody-drug conjugate," AACR Abstract No. 656, Los Angeles, CA (Apr. 4-18, 2007).
Ngo et al., "Computational Complexity, Protein Structure Prediction, and the Levinthal Paradox," The Protein Folding Problem and Tertiary Structure Prediction, Merz, Jr. et al. Editors, Birkhauser Boston, 433-506 (1994).
Nieba et al., "Disrupting the hydrophobic patches at the antibody variable/constant domain interface: improved in vivo folding and physical characterization of an engineered scFv fragment," Protein Eng., Apr. 1997;10(4):435-44.
Nishii, "CD22 antibody therapy," Current Therapy, 20:47-50 (2001) (English translation included).
Nishimoto et al., "Humanized anti-interleukin-6 receptor antibody treatment of multicentric Castleman disease," Blood, 106:2627-32 (2005).
Nishimoto et al., "Interleukin 6: from bench to bedside," Nat. Clin. Pract. Rheumatol., 2:619-626 (2006).
Nohaile et al., "Altering dimerization specificity by changes in surface electrostatics," Pro Natl Acad Sci U S A., Mar. 13, 2001;98(6):3109-14. Epub Feb. 27, 2001.
O'Shea et al., "Peptide 'Velcro': design of a heterodimeric coiled coil," Curr Biol., Oct. 1, 1993;3(10):658-67.
Ohtomo et al., "Molecular Cloning and Characterization of a Surface Antigen Preferentially Overexpressed on Multiple Myeloma Cells," Biochem. Biophys. Res. Commun., 258:583-591 (1999).
Oka, "Development of Novel Immunotoxin Using Recombinant Alpha-Sarcin and Its Application Treatment of Hematopoietic Tumor," Sankyo Seimei Kagaku Kenkyu Shinko Zaidan Kenkyu Hokokushu, 12:46-56 (1998) (English translation included).

Onda et al., "Lowering the Isoelectric Point of the Fv Portion of Recombinant Immunotoxins Leads to Decreased Nonspecific Animal Toxicity without Affecting Antitumor Activity," Cancer Res., 61:5070-77 (2001).
Ono et al., "The humanized anti-HM1.24 antibody effectively kills multiple myeloma cells by human effector cell-mediated cytotoxicity," Mol. Immunol., 36:387-395 (1999).
Orita et al., "A novel therapeutic approach for thrombocytopenia by minibody agonist of the thrombopoietin receptor," Blood, 105:562-566 (2005).
Ozaki et al., "A Recombinant HLA Class I-Specific Single Chain Fv Diabody Induces Cell Death in Human Lymphoid Malignancies," Blood, 102:933a, Abstract No. 3474 (2003).
Ozaki et al., "Humanized Anti-HM1.24 Antibody Mediates Myeloma Cell Cytotoxicity That Is Enhanced by Cytokine Stimulation of Effector Cells," Blood, 93:3922-3930 (1999).
Ozaki et al., "Immunotherapy of Multiple Myeloma With a Monoclonal Antibody Directed Against a Plasma Cell-Specific Antigen, HM1.24," Blood, 90:3179-3186 (1997).
Ozhegov et al., Tolkovyi Slovar Russkogo iazyka: 2004, p. 292 (with an English translation of the relevant passage defining "control").
Padlan et al., "Antibody Fab assembly: the interface residues between CH1 and CL," Mol Immunol., 23(9):951-60 (1986).
Pakula et al., "Genetic Analysis of Protein Stability and Function," Annu. Rev. Genet, 23:289-310 (1989).
Palacios et al., "IL-3-dependent mouse clones that express B-220 surface antigen, contain Ig genes in germ-line configuration, and generate B lymphocutes in vivo," Cell, 41:727-734 (1985).
Pan et al., "Blocking neuropilin-1 function has an additive effect with anti-VEGF to inhibit tumor growth," Cancer Cell, Jan. 2007;11(1):53-67.
Panka et al., "Variable region framework differences result in decreased or increased affinity of variant anti-digoxin antibodies," Proc. Natl. Acad. Sci. U.S.A., 85(9):3080-4 (1988).
Pardridge et al., "Enhanced endocytosis in cultured human breast carcinoma cells and in vivo biodistribution in rats of a humanized monoclonal antibody after cationization of the protein," J. Pharmacol. Exp. Ther., 286(1):548-54 (1998).
Paul, William ed., Fundamental Immunology, $3^{rd}$ edition, p. 242 (1993).
Paul, "Structure and function of immunoglobulins," Fundamental Immunology, Third Edition, 292-295 (1993).
Pavlinkova et al., "Charge-modified single chain antibody constructs of monoclonal antibody CC49: Generation, characterization, pharmacokinetics, and biodistribution analysis," Nucl. Med. Biol., 26:27-34 (1999).
Pavlou et al., "The therapeutic antibodies market to 2008," Eur. J. Pharm. Biopharm., 59:389-396 (2005).
Peipp et al., "Bispecific antibodies targeting cancer cells," Biochem. Soc. Trans., 30:507-511 (2002).
Pettersen et al., "The TCR-Binding Region of the HLA Class I $\alpha_2$ Domain Signals Rapid Fas-Independent Cell Death: A Direct Pathway for T Cell-Mediated Killing of Target Cells?" J. Immunol., 160:4343-4352 (1998).
Piétri-Rouxel et al., "The biochemical effect of the naturally occurring Trp64→Arg mutation on human β3-adrenoceptor activity," Eur. J. Biochem., 247:1174-1179 (1997).
Plückthun et al., "New protein engineering approaches to multivalent and bispecific antibody fragments," Immunotechnology, 3:83-105 (1997).
Poduslo et al., "Polyamine modification increases the permeability of proteins at the blood-nerve and blood-brain barriers," J. Neurochem., 66:1599-1609 (1996).
Pons et al., "Energetic analysis of an antigen/antibody interface: alanine scanning mutagenesis and double mutant cycles on the HyHEL-10/lysozyme interaction," Protein Sci., 8(5):958-68 (1999).
Portolano et al., "Lack of Promiscuity in Autoantigen-Specific H and L Chain Combinations as Revealed by Human H and L Chain "Roulette"," J. Immunol., 150(3):880-887 (1993).
Presta, "Engineering of therapeutic antibodies to minimize immunogenicity and optimize function," Adv. Drug Deliv. Rev., 58(5-6):640-56 (2006).

(56) References Cited

OTHER PUBLICATIONS

Presta et al., "Molecular engineering and design of therapeutic antibodies," Curr. Opin. Immunol., 20(4):460-70. doi: 10.1016/j.coi.2008.06.012 (2008).
Queen et al., "A humanized antibody that binds to the interleukin 2 receptor," Proc. Natl. Acad. Sci. U.S.A., 86(24):10029-10033 (1989).
Raffen et al., "Reengineering immunoglobulin domain interactions by introduction of charged residues," Protein Eng. Apr. 1998;11:303-9.
Rajagopal et al., "A form of anti-Tac (Fv) which is both single-chain and disulfide stabilized: comparison with its single-chain and disulfide-stabilized homologs," Protein Engineering, 10(12):1453-1459 (1997).
Rajpal et al., A general method for greatly improving the affinity of antibodies by using combinatorial libraries, Proc. Natl. Acad. Sci. USA, 102:8466-71 (2005).
Rathanaswami et al., "Demonstration of an in vivo generated sub-picomolar affinity fully human monoclonal antibody to interleukin-8," Biochem. Biophys. Res. Commun., 334:1004-13 (2005).
Reddy et al., "Elimination of Fc receptor-dependent effector functions of a modified IgG4 monoclonal antibody to human CD4," J. Immunol., 164(4):1925-33 (2000).
Reichert et al., "Monoclonal antibody successes in the clinic," Nat. Biotechnol., 23:1073-78 (2005).
Reichert et al., "Development trends for monoclonal antibody cancer therapeutics," Nat. Rev. Drug Discov., 6(5):349-56 (2007).
Reist et al., "Human IgG2 constant region enhances in vivo stability of anti-tenascin antibody 81C6 compared with its murine parent," Clin Cancer Res., Oct. 1998;4(10):2495-502.
Ridgway et al., "'Knobs-into-holes' engineering of antibody $C_H3$ domains for heavy chain heterodimerization," Protein Eng., 9:617-621 (1996).
Rispens et al., "Dynamics of inter-heavy chain interactions in human immunoglobulin G (IgG) subclasses studied by kinetic Fab arm exchange," J Biol Chem., Feb. 28, 2014;289(9):6098-109. doi: 10.1074/jbc.M113.541813. Epub Jan. 14, 2014.
Roguska et al., "Humanization of murine monoclonal antibodies through variable domain resurfacing," Proc Natl Acad Sci U.S.A., 91:969-73 (1994).
Roitt et al., Immunology, M., Mir, (2000), pp. 110-111 (in Russian, with what is believed to be a published English equivalent of those pages taken from Roitt et al., "Antibody Structure and Function," Immunology, Fifth Ed., (1998), pp. 80-81).
Roitt et al., Immunology, M., Mir, 5th Edition (2000), pp. 97-113 [In Russian: Roitt et al. (Document ID 634) is pages from a 2000 Russian edition of Immunology. In lieu of an English translation, applicant cites Male et al. (Document ID 562) which is believed to be the corresponding pages from an English language edition of Immunology].
Rossi et al., "Development of New Multivalent bispecific Agents for Pretargeting Tumor Localization and Therapy," Clin. Cancer Res., 9:3886s-3896s (2003).
Rothe et al., "Ribosome display for improved biotherapeutic molecules," Expert Opin. Biol. Ther., 6:177-187 (2006).
Rothlisberger et al., "Domain interactions in the Fab fragment: a comparative evaluation of the single-chain Fv and Fab format engineered with variable domains of different stability," J Mol Biol., 347(4):773-89 (2005).
Rousch et al., "Somatostatin displayed on filamentous phage as a receptor-specific agonist," Br. J. Pharmacol., 125:5-16 (1998).
Rudikoff et al., "Single amino acid substitution altering antigen-binding specificity," Proc. Natl. Acad. Sci. U.S.A., 79(6):1979-83 (1982).
Ruf et al., "Pharmacokinetics and in vivo stability of intraperitoneally administered therapeutic antibody catuniaxoniab," J. Clin. Oncol., 26 (May 20 suppl) (2008), abstr 14006.
Saito et al., "Factor VIII Mimetic Antibody: (1) Establishment and Characterization of Anti-factor IX/anti-factor X Bispecific Antibodies," 2005 International Society of Thrombosis and Haemostasis, vol. 3, Issue Supplement s1, p. #OR160.
Saito et al., "Establishment of Factor VIII Mimetic Antibodies and Their In Vitro Activities in Hemophilia A," 2006 National Hemophilia Foundation Symposia.
Salfeld et al., "Isotype selection in antibody engineering," Nat. Biotechnol., 25:1369-72 (2007).
Sal-Man et al., "Arginine mutations within a transmembrane domain of Tar, an *Escherichia coli* aspartate receptor, can drive homodimer dissociation and heterodimer association in vivo," Biochem J., Jan. 1, 2005;385(Pt 1):29-36.
Sampei et al., "Identification and multidimensional optimization of an asymmetric bispecific IgG antibody mimicking the function of factor VIII cofactor activity," PLoS One, 2013;8(2):e57479. doi: 10.1371/journal.pone.0057479. Epub Feb. 28, 2013.
Sarmay et al., "Mapping and comparison of the interaction sites on the Fc region of IgG responsible for triggering antibody dependent cellular cytotoxicity (ADCC) through different types of human Fc gamma receptor," Mol. Immunol., 29(5):633-9 (1992).
Sato et al., "CD22 Is Both a Positive and Negative Regulator of B Lymphocyte Antigen Receptor Signal Transduction: Altered Signaling in CD22-Deficient Mice," Immunity, 5:551-562 (1996).
Sato et al., "Reshaping a human antibody to inhibit the interleukin 6-dependent tumor cell growth," Cancer Res., 53:851-856 (1993).
Schaeffer et al., "The Rat Glomerular Filtration Bather Does Not Show Negative Charge Selectivity," Microcirculation, 9:329-342 (2002).
Schaefer et al., "Immunoglobulin domain crossover as a generic approach for the production of bispecific IgG antibodies," Proc Natl Acad Sci U S A., Jul. 5, 2011;108(27):11187-92. doi: 10.1073/pnas.1019002108. Epub Jun. 20, 2011.
Scheurle et al., "Cancer Gene Discovery Using Digital Differential Display," Cancer Res., 60:4037-4043 (2000).
Schmidt et al., "Structure-function relationships in factor IX and factor IXa," Trends Cardiovasc Med., Jan. 2003;13(1):39-45.
Schmidt et al., Human Physiology, Moscow, 2:431-436 (1996), and English translation: Schmidt et al., "Hemostatis and Coagulation," Human Physiology, R.F. Schmidt G. Thews (Eds.), Second, Completely Revised Edition, 418-423 [translated by Marguerite A. Biederman-Thorson], Springer-Verlag, 1989 (with English translation).
Schmidt et al., Human Physiology, Moscow, 3:764 (1996), and English translation: Schmidt et al., "Enzymes of the pancreatic juice," Human Physiology, R.F. Schmidt, G. Thews (Eds.), Second, Completely Revised Edition, 716 [translated by Marguerite A. Biederman-Thorson], Springer-Verlag, 1989 (with English translation).
Schmitz et al., "Phage display: a molecular tool for the generation of antibodies—a review," Placenta., 21 Suppl A:S106-12 (2000).
Schuurman et al., "Normal human immunoglobulin G4 is bispecific: it has two different antigen-combining sites," Immunology, Aug. 1999;97(4):693-8.
Schuurman et al., "The inter-heavy chain disulfide bonds of IgG4 are in equilibrium with intra-chain disulfide bonds," Mol Immunol., Jan. 2001;38(1):1-8.
Segal et al., "Bispecific antibodies in cancer therapy," Curr Opin Immunol., Oct. 1999;11(5):558-62.
Shalaby et al., "Development of Humanized Bispecific Antibodies Reactive with Cytotoxic Lymphocytes and Tumor Cells Overexpressing the HER2 Protooncogene," J. Exp. Med., 175:217-225 (1992).
Shaul, "Exploring the charge space of protein-protein association: a proteomic study," Proteins, 60:341-352 (2005).
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 276:6591-6604 (2001) (Epub Nov. 28, 2000).
Shima et al., "Factor VIII Mimetic Antibody: (2) In Vitro Assessment of Cofactor Activity in Hemophilia A," 2005 International Society of Thrombosis and Haemostasis, vol. 3, Issue Supplement s1, p. #P0038.
Shima, M., "Bispecific antibodies to coagulation factors IXa and X mimic the function of factor VIII," 2006 World Federation of Haemophilia (Haemophilia, 12(Suppl. 2):98 (2006)).

(56) References Cited

OTHER PUBLICATIONS

Shimba et al., "Comparative thermodynamic analyses of the Fv, Fab* and Fab fragments of anti-dansyl mouse monoclonal antibody," FEBS Letters, 360:247-250 (1995).
Shirahata, Minna ni yakudatsu ketsuyubyo no kiso to rinsho. Iyaku (Medicine and Drug) Journal Co., Ltd., 280-9 (2009) (with English translation).
Shire et al., "Challenges in the development of high protein concentration formulations," Journal of Pharmaceutical Sciences, 93(6):1390-1402 (2004).
Singer et al., Genes & Genomes, 1991;67-69.
Singer et al., Genes & Genomes, 1998;1:63-64.
Sinha et al., "Electrostatics in protein binding and function," Curr Protein Pept Sci., Dec. 2002;3(6):601-14.
Sinha et al., "Molecular dynamics simulation of a high-affinity antibody-protein complex: the binding site is a mosaic of locally flexible and preorganized rigid regions," Cell Biochem Biophys., 43:253-273 (2005).
Skerra, "Use of the tetracycline promoter for the tightly regulated production of a murine antibody fragment in *Escherichia coli*," Gene, 151:131-135 (1994).
Smans et al., "Bispecific antibody-mediated lysis of primary cultures of ovarian carcinoma cells using multiple target antigens," Int. J. Cancer, 83:270-277 (1999).
Smith, "Creative Expression: Mammalian Expression Vectors and Systems," The Scientist Magazine, Feb. 2, 1998, 3 pages.
Smith et al., "Inhibition of T Cell Activation by a Monoclonal Antibody Reactive Against the α3 Domain of Human MHC Class I Molecules," J. Immunol., 153:1054-1067 (1994).
Smith-Gill et al., "Contributions of immunoglobulin heavy and light chains to antibody specificity for lysozyme and two haptens," The Journal of Immunology, 139:4135-4144 (1987).
Smolen et al., "Interleukin-6: a new therapeutic target," Arthritis Res Ther., 2006;8 Suppl 2:S5. Epub Jul. 28, 2006.
Soeda et al., "Factor VIII Taitei Kotai (1) Ko FIXa/FX bispecific Kotai no Sakusei oyobi characterization," Rinsho Ketsueki, 46(8):728 (2005) (including English translation).
Soeda et al., "Phage library—ho ni yori Sakusei shita Ko-FIXa/Ko-FX bispecific Kotai no FVIII Taitei Sayo," Jpn J Thromb Hemost., 16(5):526 (2005) (including English translation).
Song et al., "Light chain of natural antibody plays a dominant role in protein antigen binding," Biochemical and Biophysical Research Communications, 268:390-394 (2000).
Souyri, M., "Mpl: from an acute myeloproliferative virus to the isolation of the long sought thrombopoietin," Seminars in Hematology, 35(3):222-231 (1998).
Spiess et al., "Bispecific antibodies with natural architecture produced by co-culture of bacteria expressing two distinct half-antibodies," Nat Biotechnol., Aug. 2013; 31(8):753-8. doi: 10.1038/nbt.2621. Epub Jul. 7, 2013.
Staerz et al., "Hybrid hybridoma producing a bispecific monoclonal antibody that can focus effector T-cell activity," Proc Natl Acad Sci U.S.A., 83:1453-7 (1986).
Strand et al., "Biologic therapies in rheumatology: lessons learned, future directions," Nat. Rev. Drug Discov., 6:75-92 (2007).
Suresh et al., "Bispecific monoclonal antibodies from hybrid hybridomas," Methods Enzymol., 1986;121:210-228.
Sun et al., "Coexpression of Gas6/Axl in human ovarian cancers," Oncology, 66(6):450-7 (2004).
Tahtis et al., "Biodistribution Properties of [111]Indium-labeled C-Functionalized trans-Cyclohexyl Diethylenetriaminepentaacetic Acid Humanized 3S193 Diabody and F(ab')$_2$ Constructs in a Breast Carcinoma Xenograft Model," Clin. Cancer Res., 7:1061-1072 (2001).
Tamura et al., "Structural correlates of an anticarcinoma antibody: identification of specificity-determining residues (SDRs) and development of a minimally immunogenic antibody variant by retention of SDRs only," J Immunol., Feb. 1, 2000;164(3):1432-41.
Tan et al., "Contributions of a highly conserved $V_H/V_L$ hydrogen bonding interaction to scFv folding stability and refolding efficiency," Biophys J., Sep. 1998; 75(3):1473-82.
Tan et al., "Engineering the isoelectric point of a renal cell carcinoma targeting antibody greatly enhances scFv solubility," Immunotechnology, 4(2):107-114 (1998).
Tang et al., "Selection of linkers for a catalytic single-chain antibody using phage display technology", The Journal of Biological Chemistry, 271(26):15682-15686 (1996).
Tarditi et al., "Selective high-performance liquid chromatographic purification of bispecific monoclonal antibodies," J. Chromatogr., 599:13-20 (1992).
Tedder et al., "CD22, a B Lymphocyte-Specific Adhesion Molecule That Regulates Antigen Receptor Signaling," Annu. Rev. Immunol., 15:481-504 (1997).
Teeling et al., "The biological activity of human CD20 monoclonal antibodies is linked to unique epitopes on CD20," J. Immunol., 177(1):362-71 (2006).
Teerinen et al., "Structure-based stability engineering of the mouse IgG1 Fab fragment by modifying constant domains," J Mol Biol., 361(4):687-97 (2006).
Ten Kate et al., "Effect of isoelectric point on biodistribution and inflammation: imaging with indium-111-labelled IgG," Eur. J. Nucl. Med., 17:305-309 (1990).
Thilenius et al., "Agonist antibody and Fas ligand mediate different sensitivity to death in the signaling pathways of Fas and cytoplasmic mutants," Eur. J. Immunol., 27:1108-1114 (1997).
Tsubaki et al., "C-terminal modification of monoclonal antibody drugs: amidated species as a general product-related substance," Int J Biol Macromol., 52:139-47. doi: 10.1016/j.ijbiomac.2012.09.016. Epub Sep. 25, 2012.
Tsuchiya, Credit Suisse Seminar, "Therapeutic Antibody," at Fuji-Gotemba Laboratories, p. 21 (2006) (with English translation).
Tsurushita et al., "Design of humanized antibodies: From anti-Tac to Zenapax," Methods, 36:69-83 (2005).
Turner et al., "Importance of the linker in expression of single-chain Fv antibody fragments: optimization of peptide sequence using phage display technology," Journal of Immunological Methods, 205:43-54 (1997).
Vaisitti et al., "Cationization of monoclonal antibodies: another step towards the "magic bullet"?," J. Biol. Regul. Homeost. Agents., 19(3-4):105-12 (2005).
Vajdos et al., "Comprehensive functional maps of the antigen-binding site of an anti-ErbB2 antibody obtained with shotgun scanning mutagenesis," J. Mol. Biol., 320(2):415-28 (2002).
Van Loghem et al., "Staphylococcal protein A and human IgG subclasses and allotypes," Scand. J. Immunol., 15(3):275-8 (1982).
Van Walle et al., "Immunogenicity screening in protein drug development," Expert Opin. Biol. Ther., 7(3):405-18 (2007).
Van Den Burg et al., "Selection of mutations for increased protein stability," Curr. Opin. Biotechnol., 13(4):333-337 (2002).
Van Der Neut Kolfschoten et al., "Anti-inflammatory activity of human IgG4 antibodies by dynamic Fab arm exchange," Science, Sep. 14, 2007;317(5844):1554-7.
Vargas-Madrazo et al., "An improved model of association for VH-VL immunoglobulin domains: asymmetries between VH and VL in the packing of some interface residues," J Mol Recognit., May-Jun. 2003;16(3):113-20.
Vaughan et al., "Human antibodies with sub-nanomolar affinities isolated from a large non-immunized phage display library," Nat Biotechnol., Mar. 1996;14(3):309-14.
Vehar et al., "Structure of human factor VIII," Nature, 312(5992):337-42 (1984).
Vieille et al., "Hyperthermophilic enzymes: sources, uses, and molecular mechanisms for thermostability," Microbiology and Molecular Biology Reviews, 65(1):1-43 (2001).
Volkel et al., "Optimized linker sequences for the expression of monomeric and dimeric bispecific single-chain diabodies," Protein Engineering, 14(10):815-823 (2001).
Wally et al., "Identification of a novel substitution in the constant region of a gene coding for an amyloidogenic kappa1 light chain," Biochim Biophys Acta., May 31, 1999;1454(1):49-56.

(56) References Cited

OTHER PUBLICATIONS

Wang et al., "Polyethylene Glycol-modified Chimeric Toxin Composed of Transforming Growth Factor alpha and Pseudomonas Exotoxin," Cancer. Res., 53:4588-4594 (1993).
Wang et al., "Conserved amino acid networks involved in antibody variable domain interactions," Proteins, Jul. 2009;76(1):99-114. doi: 10.1002/prot.22319.
Warnaar et al., "Purification of bispecific F(ab')2 from murine trinoma OC/TR with specificity for CD3 and ovarian cancer," Hybridoma, 13:519-526 (1994).
Wells, "Perspectives in Biochemistry," Biochemistry, 29(37):8509-8517 (1990).
Whitlow et al., "An improved linker for single-chain Fv with reduced aggregation and enhanced proteolytic stability," Protein Engineering, 6(8):989-995 (1993).
Wiens et al., "Somatic mutation in VH complementarity-determining region 2 and framework region 2: differential effects on antigen binding and Ig secretion," J. Immunol., 159(3):1293-302 (1997).
Wiens et al., "Mutation of a single conserved residue in VH complementarity-determining region 2 results in a severe Ig secretion defect," J. Immunol., 167(4):2179-86 (2001).
Wood et al., "Expression of active human factor VIII from recombinant DNA clones," Nature, 312(5992):330-7 (1984).
Woodle et al., "Anti-Human Class I MHC Antibodies Induce Apoptosis by a Pathway That Is Distinct from the Fas Antigen-Mediated Pathway," J. Immunol., 158:2156-2164 (1997).
Woodle et al., "Anti-Human Class I α3 Domain-Specific Monoclonal Antibody Induces Programmed Cell Death in Murine Cells Expressing Human Class I MHC Transgenes," Transplant. Proc., 30:1059-1060 (1998).
Woodle et al., "Class I MHC Mediates Programmed Cell Death in Human Lymphoid Cells," Transplantation, 64:140-146 (1997).
Worn et al., "Stability engineering of antibody single-chain Fv fragments," J Mol Biol., Feb. 2, 2001;305(5):989-1010.
Wu et al., "Development of motavizumab, an ultra-potent antibody for the prevention of respiratory syncytial virus infection in the upper and lower respiratory tract" J. Mol. Biol., 368(3):652-65 (2007).
Wu et al., "Multimerization of a chimeric anti-CD20 single-chain Fv-Fc fusion protein is mediated through variable domain exchange," Protein Eng., Dec. 2001;14(12):1025-33.
Wu et al., "Tumor localization of anti-CEA single-chain Fvs: improved targeting by non-covalent dimers," Immunotechnology, 2:21-36 (1996).
Wypych et al., "Human IgG2 antibodies display disulfide-mediated structural isoforms," J. Biol. Chem., 283(23):16194-16205 (2008).
Xiang et al., "Study of B72.3 combining sites by molecular modeling and site-directed mutagenesis," Protein Eng., 13(5):339-44 (2000).
Xiong et al., "Efficient inhibition of human B-cell lymphoma xenografts with an anti-CD20 X anti-CD3 bispecific diabody," Cancer Lett., 177:29-39 (2002).
Xu et al., "Insight into hepatocellular carcinogenesis at transcriptome level by comparing gene expression profiles of hepatocellular carcinoma with those of corresponding noncancerous liver," Proc. Natl. Acad. Sci. USA, 98:15089-15094 (2001).
Yamasaki et al., "Pharmacokinetic analysis of in vivo disposition of succinylated proteins targeted to liver nonparenchymal cells via scavenger receptors: importance of molecular size and negative charge density for in vivo recognition by receptors," J. Pharmacol. Exp. Ther., 301:467-477 (2002).
Yang et al., "Tailoring structure-function and pharmacokinetic properties of single-chain Fv proteins by site-specific PEGylation," Protein Eng., 16:761-770 (2003).
Zhu et al., "An efficient route to the production of an IgG-like bispecific antibody", Protein Eng., 13:361-367 (2000).
Zhu et al., "Remodeling domain interfaces to enhance heterodimer formation," Protein Sci., Apr. 1997;6(4):781-8.
Zhu et al., "MHC class I-related neonatal Fc receptor for IgG is functionally expressed in monocytes, intestinal macrophages, and dendritic cells," J. Immunol., 166(5):3266-76 (2001).
Zuckier et al., "Chimeric human-mouse IgG antibodies with shuffled constant region exons demonstrate that multiple domains contribute to in vivo half-life," Cancer Res., 58:3905-08 (1998).
Zuo et al., "An efficient route to the production of an IgG-like bispecific antibody," Protein Eng., 13(5):361-7 (2000).
Zwick et al., "The long third complementarity-determining region of the heavy chain is important in the activity of the broadly neutralizing anti-human immunodeficiency virus type 1 antibody 2F5," J. Virol., 78(6):3155-61 (2004).
International Search Report for App. Ser. No. PCT/JP2006/306803, dated Jul. 11, 2006, 4 pages.
International Preliminary Report on Patentability for App. Ser. No. PCT/JP2006/306803, dated Oct. 3, 2007, 6 pages.
International Search Report for App. Ser. No. PCT/JP2014/075728, dated Dec. 22, 2014, 4 pages.
International Preliminary Report on Patentability for App. Ser. No. PCT/JP2014/075728, dated Mar. 29, 2016, 15 pages.
Amersdorfer et al., GenPept Accession No. AAC26541, "anti BoNT/A Hc scFv antibody [synthetic construct]," 1 page (Aug. 1, 2001).
Asselta et al., "Factor V Deficiency," Semin. Thromb. Hemost., 35:382-389 (2009).
Bajaj et al., "A Monoclonal Antibody to Factor IX That Inhibits the Factor VIII:Ca Potentiation of Factor X Activation," J. Biol. Chem., Sep. 25, 1985;260(21):11574-11580.
Bebbington et al., "High-Level Expression of a Recombinant Antibody from Myeloma Cells Using a Glutamine Synthetase Gene as an Amplifiable Selectable Marker," Biotechnology (N Y), Feb. 1992;10:169-175.
Bessos et al., "The characterization of a panel of monoclonal antibodies to human coagulation factor IX," Thrombosis Research, Dec. 15, 1985;40:863-867.
Bian et al., "Discovery of promiscuous HLA-II-restricted T cell epitopes with TEPITOPE," Methods, Dec. 2004;34(4):468-75.
Bolton-Maggs et al., "Haemophilias A and B," The Lancet, May 24, 2003;361:1801-9.
Bos et al., "Enhanced Transfection of a Bacterial Plasmid into Hybridoma Cells by Electroporation: Application for the Selection of Hybrid Hybridoma (Quadroma) Cell Lines," Hybridoma, Feb. 1992;11:41-51.
Brennan et al., "Preparation of Bispecific Antibodies by Chemical Recombination of Monoclonal Immunoglobulin G1 Fragments," Science, Jul. 5, 1985;229:81-3.
Brinkivian et al. "Phospholipid-binding domain of factor VIII is involved in endothelial cell-mediated activation of factor X by factor IXa," Arterioscler. Thromb. Vasc. Biol., Mar. 1, 2002;22(3):511-6.
Dall'Acqua et al., "Increasing the affinity of a human IgG1 for the neonatal Fc receptor: biological consequences," J. Immunol., Nov. 1, 2002;169(9):5171-80.
Davie et al., "The coagulation cascade: Initiation, maintenance, and regulation," Biochemistry, Oct. 29, 1991;30(43):10363-70.
Dhiman et al., "Gene expression microarrays: a 21st century tool for directed vaccine design," Vaccine, Oct. 12, 2001;20(1-2):22-30.
Francois et al., "Construction of a Bispecific Antibody Reacting with the α- and β-Chains of the Human IL-2 Receptor," J. Immunol., May 15, 1993;150:4610-9.
Grosse-Hovest et al., "A recombinant bispecific single-chain antibody induces targeted, supra-agonistic CD28-stimulation and tumor cell killing", European Journal of Immunology, May 2003;33(5):1334-40.
Hämmerling et al., "Use of Hybrid Antibody with Anti-γG and Anti-Ferritin Specificities in Locating Cell Surface Antigens by Electron Microscopy," J. Exp. Med., Dec. 1, 1968;128:1461-73.
Hoad et al. "Characterization of monoclonal antibodies to human factor X.Xa: Initial observations with a quantitative ELISA procedure," J. Immunol. Methods, Feb. 15, 1991;136(2):269-78.
Hsia et al., "Treatment of acquired factor X inhibitor by plasma exchange with concomitant intravenous immunoglobulin and corticosteroids," Am. J. Hematol., Apr. 2008;83:318-20.

(56) References Cited

OTHER PUBLICATIONS

Huse et al., "Generation of a Large Combinatorial Library of the Immunoglobulin Repertoire in Phage Lambda," *Science*, Dec. 8, 1989;246:1275-81.
Kabsch et al., "On the use of sequence homologies to predict protein structure: identical pentapeptides can have completely different conformations," *Proc Natl Acad Sci U S A.*, Feb. 1984;81(4):1075-8.
Kang et al., "Linkage of recognition and replication functions by assembling combinatorial antibody Fab libraries along phage surfaces," *Proc. Natl. Acad. Sci. USA*, May 15, 1991;88:4363-6.
Karpovsky et al., "Production of Target-Specific Effector Cells Using Hetero—Cross-Linked Aggregates Containing Anti-Target Cell and Anti-Fcγ Receptor Antibodies," *J. Exp. Med.*, Dec. 1, 1984;160:1686-701.
Kim et al., "Mammalian type I interferon receptors consists of two subunits: IFNaR1 and IFNaR2," *Gene*, Sep. 1, 1997;196:279-86.
Kroesen et al., "Phase I study of intravenously applied bispecific antibody in renal cell cancer patients receiving subcutaneous interleukin 2," *Br. J. Cancer*, Oct. 1994;70:652-61.
Kurokawa et al., "Enhanced Fibrinolysis by a Bispecific Monoclonal Antibody Reactive to Fibrin and Tissue Plasminogen Activator," *Bio/Technology*, Nov. 1989;7:1163-7.
Lapan et al., "Interaction of the A1 Subunit of Factor VIIIa and the Serine Protease Domain of Factor X Identified by Zero-length Cross-linking," *Thromb. Haemost.*, Sep. 1998;80:418-22.
Le Doussal et al., "Bispecific Monoclonal Antibody-Mediated Targeting of an Indium-111-Labeled DTPA Dimer to Primary Colorectal Tumors: Pharmacokinetics, Biodistribution, Scintigraphy and Immune Response," *J. Nucl. Med.*, Oct. 1993;34:1662-71.
Lenting et al., "The life cycle of coagulation factor VIII in view of its structure and function", *Blood*, Dec. 1, 1998;92(11):3983-96.
Link et al., "Production and Characterization of a Bispecific IgG Capable of Inducing T-Cell-Mediated Lysis of Malignant B Cells," *Blood*, Jun. 15, 1993;81:3343-9.
Löfqvist et al., "Haemophilia prophylaxis in young patients—a long-term follow-up," *J. Intern. Med.*, May 1997;241:395-400.
Lu et al., "Fab-scFv fusion protein: an efficient approach to production of bispecific antibody fragments," *J. Immunol. Methods*, Sep. 15, 2002;267:213-26.
Lu et al., "Di-diabody: a novel tetravalent bispecific antibody molecule by design," *J. Immunol. Methods*, Aug. 2003;279:219-32.
Massino et al., "Quantitative analysis of the products of IgG chain recombination in hybrid hybridomas based on affinity chromatography and radioimmunoassay," *J. Immunol. Methods*, Feb. 14, 1997;201:57-66.
McCafferty et al., "Phage antibodies: filamentous phage displaying antibody variable domains," *Nature*, Dec. 6, 1990;348:552-4.
McPhee et al., "Engineering human immunodeficiency virus 1 protease heterodimers as macromolecular inhibitors of viral maturation," *Proc Natl Acad Sci U S A.*, Oct. 15, 1996;93(21):11477-81.
Menegatti et al., "Factor X Deficiency," *Semin. Thromb. Hemost.*, Jun. 2009;35:407-15.
Mertens et al., "Factor VIII-Factor IX Interactions: Molecular Sites Involved in Enzyme-Cofactor Complex Assembly," *Thromb. Haemost.*, Aug. 1999;82:209-17.
Milstein et al., "Hybrid hybridomas and their use in immunohistochemistry," *Nature*, Oct. 6-12, 1983;305:537-40.
"National Haemophilia Foundation (NHF) Medical and Scientific Advisory Council (MASAC) Recommendations Concerning Prophylaxis," *MedicalBulletin*, No. 193, 1 page (1994).
Nilsson et al., "Twenty-five years' experience of prophylactic treatment in severe haemophilia A and B," *J. Intern. Med.*, Jul. 1992;232:25-32.
Nilsson et al., "Induction of split tolerance and clinical cure in high-responding hemophiliacs with factor IX antibodies," *Proc. Natl. Acad. Sci. U S A.*, Dec. 1986;83:9169-73.
Nitta et al., "Preliminary trial of specific targeting therapy against malignant glioma," *Lancet*, Feb. 17, 1990;335:368-371.

Okubo et al. "The production and characterization of four monoclonal antibodies to human factor X," *Nara Med Assoc.*, 1987;38(1):20-28.
Piper et al., "Interferon therapy in primacy care," *Primary Care Update for Ob/Gyns*, Jul. 2001;8(4):163-69.
Pokkuluri et al., "A domain flip as a result of a single amino-acid substitution," *Structure*, Aug. 15, 1998;6(8):1067-73.
Price et al., "Tissue factor and tissue factor pathway inhibitor," *Anaesthesia*, May 2004;59:483-92.
Ruef et al., "A bispecific antifibrin-antiplatelet urokinase conjugate (BAAUC) induces enhanced clot lysis and inhibits platelet aggregation," *Thromb. Haemost.*, Jul. 1999;82(1):109-14.
Sato et al., "Properties of Two VEGF Receptors, Flt-1 and KDR, in Signal Transduction," *Ann N.Y. Acad. Sci*, May 2000;902:201-207, discussion 205-7.
Segal et al., "Introduction: bispecific antibodies," *J. Immunol. Methods*, Feb. 1, 2001;248:1-6.
Shima et al., "Factor VIII Taitei Kotai (2), Ketsuyubyo A Kanja Katsueki ni okeru in vitro Gyoko Kassei no Kento", Rinsho Ketsueki, Aug. 30, 2005;46(8):777 (#WS-36-5) (with English translation).
Stickney et al., "Bifunctional Antibody: A Binary Radiopharmaceutical Deliver), System for Imaging Colorectal Carcinoma," *Cancer Res.*, Dec. 15, 1991;51:6650-5.
Suresh et al., "Advantages of bispecific hybridomas in one-step immunocytochemistry and immunoassays," *Proc. Natl. Acad. Sci. U S A.*, Oct. 1986;83:7989-93.
Taki, *The Journal of Japanese Society on Thrombosis and Hemostasis*, Feb. 2, 2002;13:109-113.
Thies et al., "The alternatively folded state of the antibody C(H)3 domain," J Mol Biol., Jun. 22, 2001;309(5):1077-85.
Ward et al., "Effects of engineering complementary charged residues into the hydrophobic subunit interface of tyrosyl-tRNA synthetase. Appendix: Kinetic analysis of dimeric enzymes that reversibly dissociate into inactive subunits," *Biochemistry*, Jun. 30, 1987;26(13):4131-8.
Weiner et al., "A Human Tumor Xenograft Model of Therapy with a Bispecific Monoclonal Antibody Targeting c-erbB-2 and CD16," *Cancer Res.*, Jan. 1, 1993;53:94-100.
Weiner et al., "The Role of T Cell Activation in Anti-CD3 × Antitumor Bispecific Antibody Therapy," J. Immunol., Mar. 1, 1994;152:2385-92.
Choi et al., "Engineering of Immunoglobulin Fc Heterodimers Using Yeast Surface-Displayed Combinatorial Fc Library Screening," PLoS One, Dec. 16, 2015;10(12):e0145349. doi: 10.1371/journal.pone.0145349. eCollection 2015.
Coloma et al., "Position effects of variable region carbohydrate on the affinity and in vivo behavior of an anti-(1-->6) dextran antibody," J Immunol., Feb. 15, 1999;162(4):2162-70.
Hird et al., "Tumour localisation with a radioactively labelled reshaped human monoclonal antibody," Br J Cancer, Nov. 1991;64(5):911-4.
Hong et al., "Enhanced cellular uptake and transport of polyclonal immunoglobulin G and fab after their cationization," J Drug Target., 2000;8(2):67-77.
Li et al., "Construction and characterization of a humanized anti-human CD3 monoclonal antibody 12F6 with effective immunoregulation functions," Immunology, Dec. 2005;116(4):487-98.
Marshall et al., "Rational design and engineering of therapeutic proteins," Drug Discov Today, Mar. 1, 2003;8(5):212-21.
Pardridge et al., "Enhanced cellular uptake and in vivo biodistribution of a monoclonal antibody following cationization," J Pharm Sci., Aug. 1995;84(8):943-8.
Reimann et al., "A humanized form of a CD4-specific monoclonal antibody exhibits decreased antigenicity and prolonged plasma half-life in rhesus monkeys while retaining its unique biological and antiviral properties," AIDS Res Hum Retroviruses, Jul. 20, 1997;13(11):933-43.
Sarkar et al., "Rational cytokine design for increased lifetime and enhanced potency using pH-activated "histidine switching"," Nat Biotechnol., Sep. 2002;20(9):908-13. Epub Aug. 5, 2002.
Sharifi et al., "Improving monoclonal antibody pharmacokinetics via chemical modification," Q J Nucl Med., Dec. 1998;42(4):242-9.

(56) References Cited

OTHER PUBLICATIONS

Tabrizi et al., "Elimination mechanisms of therapeutic monoclonal antibodies," Drug Discov Today, Jan. 2006;11(1-2):81-8.
Verhoeyen et al., "Construction of a reshaped HMFG1 antibody and comparison of its fine specificity with that of the parent mouse antibody," *Immunology*, Mar. 1993;78(3):364-70.
Verhoeyen et al., "Monoclonal Antibodies in Clinical Oncology," 1991, Edited by AA Epenetos, Chapter 5, pp. 37-43, Chapman and Hall.
Ibragimova et al., "Stability of the beta-sheet of the WW domain: A molecular dynamics simulation study," *Biophys J.*, Oct. 1999;77(4):2191-8.
Lin et al., "Structure-function relationships in glucagon: properties of highly purified des-His-1-, monoiodo-, and (des-Asn-28, Thr-29)(homoserine lactone-27)-glucagon," *Biochemistry*, Apr. 22, 1975;14(8):1559-63.
Schwartz et al., "A superactive insulin: [B10-aspartic acid]insulin(human)," *Proc Natl Acad Sci U S A.*, Sep. 1987;84(18):6408-11.
USPTO Restriction Requirement in U.S. Appl. No. 14/127,576, dated Jun. 1, 2016, 8 pages.
Fish & Richardson P.C., Reply to Restriction Requirement dated Jun. 1, 2016 in U.S. Appl. No. 14/127,576, filed Aug. 24, 2016, 2 pages.
USPTO Non-Final Office Action in U.S. Appl. No. 14/127,576, dated Sep. 20, 2016, 17 pages.
U.S. Appl. No. 15/402,580, Hattori et al., filed Jan. 10, 2017.
U.S. Appl. No. 15/467,654, Nezu et al.
Amann et al., "Therapeutic window of an EpCAM/CD3-specific BiTE antibody in mice is determined by a subpopulation of EpCAM-expressing lymphocytes that is absent in humans," Cancer Immunol Immunother. Jan. 2009: 58 (1):95-109. Epub Jul. 2, 2008.
Bendig M. M., "Humanization of Rodent Monoclonal Antibodies by CDR Grafting," Methods: A Companion to Methods in Enzymology, 1995; 8:83-93.
Brenner et al., "Errors in genome annotation," Trends in Genetics, Apr. 1999;15:132-133.
Campoli et al., "Immunotherapy of Malignant Disease with Tumor Antigen-Specific Monoclonal Antibodies," Clin Cancer Res. Jan. 1, 2010:16 (1): 11-20. do i: 10. 1158/ 1078-0432. CCR-09-2345. Epub Dec. 22, 2009.
Chan et al., "Therapeutic antibodies for autoimmunity and inflammation," Nat Rev Immunol. May 2010 ;10(5):301-16. do i: 10.1038/ nri 2761.
Diaz et al., "Effects of engineering charged amino acids in the CH3 domains on antibody heavy chain dimerization," Philippine Science Letters. 2011;4(1):48-55.
Ejima et al, "Effects of Acid Exposure on the Conformation, Stability, and Aggregation of Monoclonal Antibodies," Proteins, Mar. 1, 2007;66(4):954-62.
Gen Bank Accession No. AAG00910.2, "recombinant IgG2 heavy chain, partial [*Homo sapiens*]," May 14, 2001, 1 page.
Hess et al., "Cancer therapy with trifunctional antibodies: linking innate and adaptive immunity," Future Oncol. Jan. 2012: 8(1):73-85. doi: 10.2217/ fon.11.138.
Janeway et al., Immunobioiogy, 5th edition. 2001 :Extract from Chapter 3, pp. 93-122.
Janeway et al., Immunobioiogy, 5th edition. 2001 :Extract from Chapter 4, pp. 123-154.
Jefferis et al., "Interaction sites on human IgG-Fc for FcγR: current models," Immunol Lett. Jun. 3, 2002:82(1-2):57-65.
Jones et al., "Growth factor receptor interplay and resistance in cancer," Endocr Relat Cancer. Dec. 2006 :13 Supp 1 1:S45-51.
Kontermann, "Dual targeting strategies with bispecific antibodies," MAbs. Mar.-Apr. 2012;4(2):182-97. do i: 10. 4161 / mabs. 4. 2. 19000. Epub Mar. 1, 2012.
Lacroix-Desmazes et al, "Dynamics of factor VIII interactions determine its immunologic fate in hemophilia A," Blood, Jul. 15, 2008;112(2):240-9. doi: 10.1182/blood-2008-02-124941. Epub May 9, 2008.

Mezzanzanica et al., "Human Ovarian Carcinoma Lysis by Cytotoxic T Cells Targeted by Bispecific Monoclonal Antibodies: Analysis of the Antibody Components," Int J Cancer. Apr. 15, 1988 :41(4):609-15.
Morrison, "Two heads are better than one," Nat Biotechnol., Nov. 2007;25(11):1233-4.
Murata et al., "Anti-Digoxin Fab Variants Generated by Phage Display," Mol Biotechnol. Jun. 2013 :54 (2) :269- 77. doi : 10. 1007/s12033-012-9564-1.
Nakano et al. "Anti-glypican 3 antibodies cause ADCC against human hepatocellular carcinoma cells," Biochem Biophys Res Commun. Jan. 9, 2009:378 (2) :279-84. doi: 10.1016/j.bbrc.2008. 11.033. Epub Nov. 18, 2008.
Natsume et al., "Improving effector functions of antibodies for cancer treatment: Enhancing ADCC and CDC," Drug Des Devel Ther., Sep. 21, 2009:3:7-16.
Newman et al, "Modification of the Fc Region of a Primatized IgG Antibody to Human CD4 Retains Its Ability to Modulate CD4 Receptors but Does Not Deplete CD4 T Cells in Chimpanzees," Clin Immunol, Feb. 2001;98(2):164-74.
Nimmerjahn et al., ".Fcγ receptors as regulators of immune responses," Nat Rev Immunol. Jan. 2008; 8(1):34-47.
Paul et al., "Immunologiya", M.:Mir, 1987-1988, vol. 1, p. 231 (with English translation).
Pejchal et al., "A Conformational Switch in Human Immunodeficiency Virus gp41 Revealed by the Structures of Overlapping Epitopes Recognized by Neutralizing Antibodies," J Virol. Sep. 2009 ; 83 (17) : 8451-62. do i : 10. 1128/ JVI. 00685-09. Epub Jun. 10, 2009.
Pritsch et al., "Can Immunoglobulin CH1 Constant Region Domain Modulate Antigen Binding Affinity of Antibodies?," J Clin Invest. Nov. 15, 1996;98(10):2235-43.
Radaev et al., "The Structure of a Human Type III Fcγ Receptor in Complex with Fc," J Biol Chem. May 11, 2001 :276 (19) :16469-77. Epub Jan. 31, 2001.
Raposo et al., "Epitope-specific antibody response is controlled by immunoglobulin Vh polymorphisms," J Exp Med. Mar. 10, 2014:211 (3):405-11. doi:10. 1084/jem. 20130968. Epub Feb. 17, 2014.
Riechelmann et al., "Adoptive therapy of head and neck squamous cell carcinoma with antibody coated immune cells: a pilot clinical trial," Cancer Immunol Immunother. Sep. 2007 :56 (9) :1397-406. Epub Feb. 2, 2007.
Roopenian et al., "FcRn: the neonatal Fc receptor comes of age," Nat Rev Immunol., Sep. 3007;7(9):715-25.
Rothe et al., Recombinant proteins in rheumatology—recent advances, N Biotechnol. Sep. 2011;28 (5) :502-10. doi: 10.1016/ j. nbt. 2011. 03. 019. Epub Apr. 5, 2011.
Schlereth et al., "T-cell activation and B-cell depletion in chimpanzees treated with a bispecific anti-CD19/anti-CD3 single-chain antibody construct," Cancer Immunol Immunother. May 2006:55 (5) :503-14. Epub Jul. 20, 2005.
Sebastian et al., "Treatment of non-small cell lung cancer patients with the trifunctional monoclonal antibody catumaxomab (anti-EpCAM x anti-CD3): a phase I study," Cancer Immunol Immunother. Oct. 2007 :56 (10) :1637-44. Epub Apr. 5, 2007.
Seimetz et al., "Development and approval of the trifunctional antibody catumaxomab (anti-EpCAM x anti-CD3) as a targeted cancer immunotherapy," Cancer Treat Rev. Oct. 2010 :36 (6) : 458-67. do i: 10. 1016/ j. ctrv. 2010. 03. 001 Epub Mar. 27, 2010.
Smith et al., "The challenges of genome sequence annotation or 'the devil is in the details'," Nature Biotechnology, Nov. 1997;15:1222-1223.
Staerz et al., "Hybrid antibodies can target sites for attack by T cells," Nature. Apr. 18-24, 1985 :314 (6012) :628-31.
Unkeless et al., "Structure and Function of Human and Murine Receptors for IgG," Annu Rev Immunol. 1988 :6:251-81.
Ward et al., "Binding activities of a repertoire of single immunoglobulin variable domains secreted from *Escherichia coli*," Nature, 1989;341:544-546.
Wozniak-Knopp et al., "Introducing antigen-binding sites in structural loops of immunoglobulin constant domains: Fc fragments with

(56) References Cited

OTHER PUBLICATIONS engineered HER2/neu-binding sites and antibody properties," Protein Eng Des Sel. Apr. 2010; 23(4):289-97. do i: 10. 1093/ prote in/ gzq005. Epub Feb. 11, 2010.
Yang et al., "CDR Walking Mutagenesis for the Affinity Maturation of a Potent Human Anti-HIV-1 Antibody into the Picomolar Range," J Mol. Biol., 254(3):392-403 (Dec. 1995).
Zeidler et al., "Simultaneous Activation of T Cells and Accessory Cells by a New Class of Intact Bispecific Antibody Results in Efficient Tumor Cell Killing," J Immunol. Aug. 1, 1999 ; 163(3) : 1246-52.
USPTO Interview Summary in U.S. Appl. No. 14/127,576, dated Dec. 23, 2016, 3 pages.
Fish & Richardson P.C., Reply to Non-Final Office Action dated Sep. 20, 2016 in U.S. Appl. No. 14/127,576, dated Mar. 16, 2017, 21 pages.
USPTO Notice of Allowance in U.S. Appl. No. 14/127,576, dated Jun. 2, 2017, 13 pages.
USPTO Notice of Allowance in U.S. Appl. No. 14/127,576, dated Jun. 21, 2017, 9 pages.
U.S. Appl. No. 15/963,345, Hattori et al., filed Apr. 26, 2018.
U.S. Appl. No. 14/680,250, Igawa et al., filed Apr. 7, 2015.
U.S. Appl. No. 14/962,293, Igawa et al., filed Dec. 8, 2015.
U.S. Appl. No. 13/497,269, Kuramochi et al., filed Jun. 1, 2012.
U.S. Appl. No. 15/875,847, Igawa et al., filed Jan. 19, 2018.
U.S. Appl. No. 15/467,654, Nezu et al., filed Mar. 23, 2017.
Canfield et al., "The Binding Affinity of Human IgG for its High Affinity Fc Receptor Is Determined by Multiple Amino Acids in the $C_H2$ Domain and Is Modulated by the Hinge Region," J Exp Med, Jun. 1, 1991, 173(6):1483-91.
Dall'Acqua et al., "Properties of Human IgG1 s Engineered for Enhanced Binding to the Neonatal Fc Receptor (FcRn)", J Biol Chem., Aug. 18, 2006, 281(33):23514-24. Epub Jun. 21, 2006.
EPO Register Extract EP 1915397 (document submitted in EP opposition and posted by EPO on Feb. 2, 2018); 4 pages.
Geneseq Accession No. AEM45140, Feb. 22, 2007, "Light chain constant region of therapeutic human IgG antibody" 1 page.
Golay et al., "Mechanism of action of therapeutic monoclonal antibodies: Promises and pitfalls of in vitro and in vivo assays," Archives of Biochemistry and Biophysics, Feb. 25, 2012, 526:141-153.
Hotzel et al., "A strategy for risk mitigation of antibodies with fast clearance," mAbs, Nov.-Dec. 2012, 4(6):753-60. doi: 10.4161/mabs. 22189.
Jaeger, "Clinical Immunology and Allergology," 2nd edition, M.: Medicina, 1990, 3 vol. 2:484-5 (with English translation).
Kabat et al., "Identical V Region Amino Acid Sequences and Segments of Sequences in Antibodies of Different Specificities," Journal of Immunology, Sep. 1, 1991, 147(5):1709-19.
Kim et al., "Antibody light chain variable domains and their biophysically improved versions for human immunotherapy," mAbs, Jan.-Feb. 2014, 6(1):219-35. doi: 10.4161/mabs.26844.
Li et al., "Framework selection can influence pharmacokinetics of a humanized therapeutic antibody through differences in molecule charge," mAbs., 2014, 6(5):1255-64. doi: 10.4161/mabs.29809. Epub Oct. 30, 2014.
Roitt et al., Immunology, M., Mir, 2000, pp. 110, 150, and 537-539 (in Russian, with what is believed to be a published English equivalent of those pages).
Ryman et al., "Pharmacokinetics of Monoclonal Antibodies," CPT Pharmacometrics Syst Pharmacol., Sep. 2017, 6(9):576-588. doi: 10.1002/psp4.12224. Epub Jul. 29, 2017.
Summary of information about antibodies in Examples of patent (document submitted in EP opposition and posted by EPO on Apr. 13, 2018); 3 pages.
Written Submissions by Opponent 1 (Alexion Pharmaceuticals, Inc.) in Opposition of EP 2006381 dated Apr. 13, 2018, 19 pages.
Written Submissions by Opponent 2 (Novo Nordisk A/S) in Opposition of EP 2006381 dated Apr. 13, 2018, 14 pages.
Written Submissions by Opponent 3 (name Unknown) in Opposition of EP 2006381 dated Apr. 13, 2018, 16 pages.
Wu et al., "Ultra-potent Antibodies Against Respiratory Syncytial Virus: Effects of Binding Kinetics and Binding Valence on Viral Neutralization," J Mol Biol., Jul. 1, 2005, 350(1):126-44.
Yarilin, "Immunology Basics", M:Medicina, 1999:169-74 (with English translation) 14 pages.
Yarilin, Fundamentals of Immunology M:Medicina, 1999, pp. 169-72, 354-8 (with English translation) 21 pages.
Yarilin, Fundamentals of Immunology M:Medicina, 1999, pp. 172-174 (with English translation), 8 pages.
Feige et al., "How antibodies fold," Trends Biochem Sci, Apr. 2010, 35(4):189-98. doi: 10.1016/j.tibs.2009.11.005. Epub Dec. 21, 2009.
Feige et al., "An Unfolded $C_H1$ Domain Controls the Assembly and Secretion of IgG Antibodies," Mol Cell, Jun. 12, 2009, 34(5):569-79. doi: 10.1016/j.molcel.2009.04.028.
Horne et al., "Noncovalent Association of Heavy and Light Chains of Human Immunoglobulins," J Immunol, Aug. 1982, 129(2):660-4.
Kabat et al., "Sequences of proteins of immunological interest," DIANE Publishing, vol. 1, 5th ed., 1991, pp. 647-652 and 661-669.
Muller et al., "The first constant domain ($C_H1$ and $C_L$ of an antibody used as heterodimerization domain for bispecific miniantibodies," FEBS Lett, Jan. 30, 1998, 422(2):259-64.
Declaration of Dr. Anette Henriksen, signed Apr. 17, 2019 (submitted by the Opponent during EPO opposition procedure for EP 2 006 381).
U.S. Appl. No. 16/226,798, Hattori et al., filed Dec. 20, 2018.
U.S. Appl. No. 14/019,712, Igawa et al., filed Sep. 6, 2013 (abandoned).
U.S. Appl. No. 15/132,996, Igawa et al., filed Apr. 19, 2016.
U.S. Pat. No. 9,828,429, Hattori et al., issued Nov. 28, 2017.
U.S. Appl. No. 13/582,073, Kuramochi et al., filed Dec. 20, 2012.
U.S. Appl. No. 14/351,654, Kuramochi et al., filed Apr. 14, 2014.
Barrabes et al., "Effect of sialic acid content on glycoprotein pI analyzed by two-dimensional electrophoresis," Electrophoresis, Sep. 2010, 31(17):2903-12. doi: 10.1002/elps.200900764.
Mariuzza, "The Structural Basis of Antigen-Antibody Recognition," Annu Rev Biophys, Biophys Chem, Jun. 1987, 16:139-159.
Davie, "A Brief Historical Review of the Waterfall/Cascade of Blood Coagulation," J Biol Chem. Dec. 19, 2003, 278(51):50819-32. Epub Oct. 21, 2003.
Decision of the Opposition Division in EP 2 275 443, dated Apr. 26, 2018 (submitted on May 24, 2019 by the Patentee during EPO Opposition Procedure for EP 2 202 245), 29 pages.
Declaration of Taichi Kuramochi (submitted on May 24, 2019 by the Patentee during EPO Opposition Procedure for EP 2 202 245), 11 pages.
Granted claims of EP 2 275 443 (submitted on May 24, 2019 by the Patentee during EPO Opposition Procedure for EP 2 202 245), 1 page.
Supplemental Material to Raposo et al., "Epitope-specific antibody response is controlled by immunoglobulin $V_H$ polymorphisms," J Exp Med, Mar. 10, 2014, 211(3):405-11. doi: 10.1084/jem. 20130968. Epub Feb. 17, 2014 (submitted on May 24, 2019 by the Patentee during EPO Opposition Procedure for EP 2 202 245), 4 pages.
De Gast et al., "CD8 T cell activation after intravenous administration of CD3 × CD19 bispecific antibody in patients with non-Hodgkin lymphoma," Cancer Immunol Immunother, Jun. 1995, 40(6):390-6.
Lazar et al., "Engineered antibody Fc variants with enhanced effector function," Proc Natl Acad Sci USA, Mar. 14, 2006, 103(11):4005-10. Epub Mar. 6, 2006.
Moiseenko, "Monoclonal Antibodies in the Treatment of Malignant Tumors," Practical Oncology, 2003, 4(3):148-56 (with English translation).
Wang et al., "A New Recombinant Single Chain Trispecific Antibody Recruits T Lymphocytes to Kill CEA (Carcinoma Embryonic Antigen) Positive Tumor Cells In Vitro Efficiently," J Biochem, Apr. 2004, 135(4):555-65.

(56) References Cited

OTHER PUBLICATIONS

Zeidler et al., "The Fc-region of a new class of intact bispecific antibody mediates activation of accessory cells and NK cells and induces direct phagocytosis of tumour cells," Br J Cancer, Jul. 2000, 83(2):261-6.
U.S. Appl. No. 10/575,905, Hattori et al., filed Apr. 30, 2017 (abandoned).
U.S. Appl. No. 13/434,643, Hattori et al., filed Mar. 29, 2012 (abandoned).
U.S. Appl. No. 15/402,80, Hattori et al., filed Jan. 10, 2017 (abandoned).
U.S. Appl. No. 15/288,965, Igawa et al., filed Oct. 7, 2016.
U.S. Appl. No. 16/155,673, Igawa et al., filed Oct. 9, 2018.
Abe et al., "Novel Protein A Resin: Synthetic Polymer Matrix Design Impact on Antibody Binding Capacity," JSR Technical Review, No. 119, 2012, pp. 1-5 [online], [retrieved on Feb. 17, 2017], retrieved from the internet: <URL:http://www.jsr.co.jp/pdf/rd/tec119-1.pdf > (with English translation).
Choi et al., "Crystal structures of immunoglobulin Fc heterodimers reveal the molecular basis for heterodimer formation," Mol Immunol, Jun. 2015, 65(2):377-83. doi: 10.1016/j.molimm.2015.02.017. Epub Mar. 2, 2015.
Cruse et al., Atlas of Immunology, CRC Press LLC, 2004, Chapter 3, "Antigens and Immunogens," p. 109.
Decision of the EPO Opposition Division for EP 2 006 381 on Jul. 25, 2018, 17 pages.
GE Healthcare Life Sciences, Dynamic binding capacity study on MabSelect SuReTM LX for capturing high-titer monoclonal antibodies, Application note 28-9875-25-AA, 2011, [online], [retrieved on Feb. 17, 2017], retrieved from the internet: ,http://www.processdevelopmentforum.com/images/articles/28-9875-22_AA_AN_DBC_study_on_MabSelect_SuRe_LX_final.pdf.
Geneseq Accession No. ARZ17615, Aug. 21, 2008, "Human antibody IgG2 heavy chain constant region SEQ ID No. 36," 1 page.
Goulet et al., "Kinetic mechanism of controlled Fab-arm exchange for the formation of bispecific immunoglobulin G1 antibodies," J Biol Chem, Jan. 12, 2018, 293(2):651-661. doi:10.1074/jbc.RA117.000303. Epub Nov. 17, 2017.
Rispens et al., "Mechanism of Immunoglobulin G4 Fab-arm Exchange," J Am Chem Soc, Jul. 6, 2011, 133(26):10302-11. doi: 10.1021/ja203638y. Epub Jun. 15, 2011.
Sampei et al, "Non—antigen-contacting region of an asymmetric bispecific antibody to factors IXa/X significantly affects factor VIII-mimetic activity," mAbs, Jan./Feb. 2015, 7(1):120-8. doi: 10.4161/19420862.2015.989028.
Sequence alignments and modification scheme (document filed during Oral Proceedings in EPO opposition for EP 2 006 381 mentioned in minutes of the Oral Proceedings posted by EPO on Jul. 25, 2018), 3 pages.
Van Den Abbeele et al., "Antigen-Binding Site Protection During Radiolabeling Leads to a Higher Immunoreactive Fraction," J Nucl Med, Jan. 1991, 32(1):116-22.
U.S. Appl. No. 10/575,905, Hattori et al., filed Apr. 30, 2007 (abandoned).
U.S. Pat. No. 8,062,635, Hattori et al., issued Nov. 22, 2011.
U.S. Appl. No. 11/910,836, Hattori et al., filed Jan. 12, 2009 (abandoned).
U.S. Appl. No. 13/34,643, Hattori et al., filed Mar. 29, 2012 (abandoned).
U.S. Appl. No. 14/921,590, Hattori et al., filed Oct. 23, 2015 (abandoned).
U.S. Appl. No. 15/172,727, Hattori et al., filed Jun. 3, 2016 (abandoned).
U.S. Appl. No. 15/402,580, Hattori et al., filed Jan. 10, 2017 (abandoned).
U.S. Appl. No. 15/701,630, Hattori et al., filed Sep. 12, 2017 (abandoned).
U.S. Appl. No. 15/963,345, Hattori et al., filed Apr. 26, 2018 (abandoned).
U.S. Appl. No. 16/226,798, Hattori et al., filed Dec. 20, 2018 (abandoned).
U.S. Appl. No. 16/536,385, Hattori et al., filed Aug. 9, 2019.
U.S. Pat. No. 9,334,331, Igawa et al., issued May 10, 2016.
U.S. Appl. No. 14/019,117, Igawa et al., filed Sep. 5, 2013 (abandoned).
U.S. Appl. No. 14/019,712, Igawa et al., filed Sep. 6, 2013.
U.S. Pat. No. 10,450,381, Igawa et al., issued Oct. 22, 2019.
U.S. Appl. No. 15/288,965, Igawa et al., filed Oct. 7, 2016 (abandoned).
U.S. Appl. No. 16/459,791, Igawa et al., filed Jul. 2, 2019.
U.S. Appl. No. 10/560,098, Miyazaki et al., filed Apr. 28, 2006 (abandoned).
U.S. Pat. No. 10,011,858, Igawa et al., issued Jul. 3, 2018.
U.S. Appl. No. 15/782,256, Igawa et al., filed Oct. 12, 2017.
U.S. Appl. No. 15/562,186, Igawa et al., filed Sep. 27, 2017.
U.S. Appl. No. 12/295,039, Igawa et al., filed Jan. 20, 2009.
U.S. Pat. No. 9,096,651, Igawa et al., issued Aug. 4, 2015.
U.S. Pat. No. 9,828,429, Igawa et al., issued Nov. 28, 2017.
U.S. Appl. No. 15/725,692, Igawa et al., filed Oct. 5, 2017.
U.S. Pat. No. 9,688,762, Igawa et al., issued Jun. 27, 2017.
U.S. Appl. No. 15/614,842, Igawa et al., filed Jun. 6, 2017.
U.S. Appl. No. 13/257,145, Igawa et al., filed Nov. 22, 2011 (abandoned).
U.S. Pat. No. 10,253,091, Igawa et al., issued Apr. 9, 2019.
U.S. Appl. No. 16/298,032, Igawa et al., filed Mar. 11, 2019.
U.S. Pat. No. 9,228,017, Igawa et al., issued Jan. 5, 2016.
U.S. Pat. No. 10,066,018, Igawa et al., issued Sep. 4, 2018.
U.S. Pat. No. 10,150,808, Kuramochi et al., issued Dec. 11, 2018.
U.S. Pat. No. 10,435,458, Kuramochi et al., issued Oct. 8, 2019.
U.S. Pat. No. 9,670,269, Igawa et al., issued Jun. 6, 2017.
U.S. Appl. No. 15/490,936, Igawa et al., filed Apr. 19, 2017.
U.S. Appl. No. 13/518,861, Igawa et al., filed Oct. 4, 2012 (abandoned).
U.S. Appl. No. 15/617,008, Igawa et al., filed Jun. 8, 2017 (abandoned).
U.S. Appl. No. 15/875,847, Igawa et al., filed Jan. 19, 2018 (abandoned).
U.S. Appl. No. 16/155,673, Igawa et al., filed Oct. 9, 2018 (abandoned).
U.S. Appl. No. 16/448,088, Igawa et al., filed Jun. 21, 2019.
U.S. Appl. No. 14/351,654, Kuramochi et al., filed Apr. 13, 2014.
U.S. Appl. No. 16/692,676, Kuramochi et al., filed Nov. 22, 2019.
U.S. Appl. No. 16/061,454, Tanaka et al., filed Jun. 12, 2018.
U.S. Appl. No. 16/093,495, Saeki et al., filed Oct. 12, 2018.
U.S. Appl. No. 16/496,089, Shima et al., filed Sep. 20, 2019.
U.S. Pat. No. 9,975,966, Nezu et al., issued May 22, 2018.
U.S. Appl. No. 15/963,221, Nezu et al., filed Apr. 26, 2018.
U.S. Appl. No. 16/083,975, Kinoshita et al., filed Sep. 11, 2018.
Do et al., "A rapid method for determining dynamic binding capacity of resins for the purification of proteins," Protein Expr Purif, Aug. 2008, 60(2):147-50. doi: 10.1016/j.pep.2008.04.009. Epub May 3, 2008.
Labrijn et al., "Therapeutic IgG4 antibodies engage in Fab-arm exchange with endogenous human IgG4 in vivo," Nat Biotechnol, Aug. 2009, 27(8):767-771.
Lund et al., "Multiple interactions of IgG with its core oligosaccharide can modulate recognition by complement and human Fc gamma receptor I and influence the synthesis of its oligosaccharide chains," The Journal of Immunology, Dec. 1, 1996, 157:4963-4969.
Pabst et al., "Engineering of novel Staphylococcal Protein A ligands to enable milder elution pH and high dynamic binding capacity," J Chromatogr A, Oct. 3, 2014, 1362:180-5. doi: 10.1016/j.chroma.2014.08.046. Epub Aug. 19, 2014.
Pabst et al., "Evaluation of recent Protein A stationary phase innovations for capture of biotherapeutics," J Chromatogr A, Jun. 15, 2018, 1554:45-60. doi: 10.1016/j.chroma.2018.03.060. Epub Apr. 7, 2018.
Wu et al., "Humanization of a Murine Monoclonal Antibody by Simultaneous Optimization of Framework and CDR Residues," J Mol Biol, Nov. 19, 1999, 294(1):151-162.
U.S. Appl. No. 11/910,128, Igawa et al., filed Oct. 7, 2008.
U.S. Appl. No. 16/815,089, Igawa et al., filed Mar. 11, 2020.

(56) References Cited

OTHER PUBLICATIONS

U.S. Appl. No. 16/825,513, Hattori et al., filed Mar. 20, 2020.
U.S. Appl. No. 17/076,938, Igawa et al., filed Oct. 22, 2020.
U.S. Appl. No. 61/467,727, Blein et al., filed Mar. 25, 2011.
Adlersberg et al., "The Immunoglobin Hinge (Interdomain) Region," Ric Clin Lab, Jul.-Sep. 1976, 6(3):191-205.
Alprolix ® Intravenous, 2019, 16 pages (with English translation).
Annex 1—Analysis of the Examples of EP 2 787 078, 3 pages (document submitted in opposition of EP 2 787 078 on Feb. 28, 2020).
Arguments filed on Oct. 12, 2016 in U.S. Appl. No. 14/351,654, 10 pages (document submitted in opposition of EP 2 787 078 on Feb. 25, 2020).
Astermark et al., "A randomized comparison of bypassing agents in hemophilia complicated by an inhibitor: the FEIBA NovoSeven Comparative (FENOC) Study," Blood, Jan. 15, 2007, 109(2):546-551. Epub Sep. 21, 2006.
Claims filed on Sep. 5, 2018 in U.S. Appl. No. 14/351,654, 7 pages (document submitted in opposition of EP 2 787 078 on Feb. 28, 2020).
Collins et al., "Implications of coagulation factor VIII and IX pharmaco-kinetics in the prophylactic treatment of haemophilia," Haemophilia, Jan. 2011, 17(1):2-10, doi: 10.1111/j.1365-2516.2010. 02370.x. Epub Aug. 22, 2010.
Coppola et al., "Acquired Inhibitors of Coagulation Factors: Part I—Acquired Hemophilia A," Semin Thromb Hemost, Jul. 2012, 38(5):433-446. doi: 10.1055/s-0032-1315757. Epub Jun. 27, 2012.
Dall'Acqua et al., "Contribution of Domain Interface Residues to the Stability of Antibody CH3 Domain Homodimers," Biochemistry, Jun. 30, 1998, 37(26):9266-9273. doi: 10.1021/bi980270i. PMID: 9649307.
Declaration of Christian Beil, signed Jun. 18, 2020, submitted by the opponent in Opposition of EP 3 050 963, 6 pages.
Filmus et al., "Glypicans," Genome Biol, May 22, 2018, 9(5):224, 6 pages. doi:10.1186/gb-2008-9-5-224.
Franchini et al., "Acquired haemophilia A: A 2013 update," Thromb Haemost, Dec. 2013, 110(6)11114-1120, doi:10.1160/TH13-05-0363. Epub Sep. 5, 2013.
Guidelines for the Management of Hemophilia, 2005, World Federation of Hemophilia, 52 pages.
Hagiwara et al., "Effect of Emicizumad in improving coagulation ability in the presence of minor amount of Factor IX," Japanese Journal of Thrombosis and Haemostasis, 2017, 28(2):190 0-012 (with English translation).
Helguera et al., "Antibody-Cytokine Fusion Proteins for the Therapy of Cancer," Methods Mol Med, 2005, 109:347-374. doi: 10.1385/1-59259-862-5:347. PMID: 15585931.
"Hemostatic Therapy Guideline for Inhibitor-negative Hemophilia Patients," Japanese Journal of Thrombosis and Hemostasis, 2013, 24(6):619-639 (with English translation).
"Hemostatic Therapy Guideline for Inhibitor-positive Hemophilia Patients," Japanese Journal of Thrombosis and Hemostasis, 2013, 24(6):640-658 (with English translation).
Hugo et al., "Functional aspects of co-variant surface charges in an antibody fragment," Protein Sci, Nov. 2002, 11(11):2697-2705. doi: 10.1110/ps.0209302. PMID: 12381851; PMCID: PMC2373727.
Kruse-Jarres, "Inhibitors: our greatest challenge. Can we minimize the incidence?," Haemophilia, Jan. 2013, 19 Suppl 1:2-7. doi: 10.111/hae. 12049.
Lillicrap, "von Willebrand disease: advances in pathogenetic understanding, diagnosis, and therapy," Blood, Nov. 28, 2013, 122(23):3735-3740. doi: 10.1182/blood-2013-06-498303. Epub Sep. 24, 2013.
Minami et al., "Bispecific Antibody ACE910 Improves Coagulation Function in Plasma of Patients with Factor XI-Deficiency," Japanese Journal of Thrombosis and Hemostasis, 2015, 26(2):188 0-024 (with English translation).
Miyata, "Factor IX Abnormality—Molecular defects of Factor IX," Japanese Journal of Thrombosis and Hemostasis, 1991, 2(1):1-11 (with English translation).
Muto et al., "Anti-factor IXa/S bispecific antibody (ACE910): hemostatic potency against ongoing bleeds in a hemophilia A model and the possibility of routine supplementations," J Thromb Haemost. Feb. 2014, 12(2):206-213. doi: 10. 1111/jth.12474.
Muto et al., "Anti-factor IXa/X bispecific antibody ACE910 prevents joint bleeds in a long-term primate model of acquired hemophilia A," Blood, Nov. 13, 2014, 124(20):3165-3171. doi: 10.1182/blood-2014-07-585737. Epub Oct. 1, 2014.
Nishimura et al., "Factor IX Furuoka—Substitution of $ASN^{92}$ by His in the second epidermal growth factor-like domain results in defective interaction with factors VIIIa/X," Journal of Biological Chemistry, Nov. 15, 1993, 268(32):24041-24046.
Nogami, "Bispecific Antibody that Substitutes for Factor VIII in the Treatment of Childhood Hemophilia A," The Japanese Journal of Pediatric Hematology/Oncology, 2016, 53(2):69-74 (with English translation).
Otomo et al., "Structure of the heterodimeric complex between CAD domains of CAD and ICAD," Nat Struct Biol, Aug. 2000, 7(8):658-662. doi: 10.1038/77957. PMID: 10932250.
Raghavan et al., "Fc Receptors and Their Interactions with Immunoglobins," Annu Rev Cell Dev Biol, Nov. 1996, 12:181-220.
Reference table: IMGT exon, EU and Kabat numbering of residues within the human IgG1 sequence: retrieved from http://www.imgt.org/IMGTScientificChart/Numbering/Hu_IGHGnber.html on Jun. 1, 2020, 4 pages (cited by the opponents in the Opposition procedure in the corresponding European Patent No. 3 050 963, which was notified to the patentee on Jul. 3, 2020).
Shima et al., "Factor VIII-Mimetic Function of Humanized Bispecific Antibody in Hemophilia A," The New England Journal of Medicine, May 26, 2016, 374(21):2044-2053. doi: 10.1052/NEJMoa11769.
Shima, "The Forefront and Prospects of Hemophilia Treatment," J Jpn Pediatr Soc, Mar. 1, 2017, 121(3):543-552 (with English translation).
Singer et al., Chapter 1.3 "Structure of Proteins," Genes & Genomes, 1998, pp. 63-64 (in Russian, which what are believed to be corresponding pages from an English version of Genes & Genomes, pp. 67-70).
Tarantineo et al., "Safety of human plasma-derived clotting factor products and their role in haemostasis in patients with haemophilia: meeting report," Haemophilia, Sep. 2007, 13(5):663-669.
Uchida et al., "A first-in-human phase 1 study of ACE910, a novel factori VIII-mimetic bispecific antibody, in healthy subjects," Blood, Mar. 2016, 127(13):1633-1641. doi:10.1182/blood-2015-06-650226. Epub Dec. 1, 2015.
Wenig et al., "Structure of the streptococcal endopeptidase IdeS, a cytesine proteinase with strict specificity for IgG," Proc Natl Acad Sci USA, Dec. 14, 2004, 101:17371-17376.
USPTO Non-Final Office Action in U.S. Appl. No. 11/910,128, dated Nov. 28, 2016, 17 pages.
USPTO Final Office Action un U.S. Appl. No. 14/351,654, dated Apr. 14, 2016, 12 pages.

* cited by examiner

[Figure 1]
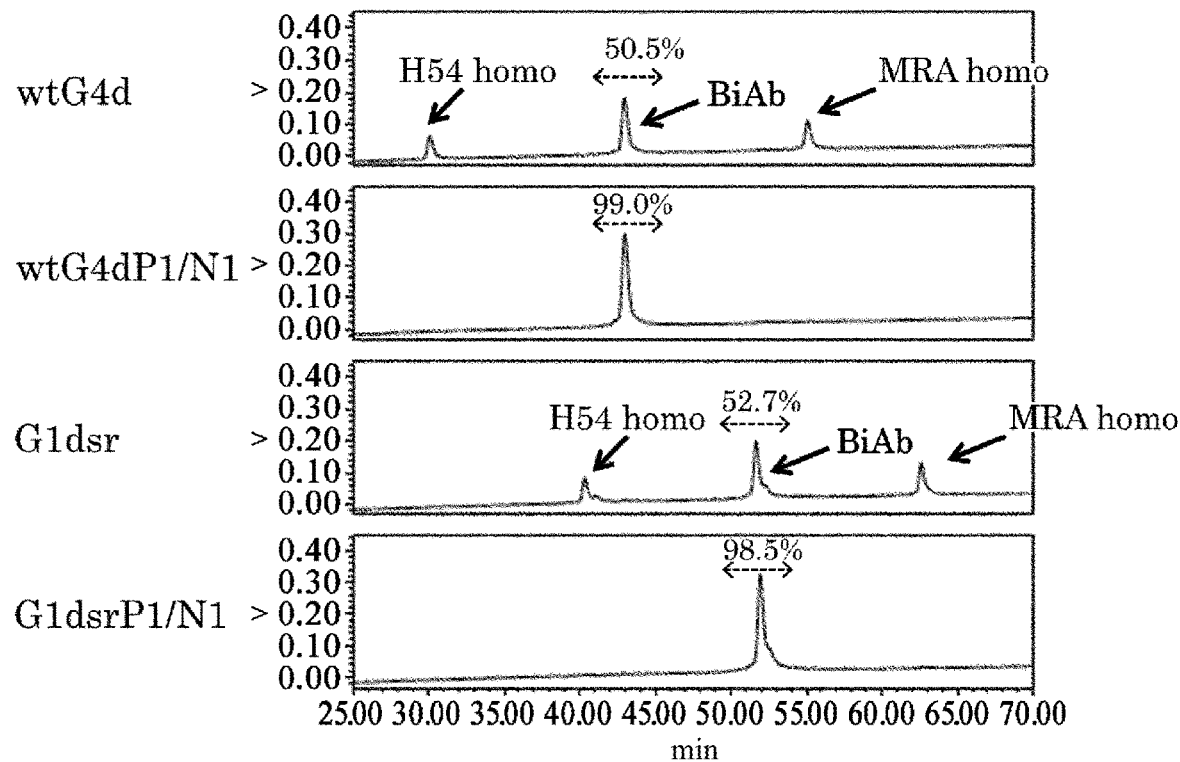
[Figure 2]
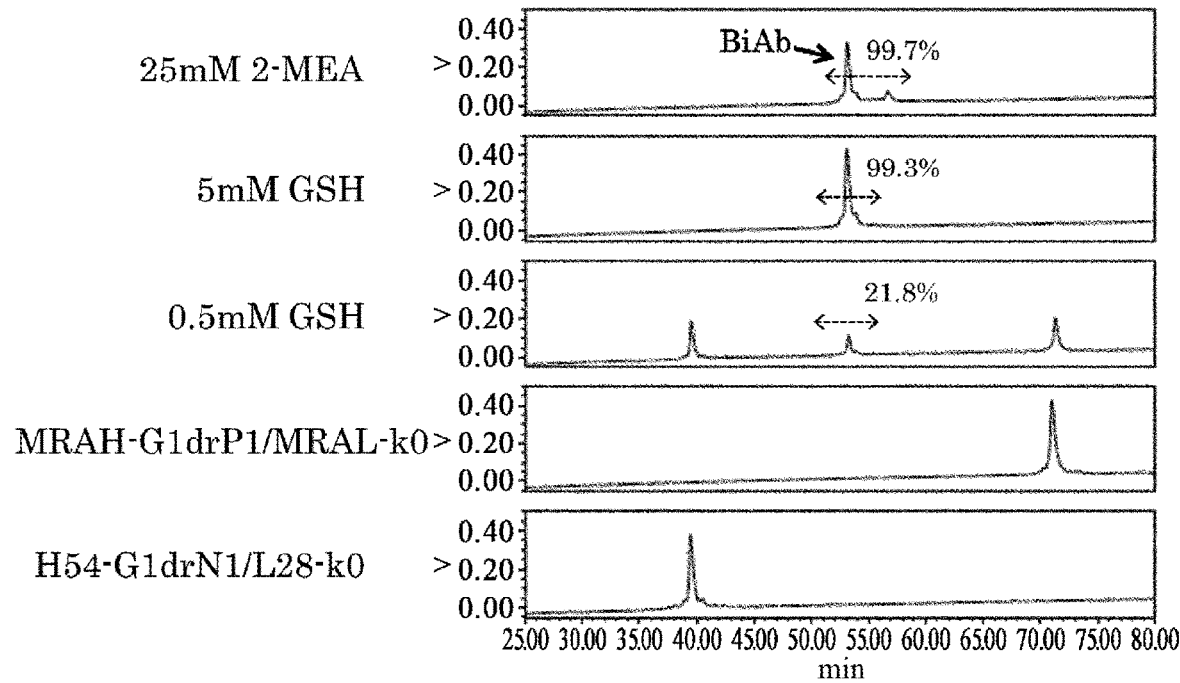

[Figure 3]
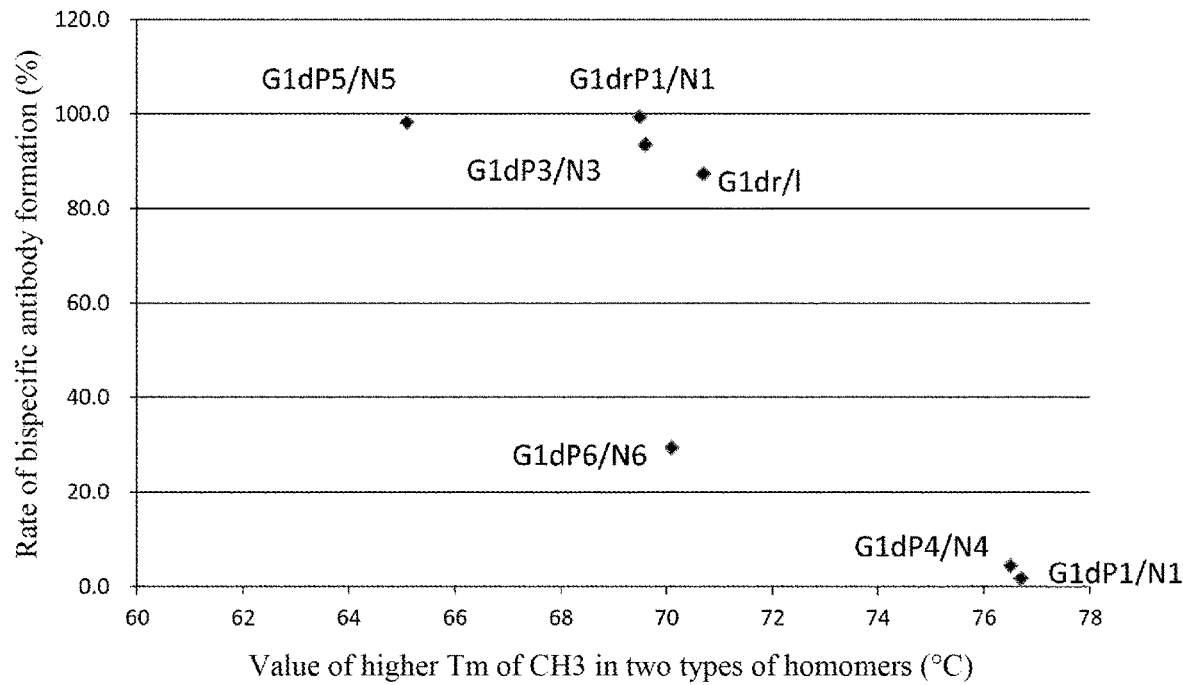
[Figure 4]
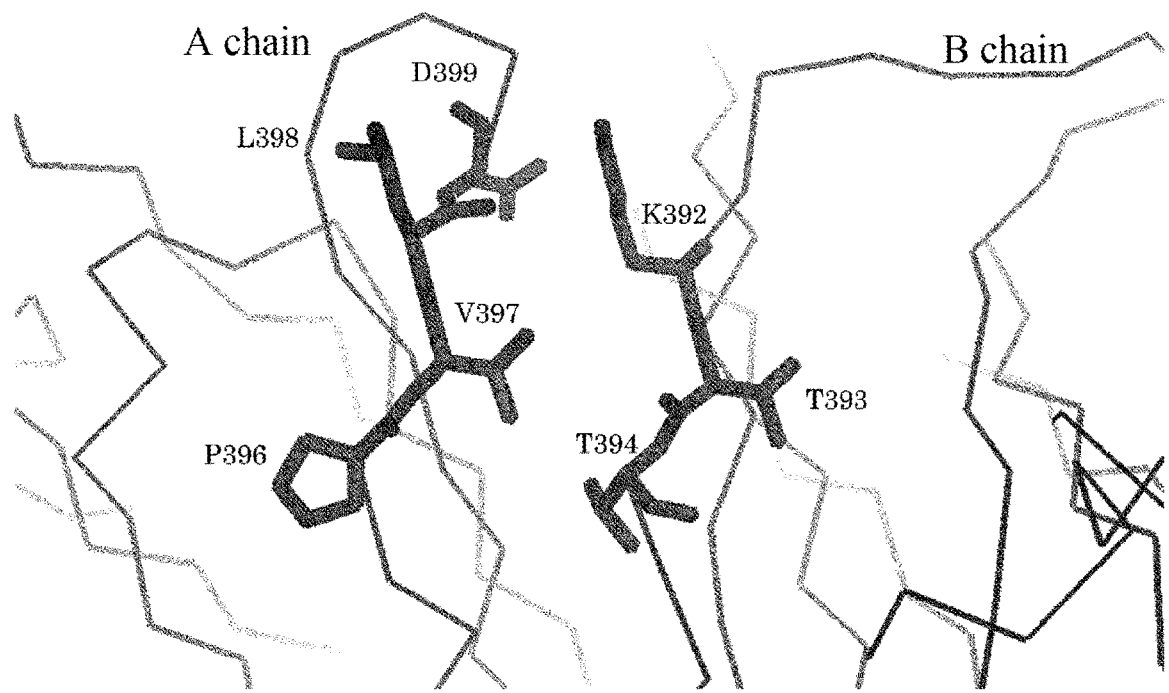

[Figure 5]
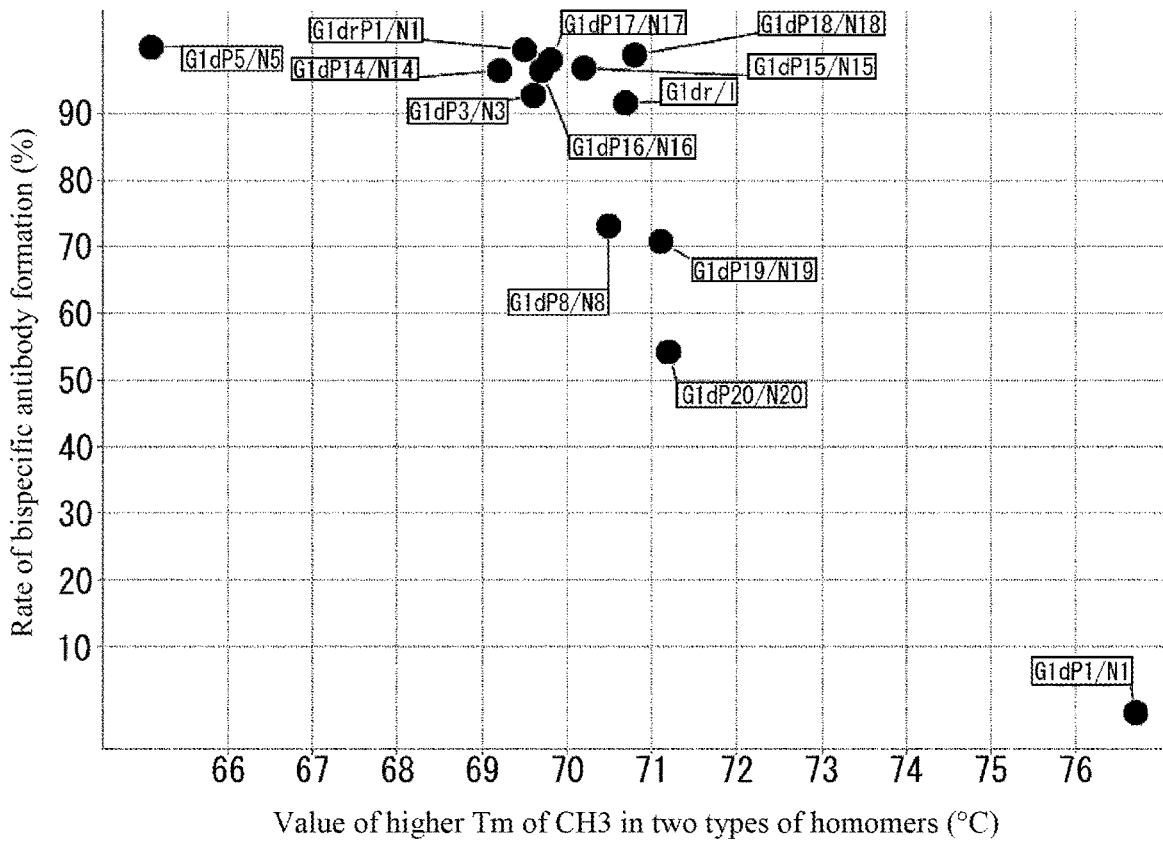
[Figure 6]
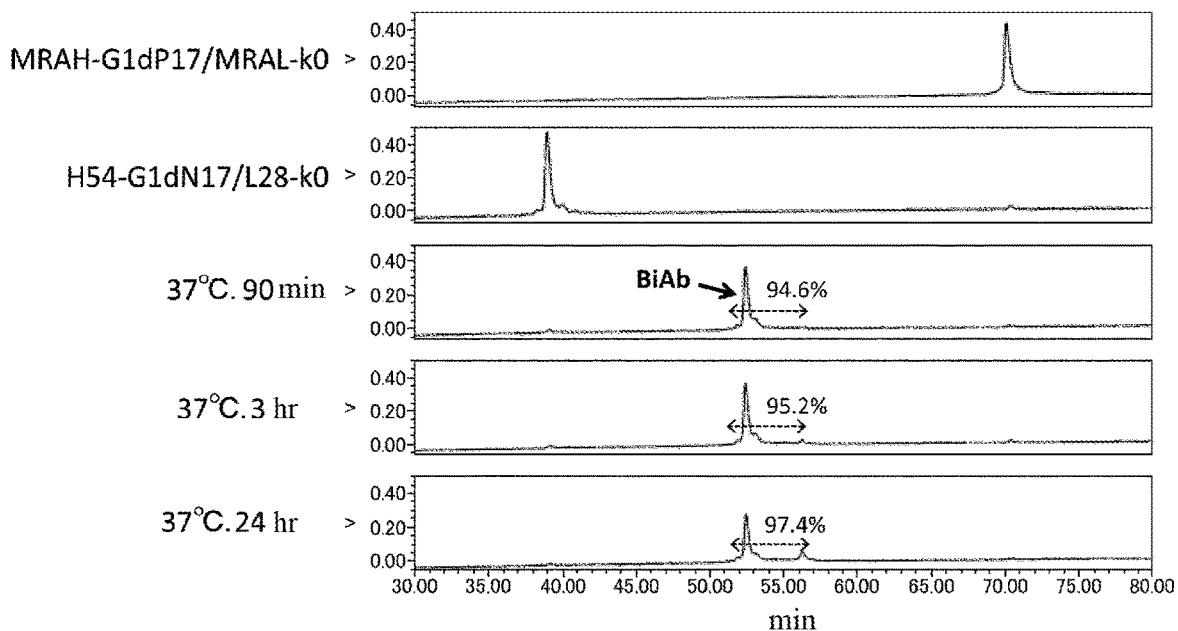

[Figure 7]
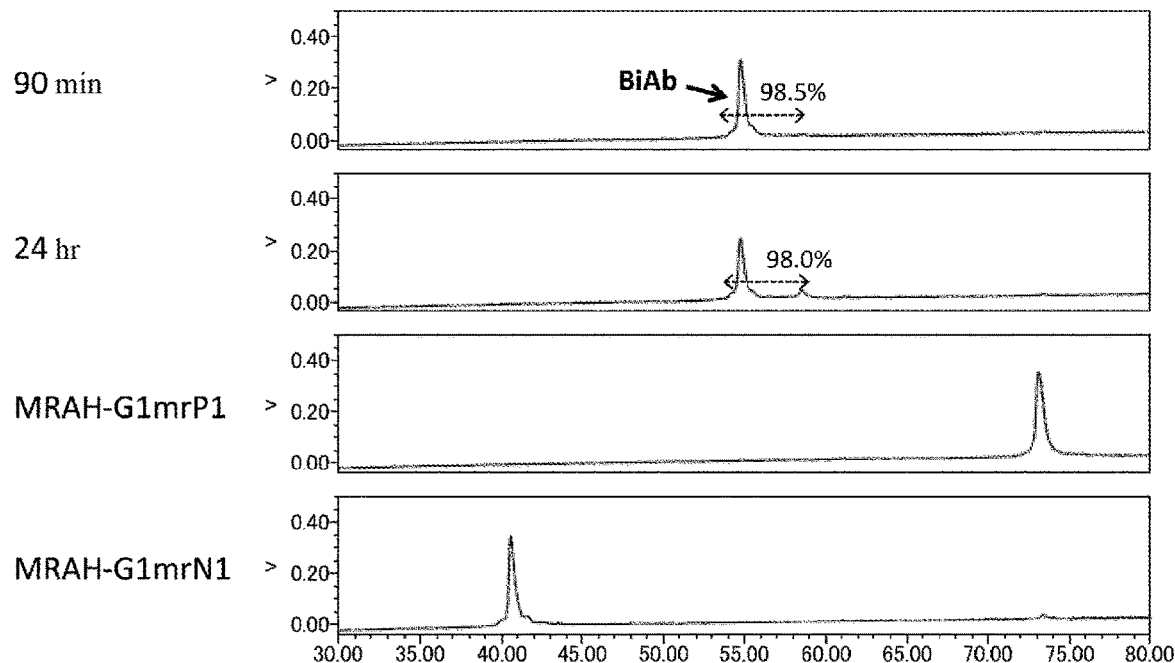
[Figure 8]
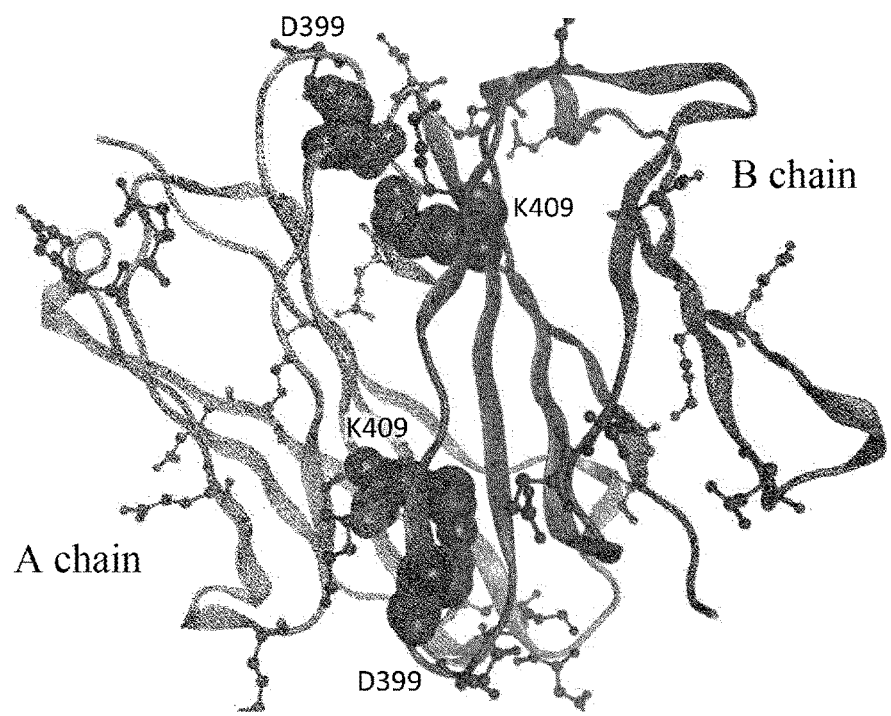

[Figure 9]
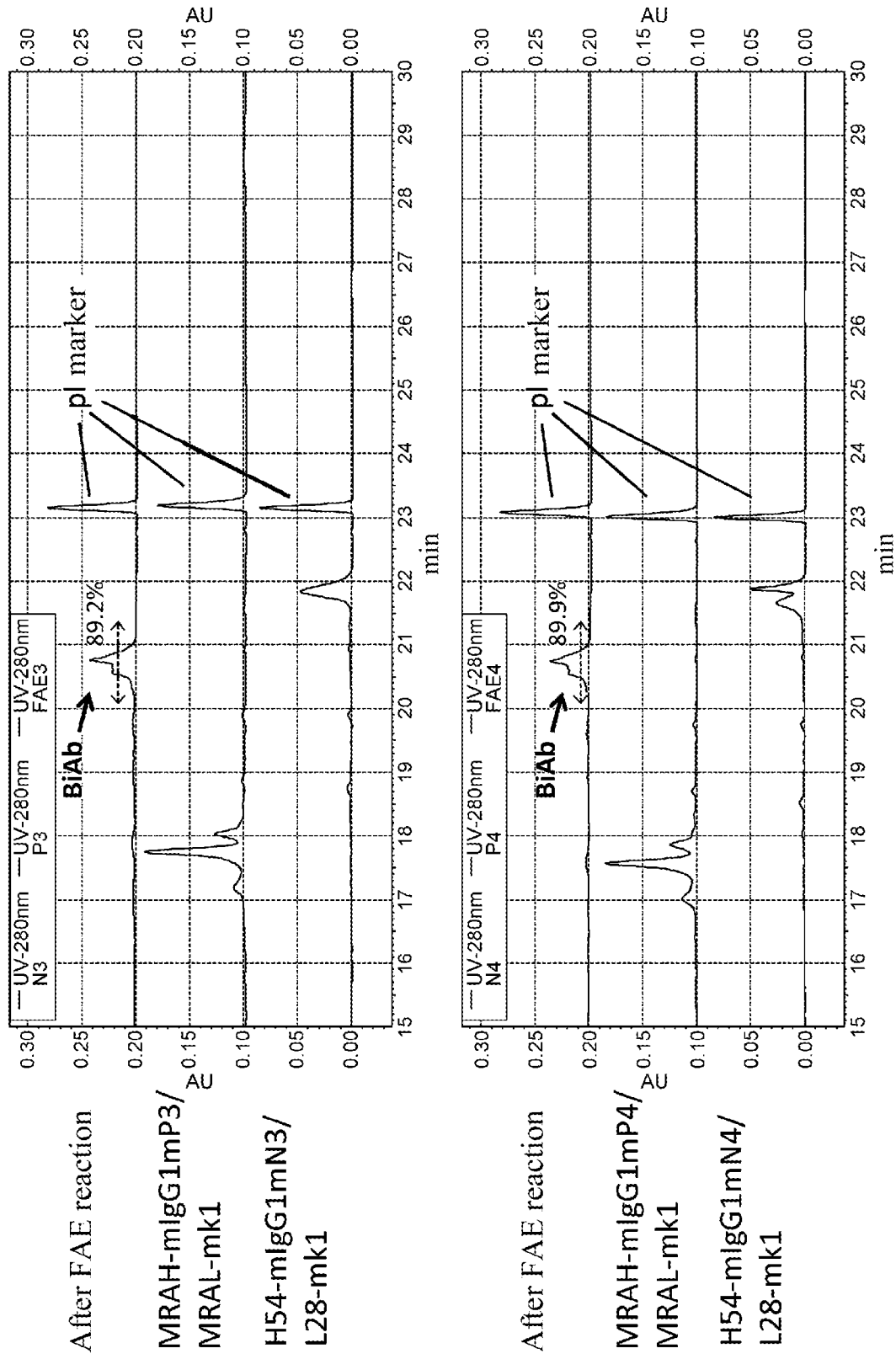

[Figure 10]
(10-1)
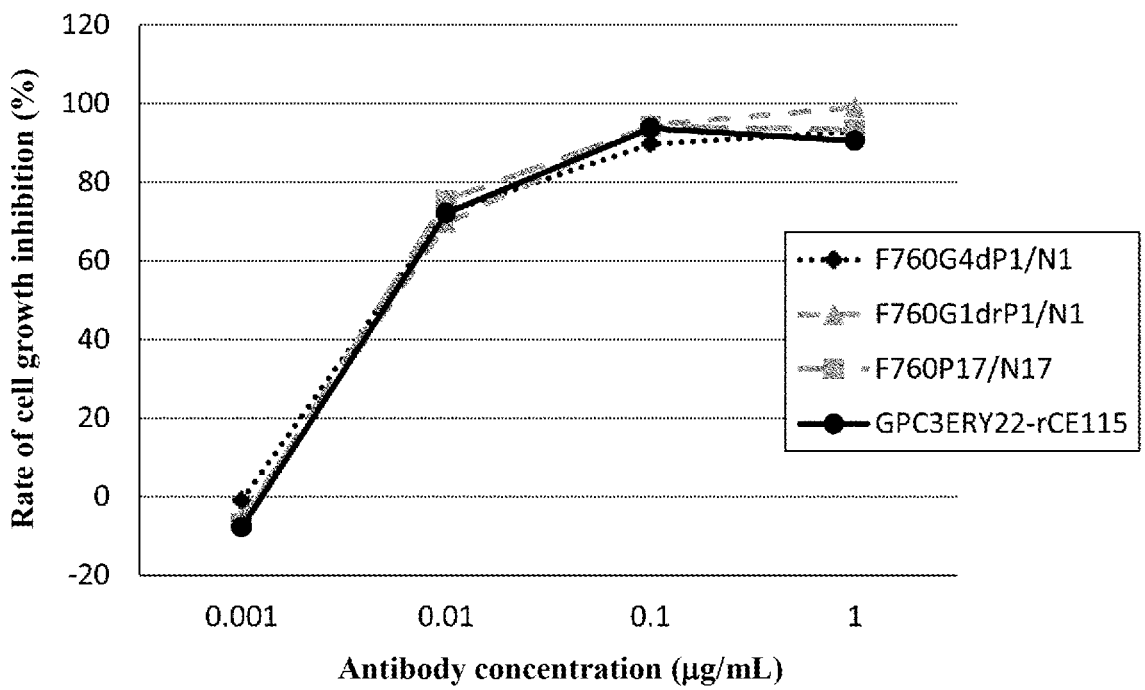
(10-2)
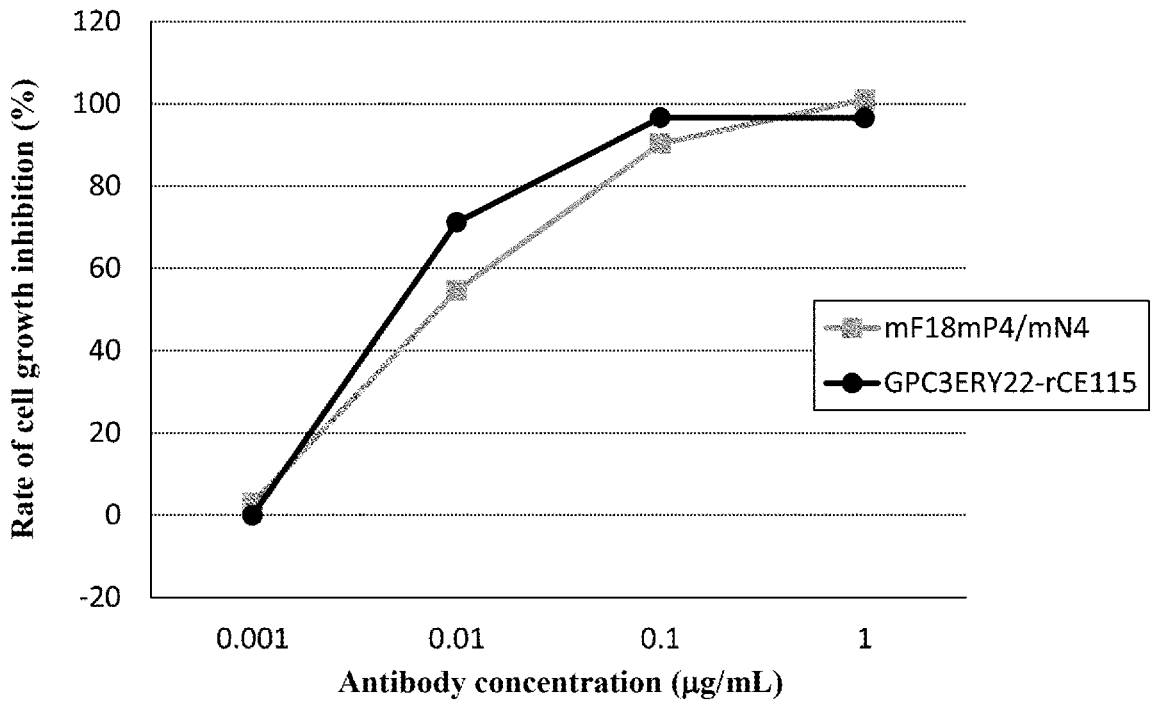

[Figure 11]
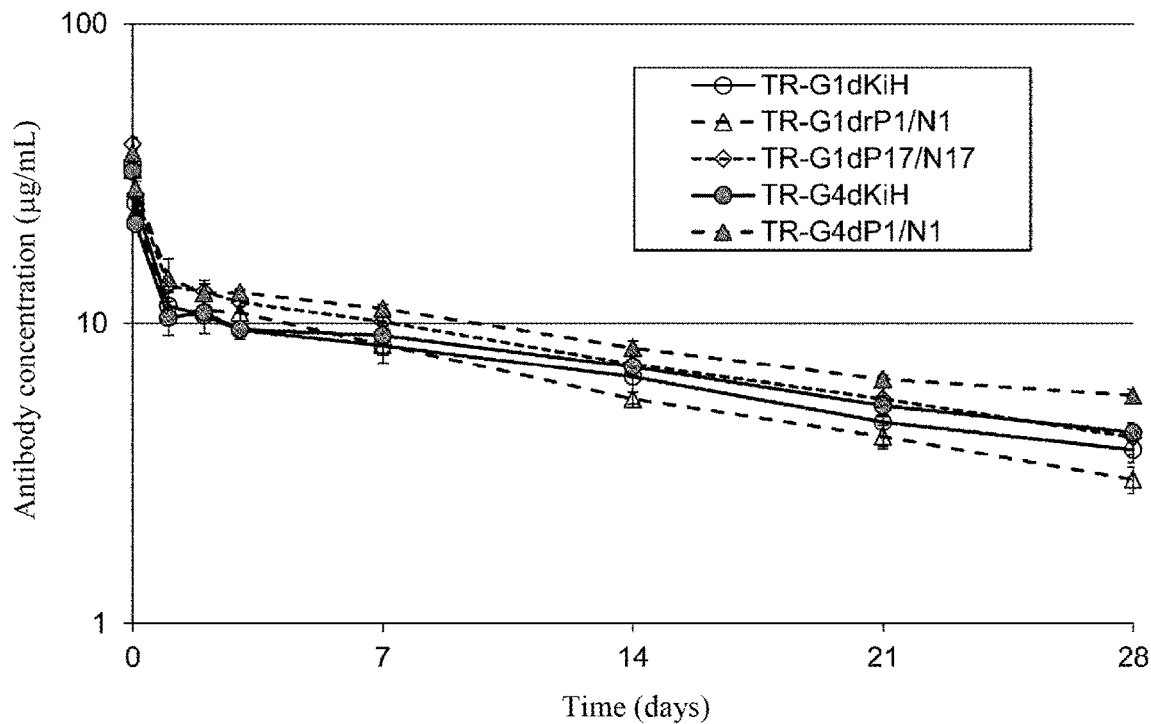
[Figure 12]
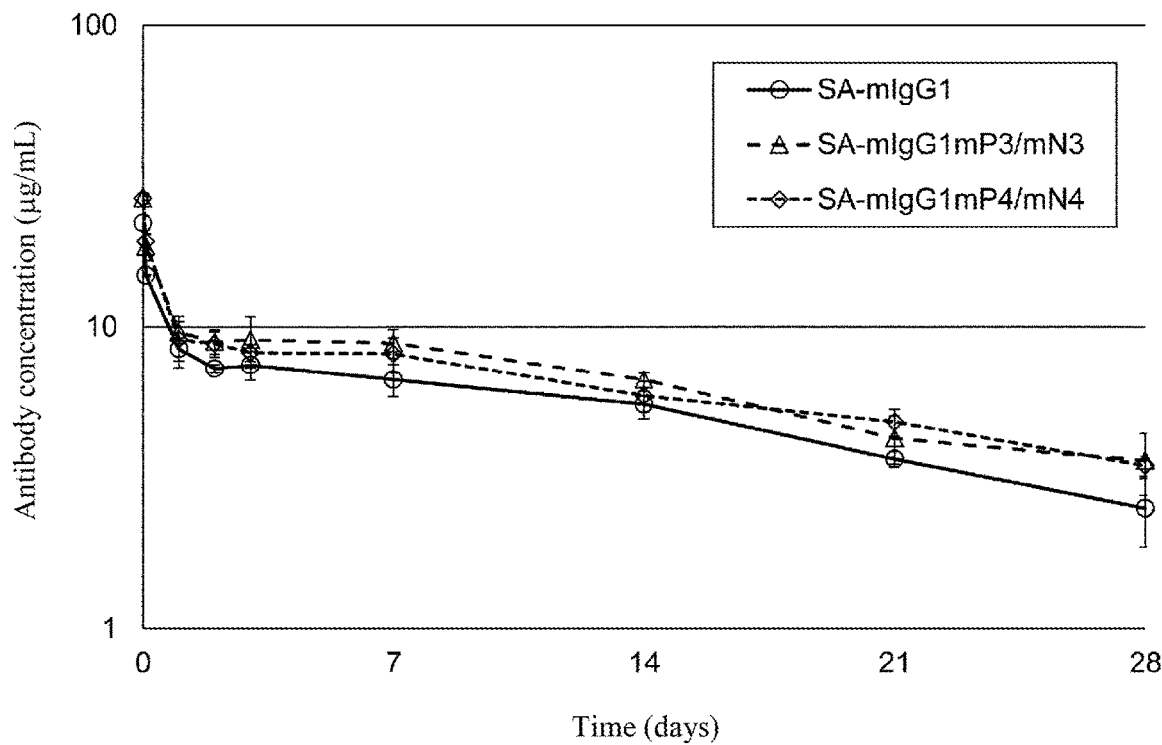

SEQUENCE LISTING

```
<160> NUMBER OF SEQ ID NOS: 81

<210> SEQ ID NO 1
<211> LENGTH: 119
<212> TYPE: PRT
<213> ORGANISM: Artificial sequence
<220> FEATURE:
<223> OTHER INFORMATION: An artificially synthesized sequence

<400> SEQUENCE: 1

Gln Val Gln Leu Gln Glu Ser Gly Pro Gly Leu Val Arg Pro Ser Gln
1               5                   10                  15
```

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser
        115

<210> SEQ ID NO 2
<211> LENGTH: 119
<212> TYPE: PRT
<213> ORGANISM: Artificial sequence
<220> FEATURE:
<223> OTHER INFORMATION: An artificially synthesized sequence

<400> SEQUENCE: 2

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser
        115

<210> SEQ ID NO 3
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 3

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 4
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 4

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
            85                  90                  95

Ala Arg Ser Leu Ala Arg Thr Thr Ala Met Asp Tyr Trp Gly Glu Gly
        100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Asp Glu Leu Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415
```

```
Ser Arg Trp Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 5
<211> LENGTH: 444
<212> TYPE: PRT
<213> ORGANISM: Artificial sequence
<220> FEATURE:
<223> OTHER INFORMATION: An artificially synthesized sequence

<400> SEQUENCE: 5

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335
```

```
Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu
            435                 440

<210> SEQ ID NO 6
<211> LENGTH: 444
<212> TYPE: PRT
<213> ORGANISM: Artificial sequence
<220> FEATURE:
<223> OTHER INFORMATION: An artificially synthesized sequence

<400> SEQUENCE: 6

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
                20                  25                  30

Gln Ala Trp Ser Trp Val Arg Gln Pro Pro Gly Glu Gly Leu Glu Trp
            35                  40                  45

Ile Gly Tyr Ile Ser Tyr Ser Gly Ile Thr Asn Tyr Asn Pro Ser Leu
        50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255
```

```
Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu
        435                 440

<210> SEQ ID NO 7
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 7

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Ser Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 8
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95
```

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Ser Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 9
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 9

Gln Val Gln Leu Gln Glu Ser Gly Pro Gly Leu Val Arg Pro Ser Gln
1               5                   10                  15

```
Thr Leu Ser Leu Thr Cys Thr Val Ser Gly Tyr Ser Ile Thr Ser Asp
             20                  25                  30

His Ala Trp Ser Trp Val Arg Gln Pro Pro Gly Arg Gly Leu Glu Trp
         35                  40                  45

Ile Gly Tyr Ile Ser Tyr Ser Gly Ile Thr Thr Tyr Asn Pro Ser Leu
     50                  55                  60

Lys Ser Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Ser Leu Ala Arg Thr Thr Ala Met Asp Tyr Trp Gly Gln Gly
             100                 105                 110

Ser Leu Val Thr Val Ser Ser Ala Ser Thr Lys Gly Pro Ser Val Phe
         115                 120                 125

Pro Leu Ala Pro Ser Ser Lys Ser Thr Ser Gly Gly Thr Ala Ala Leu
     130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
         195                 200                 205

Ser Asn Thr Lys Val Asp Lys Lys Val Glu Pro Lys Ser Cys Asp Lys
 210                 215                 220

Thr His Thr Cys Pro Ser Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                 245                 250                 255

Arg Thr Pro Glu Val Thr Cys Val Val Val Asp Val Ser His Glu Asp
             260                 265                 270

Pro Glu Val Lys Phe Asn Trp Tyr Val Asp Gly Val Glu Val His Asn
         275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                 325                 330                 335

Thr Ile Ser Lys Ala Lys Gly Gln Pro Arg Glu Pro Gln Val Tyr Thr
             340                 345                 350

Leu Pro Pro Ser Arg Lys Glu Leu Thr Lys Asn Gln Val Ser Leu Thr
         355                 360                 365

Cys Leu Val Lys Gly Phe Tyr Pro Ser Asp Ile Ala Val Glu Trp Glu
     370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                 405                 410                 415

Ser Arg Trp Gln Gln Gly Asn Val Phe Ser Cys Ser Val Met His Glu
             420                 425                 430

Ala Leu His Asn His Tyr Thr Gln Lys Ser Leu Ser Leu Ser Pro
```

<210> SEQ ID NO 10
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 10

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Ser Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
```

```
                    355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
            435                 440                 445

<210> SEQ ID NO 11
<211> LENGTH: 444
<212> TYPE: PRT
<213> ORGANISM: Artificial sequence
<220> FEATURE:
<223> OTHER INFORMATION: An artificially synthesized sequence

<400> SEQUENCE: 11

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
```

```
                    275                 280                 285
Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Lys Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu
        435                 440
```

<210> SEQ ID NO 12
<211> LENGTH: 444
<212> TYPE: PRT
<213> ORGANISM: Artificial sequence
<220> FEATURE:
<223> OTHER INFORMATION: An artificially synthesized sequence

<400> SEQUENCE: 12

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
```

```
                195                 200                 205
Ser Asn Thr Lys Val Asp Lys Arg Val Glu Ser Lys Tyr Gly Pro Pro
210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
                275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Glu Ser Leu Ser Leu Ser Leu
                435                 440

<210> SEQ ID NO 13
<211> LENGTH: 214
<212> TYPE: PRT
<213> ORGANISM: Artificial sequence
<220> FEATURE:
<223> OTHER INFORMATION: An artificially synthesized sequence

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
                115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
            195                 200                 205
Phe Asn Arg Gly Glu Cys
    210

<210> SEQ ID NO 14
<211> LENGTH: 214
<212> TYPE: PRT
<213> ORGANISM: Artificial sequence
<220> FEATURE:
<223> OTHER INFORMATION: An artificially synthesized sequence

<400> SEQUENCE: 14

Asp Ile Gln Met Thr Gln Ser Pro Ser Ser Leu Ser Ala Ser Val Gly
1               5                   10                  15
Asp Ser Val Thr Ile Thr Cys Gln Ala Ser Gln Asp Ile Ser Ser Tyr
            20                  25                  30
Leu Asn Trp Tyr Gln Gln Lys Pro Gly Lys Ala Pro Glu Leu Leu Ile
        35                  40                  45
Tyr Tyr Gly Ser Glu Leu His Ser Gly Val Pro Ser Arg Phe Ser Gly
    50                  55                  60
Ser Gly Ser Gly Thr Asp Phe Thr Phe Thr Ile Ser Ser Leu Glu Ala
65                  70                  75                  80
Glu Asp Ala Ala Thr Tyr Tyr Cys Gln Gln Gly Asn Ser Leu Pro Tyr
                85                  90                  95
Thr Phe Gly Gln Gly Thr Lys Val Glu Ile Glu Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
            195                 200                 205
Phe Asn Arg Gly Glu Cys
    210

<210> SEQ ID NO 15
<211> LENGTH: 447
<212> TYPE: PRT
<213> ORGANISM: Artificial sequence
<220> FEATURE:
<223> OTHER INFORMATION: An artificially synthesized sequence
```

<400> SEQUENCE: 15

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
```

```
                    405                 410                 415
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 16
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
```

```
                   325                 330                 335
Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Glu Ser Leu Ser Leu Ser Pro
                435                 440                 445

<210> SEQ ID NO 17
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 17

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
                20                  25                  30

His Ala Trp Ser Trp Val Arg Gln Pro Pro Gly Arg Gly Leu Glu Trp
                35                  40                  45

Ile Gly Tyr Ile Ser Tyr Ser Gly Ile Thr Thr Tyr Asn Pro Ser Leu
            50                  55                  60

Lys Ser Arg Val Thr Met Leu Arg Asp Thr Ser Lys Asn Gln Phe Ser
65              70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
                100                 105                 110

Ser Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
                210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
```

```
                    245                 250                 255
Arg Thr Pro Glu Val Thr Cys Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Lys Glu Leu Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
                435                 440                 445

<210> SEQ ID NO 18
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 18

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
        50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

```
                    165                 170                 175
Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Lys Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 19
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 19

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
                20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
        50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
```

```
                    85                  90                  95
Ala Arg Ser Leu Ala Arg Thr Thr Ala Met Asp Tyr Trp Gly Gln Gly
                100                 105                 110

Ser Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Lys Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 20
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 20

Gln Val Gln Leu Gln Glu Ser Gly Pro Gly Leu Val Arg Pro Ser Gln
```

```
1               5                    10                   15
Thr Leu Ser Leu Thr Cys Thr Val Ser Gly Tyr Ser Ile Thr Ser Asp
             20                   25                   30

His Ala Trp Ser Trp Val Arg Gln Pro Pro Gly Arg Gly Leu Glu Trp
             35                   40                   45

Ile Gly Tyr Ile Ser Tyr Ser Gly Ile Thr Thr Tyr Asn Pro Ser Leu
             50                   55                   60

Lys Ser Arg Val Thr Met Leu Arg Asp Thr Ser Lys Asn Gln Phe Ser
 65                   70                   75                   80

Leu Arg Leu Ser Ser Val Thr Ala Ala Asp Thr Ala Val Tyr Tyr Cys
             85                   90                   95

Ala Arg Ser Leu Ala Arg Thr Ala Met Asp Tyr Trp Gly Gln Gly
             100                  105                  110

Ser Leu Val Thr Val Ser Ser Ala Ser Thr Lys Gly Pro Ser Val Phe
             115                  120                  125

Pro Leu Ala Pro Ser Ser Lys Ser Thr Ser Gly Gly Thr Ala Ala Leu
             130                  135                  140

Gly Cys Leu Val Lys Asp Tyr Phe Pro Glu Pro Val Thr Val Ser Trp
145                  150                  155                  160

Asn Ser Gly Ala Leu Thr Ser Gly Val His Thr Phe Pro Ala Val Leu
             165                  170                  175

Gln Ser Ser Gly Leu Tyr Ser Leu Ser Ser Val Val Thr Val Pro Ser
             180                  185                  190

Ser Ser Leu Gly Thr Gln Thr Tyr Ile Cys Asn Val Asn His Lys Pro
             195                  200                  205

Ser Asn Thr Lys Val Asp Lys Lys Val Glu Pro Lys Ser Cys Asp Lys
             210                  215                  220

Thr His Thr Cys Pro Pro Cys Pro Ala Pro Glu Leu Leu Gly Gly Pro
225                  230                  235                  240

Ser Val Phe Leu Phe Pro Pro Lys Pro Lys Asp Thr Leu Met Ile Ser
             245                  250                  255

Arg Thr Pro Glu Val Thr Cys Val Val Val Asp Val Ser His Glu Asp
             260                  265                  270

Pro Glu Val Lys Phe Asn Trp Tyr Val Asp Gly Val Glu Val His Asn
             275                  280                  285

Ala Lys Thr Lys Pro Arg Glu Glu Gln Tyr Asn Ser Thr Tyr Arg Val
             290                  295                  300

Val Ser Val Leu Thr Val Leu His Gln Asp Trp Leu Asn Gly Lys Glu
305                  310                  315                  320

Tyr Lys Cys Lys Val Ser Asn Lys Ala Leu Pro Ala Pro Ile Glu Lys
             325                  330                  335

Thr Ile Ser Lys Ala Lys Gly Gln Pro Arg Glu Pro Gln Val Tyr Thr
             340                  345                  350

Leu Pro Pro Ser Arg Lys Glu Leu Thr Lys Asn Gln Val Ser Leu Thr
             355                  360                  365

Cys Leu Val Lys Gly Phe Tyr Pro Ser Asp Ile Ala Val Glu Trp Glu
             370                  375                  380

Ser Asn Gly Gln Pro Glu Asn Asn Tyr Lys Thr Thr Pro Pro Val Leu
385                  390                  395                  400

Lys Ser Asp Gly Ser Phe Phe Leu Tyr Ser Lys Leu Thr Val Asp Lys
             405                  410                  415

Ser Arg Trp Gln Gln Gly Asn Val Phe Ser Cys Ser Val Met His Glu
             420                  425                  430
```

```
Ala Leu His Asn His Tyr Thr Gln Lys Ser Leu Ser Leu Ser Pro
            435                 440                 445

<210> SEQ ID NO 21
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 21

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350
```

```
Leu Pro Pro Ser Arg Lys Lys Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
            435                 440                 445

<210> SEQ ID NO 22
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 22

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

-continued

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
            435                 440                 445

<210> SEQ ID NO 23
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 23

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

Ser Ser Leu Gly Thr Gln Thr Tyr Ile Cys Asn Val Asn His Lys Pro
            195                 200                 205

Ser Asn Thr Lys Val Asp Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Asp Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 24
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 24

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
            35                  40                  45

Ile Gly Tyr Ile Ser Tyr Ser Gly Ile Thr Asn Tyr Asn Pro Ser Leu
            50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
            85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Glu Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 25
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 25

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

-continued

```
Gln Ala Trp Ser Trp Val Arg Gln Pro Pro Gly Glu Gly Leu Glu Trp
         35                  40                  45
Ile Gly Tyr Ile Ser Tyr Ser Gly Ile Thr Asn Tyr Asn Pro Ser Leu
 50                  55                  60
Lys Gly Arg Val Thr Ile Ser Arg Asp Thr Ser Lys Asn Gln Phe Ser
 65                  70                  75                  80
Leu Lys Leu Ser Ser Val Thr Ala Ala Asp Thr Ala Ala Tyr Tyr Cys
                 85                  90                  95
Ala Arg Ser Leu Ala Arg Thr Thr Ala Met Asp Tyr Trp Gly Glu Gly
             100                 105                 110
Thr Leu Val Thr Val Ser Ser Ala Ser Thr Lys Gly Pro Ser Val Phe
         115                 120                 125
Pro Leu Ala Pro Ser Ser Lys Ser Thr Ser Gly Gly Thr Ala Ala Leu
     130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Asp Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Glu Ser Leu Ser Leu Ser Pro
        435                 440                 445
```

```
<210> SEQ ID NO 26
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 26

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

-continued

Cys Leu Val Glu Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
            435                 440                 445

<210> SEQ ID NO 27
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 27

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 28
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 28

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Leu Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 29
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 29

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125
```

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Lys Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
            435                 440                 445

<210> SEQ ID NO 30
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 30

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
        50                  55                  60

Lys Ser Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Lys Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 31
<211> LENGTH: 447
<212> TYPE: PRT

-continued

<213> ORGANISM: Artificial sequence
<220> FEATURE:
<223> OTHER INFORMATION: An artificially synthesized sequence

<400> SEQUENCE: 31

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Lys Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Met Leu
```

```
                385                 390                 395                 400
Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 32
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 32

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
```

```
305                 310                 315                 320
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Glu Ser Leu Ser Leu Ser Pro
                435                 440                 445

<210> SEQ ID NO 33
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 33

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
                20                  25                  30

Gln Ala Trp Ser Trp Val Arg Gln Pro Pro Gly Glu Gly Leu Glu Trp
            35                  40                  45

Ile Gly Tyr Ile Ser Tyr Ser Gly Ile Thr Asn Tyr Asn Pro Ser Leu
        50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
```

```
              225                 230                 235                 240
Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Glu Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
            435                 440                 445

<210> SEQ ID NO 34
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 34

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
                20                  25                  30

Gln Ala Trp Ser Trp Val Arg Gln Pro Pro Gly Glu Gly Leu Glu Trp
            35                  40                  45

Ile Gly Tyr Ile Ser Tyr Ser Gly Ile Thr Asn Tyr Asn Pro Ser Leu
        50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
```

```
                145                 150                 155                 160
        Asn Ser Gly Ala Leu Thr Ser Gly Val His Thr Phe Pro Ala Val Leu
                        165                 170                 175
        Gln Ser Ser Gly Leu Tyr Ser Leu Ser Ser Val Val Thr Val Pro Ser
                        180                 185                 190
        Ser Ser Leu Gly Thr Gln Thr Tyr Ile Cys Asn Val Asn His Lys Pro
                        195                 200                 205
        Ser Asn Thr Lys Val Asp Lys Lys Val Glu Pro Lys Ser Cys Asp Lys
                    210                 215                 220
        Thr His Thr Cys Pro Pro Cys Pro Ala Pro Glu Leu Leu Gly Gly Pro
        225                 230                 235                 240
        Ser Val Phe Leu Phe Pro Pro Lys Pro Lys Asp Thr Leu Met Ile Ser
                            245                 250                 255
        Arg Thr Pro Glu Val Thr Cys Val Val Val Asp Val Ser His Glu Asp
                        260                 265                 270
        Pro Glu Val Lys Phe Asn Trp Tyr Val Asp Gly Val Glu Val His Asn
                        275                 280                 285
        Ala Lys Thr Lys Pro Arg Glu Glu Gln Tyr Asn Ser Thr Tyr Arg Val
                    290                 295                 300
        Val Ser Val Leu Thr Val Leu His Gln Asp Trp Leu Asn Gly Lys Glu
        305                 310                 315                 320
        Tyr Lys Cys Lys Val Ser Asn Lys Ala Leu Pro Ala Pro Ile Glu Lys
                            325                 330                 335
        Thr Ile Ser Lys Ala Lys Gly Gln Pro Arg Glu Pro Gln Val Tyr Thr
                        340                 345                 350
        Leu Pro Pro Ser Arg Asp Glu Leu Thr Lys Asn Gln Val Ser Leu Thr
                        355                 360                 365
        Cys Leu Val Glu Gly Phe Tyr Pro Ser Asp Ile Ala Val Glu Trp Glu
                    370                 375                 380
        Ser Asn Gly Gln Pro Glu Asn Asn Tyr Lys Thr Thr Pro Pro Met Leu
        385                 390                 395                 400
        Asp Ser Asp Gly Ser Phe Phe Leu Tyr Ser Lys Leu Thr Val Asp Lys
                            405                 410                 415
        Ser Arg Trp Gln Gln Gly Asn Val Phe Ser Cys Ser Val Met His Glu
                        420                 425                 430
        Ala Leu His Asn His Tyr Thr Gln Glu Ser Leu Ser Leu Ser Pro
                        435                 440                 445

<210> SEQ ID NO 35
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 35

Gln Val Gln Leu Gln Glu Ser Gly Pro Gly Leu Val Arg Pro Ser Gln
        1               5                   10                  15
        Thr Leu Ser Leu Thr Cys Thr Val Ser Gly Tyr Ser Ile Thr Ser Asp
                        20                  25                  30
        His Ala Trp Ser Trp Val Arg Gln Pro Pro Gly Arg Gly Leu Glu Trp
                        35                  40                  45
        Ile Gly Tyr Ile Ser Tyr Ser Gly Ile Thr Thr Tyr Asn Pro Ser Leu
                    50                  55                  60
        Lys Ser Arg Val Thr Met Leu Arg Asp Thr Ser Lys Asn Gln Phe Ser
```

```
                65                  70                  75                  80
Leu Arg Leu Ser Ser Val Thr Ala Ala Asp Thr Ala Val Tyr Tyr Cys
                    85                  90                  95

Ala Arg Ser Leu Ala Arg Thr Thr Ala Met Asp Tyr Trp Gly Gln Gly
                100                 105                 110

Ser Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Lys Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Asp Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
            435                 440                 445

<210> SEQ ID NO 36
<211> LENGTH: 447
<212> TYPE: PRT
<213> ORGANISM: Artificial sequence
<220> FEATURE:
<223> OTHER INFORMATION: An artificially synthesized sequence
```

<400> SEQUENCE: 36

```
Gln Val Gln Leu Gln Glu Ser Gly Pro Gly Leu Val Arg Pro Ser Gln
1               5                   10                  15
Thr Leu Ser Leu Thr Cys Thr Val Ser Gly Tyr Ser Ile Thr Ser Asp
            20                  25                  30
His Ala Trp Ser Trp Val Arg Gln Pro Pro Gly Arg Gly Leu Glu Trp
        35                  40                  45
Ile Gly Tyr Ile Ser Tyr Ser Gly Ile Thr Thr Tyr Asn Pro Ser Leu
    50                  55                  60
Lys Ser Arg Val Thr Met Leu Arg Asp Thr Ser Lys Asn Gln Phe Ser
65                  70                  75                  80
Leu Arg Leu Ser Ser Val Thr Ala Ala Asp Thr Ala Val Tyr Tyr Cys
                85                  90                  95
Ala Arg Ser Leu Ala Arg Thr Thr Ala Met Asp Tyr Trp Gly Gln Gly
            100                 105                 110
Ser Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Lys Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Glu Thr Thr Pro Pro Met Leu
385                 390                 395                 400
Asp Ser Asp Gly Ser Phe Phe Leu Tyr Ser Lys Leu Thr Val Asp Lys
                405                 410                 415
```

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 37
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 37

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

```
Thr Ile Ser Lys Ala Lys Gly Gln Pro Arg Glu Pro Gln Val Tyr Thr
            340                 345                 350

Leu Pro Pro Ser Arg Lys Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Phe Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 38
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 38

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
        50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
            85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
            225                 230                 235                 240

Ser Val Phe Leu Phe Pro Pro Lys Pro Lys Asp Thr Leu Met Ile Ser
            245                 250                 255
```

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Tyr Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 39
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 39

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Thr Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 40
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 40

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Lys Asn Gln Phe Ser
65                  70                  75              80

Leu Arg Leu Ser Ser Val Thr Ala Ala Asp Thr Ala Val Tyr Tyr Cys
                85                  90                  95
```

```
Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Val Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 41
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 41

Gln Val Gln Leu Gln Glu Ser Gly Pro Gly Leu Val Arg Pro Ser Gln
1               5                   10                  15
```

```
Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
 50                  55                  60

Lys Ser Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
 130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
 210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
 290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Ile Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

```
Ala Leu His Asn His Tyr Thr Gln Lys Ser Leu Ser Leu Ser Pro
            435                 440                 445
```

<210> SEQ ID NO 42
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 42

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
            85                  90                  95

Ala Arg Ser Leu Ala Arg Thr Thr Ala Met Asp Tyr Trp Gly Glu Gly
        100                 105                 110

Thr Leu Val Thr Val Ser Ser Ala Ser Thr Lys Gly Pro Ser Val Phe
    115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350
```

```
Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Asp Thr Thr Pro Pro Met Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
            435                 440                 445

<210> SEQ ID NO 43
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 43

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Glu Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445

<210> SEQ ID NO 44
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 44

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
        195                 200                 205

Ser Asn Thr Lys Val Asp Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Phe Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445

<210> SEQ ID NO 45
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 45

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110
```

```
Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Tyr Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445

<210> SEQ ID NO 46
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 46

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30
```

-continued

Gln Ala Trp Ser Trp Val Arg Gln Pro Pro Gly Glu Gly Leu Glu Trp
            35                  40                  45

Ile Gly Tyr Ile Ser Tyr Ser Gly Ile Thr Asn Tyr Asn Pro Ser Leu
 50                  55                  60

Lys Gly Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Ala Tyr Tyr Cys
                 85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Thr Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
            435                 440                 445

```
<210> SEQ ID NO 47
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
```

```
                370                 375                 380
Ser Asn Gly Gln Pro Glu Asn Asn Tyr Val Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Glu Ser Leu Ser Leu Ser Pro
                435                 440                 445

<210> SEQ ID NO 48
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 48

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
                20                  25                  30

Gln Ala Trp Ser Trp Val Arg Gln Pro Pro Gly Glu Gly Leu Glu Trp
            35                  40                  45

Ile Gly Tyr Ile Ser Tyr Ser Gly Ile Thr Asn Tyr Asn Pro Ser Leu
50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
```

```
                290                 295                 300
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Ile Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Glu Ser Leu Ser Leu Ser Pro
                435                 440                 445

<210> SEQ ID NO 49
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 49

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
                20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
                100                 105                 110

Ser Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
```

```
              210                 215                 220
Thr His Thr Cys Pro Pro Cys Ala Pro Glu Leu Gly Gly Pro
225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
            435                 440                 445

<210> SEQ ID NO 50
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 50

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
                20                  25                  30

Gln Ala Trp Ser Trp Val Arg Gln Pro Pro Gly Glu Gly Leu Glu Trp
            35                  40                  45

Ile Gly Tyr Ile Ser Tyr Ser Gly Ile Thr Asn Tyr Asn Pro Ser Leu
50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
```

```
            130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 51
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 51

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
                20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
```

```
                50                  55                  60
Lys Ser Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 52
<211> LENGTH: 447
<212> TYPE: PRT
<213> ORGANISM: Artificial sequence
```

<220> FEATURE:
<223> OTHER INFORMATION: An artificially synthesized sequence

<400> SEQUENCE: 52

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Arg Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445

<210> SEQ ID NO 53
<211> LENGTH: 443
<212> TYPE: PRT
<213> ORGANISM: Artificial sequence
<220> FEATURE:
<223> OTHER INFORMATION: An artificially synthesized sequence

<400> SEQUENCE: 53

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320
```

-continued

```
Ser Ala Ala Phe Pro Ala Pro Ile Glu Lys Thr Ile Ser Lys Thr Lys
            325                 330                 335

Gly Arg Pro Lys Ala Pro Gln Val Tyr Thr Ile Pro Pro Lys Glu
        340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
        370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
            435                 440

<210> SEQ ID NO 54
<211> LENGTH: 443
<212> TYPE: PRT
<213> ORGANISM: Artificial sequence
<220> FEATURE:
<223> OTHER INFORMATION: An artificially synthesized sequence

<400> SEQUENCE: 54

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240
```

```
Pro Lys Pro Lys Asp Val Leu Thr Ile Thr Leu Thr Pro Lys Val Thr
                245                 250                 255
Cys Val Val Asp Ile Ser Lys Asp Asp Pro Glu Val Gln Phe Ser
            260                 265                 270
Trp Phe Val Asp Asp Val Glu Val His Thr Ala Gln Thr Gln Pro Arg
        275                 280                 285
Glu Glu Gln Phe Asn Ser Thr Phe Arg Ser Val Ser Glu Leu Pro Ile
    290                 295                 300
Met His Gln Asp Trp Leu Asn Gly Lys Glu Phe Lys Cys Arg Val Asn
305                 310                 315                 320
Ser Ala Ala Phe Pro Ala Pro Ile Glu Lys Thr Ile Ser Lys Thr Lys
                325                 330                 335
Gly Arg Pro Lys Ala Pro Gln Val Tyr Thr Ile Pro Pro Lys Glu
            340                 345                 350
Gln Met Ala Lys Asp Lys Val Ser Leu Thr Cys Met Ile Thr Asp Phe
        355                 360                 365
Phe Pro Glu Asp Ile Thr Val Glu Trp Gln Trp Asn Gly Gln Pro Ala
    370                 375                 380
Glu Asn Tyr Lys Asn Thr Gln Pro Ile Met Asp Thr Asp Gly Ser Tyr
385                 390                 395                 400
Phe Val Tyr Ser Lys Leu Asn Val Gln Lys Ser Asn Trp Glu Ala Gly
                405                 410                 415
Asn Thr Phe Thr Cys Ser Val Leu His Glu Gly Leu His Asn His His
            420                 425                 430
Thr Glu Lys Ser Leu Ser His Ser Pro Gly Lys
        435                 440

<210> SEQ ID NO 55
<211> LENGTH: 443
<212> TYPE: PRT
<213> ORGANISM: Artificial sequence
<220> FEATURE:
<223> OTHER INFORMATION: An artificially synthesized sequence

<400> SEQUENCE: 55

Gln Val Gln Leu Gln Glu Ser Gly Pro Gly Leu Val Arg Pro Ser Gln
1               5                   10                  15
Thr Leu Ser Leu Thr Cys Thr Val Ser Gly Tyr Ser Ile Thr Ser Asp
            20                  25                  30
His Ala Trp Ser Trp Val Arg Gln Pro Pro Gly Arg Gly Leu Glu Trp
        35                  40                  45
Ile Gly Tyr Ile Ser Tyr Ser Gly Ile Thr Thr Tyr Asn Pro Ser Leu
    50                  55                  60
Lys Ser Arg Val Thr Met Leu Arg Asp Thr Ser Lys Asn Gln Phe Ser
65                  70                  75                  80
Leu Arg Leu Ser Ser Val Thr Ala Ala Asp Thr Ala Val Tyr Tyr Cys
                85                  90                  95
Ala Arg Ser Leu Ala Arg Thr Thr Ala Met Asp Tyr Trp Gly Gln Gly
            100                 105                 110
Ser Leu Val Thr Val Ser Ser Ala Lys Thr Thr Pro Pro Ser Val Tyr
        115                 120                 125
Pro Leu Ala Pro Gly Ser Ala Ala Gln Thr Asn Ser Met Val Thr Leu
    130                 135                 140
Gly Cys Leu Val Lys Gly Tyr Phe Pro Glu Pro Val Thr Val Thr Trp
145                 150                 155                 160
```

```
Asn Ser Gly Ser Leu Ser Ser Gly Val His Thr Phe Pro Ala Val Leu
            165                 170                 175

Gln Ser Asp Leu Tyr Thr Leu Ser Ser Ser Val Thr Val Pro Ser Ser
        180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
                260                 265                 270

Trp Phe Val Asp Asp Val Glu Val His Thr Ala Gln Thr Gln Pro Arg
            275                 280                 285

Glu Glu Gln Phe Asn Ser Thr Phe Arg Ser Val Ser Glu Leu Pro Ile
        290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
                340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Lys Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 56
<211> LENGTH: 443
<212> TYPE: PRT
<213> ORGANISM: Artificial sequence
<220> FEATURE:
<223> OTHER INFORMATION: An artificially synthesized sequence

<400> SEQUENCE: 56

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80
```

Leu Arg Leu Ser Ser Val Thr Ala Ala Asp Thr Ala Val Tyr Tyr Cys
            85                  90                  95

Ala Arg Ser Leu Ala Arg Thr Thr Ala Met Asp Tyr Trp Gly Gln Gly
            100                 105                 110

Ser Leu Val Thr Val Ser Ser Ala Lys Thr Thr Pro Pro Ser Val Tyr
            115                 120                 125

Pro Leu Ala Pro Gly Ser Ala Ala Gln Thr Asn Ser Met Val Thr Leu
130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
            165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
            195                 200                 205

Ser Thr Lys Val Asp Lys Lys Ile Val Pro Arg Asp Cys Gly Cys Lys
            210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
            245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
            275                 280                 285

Glu Glu Gln Phe Asn Ser Thr Phe Arg Ser Val Ser Glu Leu Pro Ile
            290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
            325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Arg Thr Asp Gly Ser Tyr
385                 390                 395                 400

Phe Val Tyr Ser Lys Leu Asn Val Gln Lys Ser Asn Trp Glu Ala Gly
            405                 410                 415

Asn Thr Phe Thr Cys Ser Val Leu His Glu Gly Leu His Asn His His
            420                 425                 430

Thr Glu Lys Ser Leu Ser His Ser Pro Gly Lys
            435                 440

<210> SEQ ID NO 57
<211> LENGTH: 443
<212> TYPE: PRT
<213> ORGANISM: Artificial sequence
<220> FEATURE:
<223> OTHER INFORMATION: An artificially synthesized sequence

<400> SEQUENCE: 57

-continued

```
Gln Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Ser Asp Asp
             20                  25                  30

Gln Ala Trp Ser Trp Val Arg Gln Pro Pro Gly Glu Gly Leu Glu Trp
             35                  40                  45

Ile Gly Tyr Ile Ser Tyr Ser Gly Ile Thr Asn Tyr Asn Pro Ser Leu
 50                  55                  60

Lys Gly Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Ala Tyr Tyr Cys
             85                  90                  95

Ala Arg Ser Leu Ala Arg Thr Thr Ala Met Asp Tyr Trp Gly Glu Gly
            100                 105                 110

Thr Leu Val Thr Val Ser Ser Ala Lys Thr Thr Pro Pro Ser Val Tyr
            115                 120                 125

Pro Leu Ala Pro Gly Ser Ala Ala Gln Thr Asn Ser Met Val Thr Leu
            130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
                180                 185                 190

Thr Trp Pro Ser Glu Thr Val Thr Cys Asn Val Ala His Pro Ala Ser
                195                 200                 205

Ser Thr Lys Val Asp Lys Lys Ile Val Pro Arg Asp Cys Gly Cys Lys
210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
                260                 265                 270

Trp Phe Val Asp Asp Val Glu Val His Thr Ala Gln Thr Gln Pro Arg
                275                 280                 285

Glu Glu Gln Phe Asn Ser Thr Phe Arg Ser Val Ser Glu Leu Pro Ile
290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
                340                 345                 350

Gln Met Ala Lys Asp Lys Val Ser Leu Thr Cys Met Ile Thr Asp Phe
                355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Val Tyr Ser Asp Leu Asn Val Gln Lys Ser Asn Trp Glu Ala Gly
                405                 410                 415
```

-continued

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 58
<211> LENGTH: 443
<212> TYPE: PRT
<213> ORGANISM: Artificial sequence
<220> FEATURE:
<223> OTHER INFORMATION: An artificially synthesized sequence

<400> SEQUENCE: 58

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

```
Gly Arg Pro Lys Ala Pro Gln Val Tyr Thr Ile Pro Pro Lys Glu
                340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Val Tyr Ser Glu Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
            435                 440

<210> SEQ ID NO 59
<211> LENGTH: 214
<212> TYPE: PRT
<213> ORGANISM: Artificial sequence
<220> FEATURE:
<223> OTHER INFORMATION: An artificially synthesized sequence

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 60
<211> LENGTH: 214
<212> TYPE: PRT
<213> ORGANISM: Artificial sequence
<220> FEATURE:
```

-continued

<223> OTHER INFORMATION: An artificially synthesized sequence

<400> SEQUENCE: 60

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu His Ser Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Ser Leu Pro Tyr
                85                  90                  95

Thr Phe Gly Gln Gly Thr Lys Val Glu Ile Glu Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 61
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 61

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Ser Ser Ala Ser Thr Lys Gly Pro Ser Val Phe Pro Leu Ala Pro Cys
        115                 120                 125

Ser Arg Ser Thr Ser Glu Ser Thr Ala Ala Leu Gly Cys Leu Val Lys
            130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Lys Thr Tyr Thr Cys Asn Val Asp His Lys Pro Ser Asn Thr Lys Val
        195                 200                 205

Asp Lys Arg Val Glu Ser Lys Tyr Gly Pro Pro Cys Pro Pro Cys Pro
210                 215                 220

Ala Pro Glu Ala Ala Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Ala Ser Thr Tyr Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Cys Thr Leu Pro Pro Ser Gln Glu Glu Met
            340                 345                 350

Thr Lys Asn Gln Val Ser Leu Trp Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
            420                 425                 430

Lys Ser Leu Ser Leu Ser Leu His His His His His His
        435                 440                 445

<210> SEQ ID NO 62
<211> LENGTH: 455
<212> TYPE: PRT
<213> ORGANISM: Artificial sequence
<220> FEATURE:
<223> OTHER INFORMATION: An artificially synthesized sequence

<400> SEQUENCE: 62

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

```
Ala Gln Ile Lys Ala Lys Ser Asn Asn Tyr Ala Thr Tyr Tyr Ala Glu
 50                  55                  60

Ser Val Lys Gly Arg Phe Thr Ile Ser Arg Asp Asp Ser Lys Ser Asn
 65                  70                  75                  80

Ile Tyr Leu Gln Met Asn Ser Leu Lys Glu Glu Asp Thr Ala Val Tyr
                 85                  90                  95

Tyr Cys Arg Tyr Val His Tyr Gly Ala Tyr Gly Val Asp Ala Trp
                100                 105                 110

Gly Gln Gly Thr Ser Val Thr Val Ser Ser Ala Ser Thr Lys Gly Pro
                115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Lys Thr Tyr Thr Cys Asn Val Asp
                195                 200                 205

His Lys Pro Ser Asn Thr Lys Val Asp Lys Arg Val Glu Ser Lys Tyr
                210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
                275                 280                 285

Ala Lys Thr Lys Pro Arg Glu Glu Gln Phe Ala Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Cys Glu Met Thr Lys Asn Gln Val Ser Leu Ser
                355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Asp
                435                 440                 445

Tyr Lys Asp Asp Asp Lys
        450                 455
```

<210> SEQ ID NO 63
<211> LENGTH: 222
<212> TYPE: PRT
<213> ORGANISM: Artificial sequence
<220> FEATURE:
<223> OTHER INFORMATION: An artificially synthesized sequence

<400> SEQUENCE: 63

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Ile Arg Gln Pro Gly Gln Gly Leu Glu Trp Ile
        35                  40                  45

Gly Ala Ile Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Arg Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Cys
    210                 215                 220
```

<210> SEQ ID NO 64
<211> LENGTH: 219
<212> TYPE: PRT
<213> ORGANISM: Artificial sequence
<220> FEATURE:
<223> OTHER INFORMATION: An artificially synthesized sequence

<400> SEQUENCE: 64

```
Asp Val Val Met Thr Gln Thr Pro Val Ser Met Ser Val Ser Leu Gly
1               5                   10                  15

Gly Gln Val Ser Ile Ser Cys Arg Ser Ser Gln Ser Leu Val His Asn
            20                  25                  30

Asn Gly Asn Thr Tyr Val Ser Trp Tyr Ile Gln Lys Pro Ser Gln Ser
        35                  40                  45

Pro Gln Leu Leu Ile Tyr Lys Val Ser Asn Arg Phe Ser Gly Ile Ser
    50                  55                  60

Asp Arg Phe Ser Gly Ser Gly Ser Gly Thr Asp Phe Thr Leu Lys Ile
65                  70                  75                  80

Ser Arg Val Glu Pro Asp Asp Leu Gly Val Tyr Tyr Cys Gly Gln Gly
                85                  90                  95
```

```
Thr Gln Asp Pro Tyr Thr Phe Gly Ala Gly Thr Lys Leu Glu Leu Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
            210                 215

<210> SEQ ID NO 65
<211> LENGTH: 443
<212> TYPE: PRT
<213> ORGANISM: Artificial sequence
<220> FEATURE:
<223> OTHER INFORMATION: An artificially synthesized sequence

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Ile Arg Gln Pro Pro Gly Gln Gly Leu Glu Trp Ile
        35                  40                  45

Gly Ala Ile Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Lys Val Glu Pro Lys Ser Cys Asp Lys Thr His Thr Cys
            210                 215                 220

Pro Pro Cys Pro Ala Pro Glu Leu Arg Gly Gly Pro Lys Val Phe Leu
225                 230                 235                 240
```

```
Phe Pro Pro Lys Pro Lys Asp Thr Leu Met Ile Ser Arg Thr Pro Glu
                245                 250                 255

Val Thr Cys Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Tyr Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Glu Ser Leu Ser Leu Ser Pro
            435                 440

<210> SEQ ID NO 66
<211> LENGTH: 443
<212> TYPE: PRT
<213> ORGANISM: Artificial sequence
<220> FEATURE:
<223> OTHER INFORMATION: An artificially synthesized sequence

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Ile Arg Gln Pro Pro Gly Gln Gly Leu Glu Trp Ile
        35                  40                  45

Gly Ala Ile Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160
```

```
Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Arg Gly Gly Pro Lys Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Glu Ser Leu Ser Leu Ser Pro
        435                 440

<210> SEQ ID NO 67
<211> LENGTH: 440
<212> TYPE: PRT
<213> ORGANISM: Artificial sequence
<220> FEATURE:
<223> OTHER INFORMATION: An artificially synthesized sequence

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Ile Arg Gln Pro Pro Gly Gln Gly Leu Glu Trp Ile
        35                  40                  45

Gly Ala Ile Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80
```

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Arg Gly Gly Pro Lys Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Glu Ser Leu Ser Leu Ser Leu
        435                 440

<210> SEQ ID NO 68
<211> LENGTH: 439
<212> TYPE: PRT
<213> ORGANISM: Artificial sequence
<220> FEATURE:
<223> OTHER INFORMATION: An artificially synthesized sequence

<400> SEQUENCE: 68

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Ile Arg Gln Pro Gly Gln Gly Leu Glu Trp Ile
            35                  40                  45

Gly Ala Ile Asp Pro Lys Thr Gly Asp Thr Ala Tyr Ser Gln Lys Phe
50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
                100                 105                 110

Val Ser Ser Ala Lys Thr Thr Pro Pro Ser Val Tyr Pro Leu Ala Pro
            115                 120                 125

Gly Ser Ala Ala Gln Thr Asn Ser Met Val Thr Leu Gly Cys Leu Val
130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
                180                 185                 190

Glu Thr Val Thr Cys Asn Val Ala His Pro Ala Ser Ser Thr Lys Val
                195                 200                 205

Asp Lys Lys Ile Val Pro Arg Asp Cys Gly Cys Lys Pro Cys Ile Cys
            210                 215                 220

Thr Val Lys Glu Val Ser Lys Val Phe Ile Phe Pro Pro Lys Pro Lys
225                 230                 235                 240

Asp Val Leu Thr Ile Thr Leu Thr Pro Lys Val Thr Cys Val Val Val
                245                 250                 255

Asp Ile Ser Lys Asp Asp Pro Glu Val Gln Phe Ser Trp Phe Val Asp
                260                 265                 270

Asp Val Glu Val His Thr Ala Gln Thr Gln Pro Arg Glu Glu Gln Phe
                275                 280                 285

Asn Ser Thr Phe Arg Ser Val Ser Glu Leu Pro Ile Met His Gln Asp
            290                 295                 300

Trp Leu Asn Gly Lys Glu Phe Lys Cys Arg Val Asn Ser Ala Ala Phe
305                 310                 315                 320

Pro Ala Pro Ile Glu Lys Thr Ile Ser Lys Thr Lys Gly Arg Pro Lys
                325                 330                 335

Ala Pro Gln Val Tyr Thr Ile Pro Pro Pro Lys Glu Gln Met Ala Lys
                340                 345                 350

Asp Lys Val Ser Leu Thr Cys Met Ile Thr Asp Phe Phe Pro Glu Asp
                355                 360                 365

Ile Thr Val Glu Trp Gln Trp Asn Gly Gln Pro Ala Glu Asn Tyr Lys
                370                 375                 380

Asn Thr Gln Pro Ile Met Asp Thr Asp Gly Ser Tyr Phe Val Tyr Ser
385                 390                 395                 400

Glu Leu Asn Val Gln Lys Ser Asn Trp Glu Ala Gly Asn Thr Phe Thr
                405                 410                 415
```

-continued

```
Cys Ser Val Leu His Glu Gly Leu His Asn His His Thr Glu Lys Ser
            420                 425                 430

Leu Ser His Ser Pro Gly Lys
            435

<210> SEQ ID NO 69
<211> LENGTH: 450
<212> TYPE: PRT
<213> ORGANISM: Artificial sequence
<220> FEATURE:
<223> OTHER INFORMATION: An artificially synthesized sequence

<400> SEQUENCE: 69

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Asn
65                  70                  75                  80

Ile Tyr Leu Gln Met Asn Ser Leu Lys Glu Glu Asp Thr Ala Val Tyr
                85                  90                  95

Tyr Cys Arg Tyr Val His Tyr Gly Ala Tyr Tyr Gly Val Asp Ala Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Arg
225                 230                 235                 240

Gly Gly Pro Lys Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335
```

```
Ile Glu Lys Thr Ile Ser Lys Ala Lys Gly Gln Pro Arg Glu Pro Gln
                340                 345                 350

Val Tyr Thr Leu Pro Pro Ser Arg Lys Glu Leu Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Tyr Leu Asp Ser Asp Gly Ser Phe Phe Leu Tyr Ser Lys Leu Thr
                405                 410                 415

Val Asp Lys Ser Arg Trp Gln Gln Gly Asn Val Phe Cys Ser Val
            420                 425                 430

Met His Glu Ala Leu His Asn His Tyr Thr Gln Lys Ser Leu Ser Leu
        435                 440                 445

Ser Pro
    450

<210> SEQ ID NO 70
<211> LENGTH: 450
<212> TYPE: PRT
<213> ORGANISM: Artificial sequence
<220> FEATURE:
<223> OTHER INFORMATION: An artificially synthesized sequence

<400> SEQUENCE: 70

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Asn
65                  70                  75                  80

Ile Tyr Leu Gln Met Asn Ser Leu Lys Glu Glu Asp Thr Ala Val Tyr
                85                  90                  95

Tyr Cys Arg Tyr Val His Tyr Gly Ala Tyr Tyr Gly Val Asp Ala Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Arg
225                 230                 235                 240
```

```
Gly Gly Pro Lys Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Lys Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro
    450

<210> SEQ ID NO 71
<211> LENGTH: 447
<212> TYPE: PRT
<213> ORGANISM: Artificial sequence
<220> FEATURE:
<223> OTHER INFORMATION: An artificially synthesized sequence

<400> SEQUENCE: 71

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

Ser Val Lys Gly Arg Phe Thr Ile Ser Arg Asp Asp Ser Lys Ser Asn
65                  70                  75                  80

Ile Tyr Leu Gln Met Asn Ser Leu Lys Glu Glu Asp Thr Ala Val Tyr
                85                  90                  95

Tyr Cys Arg Tyr Val His Tyr Gly Ala Tyr Tyr Gly Val Asp Ala Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140
```

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Arg Gly Gly Pro
225                 230                 235                 240

Lys Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Lys Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu
            435                 440                 445

<210> SEQ ID NO 72
<211> LENGTH: 446
<212> TYPE: PRT
<213> ORGANISM: Artificial sequence
<220> FEATURE:
<223> OTHER INFORMATION: An artificially synthesized sequence

<400> SEQUENCE: 72

Glu Val Gln Leu Val Glu Thr Gly Gly Ser Leu Val Gln Pro Gly Lys
1               5                   10                  15

Ser Leu Lys Leu Thr Cys Ala Thr Ser Gly Phe Thr Phe Ser Asn Ala
            20                  25                  30

Trp Met His Trp Val Arg Gln Ser Pro Glu Lys Gln Leu Glu Trp Val
        35                  40                  45

Ala Gln Ile Lys Ala Lys Ser Asn Asn Tyr Ala Thr Tyr Tyr Ala Glu
    50                  55                  60

```
Ser Val Lys Gly Arg Phe Thr Ile Ser Arg Asp Asp Ser Lys Ser Asn
 65                  70                  75                  80

Ile Tyr Leu Gln Met Asn Ser Leu Lys Glu Glu Asp Thr Ala Val Tyr
                 85                  90                  95

Tyr Cys Arg Tyr Val His Tyr Gly Ala Tyr Gly Val Asp Ala Trp
            100                 105                 110

Gly Gln Gly Thr Ser Val Thr Val Ser Ser Ala Lys Thr Thr Pro Pro
            115                 120                 125

Ser Val Tyr Pro Leu Ala Pro Gly Ser Ala Ala Gln Thr Asn Ser Met
            130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
                180                 185                 190

Pro Ser Ser Thr Trp Pro Ser Glu Thr Val Thr Cys Asn Val Ala His
            195                 200                 205

Pro Ala Ser Ser Thr Lys Val Asp Lys Lys Ile Val Pro Arg Asp Cys
210                 215                 220

Gly Cys Lys Pro Cys Ile Cys Thr Val Lys Glu Val Ser Lys Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
            275                 280                 285

Gln Pro Arg Glu Glu Gln Phe Asn Ser Thr Phe Arg Ser Val Ser Glu
            290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
            355                 360                 365

Thr Asp Phe Phe Pro Glu Asp Ile Thr Val Glu Trp Gln Trp Asn Gly
370                 375                 380

Gln Pro Ala Glu Asn Tyr Lys Asn Thr Gln Pro Ile Met Arg Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
            435                 440                 445

<210> SEQ ID NO 73
<211> LENGTH: 443
<212> TYPE: PRT
<213> ORGANISM: Artificial sequence
<220> FEATURE:
<223> OTHER INFORMATION: An artificially synthesized sequence
```

<400> SEQUENCE: 73

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly

```
                        405                 410                 415
Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 74
<211> LENGTH: 443
<212> TYPE: PRT
<213> ORGANISM: Artificial sequence
<220> FEATURE:
<223> OTHER INFORMATION: An artificially synthesized sequence

<400> SEQUENCE: 74

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
```

```
                   325                 330                 335
Gly Arg Pro Lys Ala Pro Gln Val Tyr Thr Ile Pro Pro Lys Glu
                340                 345                 350
Gln Met Ala Lys Asp Lys Val Ser Leu Thr Cys Met Ile Thr Asp Phe
                355                 360                 365
Phe Pro Glu Asp Ile Thr Val Glu Trp Gln Trp Asn Gly Gln Pro Ala
370                 375                 380
Glu Asn Tyr Lys Asn Thr Gln Pro Ile Met Lys Thr Asp Gly Ser Tyr
385                 390                 395                 400
Phe Val Tyr Ser Lys Leu Asn Val Gln Lys Ser Asn Trp Glu Ala Gly
                405                 410                 415
Asn Thr Phe Thr Cys Ser Val Leu His Glu Gly Leu His Asn His His
                420                 425                 430
Thr Glu Lys Ser Leu Ser His Ser Pro Gly Lys
                435                 440
```

<210> SEQ ID NO 75
<211> LENGTH: 443
<212> TYPE: PRT
<213> ORGANISM: Artificial sequence
<220> FEATURE:
<223> OTHER INFORMATION: An artificially synthesized sequence

<400> SEQUENCE: 75

```
Gln Val Gln Leu Gln Glu Ser Gly Pro Gly Leu Val Lys Pro Ser Glu
1               5                   10                  15
Thr Leu Ser Leu Thr Cys Ala Val Ser Gly His Ser Ile Ser His Asp
                20                  25                  30
His Ala Trp Ser Trp Val Arg Gln Pro Pro Gly Glu Gly Leu Glu Trp
            35                  40                  45
Ile Gly Phe Ile Ser Tyr Ser Gly Ile Thr Asn Tyr Asn Pro Ser Leu
        50                  55                  60
Gln Gly Arg Val Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Leu Ala Arg Thr Thr Ala Met Asp Tyr Trp Gly Glu Gly
                100                 105                 110
Thr Leu Val Thr Val Ser Ser Ala Lys Thr Thr Pro Pro Ser Val Tyr
                115                 120                 125
Pro Leu Ala Pro Gly Ser Ala Ala Gln Thr Asn Ser Met Val Thr Leu
            130                 135                 140
Gly Cys Leu Val Lys Gly Tyr Phe Pro Glu Pro Val Thr Val Thr Trp
145                 150                 155                 160
Asn Ser Gly Ser Leu Ser Ser Gly Val His Thr Phe Pro Ala Val Leu
                165                 170                 175
Gln Ser Asp Leu Tyr Thr Leu Ser Ser Val Thr Val Pro Ser Ser
            180                 185                 190
Thr Trp Pro Ser Glu Thr Val Thr Cys Asn Val Ala His Pro Ala Ser
                195                 200                 205
Ser Thr Lys Val Asp Lys Lys Ile Val Pro Arg Asp Cys Gly Cys Lys
            210                 215                 220
Pro Cys Ile Cys Thr Val Pro Glu Val Ser Ser Val Phe Ile Phe Pro
225                 230                 235                 240
Pro Lys Pro Lys Asp Val Leu Thr Ile Thr Leu Thr Pro Lys Val Thr
```

```
                245                 250                 255
    Cys Val Val Asp Ile Ser Lys Asp Asp Pro Glu Val Gln Phe Ser
                260                 265                 270

Trp Phe Val Asp Val Glu Val His Thr Ala Gln Thr Gln Pro Arg
                275                 280                 285

Glu Glu Gln Phe Asn Ser Thr Phe Arg Ser Val Ser Glu Leu Pro Ile
        290                 295                 300

Met His Gln Asp Trp Leu Asn Gly Lys Glu Phe Lys Cys Arg Val Asn
    305                 310                 315                 320

Ser Ala Ala Phe Pro Ala Pro Ile Glu Lys Thr Ile Ser Lys Thr Lys
                    325                 330                 335

Gly Arg Pro Lys Ala Pro Gln Val Tyr Thr Ile Pro Pro Lys Glu
                340                 345                 350

Gln Met Ala Lys Asp Lys Val Ser Leu Thr Cys Met Ile Thr Asp Phe
                    355                 360                 365

Phe Pro Glu Asp Ile Thr Val Glu Trp Gln Trp Asn Gly Gln Pro Ala
                370                 375                 380

Glu Asn Tyr Lys Asn Thr Gln Pro Ile Met Asp Thr Asp Gly Ser Tyr
    385                 390                 395                 400

Phe Val Tyr Ser Asp Leu Asn Val Gln Lys Ser Asn Trp Glu Ala Gly
                    405                 410                 415

Asn Thr Phe Thr Cys Ser Val Leu His Glu Gly Leu His Asn His His
                    420                 425                 430

Thr Glu Lys Ser Leu Ser His Ser Pro Gly Lys
                    435                 440

<210> SEQ ID NO 76
<211> LENGTH: 443
<212> TYPE: PRT
<213> ORGANISM: Artificial sequence
<220> FEATURE:
<223> OTHER INFORMATION: An artificially synthesized sequence

<400> SEQUENCE: 76

Gln Val Gln Leu Gln Glu Ser Gly Pro Gly Leu Val Lys Pro Ser Glu
    1               5                   10                  15

Thr Leu Ser Leu Thr Cys Ala Val Ser Gly His Ser Ile Ser His Asp
                    20                  25                  30

His Ala Trp Ser Trp Val Arg Gln Pro Pro Gly Glu Gly Leu Glu Trp
                35                  40                  45

Ile Gly Phe Ile Ser Tyr Ser Gly Ile Thr Asn Tyr Asn Pro Ser Leu
        50                  55                  60

Gln Gly Arg Val Thr Ile Ser Arg Asp Asn Ser Lys Asn Thr Leu Tyr
    65                  70                  75                  80

Leu Gln Met Asn Ser Leu Arg Ala Glu Asp Thr Ala Val Tyr Tyr Cys
                    85                  90                  95

Ala Arg Ser Leu Ala Arg Thr Thr Ala Met Asp Tyr Trp Gly Glu Gly
                100                 105                 110

Thr Leu Val Thr Val Ser Ser Ala Lys Thr Thr Pro Pro Ser Val Tyr
                115                 120                 125

Pro Leu Ala Pro Gly Ser Ala Ala Gln Thr Asn Ser Met Val Thr Leu
            130                 135                 140

Gly Cys Leu Val Lys Gly Tyr Phe Pro Glu Pro Val Thr Val Thr Trp
    145                 150                 155                 160

Asn Ser Gly Ser Leu Ser Ser Gly Val His Thr Phe Pro Ala Val Leu
```

```
                    165                 170                 175

Gln Ser Asp Leu Tyr Thr Leu Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Arg Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 77
<211> LENGTH: 443
<212> TYPE: PRT
<213> ORGANISM: Artificial sequence
<220> FEATURE:
<223> OTHER INFORMATION: An artificially synthesized sequence

<400> SEQUENCE: 77

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                    85                  90                  95
Ala Arg Ser Leu Ala Arg Thr Thr Ala Met Asp Tyr Trp Gly Glu Gly
                100                 105                 110

Thr Leu Val Thr Val Ser Ser Ala Lys Thr Thr Pro Pro Ser Val Tyr
            115                 120                 125

Pro Leu Ala Pro Gly Ser Ala Ala Gln Thr Asn Ser Met Val Thr Leu
        130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Pro Ser Ser
                180                 185                 190

Thr Trp Pro Ser Glu Thr Val Thr Cys Asn Val Ala His Pro Ala Ser
            195                 200                 205

Ser Thr Lys Val Asp Lys Lys Ile Val Pro Arg Asp Cys Gly Cys Lys
        210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Val Tyr Ser Glu Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 78
<211> LENGTH: 214
<212> TYPE: PRT
<213> ORGANISM: Artificial sequence
<220> FEATURE:
<223> OTHER INFORMATION: An artificially synthesized sequence

<400> SEQUENCE: 78

Asp Ile Gln Met Thr Gln Ser Pro Ser Ser Leu Ser Ala Ser Val Gly
```

```
            1               5                  10                 15
Asp Ser Val Thr Ile Thr Cys Gln Ala Ser Thr Asp Ile Ser Ser His
                20                  25                 30

Leu Asn Trp Tyr Gln Gln Lys Pro Gly Lys Ala Pro Glu Leu Leu Ile
        35                  40                 45

Tyr Tyr Gly Ser His Leu Leu Ser Gly Val Pro Ser Arg Phe Ser Gly
    50                  55                 60

Ser Gly Ser Gly Thr Asp Phe Thr Phe Thr Ile Ser Ser Leu Glu Ala
65                  70                 75                  80

Glu Asp Ala Ala Thr Tyr Tyr Cys Gly Gln Gly Asn Arg Leu Pro Tyr
                85                  90                 95

Thr Phe Gly Gln Gly Thr Lys Val Glu Ile Glu Arg Ala Asp Ala Ala
                100                 105                110

Pro Thr Val Ser Ile Phe Pro Pro Ser Glu Gln Leu Thr Ser Gly
                115                 120                125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                175

Ser Thr Leu Thr Leu Thr Lys Asp Glu Tyr Glu Arg His Asn Ser Tyr
                180                 185                190

Thr Cys Glu Ala Thr His Lys Thr Ser Thr Ser Pro Ile Val Lys Ser
                195                 200                205

Phe Asn Arg Asn Glu Cys
        210

<210> SEQ ID NO 79
<211> LENGTH: 219
<212> TYPE: PRT
<213> ORGANISM: Artificial sequence
<220> FEATURE:
<223> OTHER INFORMATION: An artificially synthesized sequence

<400> SEQUENCE: 79

Asp Ile Val Met Thr Gln Ser Pro Leu Ser Leu Pro Val Thr Pro Gly
1               5                  10                 15

Glu Pro Ala Ser Ile Ser Cys Arg Ser Ser Gln Ser Leu Val His Ser
                20                  25                 30

Asn Arg Asn Thr Tyr Leu His Trp Tyr Gln Gln Lys Pro Gly Gln Ala
        35                  40                 45

Pro Arg Leu Leu Ile Tyr Lys Val Ser Asn Arg Phe Ser Gly Val Pro
    50                  55                 60

Asp Arg Phe Ser Gly Ser Gly Ser Gly Thr Asp Phe Thr Leu Lys Ile
65                  70                 75                  80

Ser Arg Val Glu Ala Glu Asp Val Gly Val Tyr Tyr Cys Ser Gln Asn
                85                  90                 95

Thr His Val Pro Pro Thr Phe Gly Gln Gly Thr Lys Leu Glu Ile Lys
                100                 105                110

Arg Thr Val Ala Ala Pro Ser Val Phe Ile Phe Pro Pro Ser Asp Glu
                115                 120                125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
```

```
                145                 150                 155                 160
        Ser Gly Asn Ser Gln Glu Ser Val Thr Glu Gln Asp Ser Lys Asp Ser
                        165                 170                 175

Thr Tyr Ser Leu Ser Ser Thr Leu Thr Leu Ser Lys Ala Asp Tyr Glu
                        180                 185                 190

Lys His Lys Val Tyr Ala Cys Glu Val Thr His Gln Gly Leu Ser Ser
                        195                 200                 205

Pro Val Thr Lys Ser Phe Asn Arg Gly Glu Cys
                        210                 215

<210> SEQ ID NO 80
<211> LENGTH: 219
<212> TYPE: PRT
<213> ORGANISM: Artificial sequence
<220> FEATURE:
<223> OTHER INFORMATION: An artificially synthesized sequence

<400> SEQUENCE: 80

Asp Ile Val Met Thr Gln Ser Pro Leu Ser Leu Pro Val Thr Pro Gly
        1               5                   10                  15

Glu Pro Ala Ser Ile Ser Cys Arg Ser Ser Gln Ser Leu Val His Ser
                        20                  25                  30

Asn Arg Asn Thr Tyr Leu His Trp Tyr Gln Gln Lys Pro Gly Gln Ala
                        35                  40                  45

Pro Arg Leu Leu Ile Tyr Lys Val Ser Asn Arg Phe Ser Gly Val Pro
                50                  55                  60

Asp Arg Phe Ser Gly Ser Gly Ser Gly Thr Asp Phe Thr Leu Lys Ile
        65                  70                  75                  80

Ser Arg Val Glu Ala Glu Asp Val Gly Val Tyr Tyr Cys Ser Gln Asn
                        85                  90                  95

Thr His Val Pro Pro Thr Phe Gly Gln Gly Thr Lys Leu Glu Ile Lys
                        100                 105                 110

Arg Ala Asp Ala Ala Pro Thr Val Ser Ile Phe Pro Pro Ser Ser Glu
                        115                 120                 125

Gln Leu Thr Ser Gly Gly Ala Ser Val Val Cys Phe Leu Asn Asn Phe
                130                 135                 140

Tyr Pro Lys Asp Ile Asn Val Lys Trp Lys Ile Asp Gly Ser Glu Arg
        145                 150                 155                 160

Gln Asn Gly Val Leu Asn Ser Trp Thr Asp Gln Asp Ser Lys Asp Ser
                        165                 170                 175

Thr Tyr Ser Met Ser Ser Thr Leu Thr Leu Thr Lys Asp Glu Tyr Glu
                        180                 185                 190

Arg His Asn Ser Tyr Thr Cys Glu Ala Thr His Lys Thr Ser Thr Ser
                        195                 200                 205

Pro Ile Val Lys Ser Phe Asn Arg Asn Glu Cys
                        210                 215

<210> SEQ ID NO 81
<211> LENGTH: 219
<212> TYPE: PRT
<213> ORGANISM: Artificial sequence
<220> FEATURE:
<223> OTHER INFORMATION: An artificially synthesized sequence

<400> SEQUENCE: 81

Asp Val Val Met Thr Gln Thr Pro Val Ser Met Ser Val Ser Leu Gly
        1               5                   10                  15
```

-continued

```
Gly Gln Val Ser Ile Ser Cys Arg Ser Ser Gln Ser Leu Val His Asn
            20                  25                  30

Asn Gly Asn Thr Tyr Val Ser Trp Tyr Ile Gln Lys Pro Ser Gln Ser
        35                  40                  45

Pro Gln Leu Leu Ile Tyr Lys Val Ser Asn Arg Phe Ser Gly Ile Ser
    50                  55                  60

Asp Arg Phe Ser Gly Ser Gly Ser Gly Thr Asp Phe Thr Leu Lys Ile
65                      70                  75                  80

Ser Arg Val Glu Pro Asp Leu Gly Val Tyr Tyr Cys Gly Gln Gly
                85                  90                  95

Thr Gln Asp Pro Tyr Thr Phe Gly Ala Gly Thr Lys Leu Glu Leu Lys
            100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215
```

METHOD FOR PRODUCING POLYPEPTIDE HETEROMULTIMER

CROSS-REFERENCE TO RELATED APPLICATIONS

This application is the National Stage of International Application Serial No. PCT/JP2014/075728, filed on Sep. 26, 2014, which claims the benefit of Japanese Application Serial No. 2013-200845, filed on Sep. 27, 2013.

TECHNICAL FIELD

The present invention relates to, for example, a method for producing a polypeptide heteromultimer and a polypeptide heteromultimer having an altered amino acid in an Fc region so as to promote polypeptide heteromultimerization.

BACKGROUND ART

Antibodies have received attention as drugs because of having high stability in blood and few adverse reactions (Non Patent Literatures 1 and 2). Among these antibodies, there exist bispecific antibodies that can each recognize two types of antigens or epitopes at the same time. These bispecific antibodies are expected to have high target specificity and the function of inhibiting a plurality of pathways at the same time (Non Patent Literature 3). For example, already launched catumaxomab is a bispecific antibody binding to an endothelial cell adhesion factor EpCAM and CD3 expressed on T cells, and is used as a therapeutic drug for malignant ascites.

Some reports on the production of IgG-type bispecific antibodies give findings about the low efficiency of obtainment of a bispecific antibody of interest or efficient production, albeit with a high degree of difficulty due to difficult purification (Non Patent Literature 3). In the case of transfecting, for example, 4 types in total of genes, i.e., genes of H chains and L chains constituting IgG having two types of variable regions, to cells and secreting these chains by coexpression, the covalent bond between the two types of H chains or the noncovalent bond between the H chain and the L chain occurs at random. Therefore, the ratio of the bispecific antibody of interest is exceedingly low with remarkably reduced production efficiency. A reported approach to solve this problem involves applying amino acid substitution to the CH3 regions of IgG H chains, whereby IgG having different types of H chains in combination can be preferentially secreted (Patent Literature 1 and Non Patent Literatures 4 and 5). This approach is a method which involves substituting an amino acid side chain present in the CH3 region of one H chain with a larger side chain (knob), and substituting its counterpart amino acid side chain present in the CH3 region of another H chain with a smaller side chain (hole) so that the knob is inserted into the hole to promote the heterodimerization of the H chains and to inhibit the homodimerization of H chains. Also, a method for introducing different charges to the respective CH3 regions of IgG H chains has been reported (Patent Literature 2). Specifically, this method involves substituting an amino acid present in the CH3 region of one H chain with an amino acid having a positive charge, and substituting its counterpart amino acid present in the CH3 region of another H chain with an amino acid having a negative charge to promote the heterodimerization of the H chains and to inhibit the homodimerization of H chains. Meanwhile, a technique of controlling H and L chain pairing has also been reported (Non Patent Literature 6). This approach exploits antibodies prepared by the exchange of an L chain constant region (CL) and an H chain CH1 region in one Fab to efficiently induce the H and L chain pairing of interest. In addition, there also exists an approach using common L chains in both Fabs. In this case, use of the common L chains allows only one type of L chain gene to be introduced into cells, and yields a bispecific antibody without the need of taking H and L chain pairing into consideration. Currently, bispecific antibodies can be formed with high efficiency by combining the H chain heterodimerization technique and the H-L chain pairing control technique. Nevertheless, it is difficult to completely control H and L chain pairing, and a complicated molecular design is required. Another problem is a high degree of difficulty in maintaining the high affinity of the common L chains for two types of antigens.

Meanwhile, instead of the gene recombination methods described above, an approach called Fab arm exchange has been reported as a method for preparing a bispecific antibody using monoclonal antibodies separately prepared in advance. This technique has been developed on the basis of the finding that the in vivo exchange of an IgG4 half-molecule with a half-molecule of endogenous IgG4 yields a bispecific antibody (BiAb) (Non Patent Literature 7). According to the reports, two types of naturally occurring human IgG4 antibodies are mixed in vitro to produce a bispecific antibody (Patent Literature 3), and this reaction occurs more efficiently under a reducing condition (Non Patent Literature 8). Two sites characteristic of IgG4, i.e., amino acid residues at position 228 in the hinge region and at position 409 in the CH3 region have been identified as amino acid residues important for this reaction. It has been found that even in IgG1, the substitution of these two sites with IgG4-type amino acids causes the reaction with efficiency equivalent to that of IgG4 (Patent Literature 4). The Fab arm exchange produces a bispecific antibody of interest by merely mixing in vitro monoclonal antibodies prepared by a general method and is thus highly versatile. The half-molecule exchange reaction, however, occurs at random. Therefore, the bispecific antibody obtained by mixing two types of antibodies is theoretically 50% of the total amount of antibodies present in the system. Hence, a method for improving the rate of bispecific antibody formation has been studied. The reaction efficiency can be reportedly improved by introducing asymmetric amino acid alteration to two types of antibodies, i.e., K409R alteration to the H chains of one antibody and F405L alteration to the H chains of the other antibody, but still remains at approximately 95% (Patent Literature 5 and Non Patent Literature 9). The efficient and stable production of bispecific antibodies inevitably requires convenient purification and minimized lot-to-lot variation. Thus, there has been a demand for the development of an excellent approach that achieves higher reaction efficiency.

CITATION LIST

Patent Literature

Patent Literature 1: WO1996/027011
Patent Literature 2: WO2006/106905
Patent Literature 3: WO2005/062916
Patent Literature 4: WO2008/119353
Patent Literature 5: WO2011/131746

Non Patent Literature

Non Patent Literature 1: Nat Biotechnol., 23, 1073-1078, 2005
Non Patent Literature 2: Eur J Pharm Biopharm, 59 (3), 389-396, 2005
Non Patent Literature 3: mAbs, 4, 653-663, 2012
Non Patent Literature 4: Protein Engineering, 9, 617-621, 1996
Non Patent Literature 5: Nature Biotechnol., 16, 677-681, 1998
Non Patent Literature 6: Proc. Natl. Acad. Sci., 108, 11187-11192, 2011
Non Patent Literature 7: Immunology. 97, 693-698, 1999
Non Patent Literature 8: Science, 317, 1554-1557, 2007
Non Patent Literature 9: Proc. Natl. Acad. Sci., 110, 5145-5150, 2013

SUMMARY OF INVENTION

Technical Problem

The present invention has been made in light of these circumstances, and an object of the present invention is to provide an excellent approach for the efficient and stable production of a heteromultimer with high reaction efficiency, whereby the desired heteromultimer is obtained through the promotion of polypeptide heteromultimerization under a reducing condition.

Solution to Problem

The present inventors have conducted diligent studies on a method for controlling the dissociation and association of Fc regions by selecting polypeptides having the Fc regions as polypeptides to be included in a heteromultimer. As a result, the present inventors have found that: the promotion of the dissociation of Fc regions and the control of the association thereof under a reducing condition can be achieved by the substitution of a particular amino acid present in a heavy chain CH3 region; and a desired heteromeric molecule is formed efficiently as compared with the conventional techniques.

The present invention is based on these findings and specifically provides the following [1] to [25].
[1] A method for producing a heteromultimer, comprising the steps of:
a) providing a homo variant of first polypeptides each having a first antigen-binding activity and comprising an Fc region;
b) providing a homo variant of second polypeptides each having a second antigen-binding activity different from the first antigen-binding activity and comprising an Fc region;
c) incubating the homo variant of the first polypeptides and the homo variant of the second polypeptides together under a reducing condition that allows cysteines in hinge regions to cause disulfide bond isomerization; and
d) obtaining a heteromultimer comprising the first and second polypeptides, wherein
1 to 3 sets of amino acid residues selected from the following amino acid residue sets:
(1) amino acid residues at EU numbering positions 356 and 439,
(2) amino acid residues at EU numbering positions 357 and 370, and
(3) amino acid residues at EU numbering positions 399 and 409 in a CH3 region contained in the Fc region of the first and/or second polypeptide have the same type of charge, and
when the amino acid residues in the same set among the amino acid residue sets (1) to (3) have the same type of charge as each other both in the CH3 region of the first polypeptide and in the CH3 region of the second polypeptide, the amino acid residues in this set in the CH3 region of the second polypeptide have a charge opposite to that of the amino acid residues in this set in the CH3 region of the first polypeptide.
[2] The method according to [1], wherein the step a) in [1] comprises the step of providing a third polypeptide that forms a multimer with the first polypeptide, and the step b) comprises the step of providing a fourth polypeptide that forms a multimer with the second polypeptide.
[3] The method according to [1] or [2], wherein the amino acid residues having the same type of charge are selected from one or more amino acid residues included in any of the following groups (A) and (B):
(A) glutamic acid (E) and aspartic acid (D); and
(B) lysine (K), arginine (R), and histidine (H).
[4] The method according to any one of [1] to [3], wherein the set(s) of the amino acid residues having the same type of charge as each other in each of the first and second polypeptides is any one of the following amino acid residue sets (1) to (4):
(1) amino acid residues at EU numbering positions 356 and 439,
(2) amino acid residues at EU numbering positions 357 and 370,
(3) amino acid residues at EU numbering positions 399 and 409, and
(4) (i) amino acid residues at EU numbering positions 399 and 409 and
(ii) amino acid residues at EU numbering positions 356 and 439.
[5] The method according to any one of [1] to [4], wherein the set(s) of the amino acid residues having the same type of charge as each other in each of the first and second polypeptides is the following amino acid residue sets:
(i) amino acid residues at EU numbering positions 399 and 409 and
(ii) amino acid residues at EU numbering positions 356 and 439.
[6] The method according to any one of [1] to [5], wherein in the first and/or second polypeptide, an amino acid is altered so as to destabilize the stability of the CH3 region of the first and/or second polypeptide.
[7] The method according to any one of [1] to [6], wherein in the first and/or second polypeptide, an amino acid at EU numbering position 397 and/or 392 is altered.
[8] The method according to any one of [1] to [7], wherein the Fc region of the first and/or second polypeptide is of IgG1. IgG2. IgG3, or IgG4 type.
[9] The method according to any one of [1] to [7], wherein the Fc region of the first and/or second polypeptide is a mouse-derived Fc region.
[10] The method for producing a heteromultimer according to [9], wherein
1 to 3 sets of amino acid residues selected from the following amino acid residue sets:
(1) amino acid residues at EU numbering positions 356 and 439,
(2) amino acid residues at EU numbering positions 360 and 371, and (3) amino acid residues at EU numbering positions 399 and 409 in the CH3 region contained in the Fc region of the first and/or second polypeptide have the same type of charge, and when the amino acid residues in the same set among the amino acid residue sets (1) to (3) have the same type of charge as each other both in the CH3 region of the first polypeptide and in the CH3 region of the second polypeptide, the amino acid residues in this set in the CH3 region of the second polypeptide have a charge opposite to that of the amino acid residues in this set in the CH3 region of the first polypeptide.

[11] A method for producing a heteromultimer, comprising the steps of:

a) providing a homo variant of first polypeptides each having a first antigen-binding activity and comprising an Fc region;

b) providing a homo variant of second polypeptides each having a second antigen-binding activity different from the first antigen-binding activity and comprising an Fc region;

c) incubating the homo variant of the first polypeptides and the homo variant of the second polypeptides together under a reducing condition that allows cysteines in hinge regions to cause disulfide bond isomerization; and d) obtaining a heteromultimer comprising the first and second polypeptides, wherein an amino acid at EU numbering position 397 and/or 392 in a CH3 region contained in the Fc region of the first and/or second polypeptide is altered.

[12] The method according to any one of [1] to [11], wherein in the first and/or second polypeptide, the amino acid at EU numbering position 397 is altered to Met (M), Phe (F), or Tyr (Y), and/or the amino acid at EU numbering position 392 is altered to Asp (D), Glu (E), Thr (T), Val (V), or Ile (I).

[13] The method according to any one of [1] to [12], wherein in the first and/or second polypeptide, the amino acid at EU numbering position 397 is altered to Phe (F) or Tyr (Y).

[14] The method according to any one of [1] to [13], wherein in the first polypeptide, the amino acid at EU numbering position 356 is altered to Lys (K), and the amino acid at EU numbering position 397 is altered to Phe (F) or Tyr (Y); and in the second polypeptide, the amino acid at EU numbering position 397 is altered to Phe (F) or Tyr (Y), and the amino acid at EU numbering position 439 is altered to Glu (E).

[15] The method according to any one of [1] to [14], wherein the steps a) and b) are carried out by mixing a cell line producing the homo variant of the first polypeptides with a cell line producing the homo variant of the second polypeptides, and the step c) is carried out in the culture supernatant.

[16] The method according to any one of [1] to [15], wherein the heteromultimer is a multispecific antibody or a hetero-Fc fusion protein.

[17] The method according to any one of [1] to [16], wherein the heteromultimer is a bispecific antibody.

[18] The method according to any one of [1] to [17], wherein the step c) described in [1] or [11] involves contact with a reducing agent.

[19] The method according to [18], wherein the step c) involves the addition of an active substance selected from the group consisting of glutathione, L-cysteine, dithiothreitol, β-mercapto-ethanol, TCEP, and 2-MEA.

[20] The method according to [19], wherein the step c) involves the addition of an active substance selected from glutathione and 2-MEA.

[21] A heteromultimer produced by a method according to any one of [1] to [20].

[22] The heteromultimer according to [21], wherein the heteromultimer is a bispecific antibody.

[23] A composition comprising a heteromultimer according to [21] or [22] and a pharmaceutically acceptable carrier.

[24] A heteromultimer comprising a first polypeptide having a first antigen-binding activity and comprising a first Fc region, and a second polypeptide having a second antigen-binding activity different from the first antigen-binding activity and comprising a second Fc region, the heteromultimer being obtained by incubating a homo variant of the first polypeptides and a homo variant of the second polypeptides together under a reducing condition that allows cysteines in hinge regions to cause disulfide bond isomerization, wherein 1 to 3 sets of amino acid residues in selected from the following amino acid residue sets:

(1) amino acid residues at EU numbering positions 356 and 439, (2) amino acid residues at EU numbering positions 357 and 370, and (3) amino acid residues at EU numbering positions 399 and 409 in a CH3 region contained in the Fc region of the first and/or second polypeptide have the same type of charge, when the amino acid residues in the same set among the amino acid residue sets (1) to (3) have the same type of charge as each other both in the CH3 region of the first polypeptide and in the CH3 region of the second polypeptide, the amino acid residues in this set in the CH3 region of the second polypeptide have a charge opposite to that of the amino acid residues in this set in the CH3 region of the first polypeptide, and in the first and/or second polypeptide, an amino acid is altered so as to destabilize the stability of the CH3 region of the first and/or second polypeptide.

[25] A heteromultimer produced by a method comprising the steps of:

a) providing a homo variant of first polypeptides each having a first antigen-binding activity and comprising an Fc region;

b) providing a homo variant of second polypeptides each having a second antigen-binding activity different from the first antigen-binding activity and comprising an Fc region;

c) incubating the homo variant of the first polypeptides and the homo variant of the second polypeptides together under a reducing condition that allows cysteines in hinge regions to cause disulfide bond isomerization; and d) obtaining a heteromultimer comprising the first and second polypeptides, wherein 1 to 3 sets of amino acid residues selected from the following amino acid residue sets:

(1) amino acid residues at EU numbering positions 356 and 439, (2) amino acid residues at EU numbering positions 357 and 370, and (3) amino acid residues at EU numbering positions 399 and 409 in a CH3 region contained in the Fc region of the first and/or second polypeptide have the same type of charge, when the amino acid residues in the same set among the amino acid residue sets (1) to (3) have the same type of charge as each other both in the CH3 region of the first polypeptide and in the CH3 region of the second polypeptide, the amino acid residues in this set in the CH3 region of the second polypeptide have a charge opposite to that of the amino acid residues in this set in the CH3 region of the first polypeptide, and in the first and/or second polypeptide, an amino acid is altered so as to destabilize the stability of the CH3 region of the first and/or second polypeptide.

Advantageous Effects of Invention

According to the present invention, the promotion of the dissociation of Fc regions and the control of the association thereof under a reducing condition can be achieved by the substitution of a particular amino acid present in a heavy chain CH3 region. A production method for efficiently forming a desired heteromeric molecule as compared with the conventional techniques can be provided.

By use of the method of the present invention, convenience in the purification of a bispecific antibody can be improved, and lot-to-lot variation can be minimized, as compared with the conventional techniques.

A feature of the method for producing a heteromultimer according to the present invention is to alter an amino acid residue in a heavy chain CH3 region. Dissociation and association between polypeptides are promoted by introducing the amino acid residue alteration of the present invention into this region. As a result, a desired heteromultimer can be efficiently obtained as compared with the conventional techniques.

BRIEF DESCRIPTION OF DRAWINGS

FIG. 1 is a diagram showing results of analyzing a Fab arm exchange reaction product by ion-exchange chromatography. In the diagram. "BiAb" denotes purified bispecific antibody; "H54 homo" denotes a monoclonal antibody having variable regions H54/L28; and "MRA homo" denotes a monoclonal antibody having variable regions MRAH/MRAL. The numeric values indicated by percentage in the diagram represent the rate of bispecific antibody formation and were calculated by dividing the area of a peak corresponding to the bispecific antibody by the area of all antibodies present in the system, followed by multiplication by 100.

FIG. 2 is a diagram showing results of analyzing a Fab arm exchange reaction product by ion-exchange chromatography. This diagram shows results of the reaction under 3 types of reducing conditions using MRAH-G1drP1/MRAL-k0 and H54-G1drN1/L28-k0 as homo variants. The numeric values indicated by percentage in the diagram represent the rate of bispecific antibody formation and were calculated by dividing the area of a peak corresponding to the bispecific antibody by the area of all antibodies present in the system, followed by multiplication by 100.

FIG. 3 is a diagram showing the correlation between the rate of bispecific antibody formation in Fab arm exchange using 5 mM GSH as a reducing agent and the stability of CH3 of the homo variant used. In the diagram, the phrase "Value of higher Tm of CH3 in two types of homo variants" means Tm of CH3 in a homo variant having higher Tm of CH3, i.e., having more stable CH3, between two homo variants used in the reaction.

FIG. 4 is a diagram showing the conformation of human IgG1 (PDB code: 3DO3) at and around V397.

FIG. 5 is a diagram showing the correlation between the rate of bispecific antibody formation in Fab arm exchange using 25 mM 2MEA as a reducing agent and the stability of CH3 of the homo variant used. In the diagram, the phrase "Value of higher Tm of CH3 in two types of homo variants" means Tm of CH3 in a homo variant having higher Tm of CH3, i.e., having more stable CH3, between two homo variants used in the reaction.

FIG. 6 is a diagram showing results of analyzing a Fab arm exchange reaction product by ion-exchange chromatography. This diagram shows results of carrying out the reaction for different reaction times using MRAH-G1dP17/MRAL-k0 and H54-G1dN17/L28-k0 as homo variants. The numeric values indicated by percentage in the diagram represent the rate of bispecific antibody formation and were calculated by dividing the area of a peak corresponding to the bispecific antibody by the area of all antibodies present in the system, followed by multiplication by 100.

FIG. 7 is a diagram showing results of analyzing a Fab arm exchange reaction product by ion-exchange chromatography. This diagram shows results of the reaction in a cell culture supernatant using MRAH-G1mrP1/MRAL-k0 and H54-G1mrN1/L28-k0 as homo variants. The numeric values indicated by percentage in the diagram represent the rate of bispecific antibody formation and were calculated by dividing the area of a peak corresponding to the bispecific antibody by the area of all antibodies present in the system, followed by multiplication by 100.

FIG. 8 is a diagram showing the conformation of mouse IgG1 (PDB code: IGY) at and around the interacting interface between the CH3 domains.

FIG. 9 is a diagram showing results of analyzing a mouse IgG-type Fab arm exchange reaction product by CE-IEF. The numeric values indicated by percentage in the diagram represent the rate of bispecific antibody formation and were calculated by dividing the area of a peak corresponding to the bispecific antibody by the area of all antibodies present in the system, followed by multiplication by 100.

FIG. 10 is a diagram showing the comparison of the cytotoxic activity of an anti-human glypican 3/anti-human CD3 bispecific antibody. A bispecific antibody prepared using human IgG-type Fab arm exchange (FIG. 10-1) or mouse IgG-type Fab arm exchange (FIG. 10-2) was compared with a bispecific antibody prepared by CrossMab technology.

FIG. 11 is a diagram showing change in concentration in blood of an anti-human glypican 3/anti-human CD3 bispecific antibody prepared by human IgG-type Fab arm exchange and a bispecific antibody prepared by Knobs-into-Holes technology in normal mice.

FIG. 12 is a diagram showing change in concentration in blood of an anti-human IL-6 receptor antibody prepared by mouse IgG-type Fab arm exchange and an anti-human IL-6 receptor antibody having the sequence of naturally occurring mouse IgG1.

DESCRIPTION OF EMBODIMENTS

The present invention relates to a method for producing a desired heteromultimer by altering an amino acid residue in a heavy chain CH3 region in order to promote the dissociation under a reducing condition of the respective homo variants of polypeptides each having a first antigen-binding activity and polypeptides each having a second antigen-binding activity different from the first antigen-binding activity and to control the hetero-association thereof under the reducing condition. The present invention further relates to a method for selecting a desired heteromultimer.

DEFINITION OF TERMS

In the present invention, the "polypeptide" refers to a polypeptide (Fc region-containing polypeptide) or a protein (Fc region-containing protein) comprising a heavy chain Fc region in the amino acid sequence. The polypeptide is usually an organism-derived polypeptide, though the polypeptide of the present invention is not particularly limited thereto. The polypeptide may be, for example, a polypeptide consisting of an artificially designed sequence.

Alternatively, a natural polypeptide, a synthetic polypeptide, a recombinant polypeptide, or the like may be used. In addition, fragments of these polypeptides are also included in the polypeptide of the present invention.

In the present specification, the "antibody" refers to a natural immunoglobulin or an immunoglobulin produced by partial or complete synthesis. The antibody may be isolated from a natural resource (e.g., plasma or serum containing naturally occurring antibodies) or the culture supernatant of antibody-producing hybridoma cells or may be partially or completely synthesized by use of an approach such as gene recombination. Preferred examples of the antibody include isotypes of immunoglobulins and subclasses of these isotypes. Nine types of classes (isotypes), i.e., IgG1, IgG2, IgG3, IgG4, IgA1, IgA2, IgD, IgE, and IgM, are known as human immunoglobulins. Four types of classes, i.e., IgG1, IgG2a, IgG2b, and IgG3, are known as mouse immunoglobulins. Of these isotypes, human immunoglobulins IgG1, IgG2, IgG3, and IgG4 and mouse immunoglobulins IgG1, IgG2a, IgG2b, and IgG3 can be included in the antibody of the present invention. IgG1 is preferred as a mouse immunoglobulin. A plurality of allotype sequences based on gene polymorphism are described as human IgG1, human IgG2, human IgG3, and human IgG4 constant regions in Sequences of proteins of immunological interest, NIH Publication No. 91-3242. Any of these sequences can be used in the present invention. Particularly, an amino acid sequence from EU numbering positions 356 to 358 in the sequence of human IgG1 may be DEL or may be EEM. A plurality of allotype sequences based on gene polymorphism are described as a human Igκ (kappa) constant region and a human Igλ (lambda) constant region in Sequences of proteins of immunological interest, NIH Publication No. 91-3242. Any of these sequences can be used in the present invention.

The term "Fc region" is used for defining the C-terminal region of an immunoglobulin heavy chain and includes a natural Fc region sequence and a variant Fc region. Although the boundary of the Fc region of an immunoglobulin heavy chain may vary, the Fc region refers to a region comprising hinges or a portion thereof and CH2 and CH3 domains in an antibody molecule. The heavy chain Fc region of human IgG is usually defined as extending from the amino acid residue Cys226 to the carboxyl terminus of the Fc region, though the Fc region of the present invention is not limited thereto. The immunoglobulin Fc region contains two constant regions, i.e., CH2 and CH3. The "CH2" domain of the human IgG Fc region usually extends from amino acid 231 to amino acid 340. The "CH3" domain extends from the carboxyl terminus of the Fc region to before the CH2 region, i.e., extends from amino acid 341 to about amino acid 447 of IgG.

The Fc region can be preferably obtained by the partial digestion of an IgG monoclonal antibody or the like with a proteolytic enzyme such as pepsin followed by the re-elution of a fraction adsorbed on a protein A or protein G column. Such a proteolytic enzyme is not particularly limited as long as the enzyme is capable of digesting a whole antibody so as to restrictively form Fab or F(ab')2 under appropriately set reaction conditions (e.g., pH) of the enzyme. Examples thereof can include pepsin and papain.

The position of each alteration site is represented using the EU numbering system (Kabat E A et al., 1991. Sequences of Proteins of Immunological Interest. NIH).

In the present invention, the "association" of polypeptides can refer to, for example, a state where two or more polypeptide regions interact with each other.

In the present invention, the phrase "controlling association" refers to control so as to attain a desired associated state and more specifically refers to control so as to prevent undesired association between polypeptides (preferably, association between polypeptides having identical amino acid sequences).

In the present invention, the "interface" usually refers to the location of association at which polypeptides associate (interact) with each other. Amino acid residues that form the interface are usually one or more amino acid residues contained in the polypeptide regions subjected to this association and are more preferably amino acid residues that are placed close during the association to participate in the interaction. The interaction specifically includes, for example, the case where the amino acid residues that are placed close during the association form a hydrogen bond, an electrostatic interaction, or a salt bridge therebetween.

In the present invention, the "homo variant" of polypeptides refers to the associated form of polypeptides having identical amino acid sequences.

In the present invention, the "heteromer" of polypeptides refers to the associated form of a first polypeptide and a second polypeptide differing in amino acid sequence by at least one amino acid residue from the first polypeptide.

In the present invention, the "dissociation" between polypeptides refers to a state where the associated form of two or more polypeptides in the polypeptide homo variant is separated into the single polypeptides.

In the present invention, the "heteromultimer" refers to a protein multimer that is constituted by plural types of polypeptides capable of associating with each other. More specifically, the "heteromultimer" has at least a first polypeptide and a second polypeptide. In this context, the second polypeptide is a molecule differing in amino acid sequence by at least one amino acid residue from the first polypeptide. The heteromultimer preferably has antigen-binding activities against at least two different types of ligands, antigens, receptors, or substrates, etc., though the heteromultimer of the present invention is not particularly limited thereto. The heteromultimer may contain an additional type of polypeptide in addition to the "heterodimer" formed by the first and second polypeptides. Specifically, the "heteromultimer" of the present invention is not limited to the heterodimer and also includes, for example, a heterotrimer and a heterotetramer.

In the polypeptide multimer of the present invention comprising the first polypeptide, the second polypeptide, and one or two third polypeptides, the first polypeptide and the second polypeptide can respectively form multimers (dimers) with the third polypeptides. Furthermore, the formed dimers can form a multimer (tetramer) with each other. The two third polypeptides may have completely identical amino acid sequences (which may have a binding activity against the same antigen). Alternatively, the two third polypeptides may have identical amino acid sequences, but have two or more activities (which may have, for example, binding activities against two or more different antigens). In the case of one third polypeptide, this third polypeptide can form a dimer with any one of the first polypeptide and the second polypeptide to form a polypeptide multimer.

In the polypeptide multimer of the present invention, the first polypeptide and the second polypeptide preferably have binding activities against different antigens. On the other hand, the third polypeptide may be a polypeptide having a binding activity against the same antigen as that of either of the first polypeptide or the second polypeptide, or both. Alternatively, the third polypeptide may be a polypeptide having a binding activity against an antigen different from that of the first polypeptide and the second polypeptide.

Alternatively, the polypeptide multimer of the present invention may be a polypeptide multimer comprising the first polypeptide, the second polypeptide, the third polypeptide, and a fourth polypeptide. In such a polypeptide multimer, the first polypeptide and the second polypeptide can form multimers (dimers) with the third polypeptide and the fourth polypeptide, respectively. For example, a disulfide bond can be formed between the first polypeptide and the third polypeptide and between the second polypeptide and the fourth polypeptide to form dimers.

In the polypeptide multimer of the present invention, the first polypeptide and the second polypeptide preferably have binding activities against different antigens. On the other hand, the third polypeptide may be a polypeptide having a binding activity against the same antigen as that of either of the first polypeptide or the second polypeptide, or both. Alternatively, the third polypeptide may be a polypeptide having a binding activity against an antigen different from that of the first polypeptide and the second polypeptide. The fourth polypeptide may be a polypeptide having a binding activity against the same antigen as that of either of the first polypeptide or the second polypeptide, or both. Alternatively, the fourth polypeptide may be a polypeptide having a binding activity against an antigen different from that of the first polypeptide and the second polypeptide.

When the "heteromultimer" according to the present invention is a bispecific antibody, the first polypeptide and the second polypeptide may be, for example, a polypeptide comprising the amino acid sequence of an antibody heavy chain against antigen A and a polypeptide comprising the amino acid sequence of an antibody heavy chain against antigen B, respectively. In this case, the third polypeptide can be a polypeptide comprising the amino acid sequence of an antibody light chain against the antigen A, while the fourth polypeptide can be a polypeptide comprising the amino acid sequence of an antibody light chain against the antigen B.

In the present invention, the "polypeptide having an antigen-binding activity" refers to a peptide or a protein of 5 or more amino acids in length having a domain (or region) capable of binding to a protein or a peptide such as an antigen or a ligand, and includes, for example, an antibody heavy chain or light chain variable region, a receptor, a fusion peptide of a receptor and an Fc region, a scaffold, and their fragments. Specifically, the polypeptide having an antigen-binding activity can comprise the amino acid sequence of an antibody variable region, a receptor, a fusion peptide of a receptor and an Fc region, a scaffold, or any of their fragments.

Any polypeptide can be used as the scaffold as long as the polypeptide is conformationally stable and can bind to at least one antigen. Examples of such a polypeptide include, but are not limited to, antibody variable region fragments, fibronectin, protein A domains, LDL receptor A domains, and lipocalin as well as molecules described in Nygren et al. (Current Opinion in Structural Biology, 7: 463-469 (1997); and Journal of Immunol Methods, 290: 3-28 (2004)), Binz et al. (Nature Biotech 23: 1257-1266 (2005)), and Hosse et al. (Protein Science 15: 14-27 (2006)).

Method for obtaining the antibody variable region, the receptor, the fusion peptide of a receptor and an Fc region, the scaffold, and their fragments are well known to those skilled in the art. A polypeptide comprising the amino acid sequence of such a region and the amino acid sequence of an antibody light chain constant region can also be used.

In the present invention, the "reducing condition" refers to a condition or an environment where cysteine residues forming an inter-heavy chain disulfide bond in the heavy chain hinge regions are more likely to be reduced than oxidized. The reducing condition preferably refers to a condition or an environment that allows cysteines in hinge regions to cause disulfide bond isomerization between the heavy chains, and particularly preferably refers to a condition or an environment that allows cysteines in heavy chain hinge regions to cause disulfide bond isomerization without causing significant disulfide bond isomerization of cysteines outside the hinge regions (i.e., while conserving the disulfide bond between the heavy chain and the light chain). In the present invention, for example, the time of incubating together the homo variant of the first polypeptides each comprising an Fc region and the second polypeptides each comprising an Fc region under the reducing condition can be appropriately set by those skilled in the art.

In the present invention, the "reducing agent" refers to a compound that reduces a molecule in the environment, i.e., a compound that shifts a molecule into a state where the molecule has been more reduced or is being more reduced in the environment. The reducing agent acts by donating an electron so that the reducing agent itself becomes an oxidized state after reduction of a substrate. Thus, the reducing agent is an active substance donating an electron. Examples of the reducing agent include dithiothreitol (DTT), mercaptoethanol, cysteine, thioglycolic acid, cysteamine (2-mercaptoethylamine: 2-MEA), glutathione (GSH), TCEP (tris (2-carboxyethyl)phosphine), and sodium borohydride.

In the present invention, the "inter-heavy chain disulfide bond isomerization" refers to the exchange of the disulfide bond, i.e., the reorganization of the disulfide bond, between cysteines contained in different heavy chains.

The "disulfide bond formation" refers to the process of forming a covalent bond between two cysteines present in one or two polypeptides. This bond is schematized by "—S—S—".

The "reduction of the disulfide bond" refers to the process of cleaving the disulfide bond into two thiol groups (—SH groups).

In the present invention, the term "FcγR" or "FcgR" refers to an Fcγ receptor which is a receptor capable of binding to the Fc region of an IgG1, IgG2, IgG3, or IgG4 monoclonal antibody, and means any member of the protein family substantially encoded by Fcγ receptor genes. In humans, this family includes, for example: FcγRI (CD64) including isoforms FcγRIa, FcγRIb, and FcγRIc; FcγRII (CD32) including isoforms FcγRIIa (including allotypes H131 (H type) and R131 (R type)), FcγRIIb (including FcγRIIb-1 and FcγRIIb-2), and FcγRIIc; and FcγRIII (CD16) including isoforms FcγRIIIa (including allotypes V158 and F158) and FcγRIIIb (including allotypes FcγRIIIb-NA1 and FcγRIIIb-NA2); and any yet-to-be-discovered human FcγR or FcγR isoform or allotype. The FcγR includes those derived from humans, mice, rats, rabbits, and monkeys. The FcγR is not limited to these molecules and may be derived from any organism. The mouse FcγRs include, for example, FcγRI (CD64), FcγRII (CD32), FcγRIII (CD16) and FcγRIII-2

(CD16-2), and FcγRIV, and any yet-to-be-discovered mouse FcγR or FcγR isoform or allotype.

Method for Producing Heteromultimer by Alteration Using Charge Repulsion of Amino Acid Residues In a preferred embodiment, the method of the present invention is a method for producing a heteromer of desired polypeptides by altering amino acid residues that form the interface between polypeptides in order to promote the dissociation of the homo variants of the first and second polypeptides for a heteromultimer capable of forming two or more types of multimers and to control association between the polypeptides constituting one or more types of multimers.

The polypeptide having a first antigen-binding activity and the polypeptide having a second antigen-binding activity according to the present invention can each comprise the amino acid sequence of an antibody heavy chain constant region or the amino acid sequence of an antibody Fc region. Examples of the amino acid sequence of the antibody Fc region or the antibody heavy chain constant region include, but are not limited to, the amino acid sequences of human IgG-type constant regions or Fc regions. The IgG-type constant regions or Fc regions can be any of naturally occurring isotypes IgG1, IgG2, IgG3, and IgG4. Alternatively, their altered forms may be used. Lysine at EU numbering position 447 and glycine at EU numbering position 446 in the Fc region may be removed by the recombinant gene manipulation of nucleic acids encoding these amino acids.

The polypeptide having a third antigen-binding activity and the polypeptide having a fourth antigen-binding activity according to the present invention can each comprise the amino acid sequence of an antibody light chain constant region. Examples of the amino acid sequence of the antibody light chain constant region can include, but are not limited to, the amino acid sequences of human kappa- and human lambda-type constant regions. Alternatively, their altered forms may be used.

The polypeptide having an antigen-binding activity according to the present invention can comprise the amino acid sequence of an antibody variable region (e.g., the amino acid sequences of CDR1, CDR2. CDR3, FR1. FR2, FR3, and FR4).

In a preferred embodiment of the method for controlling dissociation and/or association between polypeptides according to the present invention, examples of the method include a method which involves introducing charge repulsion to the interface between the constant regions of heavy chains to suppress the association between the heavy chains. Examples of the amino acid residues coming in contact with each other at the interface between the heavy chain constant regions can include pairs at positions 356 and 439, at positions 357 and 370, and at positions 399 and 409 in CH3 regions. The sites in the heavy chain constant regions are represented by the EU numbering system.

As shown in Examples mentioned later, the method of the present invention is carried out by the alteration of these amino acid residues to control dissociation and/or association between heavy chain polypeptides. As a result, the desired heteromultimer can be preferentially obtained. In a preferred aspect, the present invention provides a polypeptide which is an antibody or an Fc region-containing protein (e.g., an IgG-type antibody, minibody (Alt M et al., FEBS Letters 199, 9; 454: 90-94), and immunoadhesin (Non Patent Literature 2)) comprising two or more types of heavy chain Fc regions, wherein 1 to 3 sets of amino acid residues sets selected from the following amino acid residue sets (1) to (3):

(1) amino acid residues at EU numbering positions 356 and 439, (2) amino acid residues at EU numbering positions 357 and 370, and (3) amino acid residues at EU numbering positions 399 and 409 in a first heavy chain Fc region have the same type of charge.

The present invention further provides a polypeptide wherein 1 to 3 sets of amino acid residues selected from the amino acid residue sets (1) to (3) in a second heavy chain Fc region different from the first heavy chain Fc region have a charge opposite to that of the counterpart amino acid residues having the same type of charge as each other in the corresponding set(s) among the amino acid residue sets (1) to (3) in the first heavy chain Fc region.

In the polypeptide, the "amino acid residues having a charge" are preferably selected from, for example, amino acid residues included in any of the following groups (a) and (b):

(a) glutamic acid (E) and aspartic acid (D); and
(b) lysine (K), arginine (R), and histidine (H).

In the polypeptide, the phrase "having the same type of charge" means that, for example, all of two or more amino acid residues are amino acid residues included in any one of the groups (a) and (b). The phrase "having a charge opposite" means that, for example, when at least one amino acid residue among two or more amino acid residues is an amino acid residue included in any one of the groups (a) and (b), the remaining amino acid residue(s) is an amino acid residue included in the other group.

In a preferred embodiment, the polypeptide may have the cross-link between the first heavy chain CH3 region and the second heavy chain CH3 region through a disulfide bond.

In the present invention, examples of the "association interface-controlling alteration" include the following alterations:

(1) the alteration of Asp (D) at EU numbering position 356 in the first heavy chain Fc region to Lys (K), Arg (R), or His (H), and the alteration of Lys (K) at EU numbering position 439 in the second heavy chain Fc region to Glu (E) or Asp (D);

(2) the alteration of Glu (E) at EU numbering position 357 in the first heavy chain Fc region to Lys (K), Arg (R), or His (H), and the alteration of Lys (K) at EU numbering position 370 in the second heavy chain Fc region to Glu (E) or Asp (D); and (3) the alteration of Asp (D) at EU numbering position 399 in the first heavy chain Fc region to Lys (K), Arg (R), or His (H), and the alteration of Lys (K) at EU numbering position 409 in the second heavy chain Fc region to Glu (E) or Asp (D).

In a non-limiting embodiment, the method for controlling dissociation and/or association between polypeptides according to the present invention is associated with a method for producing a mouse heteromultimer. In a preferred embodiment of this method, examples of the method include a method which involves introducing charge repulsion to the interface between the constant regions of heavy chains to suppress the association between the heavy chains. In the method, examples of the amino acid residues coming in contact with each other at the interface between the heavy chain constant regions can include pairs at positions 356 and 439, at positions 360 and 371, and at positions 399 and 409 in CH3 regions. The sites in the heavy chain constant regions are represented by the EU numbering system.

As shown in Examples mentioned later, the method of the present invention is carried out by the alteration of these amino acid residues in the mouse-derived CH3 regions to control dissociation and/or association between heavy chain polypeptides. As a result, the desired heteromultimer can be preferentially obtained. In a preferred aspect, the present invention provides a polypeptide which is an antibody or an Fc region-containing protein (e.g., an IgG-type antibody, minibody (Alt M et al., FEBS Letters 1999; 454: 90-94), and immunoadhesin (Non Patent Literature 2)) comprising two or more types of heavy chain Fc regions, wherein 1 to 3 sets of amino acid residues selected from the following amino acid residue sets (1) to (3):
(1) amino acid residues at EU numbering positions 356 and 439,
(2) amino acid residues at EU numbering positions 360 and 371, and
(3) amino acid residues at EU numbering positions 399 and 409 in a first heavy chain Fc region have the same type of charge.

The present invention further provides a polypeptide wherein 1 to 3 sets of amino acid residues selected from the amino acid residue sets (1) to (3) in a second heavy chain Fc region different from the first heavy chain Fc region have a charge opposite to that of the counterpart amino acid residues having the same type of charge as each other in the corresponding set(s) among the amino acid residue sets (1) to (3) in the first heavy chain Fc region.

In the polypeptide, the "amino acid residues having a charge" are preferably selected from, for example, amino acid residues included in any of the following groups (a) and (b):
(a) glutamic acid (E) and aspartic acid (D); and
(b) lysine (K), arginine (R), and histidine (H).

In the polypeptide, the phrase "having the same type of charge" means that, for example, all of two or more amino acid residues are amino acid residues included in any one of the groups (a) and (b). The phrase "having a charge opposite" means that, for example, when at least one amino acid residue among two or more amino acid residues is an amino acid residue included in any one of the groups (a) and (b), the remaining amino acid residue(s) is an amino acid residue included in the other group.

In a preferred embodiment, the polypeptide may have the cross-link between the first heavy chain CH3 region and the second heavy chain CH3 region through a disulfide bond.

In the present invention, examples of the "association interface-controlling alteration" include the following alterations:
(1) the alteration of Asp (D) at EU numbering position 356 in the first heavy chain Fc region to Lys (K), Arg (R), or His (H), and the alteration of Lys (K) at EU numbering position 439 in the second heavy chain Fc region to Glu (E) or Asp (D);
(2) the alteration of Glu (E) at EU numbering position 360 in the first heavy chain Fc region to Lys (K), Arg (R), or His (H), and the alteration of Lys (K) at EU numbering position 371 in the second heavy chain Fc region to Glu (E) or Asp (D); and
(3) the alteration of Asp (D) at EU numbering position 399 in the first heavy chain Fc region to Lys (K), Arg (R), or His (H), and the alteration of Lys (K) at EU numbering position 409 in the second heavy chain Fc region to Glu (E) or Asp (D).

The amino acid residues to be "altered" according to the present invention are not limited to the amino acid residues in the polypeptide constant regions. Those skilled in the art can find amino acid residues that form the interface in a polypeptide variant or a heteromultimer by homology modeling or the like using commercially available software, and can alter amino acid residues at the sites so as to control association.

The "alteration" of amino acid residues in the method of the present invention specifically refers to, for example, the substitution of the original amino acid residues by other amino acid residues, the deletion of the original amino acid residues, or the addition of a new amino acid residue and preferably refers to the substitution of the original amino acid residues by other amino acid residues.

Method for Producing Heteromultimer by Amino Acid Alteration at Position 397 and/or 392

In a more preferred embodiment of the method for controlling dissociation and/or association between polypeptides according to the present invention, the method is a method comprising introducing a mutation of an amino acid residue to a heavy chain Fc region so as to destabilize the stability of the heavy chain CH3 region. This method may further comprise the optional step of introducing the aforementioned amino acid alteration related to interface control using charge repulsion or the like.

In the present invention, the "destabilization of the stability of the CH3 region" means that a polypeptide homo variant with at least one or more amino acid residues altered in the Fc region becomes more susceptible to separation into the single polypeptides than the unaltered polypeptide homo variant.

In the present invention, the "destabilization of the stability of the CH3 region" preferably means that the intermediate temperature of thermal denaturation (Tm) of the heavy chain CH3 region having the altered amino acid residues at pH 7.4 is 72.5° C. or lower, 72.0° C. or lower, 71.5° C. or lower, 71.0° C. or lower, or 70.5° C. or lower, more preferably 70.4° C. or lower, 70.3° C. or lower, 70.2° C. or lower, 70.1° C. or lower, 70.0° C. or lower, 69.9° C. or lower, 69.8° C. or lower, 69.7° C. or lower, 69.6° C. or lower, 69.5° C. or lower, 69.0° C. or lower, 68.5° C. or lower, 68.0° C. or lower, or 67.5° C. or lower.

The Tm of the heavy chain CH3 region can be measured by, for example, a method described in Reference Example 3 in the present specification. A buffer solution or the like for use in this measurement can be appropriately selected.

In a further preferred embodiment of the method for controlling dissociation and/or association between polypeptides according to the present invention, the method is a method comprising introducing a mutation to an amino acid residue at EU numbering position 397 and/or 392 in a heavy chain CH3 region. This method may further comprise the optional step of introducing the aforementioned amino acid alteration related to interface control using charge repulsion or the like.

In a non-limiting embodiment of the present invention, a mutation can also be introduced to an amino acid residue at EU numbering position 397 and/or 392 in a heavy chain CH3 region in the method for controlling dissociation and/or association between mouse-derived polypeptides. This method may further comprise the optional step of introducing the aforementioned amino acid alteration related to interface control using charge repulsion or the like.

The amino acid residue for the introduction of a mutation at position 397 is preferably altered to an amino acid having a bulky side chain or an amino acid having a branched side chain.

The amino acid residue for the introduction of a mutation at position 392 is preferably altered to an amino acid having a negative charge, an amino acid having a bulky side chain, or an amino acid having a branched side chain.

In the present invention, examples of the "amino acid having a bulky side chain" include Met (M), Phe (F), Tyr (Y), Val (V), Leu (L), Ile (I), Trp (W), Arg (R), His (H), Glu (E), Lys (K), Gin (Q), Asp (D), Asn (N), Cys (C), and Thr (T) and preferably include Met (M), Phe (F), Thr (T), and Tyr (Y).

In the present invention, examples of the "amino acid having a branched side chain" include Val (V), Ile (I), and Leu (L) and preferably include Val (V) and Ile (I).

In the present invention, examples of the "amino acid having a negative charge" include Asp (D) and Glu (E).

In the present invention, preferred examples of the "heteromultimer" can include multispecific antibodies and hetero-fusion proteins.

In a non-limiting aspect, the present invention provides the amino acid alteration of a heteromultimer to enhance binding to FcγR. Preferred examples of the amino acid alteration site include, but are not limited to, an amino acid at EU numbering position 397. The amino acid residue for the introduction of a mutation at position 397 is preferably altered to an amino acid having a bulky side chain or an amino acid having a branched side chain.

In the present invention, more preferred examples of the multispecific antibody include IgG type, scFv-IgG, Tandem scFv-Fc, DVD-Ig, Diabody-Fc, Single chain Diabody-Fc, IgG-scFv, sVD-IgG, Tandemab, scFv light chain C-terminal fusion, Tri-specific C-terminal fusion, Tri-specific N-terminal fusion, and IgG-Fab (Bispecific Antibodies, Roland E. Kontermann, 2011, WO2010034441, and WO02010145792).

In the present invention, the term "antibody" is used in the broadest sense and includes monoclonal antibodies, polyclonal antibodies, and antibody variants (chimeric antibodies, humanized antibodies, low-molecular antibodies (also including antibody fragments), multispecific antibodies, etc.) as long as the antibody exhibits a desired biological activity. In the present invention, the "antibody" may be a polypeptide or may be a heteromultimer. The antibody is preferably a monoclonal antibody, a chimeric antibody, a humanized antibody, or a low-molecular antibody such as an antibody fragment. In the present invention, the method for controlling dissociation and/or association according to the present invention can be preferably used for obtaining (preparing) these antibodies.

Preferred examples of the polypeptide or the heteromultimer subjected to the method of the present invention can include a polypeptide or a heteromultimer having an antibody heavy chain variable region and light chain variable region. In a more preferred aspect, the present invention provides a method for controlling the dissociation and/or association of the polypeptide or the heteromultimer of the present invention comprising two or more types of heavy chain variable regions and two or more types of light chain variable regions.

The polypeptide having an antigen-binding activity according to the present invention can comprise the amino acid sequence of an antibody heavy chain or the amino acid sequence of an antibody light chain. More specifically, the polypeptide having a first antigen-binding activity and the polypeptide having a second antigen-binding activity can each comprise the amino acid sequence of an antibody heavy chain. The polypeptide having a third antigen-binding activity and the polypeptide having a fourth antigen-binding activity can each comprise the amino acid sequence of an antibody light chain.

When the polypeptide multimer of interest is a tetramer which is a multimer formed by a dimer formed between the first polypeptide and the third polypeptide and a dimer formed between the second polypeptide and the fourth polypeptide, for example, a polypeptide multimer in which the polypeptides having the first and second antigen-binding activities are polypeptides each comprising the amino acid sequence of an antibody heavy chain while the polypeptides having the third and fourth antigen-binding activities are polypeptides each comprising the amino acid sequence of an antibody light chain can also be used as the polypeptide multimer of the present invention.

Further preferred examples of the multispecific antibody of the present invention can include bispecific antibodies.

In a preferred aspect of the present invention, the present invention relates to, for example, a method for controlling dissociation and/or association as to a bispecific antibody comprising two types of heavy chains (the first polypeptide and the second polypeptide in the polypeptide multimer according to the present invention) and two types of light chains (the third polypeptide and the fourth polypeptide in the polypeptide multimer according to the present invention).

The "bispecific antibody" according to a preferred aspect of the present invention will be described in more detail. The "first polypeptide and the second polypeptide" refer to one (first H chain) of two heavy chains (H chains) constituting the antibody and the other H chain (second H chain) different from the first H chain. In short, any one of the two H chains can be arbitrarily selected as the first H chain, and the other H chain can be set to the second H chain. Likewise, the "third polypeptide and the fourth polypeptide" refer to one (first L chain) of two light chains (L chains) constituting the bispecific antibody and the other L chain (second L chain) different from the first L chain. Any one of the two L chains can be arbitrarily selected as the first L chain, and the other H chain can be set to the second L chain. Usually, the first L chain and the first H chain are derived from the same antibody that recognizes a certain antigen (or epitope). The second L chain and the second H chain are also derived from the same antibody that recognizes a certain antigen (or epitope). In this context, an L-H chain pair formed by the first H chain and L chain is referred to as a first pair (or first HL molecule). An L-H chain pair formed by the second H chain and L chain is referred to as a second pair (or second HL molecule). The first pair and the second pair may recognize the same antigen and preferably recognize different epitopes. In this case, the H chains or the L chains in the first pair and the second pair preferably have amino acid sequences different from each other. When the first pair and the second pair recognize different epitopes, the first pair may recognize an antigen totally different from that of the second pair, or the first pair and the second pair may recognize different sites (different epitopes) on the same antigen (e.g., when the antigen is a heteromeric receptor, the multispecific antibody recognizes different domains constituting the heteromeric receptor; or when the antigen is a monomer, the multispecific antibody recognizes a plural sites in the monomer antigen). Such a molecule usually binds to two antigens, but may have specificities for two or more (e.g., 3 types of) antigens. Alternatively, one of the pairs may recognize an antigen such as a protein, a peptide, a gene, or a sugar, and the other pair may recognize, for example, a cytotoxic substance such as a radioactive substance, a chemotherapeutic agent, or a cell-derived toxin. In the case of preparing a desired antibody having pairs formed by particular H chains and L chains in combination, the particular H chains and L chains can be arbitrarily determined as the first pair and the second pair.

In the present invention, the "fusion protein" refers to a protein in which two or more identical or substantially analogous protein molecules are joined via an Ig hinge region amino acid sequence linker. The prefix "hetero-" is used for describing a fusion protein containing more than one type of proteins. The "hetero-fusion protein" contains, for example, two or more proteins which are one or more residual proteins and one or more different proteins joined together.

The "antibody" according to the present invention includes those obtained by further altering the amino acid sequence of the aforementioned antibody by amino acid substitution, deletion, addition and/or insertion, or chimerization, humanization, etc. The alteration of an amino acid sequence by amino acid substitution, deletion, addition and/or insertion, or humanization, chimerization, etc., can be practiced by a method generally known to those skilled in the art. Likewise, the amino acid sequences of antibody variable regions and constant regions for use in preparing the antibody according to the present invention as a recombinant antibody may be altered by amino acid substitution, deletion, addition and/or insertion, or chimerization, humanization, etc.

The antibody according to the present invention may be an antibody derived from any animal, such as a mouse antibody, a human antibody, a rat antibody, a rabbit antibody, a goat antibody, or a camel antibody. The antibody according to the present invention may be an altered antibody prepared by the substitution of the amino acid sequence of, for example, a chimeric antibody, particularly, a humanized antibody. Alternatively, any antibody such as a modified antibody conjugated with various molecules, an antibody fragment, or a low-molecular antibody can be used.

The "chimeric antibody" is an antibody prepared from a combination of sequences derived from different animals. Examples thereof can include an antibody composed of heavy chain and light chain variable (V) regions of a mouse antibody and heavy chain and light chain constant (C) regions of a human antibody. The preparation of the chimeric antibody is known in the art. The chimeric antibody can be obtained, for example, by: ligating DNAs encoding the antibody V regions with DNAs encoding the human antibody C regions; incorporating the resulting ligation products into expression vectors; and transferring the vectors into hosts for antibody production.

The "humanized antibody", also called reshaped human antibody, is obtained by grafting complementarity-determining regions (CDRs) of an antibody derived from a non-human mammal, for example, a mouse antibody, to CDRs of a human antibody. A method for identifying CDRs is known in the art (Kabat et al., Sequence of Proteins of Immunological Interest (1987), National Institute of Health, Bethesda, Md.; and Chothia et al., Nature (1989) 342: 877). A general gene recombination approach therefor is also known in the art (see European Patent Application Publication No. EP 125023 and WO 96/02576). Accordingly, for example, mouse antibody CDRs are determined by a method known in the art. A DNA encoding an antibody having these CDRs linked to human antibody framework regions (FRs) is obtained. The humanized antibody can be produced in a system using usual expression vectors.

Such a DNA can be synthesized by PCR using several oligonucleotide primers prepared so as to have a portion overlapping the terminal regions of both CDR and FR (see a method described in WO98/13388). The human antibody FRs connected via the CDRs are selected such that the CDRs form a favorable antigen-binding site. If necessary, amino acids in the FRs of antibody variable regions may be altered such that the CDRs of the resulting reshaped human antibody form an appropriate antigen-binding site (Sato et al., Cancer Res. (1993) 53: 851-6). The amino acid residues in the FRs that can be altered include moieties binding directly to an antigen through a noncovalent bond (Amit et al., Science (1986) 233: 747-53), moieties influencing or acting on CDR structures (Chothia et al., J. Mol. Biol. (1987) 196: 901-17), and moieties related to VH-VL interaction (EP239400).

When the antibody according to the present invention is a chimeric antibody or a humanized antibody, human antibody-derived constant regions are preferably used as the C regions of the antibody. For example, Cγ1, Cγ2, Cγ3, or Cγ4 can be used for an H chain, and Cκ or Cλ can be used for an L chain. Also, the human antibody C regions may be modified, if necessary, in order to improve the antibody or the stability of its production. The chimeric antibody according to the present invention preferably comprises variable regions of a non-human mammal-derived antibody and constant regions derived from a human antibody. On the other hand, the humanized antibody preferably comprises CDRs of a non-human mammal-derived antibody and FRs and C regions derived from a human antibody. The constant regions derived from a human antibody have amino acid sequences specific for each isotype such as IgG (IgG1, IgG2, IgG3, or IgG4), IgM, IgA, IgD, or IgE. The constant regions used in the humanized antibody according to the present invention may be constant regions of an antibody belonging to any isotype. Preferably, human IgG constant regions are used, though the constant regions according to the present invention are not limited thereto. The FRs derived from a human antibody used in the humanized antibody are not particularly limited and may be derived from an antibody belonging to any isotype.

The variable regions and the constant regions of the chimeric antibody or the humanized antibody according to the present invention may be altered by deletion, substitution, insertion and/or addition, etc., as long as the resulting antibody exhibits the binding specificity of the original antibody.

The chimeric antibody or the humanized antibody containing a human-derived sequence exhibits reduced antigenicity in a human body and is therefore considered to be useful when administered to humans for a therapeutic purpose or the like.

Combination with Isoelectric Point Alternation Technique, Etc.

In a further preferred embodiment of the present invention, an amino acid mutation that alters the isoelectric point (pI value) of a polypeptide can be introduced to the polypeptide of the present invention to thereby purify or produce the polypeptide multimer having the first to fourth polypeptides of interest with higher purity and higher efficiency (WO2007114325 and US20130171095). For example, a method for hetero-associating polypeptides comprising two types of heavy chain constant regions by altering the CH3 domains of the heavy chain constant regions (which is described in, e.g., Protein Eng. 1996 July; 9 (7): 617-21;

Protein Eng Des Sel. 2010 April; 23 (4): 195-202; J Biol Chem. 2010 Jun. 18; 285 (25): 19637-46; WO2009080254; and US20130195849) and a method for promoting the association of a heavy chain and a light chain in a particular combination (which is described in, e.g., WO2009080251, WO2009080252, and WO2009080253) may be used for the amino acid mutation that is introduced for promoting association between polypeptides.

Combination with Technique Related to Target Tissue-Specific Antigen-Binding Molecule In a non-limiting embodiment of the present invention, the method of the present invention can be combined with an antibody technique for dissociation from or binding to an antigen in a concentration-dependent manner of a molecule present specifically for a target tissue (WO2013/180200).

Combination with Other Constant Region and/or Variable Region Alteration Techniques In a non-limiting embodiment of the present invention, the method of the present invention can be combined with a technique of altering constant regions with the aim of enhancing binding to FcγR (WO2013047752).

In an alternative embodiment, examples of the combination of the method of the present invention with other constant region alteration techniques include its combination with a technique of controlling binding to a complement. Any complement component can be used as the complement as long as the complement is a polypeptide that forms a complement cascade. Preferred examples of the complement include complement components C1q, C1r, and C1s involved in the binding of opsonin. An Fc region having a higher binding activity against a complement than that of a naturally occurring Fc region against the complement can be prepared by the amino acid alteration of the naturally occurring Fc region. In this context, the naturally occurring Fc region refers to a human IgG1, IgG2, IgG3, or IgG4 Fc region. Whether or not the Fc region has a higher binding activity against a complement than that of a naturally occurring Fc region against the complement can be appropriately confirmed by use of an immunological method known in the art such as FACS or ELISA. The term "alteration of amino acid(s)" or "amino acid alteration" of the Fc region includes the alteration of the amino acid sequence of a starting Fc region to a different amino acid sequence. Any Fc region can be used as the starting domain as long as the resulting modified or altered form of the starting Fc region can bind to the complement in a neutral pH region. An Fc region prepared by further altering an already altered Fc region as a starting Fc region can also be preferably used as the Fc region of the present invention. The starting Fc region can mean the polypeptide itself, a composition containing the starting Fc region, or an amino acid sequence encoding the starting Fc region. The starting Fc region may include an IgG antibody Fc region known in the art, which is produced by the recombination summarized in the section about the antibody. The origin of the starting Fc region is not limited, and the starting Fc region can be obtained from an arbitrary organism of a non-human animal or a human. Preferred examples of the arbitrary organism include organisms selected from mice, rats, guinea pigs, hamsters, gerbils, cats, rabbits, dogs, goats, sheep, cattle, horses, camels, and non-human primates. In another embodiment, the starting Fc region may be obtained from a cynomolgus monkey, a marmoset, a rhesus monkey, a chimpanzee, or a human. Preferably, the starting Fc region can be obtained from human IgG1, but is not limited by the particular class of IgG. This means that a human IgG1, IgG2, IgG3, or IgG4 Fc region can be appropriately used as the starting Fc region. This also means that an Fc region of any IgG class or subclass from the arbitrary organism can be preferably used as the starting Fc region in the present specification. Examples of variants or engineered models of naturally occurring IgG are described in publicly known literatures (Curr. Opin. Biotechnol. (2009) 20 (6), 685-91; Curr. Opin. Immunol. (2008) 20 (4), 460-470; Protein Eng. Des. Sel. (2010) 23 (4), 195-202; and WO2009086320, WO2008092117, WO2007041635, and WO2006105338), though the Fc region according to the present invention is no limited thereto.

An amino acid at any position can be altered as long as the amino acid alteration can confer the binding activity against the complement or can enhance binding activity for binding to the complement. The antigen-binding molecule comprising a human IgG Fc region as a human Fc region preferably contains the alteration to bring about the effect of enhancing its binding activity against the complement over the binding activity of the starting Fc region of human IgG1. Examples of the amino acid for altering the binding activity against the complement include amino acids in Fc region with altered binding activity against C1q reported in, for example, Duncan et al. (Nature (1988) 332, 738-740), Tao et al. (J. Exp. Med. (1993) 178, 661-667), Brekke et al. (Eur. J. Immunol. (1994) 24, 2542-2547), Xu et al. (Immunol. (1993) 150, 152A), WO1994029351, WO2000042072, and WO2011091078.

Examples of such an amino acid that permits the alteration to enhance the binding activity against C1q include at least one or more amino acids selected from EU numbering positions 231 to 238 and positions 318 to 337. One non-limiting example of the amino acid includes at least one or more amino acids selected from the group consisting of positions 235, 237, 267, 268, 276, 318, 320, 322, 324, 327, 331, and 333. The alteration of these amino acids enhances the binding of an IgG-type immunoglobulin Fc region to the complement.

Particularly preferred examples of the alteration include the alteration of an amino acid at EU numbering position 267 to Glu,
an amino acid at EU numbering position 268 to any of Phe and Tyr,
an amino acid at EU numbering position 276 to Arg,
an amino acid at EU numbering position 324 to Thr,
an amino acid at EU numbering position 327 to Gly,
an amino acid at EU numbering position 331 to Pro, or
an amino acid at EU numbering position 333 to any of Ala, Asp, Gly, Ser, and Val
in the Fc region.

The number of amino acids to be altered is not particularly limited. An amino acid at only one site may be altered, or amino acids at two or more sites in arbitrary combination selected from those described above may be altered.

In an alternative embodiment, examples of the combination of the method of the present invention with other constant region alteration techniques include its combination with antibody alteration techniques such as an Fc alteration technique of enhancing binding to FcRn at acidic pH (WO2002060919, WO2004035752, and WO2000042072), an Fc alteration technique of enhancing binding to FcRn at neutral pH (WO2011122011 and WO02012133782), a technique of enhancing selective binding to inhibitory Fcγ receptors (WO2012115241 and WO2013125667), a technique of enhancing selective binding to active Fcγ receptors (ADCC activity enhancement technique) (WO02013002362), and a technique of reducing binding activity against rheumatoid factors (WO2013046704).

In a non-limiting embodiment, examples of the combination of the method of the present invention with a variable region alteration technique include its combination with alteration techniques such as a pH-dependent antibody (WO02009125825) and a calcium-dependent antibody (WO2012073992).

Antibody Library, Immunization, and Hybridoma Preparation

A known sequence may be used as a gene encoding the H chain or the L chain of the antibody before the introduction of a mutation (in the present specification, also simply referred to as the "antibody of the present invention") in the method of the present invention. Alternatively, the gene may be obtained by a method generally known to those skilled in the art. For example, the gene may be obtained from an antibody library or may be obtained by the cloning of an antibody-encoding gene from monoclonal antibody-producing hybridomas.

Many antibody libraries have already been known in the art as such an antibody library. Also, methods for preparing the antibody library are known in the art. Thus, those skilled in the art can appropriately obtain the antibody library. For an antibody phage library, for example, see literatures such as Clackson et al., Nature 1991, 352: 624-8, Marks et al., J. Mol. Biol. 1991, 222: 581-97, Waterhouses et al., Nucleic Acids Res. 1993, 21: 2265-6, Griffiths et al., EMBO J. 1994, 13: 3245-60, Vaughan et al., Nature Biotechnology 1996, 14: 309-14, and National Publication of International Patent Application No. 2008-504970. In addition, a method known in the art such as a method for preparing a library using eukaryotic cells (WO95/15393) or a ribosome display method may be used. In addition, a technique of obtaining a human antibody by panning using a human antibody library is also known. For example, human antibody variable regions are expressed as a single-chain antibody (scFv) on the surface of phages by a phage display method. A phage expressing scFv binding to the antigen can be selected. The gene of the selected phage can be analyzed to determine DNA sequences encoding the variable regions of the human antibody binding to the antigen. If the DNA sequence of the scFv binding to the antigen can be determined, appropriate expression vectors can be prepared on the basis of this sequence and used to obtain the human antibody. These methods have already been well known. See WO92/01047, WO92/20791, WO93/06213, WO93/11236, WO93/19172, WO95/01438, and WO95/15388.

Basically, a technique known in the art is used in a method for obtaining the antibody-encoding gene from hybridomas. A desired antigen or cells expressing the desired antigen are used as a sensitizing antigen. Animals are immunized with this sensitizing antigen according to a usual immunization method. Immunocytes thus obtained are fused with parental cells known in the art by a usual cell fusion method. Monoclonal antibody-producing cells (hybridomas) are screened for by a usual screening method. From mRNAs of the obtained hybridomas, cDNAs of antibody variable regions (V regions) can be synthesized using reverse transcriptase and ligated with DNAs encoding desired antibody constant regions (C regions) to obtain the antibody-encoding gene.

More specifically, although the present invention is not limited by examples below, the sensitizing antigen for obtaining the genes encoding the antibody H chain and L chain includes both of a complete antigen having immunogenicity and an incomplete antigen (including hapten, etc.) that exhibits no immunogenicity. For example, a full-length protein or a partial peptide of the protein of interest can be used. In addition, a substance constituted by a polysaccharide, a nucleic acid, a lipid, or the like is known to serve as an antigen. The antigen for the antibody of the present invention is not particularly limited. The antigen can be prepared by a method generally lknown to those skilled in the art and can be obtained according to, for example, a method using baculovirus (e.g., WO98/46777). The hybridomas can be prepared according to, for example, the method of Milstein et al. (G. Kohler and C. Milstein, Methods Enzymol. 1981, 73: 3-46). When the antigen has low immunogenicity, this antigen can be bound to an immunogenic macromolecule such as albumin for immunization. If necessary, the antigen may be bound to another molecule to form a soluble antigen. In the case of using a transmembrane molecule such as a receptor as the antigen, a portion of the extracellular region of the receptor may be used as a fragment, or cells expressing the transmembrane molecule on their surface may be used as the immunogen.

The antibody-producing cells can be obtained by the immunization of animals with any of the appropriate sensitizing antigens mentioned above. Alternatively, lymphocytes capable of producing antibodies may be immunized in vitro and used as the antibody-producing cells. Various mammals can be used as the animals to be immunized. An animal of the order Rodentia, Lagomorpha, or Primates is generally used. Examples thereof can include: Rodentia animals such as mice, rats, and hamsters; Lagomorpha animals such as rabbits; and Primates animals such as monkeys including cynomolgus monkeys, rhesus monkeys, hamadryas baboons, and chimpanzees. In addition, transgenic animals having repertoires of human antibody genes are also known, and such animals can also be used to obtain the human antibody (see WO96/34096; and Mendez et al., Nat. Genet. 1997, 15: 146-56). Instead of using such transgenic animals, for example, human lymphocytes are sensitized in vitro with the desired antigen or cells expressing the desired antigen, and the sensitized lymphocytes can be fused with human myeloma cells, for example, U266, to obtain the desired human antibody having binding activity against the antigen (see Japanese Patent Publication No. 1-59878). Furthermore, transgenic animals having all repertoires of human antibody genes can be immunized with the desired antigen to obtain the desired human antibody (see WO93/12227, WO092/03918, WO094/02602, WO096/34096, and WO096/33735).

For the innmunization of these animals, for example, the sensitizing antigen is appropriately diluted with or suspended in phosphate-buffered saline (PBS), saline, or the like, mixed with an adjuvant, if necessary, and emulsified. Then, the resulting sensitizing antigen is intraperitoneally or subcutaneously injected to the animals. Then, the sensitizing antigen, preferably, mixed with a Freund's incomplete adjuvant, is administered to the animals several times at 4- to 21-day intervals. The antibody production can be confirmed by measuring the antibody titer of interest in the serum of the animals by a method routinely used.

The hybridomas can be prepared by fusing the antibody-producing cells obtained from the animals or the lymphocytes immunized with the desired antigen with myeloma cells using a fusion agent (e.g., polyethylene glycol) routinely used (Goding, Monoclonal Antibodies: Principles and Practice, Academic Press, 1986, 59-103). If necessary, the hybridoma cells are cultured for growth, and the binding specificity of antibodies produced by the hybridomas is measured by an analysis method known in the art such as immunoprecipitation, radioimmunoassay (RIA), or enzyme-linked immunosorbent assay (ELISA). Then, the hybridoma producing the antibody confirmed by the measurement to have the specificity, affinity, or activity of interest can also be subcloned, if necessary, by an approach such as a limiting dilution method.

Subsequently, a gene encoding the selected antibody can be cloned from the hybridoma or the antibody-producing cells (sensitized lymphocytes, etc.) using a probe (e.g., an oligonucleotide complementary to a sequence encoding an antibody constant region) capable of specifically binding to the antibody gene. The gene can also be cloned from mRNA by RT-PCR. Immunoglobulins are classified into five different classes: IgA, IgD, IgE, IgG, and IgM. These classes are further divided into some subclasses (isotypes) (e.g., IgG-1, IgG-2, IgG-3, and IgG-4; and IgA-1 and IgA-2). In the present invention, the H chain and the L chain used in the antibody production can be derived from an antibody belonging to any of these classes and subclasses. Such an antibody is not particularly limited and is particularly preferably IgG.

In this context, the genes encoding the H chain and the L chain may be altered by a genetic engineering approach. For example, a generically recombinant antibody, for example, a chimeric antibody or a humanized antibody, can be appropriately prepared by artificially altering an antibody such as a mouse antibody, a rat antibody, a rabbit antibody, a hamster antibody, a sheep antibody, or a camel antibody for the purpose of, for example, reducing hetero-antigenicity in humans. The chimeric antibody is an antibody composed of H chain and L chain variable regions of a non-human mammal antibody, for example, a mouse antibody, and H chain and L chain constant regions of a human antibody. The chimeric antibody can be obtained by: ligating DNAs encoding the mouse antibody variable regions with DNAs encoding the human antibody constant regions; incorporating the resulting ligation products into expression vectors; and transferring the vectors into hosts for antibody production. The humanized antibody is also called reshaped human antibody. DNA sequences designed to connect complementarity-determining regions (CDRs) of a non-human mammal antibody, for example, a mouse antibody, are synthesized by PCR from several prepared oligonucleotides having overlapping terminal portions. The obtained DNAs are ligated with DNAs encoding human antibody constant regions, and the resulting ligation products are subsequently incorporated to expression vectors, which are then transferred to hosts for antibody production (see EP239400; and WO096/02576). The human antibody FRs connected via the CDRs are selected such that the complementarity-determining regions form a favorable antigen-binding site. If necessary, amino acids in the framework regions of antibody variable regions may be substituted such that the complementarity-determining regions of the resulting reshaped human antibody form an appropriate antigen-binding site (K. Sato et al., Cancer Res. 1993, 53: 851-856).

In addition to the aforementioned humanization, for example, alteration is also possible for improving the biological properties of the antibody such as binding activity against the antigen. Such alteration can be carried out by a method such as site-directed mutagenesis (see e.g., Kunkel (1985) Proc. Natl. Acad. Sci. USA 82: 488), PCR mutagenesis, or cassette mutagenesis. In general, such an antibody variant having the improved biological properties has 70% or higher, more preferably 80% or higher, further preferably 90% or higher (e.g., 95% or higher, 97%, 98%, or 99%) amino acid sequence homology and/or similarity to the variable region amino acid sequences of the original antibody. In the present specification, the sequence homology and/or similarity is defined as the percentage of amino acid residues homologous (identical amino acid residues) or similar (amino acid residues classified into the same group on the basis of the side chain properties of general amino acids) to the original antibody residues after sequence alignment and gap introduction as needed so as to attain the largest value of sequence homology. Typically, natural amino acid residues are classified on the basis of the properties of their side chains into (1) hydrophobic group: alanine, isoleucine, norleucine, valine, methionine, and leucine; (2) neutral hydrophilic group: asparagine, glutamine, cysteine, threonine, and serine; (3) acidic group: aspartic acid and glutamic acid; (4) basic group: arginine, histidine, and lysine; (5) group of residues influencing chain orientation: glycine and proline; and (6) aromatic group: tyrosine, tryptophan, and phenylalanine.

A total of six complementarity determining regions (hypervariable domains; CDRs) present in H chain and L chain variable regions usually interact with each other to form an antigen-binding site in the antibody. Even one of these variable regions is known to have the ability to recognize and bind to the antigen, albeit with lower affinity than that of a molecule containing the whole binding site. Thus, the genes encoding the H chain and the L chain of the antibody of the present invention can encode fragments or moieties containing the respective antigen-binding sites of the H chain and the L chain as long as the polypeptides encoded by the genes should maintain the binding activity against the desired antigen.

Activity of Polypeptide and Examples of Antigen

For example, an antibody or a polypeptide having an activity can be efficiently prepared by use of the method for controlling dissociation and/or association according to the present invention. Examples of the activity can include binding activity, neutralizing activity, cytotoxic activity, agonistic activity, antagonistic activity, and enzymatic activity. The agonistic activity is an activity of intracellularly transducing signals, for example, through the binding of an antibody to an antigen such as a receptor to induce change in some physiological activity. Examples of the physiological activity can include, but are not limited to, proliferative activity, survival activity, differentiation activity, transcriptional activity, membrane transport activity, binding activity, proteolytic activity, phosphoiylating/dephosphorylating activity, redox activity, transfer activity, nucleolytic activity, dehydration activity, cell death-inducing activity, and apoptosis-inducing activity.

Also, an antibody or a polypeptide that recognizes a desired antigen or binds to a desired receptor can be efficiently prepared by the method of the present invention.

In the present specification, the antigen is not particularly limited, and any antigen can be used. Preferred examples of the antigen include ligands (cytokines, chemokines, etc.), receptors, cancer antigens, MHC antigens, differentiation antigens, immunoglobulins, and immunocomplexes partially containing an immunoglobulin.

Examples of the cytokines can include interleukins 1 to 18, colony-stimulating factors (G-CSF, M-CSF, GM-CSF, etc.), interferons (IFN-α, IFN-β, IFN-γ, etc.), growth factors (EGF, FGF, IGF, NGF, PDGF, TGF, HGF, etc.), tumor necrosis factors (TNF-α and TNF-β), lymphotoxin, erythropoietin, leptin, SCF, TPO, MCAF, and BMP.

Examples of the chemokines can include CC chemokines such as CCL1 to CCL28, CXC chemokines such as CXCL1 to CXCL17, C chemokines such as XCL1 to XCL2, and CX3C chemokines such as CX3CL1.

Examples of the receptors can include receptors belonging to receptor families such as hematopoietic factor receptor family, cytokine receptor family, tyrosine kinase receptor family, serine/threonine kinase receptor family, TNF receptor family, G protein-coupled receptor family, GPI-anchored receptor family, tyrosine phosphatase receptor family, adhesion factor family, and hormone receptor family. The receptors belonging to these receptor families and features thereof are described in many literatures, for example, Cooke B A., King R J B., van der Molen H J, ed. New Comprehensive Biochemistry Vol. 18B "Hormones and their Actions Part II" pp. 1-46 (1988) Elsevier Science Publishers BV., Patthy (Cell (1990) 61 (1), 13-14), Ullrich et al. (Cell (1990) 61 (2), 203-212), Massague (e carries an acute accent) (Cell (1992) 69 (6), 1067-1070), Miyajima et al. (Annu. Rev. Immunol. (1992) 10, 295-331), Taga et al. (FASEB J. (1992) 6, 3387-3396), Fantl et al. (Annu. Rev. Biochem. (1993), 62, 453-481), Smith et al. (Cell (1994) 76 (6) 959-962), and Flower D R. (Biochim. Biophys. Acta (1999) 1422 (3) 207-234).

Preferred examples of specific receptors belonging to the receptor families include human or mouse erythropoietin (EPO) receptor (Blood (1990) 76 (1), 31-35; and Cell (1989) 57 (2), 277-285), human or mouse granulocyte colony-stimulating factor (G-CSF) receptor (Proc. Natl. Acad. Sci. USA. (1990) 87 (22), 8702-8706; mG-CSFR; and Cell (1990) 61 (2), 341-350), human or mouse thrombopoietin (TPO) receptor (Proc Natl Acad Sci USA. (1992) 89 (12), 5640-5644; and EMBO J. (1993) 12 (7), 2645-53), human or mouse insulin receptor (Nature (1985) 313 (6005), 756-761), human or mouse Flt-3 ligand receptor (Proc. Natl. Acad. Sci. USA. (1994) 91 (2), 459-463), human or mouse platelet-derived growth factor (PDGF) receptor (Proc. Natl. Acad. Sci. USA. (1988) 85 (10) 3435-3439), human or mouse interferon (IFN)-α/β receptor (Cell (1990) 60 (2), 225-234; and Cell (1994) 77 (3), 391-400), human or mouse leptin receptor, human or mouse growth hormone (GH) receptor, human or mouse interleukin (IL)-10 receptor, human or mouse insulin-like growth factor (IGF)-I receptor, human or mouse leukemia inhibitory factor (LIF) receptor, and human or mouse ciliary neurotrophic factor (CNTF) receptor.

The cancer antigens are antigens that are expressed with the malignant transformation of cells, and are also called tumor-specific antigens. Abnormal sugar chains that appear on cell surface or protein molecules when cells are cancerated are also included in the cancer antigens and are also called cancer carbohydrate antigens. Preferred examples of the cancer antigens include GPC3 that belongs to the GPI-anchored receptor family as the aforementioned receptors but is expressed in some cancers including liver cancer (Int J Cancer. (2003) 103 (4), 455-65), EpCAM that is expressed in a plurality of cancers including lung cancer (Proc Natl Acad Sci USA. (1989) 86 (1), 27-31), CA19-9, CA15-3, and sialyl SSEA-1 (SLX).

The MHC antigens are mainly classified into MHC class I antigens and MHC class II antigens. The MHC class I antigens include HLA-A, -B, -C, -E, -F, -G, and -H. The MHC class II antigens include HLA-DR, -DQ, and -DP.

The differentiation antigens can include CD1, CD2, CD4, CD5, CD6, CD7, CD8, CD10, CD11a, CD11b, CD11c, CD13, CD14, CD15s, CD16, CD18, CD19, CD20, CD21, CD23, CD25, CD28, CD29, CD30, CD32, CD33, CD34, CD35, CD38, CD40, CD41a, CD41b, CD42a, CD42b, CD43, CD44, CD45, CD45RO, CD48, CD49a, CD49b, CD49c, CD49d, CD49e, CD49f, CD51, CD54, CD55, CD56, CD57, CD58, CD61, CD62E, CD62L, CD62P, CD64, CD69, CD71, CD73, CD95, CD102, CD106, CD122, CD126, and CDw130.

The immunoglobulins include IgA, IgM, IgD, IgG, and IgE. The immunocomplexes contain at least any component of immunoglobulins.

Other examples of the antigen can include the following molecules: 17-IA, 4-1BB, 4Dc, 6-keto-PGF1a, 8-iso-PGF2a, 8-oxo-dG, A1 adenosine receptor, A33, ACE, ACE-2, activin, activin A, activin AB, activin B, activin C, activin RIA, activin RIA ALK-2, activin RIB ALK-4, activin RIIA, activin RIIB, ADAM, ADAM10, ADAM12, ADAM15, ADAM17/TACE, ADAM8, ADAM9, ADAMTS, ADAMTS4, ADAMTS5, addressin, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, artemin, anti-Id, ASPARTIC, atrial natriuretic factor, av/b3 integrin, Axl, b2M, B7-1, B7-2, B7-H, B-lymphocyte-stimulating factor (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 (osteogenin), BMP-4 BMP-2b, BMP-5, BMP-6 Vgr-1, BMP-7 (OP-1), BMP-8 (BMP-8a, OP-2), BMPR, BMPR-LA (ALK-3), BMPR-IB (ALK-6), BRK-2, RPK-1, BMPR-II (BRK-3), BMP, b-NGF, BOK, bombesin, bone-derived neurotrophic factor, BPDE, BPDE-DNA, BTC, complement factor 3 (C3), C3a, C4, C10, CA125, CAD-8, calcitonin, cAMP, carcinoembryonic antigen (CEA), cancer-associated antigen, cathepsin A, cathepsin B, cathepsin C/DPPI, cathepsin D, cathepsin E, cathepsin H, cathepsin L, cathepsin 0, cathepsin S, cathepsin V, cathepsin X/Z/P, CBL, CC1, CCK2, CCL, CCL1, CCL11, CCL12, CCL13, CCL14, CCL15, CCL16, CCL17, CCL18, CCL19. CCL2, CCL20, CCL21, CCL22, CCL23, CCL24, CCL25, CCL26, CCL27, CCL28, CCL3, CCL4, CCL5, CCL6, CCL7, CCL8, CCL9/10. CCR, CCR1, CCR10, CCR10, CCR2. CCR3, CCR4, CCR5, CCR6, CCR7, CCR8, CCR9, CD1, CD2, CD3, CD3E, CD4, CD5, CD6, CD7, CD8. CD10, CD11a, CD11b, CD11c, CD13. CD14. CD15, CD16, CD18, CD19, CD20, CD21, CD22, CD23, CD25, CD27L, CD28, CD29, CD30, CD30L, CD32, CD33 (p67 protein), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium peifringens* toxin, CKb8-1, CLC, CMV, CMV UL, CNTF, CNTN-1, COX, C-Ret, CRG-2, CT-1. CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, decay accelerating factor, des(1-3)-IGF-1 (brain IGF-1), Dhh, digoxin, DNAM-1, Dnase, Dpp, DPPIV/CD26, Dtk, ECAD, EDA. EDA-A1, EDA-A2, EDAR, EGF, EGFR (ErbB-1), EMA, EMMPRIN. ENA, endothelin receptor, enkephalinase, eNOS, Eot, eotaxin 1, EpCAM, ephrin B2/EphB4, EPO, ERCC, E-selectin, ET-1, factor IIa, factor VII, factor VIIIc, factor IX, fibroblast-activating protein (FAP), Fas, FcR1, FEN-1, ferritin, FGF, FGF-19, FGF-2, FGF3, FGF-8, FGFR, FGFR-3, fibrin, FL, FLIP, Flt-3, Flt-4, follicle-stimulating hormone, fractalkine, FZD1, FZD2, FZD3, FZD4, FZD5, FZD6, FZD7, FZD8, FZD9, FZD10, G250, Gas6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), GDNF. GDNF, GFAP, GFRa-1, GFR-alpha 1, GFR-alpha 2, GFR-alpha 3, GITR, glucagon, Glut4, glycoprotein IIb/IIIa (GPIIb/IIIa), GM-CSF, gp130, gp72, GRO, growth hormone-releasing factor, hapten (NP-cap or NIP-cap), HB-EGF, HCC, HCMV gB envelope glycoprotein, HCMV gH envelope glycoprotein, HCMV UL, hematopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, high-molecular-weight melanoma-associated antigen (HMW-MAA), HIV gp120, HIV IIIB gp 120 V3 loop, HLA, HLA-DR, HM1.24, HMFG PEM. HRG, Hrk, human heart myosin, human cytomegalovirus (HCMV), human growth hormone (HGH), HVEM, 1-309, IAP, ICAM, ICAM-1, ICAM-3, ICE, ICOS. IFNg, Ig, IgA receptor, IgE, IGF, IGF-binding protein, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, inhibin, iNOS, insulin A chain, insulin B chain, insulin-like growth factor 1, integrin alpha 2, integrin alpha 3, integrin alpha 4, integrin alpha 4/beta 1, integrin alpha 4/beta 7, integrin alpha 5 (alpha V), integrin alpha 5/beta 1, integrin alpha 5/beta 3, integrin alpha 6, integrin beta 1, integrin beta 2, interferon gamma, IP-10, I-TAC, JE, kallikrein 2, kallikrein 5, kallikrein 6, kallikrein 11, kallikrein 12, kallikrein 14, kallikrein 15, kallikrein L1, kallikrein L2, kallikrein L3, kallikrein L4, KC, KDR, keratinocyte growth factor (KGF), laminin 5, LAMP, LAP, LAP (TGF-1), latent TGF-1, latent TGF-1 bp1, LBP, LDGF, LECT2, lefty, Lewis-Y antigen, Lewis-Y-related antigen, LFA-1, LFA-3, Lfo, LIF, LIGHT, lipoprotein, LIX, LKN, Lptn, L-selectin, LT-a, LT-b, LTB4, LTBP-1, lung surfactant, luteinizing hormone, lymphotoxin beta receptor, Mac-1, MAdCAM, MAG, MAP2, MARC, MCAM, MCAM, MCK-2, MCP, M-CSF, MDC, Mer, metalloprotease, MGDF receptor. MGMT, MHC (HLA-DR), MIF, MIG, MIP, MIP-1-alpha, MK, MMAC1, MMP, MMP-1, MMP-10, MMP-11, MMP-12, MMP-13, MMP-14. MMP-15. MMP-2. MMP-24. MMP-3, MMP-7, MMP-8, MMP-9, MPIF, Mpo, MSK, MSP, mucin (Muc 1), MUC18, mullerian-inhibiting factor, Mug, MuSK, NAIP, NAP, NCAD, N-cadherin, NCA 90, NCAM, NCAM, neprilysin, neurotrophin-3, -4, or -6, neurturin, nerve growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, parathyroid hormone, PARC, PARP, PBR, PBSF, PCAD, P-cadherin, PCNA, PDGF, PDGF, PDK-1, PECAM. PEM. PF4, PGE, PGF, PGI2, PGJ2, PIN, PLA2, placental alkaline phosphatase (PLAP), P1GF, PLP, PP14, proinsulin, prorelaxin, protein C, PS, PSA, PSCA, prostate-specific membrane antigen (PSMA), PTEN, PTHrp, Ptk, PTN, R51, RANK, RANKL, RANTES, RANTES, relaxin A chain, relaxin B chain, renin, respiratory syncytial virus (RSV) F, RSV Fgp, Ret, rheumatoid factor, RLIP76, RPA2, RSK, S100, SCF/KL, SDF-1, SERINE, serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T cell receptor (e.g., T cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta RI (ALK-5), TGF-beta RII, TGF-beta RIIb, TGF-beta RIII, TGF-beta 1, TGF-beta 2, TGF-beta 3, TGF-beta 4, TGF-beta 5, thrombin, thymus Ck-1, thyroid stimulating hormone, Tie, TIMP, TIQ, tissue factor, TMEFF2. Tmpo, TMPRSS2, TNF, TNF-alpha, TNF-alpha/beta, TNF-beta 2, TNFc, TNF-R1, TNF-RII, TNFRSFIOA (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSFI2 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF I9L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (Dc-TRAIL R1 TNFRH1), TNFRSF25 (DR3 Apo-3, LARD, TR-3, TRAMP, WSL-1), TNFSF10 (TRAIL Apo-2 ligand, TL2), TNFSF11 (TRANCE/RANK ligand ODF, OPG ligand), TNFSF12 (TWEAK Apo-3 ligand, DR3 ligand). TNFSF13 (APRIL TALL2), TNFSF13B (BAFF BLYS, TALL1, THANK, TNFSF20), TNFSF14 (LIGHT HVEM ligand, LTg), TNFSF15 (TLIA/VEGI), TNFSF18 (GITR ligand AITR ligand, TL6), TNFSF1A (TNF-α conectin, DIF, TNFSF2), TNFSFIB (TNF-b LTa, TNFSF). TNFSF3 (LTb TNFC, p33), TNFSF4 (OX40 ligand gp34, TXGP1), TNFSF5 (CD40 ligand CD154, gp39, HIGM1, IMD3, TRAP), TNFSF6 (Fas ligand Apo-1 ligand, APT1 ligand), TNFSF7 (CD27 ligand CD70), TNFSF8 (CD30 ligand CD153), TNFSF9 (4-1BB ligand CD137 ligand), TP-1, t-PA, Tpo, TRAIL, TRAIL R, TRAIL-R1, TRAIL-R2, TRANCE, transferrin receptor, TRF, Trk, TROP-2, TSG, TSLP, tumor-associated antigen CA125, tumor-associated antigen exhibiting Lewis Y-related carbohydrate, TWEAK, TXB2, Ung, uPAR, uPAR-1, urokinase, VCAM, VCAM-1, VECAD, VE-cadherin, VE-cadherin-2, VEFGR-1 (fit-1), VEGF, VEGFR, VEGFR-3 (fit-4). VEGI. VIM, viral antigen, VLA, VLA-1. VLA-4, VNR integrin, von Willebrand factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A. WNT9B, WNT10A, WNT1B, WNT11, WNT16, XCL1, XCL2, XCR1, XCR1, XEDAR, XLAP, XPD, HMGB1, IgA, Aβ, CD81, CD97, CD98, DDR1, DKKI, EREG, Hsp90, IL-17/IL-17R, IL-20/IL-20R, oxidized LDL, PCSK9, prekallikrein, RON, TMEM16F, SOD1, Chromogranin A, Chromogranin B, tau, VAP1, high-molecular-weight kininogen, IL-31, IL-31R, Nav1.1, Nav1.2, Nav1.3, Nav1.4, Nav1.5, Nav1.6, Nav1.7, Nav1.8, Nav1.9, EPCR, C1, Clq, Cir, Cls, C2, C2a, C2b, C3, C3a, C3b, C4, C4a, C4b, C5, C5a, C5b, C6, C7, C8, C9, factor B, factor D, factor H, properdin, sclerostin, fibrinogen, fibrin, prothrombin, thrombin, tissue factor, factor V, factor Va, factor VII, factor VIIa, factor VIII, factor VIIIa, factor IX, factor IXa, factor X, factor Xa, factor XI, factor XIa, factor XII, factor XIIa, factor XIII, factor XIIIa, TFPI, antithrombin III, EPCR, thrombomodulin, TAPI, tPA, plasminogen, plasmin, PAI-1, PAI-2, GPC3, Syndecan-1, Syndecan-2, Syndecan-3, Syndecan-4, LPA, S P, and receptors for hormones and growth factors.

In a non-limiting embodiment of the present invention, one specificity of the bispecific antibody can target a cancer antigen, and the other specificity can target an antigen expressed on CTL (cytotoxic T lymphocyte), for example, CD3 or TNFRSF (tumor necrosis factor receptor super family), though these specificities are not limited to this combination. Examples of the TNFRSF include TNFRSF9 (CD137), TNFRSF5 (CD40), and TNFRSF4 (OX40).

Alteration of Nucleic Acid

In another aspect of the production method of the present invention, the present invention provides a method for producing a heteromultimer having a mutation in amino acid residues that form the interface between polypeptides (e.g., amino acid residues at EU numbering positions 356 and 439, positions 357 and 370, and positions 399 and 409), and/or an amino acid residue at EU numbering position 397 and/or 392 so as to control dissociation and/or association between the polypeptides, the production method comprising the steps of: (a) altering nucleic acids encoding the amino acid residues that form the interface between polypeptides, etc., from their original nucleic acids so as to control dissociation and association between the polypeptides; (b) culturing a host cell having the nucleic acids to express the polypeptides; (c) recovering the polypeptides from the cultures of the host cell; and (d) incubating these polypeptides under a reducing condition to recover a heteromer of the desired polypeptides.

In a preferred embodiment, the production method of the present invention is also a method comprising the step of altering nucleic acids encoding the amino acid residues that form the interface between polypeptides from their original nucleic acids by use of the aforementioned method for controlling dissociation and/or association according to the present invention so as to inhibit association between the polypeptides.

In the method of the present invention, the phrase "altering nucleic acids" means to alter nucleic acids so as to correspond to the amino acid residues that are introduced by the "alteration" according to the present invention. More specifically, the phrase "altering nucleic acids" means to alter nucleic acids encoding the original amino acid residues (amino acid residues before the alteration) to nucleic acids encoding the amino acid residues that are introduced by the alteration. Usually, this phrase means to carry out gene manipulation or mutation treatment for the insertion, deletion, or substitution of at least one base in the original nucleic acids so as to become codons encoding the amino acid residues of interest. Specifically, the codons encoding the original amino acid residues are substituted by codons encoding the amino acid residues that are introduced by the alteration. Such nucleic acid alteration can be appropriately carried out using a technique generally known to those skilled in the art, for example, site-directed mutagenesis or PCR mutagenesis.

The nucleic acids according to the present invention are usually carried by (or inserted in) appropriate vectors and transferred to host cells. The vectors are not particularly limited as long as the vectors can stably retain the inserted nucleic acids. For example, when *E. coli* is used as the host, pBluescript vectors (manufactured by Stratagene Corp.) or the like are preferred as vectors for cloning. Various commercially available vectors can be used. In the case of using the vectors for the purpose of producing the polypeptide of the present invention, expression vectors are particularly useful. The expression vectors are not particularly limited as long as the vectors permit expression of the polypeptide in vitro, in *E. coli*, in cultured cells, or in organism individuals. The expression vectors are preferably, for example, pBEST vectors (manufactured by Promega K.K.) for in vitro expression, pET vectors (manufactured by Invitrogen Corp.) for *E. coli*, pME18S-FL3 vectors (GenBank Accession No. AB009864) for cultured cells, and pME18S vectors (Mol Cell Biol. 8: 466-472 (1988)) for organism individuals. The insertion of the DNAs of the present invention into the vectors can be carried out by a routine method, for example, ligase reaction using restriction sites (Current protocols in Molecular Biology edit. Ausubel et al. (1987) Publish. John Wiley & Sons. Section 11.4-11.11).

The host cells are not particularly limited, and various host cells are used according to the purpose. Examples of the cells for polypeptide expression can include bacterial cells (e.g., *Streptococcus, Staphylococcus, E. coli, Streptomyces,* and *Bacillus subtilis*), fungus cells (e.g., yeasts and *Aspergillus*), insect cells (e.g., *Drosophila* S2 and *Spodoptera* SF9), animal cells (e.g., CHO, COS, HeLa, C127, 3T3, BHK, HEK293, and Bowes melanoma cells), and plant cells. The transfer of the vectors to the host cells can be carried out by a method known in the art, for example, a calcium phosphate precipitation method, an electroporation method (Current protocols in Molecular Biology edit. Ausubel et al., (1987) Publish. John Wiley & Sons. Section 9.1-9.9), a Lipofectamine method (manufactured by GIBCO-BRL/Life Technologies, Inc.), or a microinjection method.

An appropriate secretory signal can be incorporated into the polypeptide of interest in order to secrete the polypeptide expressed in the host cells to the lumen of the endoplasmic reticulum, periplasmic space, or an extracellular environment. The signal may be endogenous to the polypeptide of interest or may be a foreign signal.

When the polypeptide of the present invention is secreted into a medium, the recovery of the polypeptide in the production method is carried out by the recovery of the medium. When the polypeptide of the present invention is produced into cells, the cells are first lysed and then the polypeptide is recovered.

A method known in the art including ammonium sulfate or ethanol precipitation, acid extraction, anion- or cation-exchange chromatography, phosphocellulose chromatography, hydrophobic interaction chromatography, affinity chromatography, hydroxyapatite chromatography, and lectin chromatography can be used for recovering and purifying the polypeptide of the present invention from the recombinant cell cultures.

In a non-limiting embodiment of the present invention, examples of the production method include: a method which involves separately culturing cell lines respectively producing the homo variants of the first and second polypeptides, and purifying the culture supernatants, followed by FAE (Fab arm exchange) reaction using the purified antibodies; a method which involves separately culturing cell lines respectively producing the homo variants of the first and second polypeptides, mixing the culture supernatants without purification, and causing FAE reaction in the mixed culture supernatant, followed by purification; a method which involves mixing a cell line producing the homo variant of the first polypeptides with a cell line producing the homo variant of the second polypeptides, culturing the mixture, and purifying the culture supernatant, followed by FAE reaction using the purified antibodies; and a method which involves mixing a cell line producing the homo variant of the first polypeptides with a cell line producing the homo variant of the second polypeptides, culturing the mixture, and causing FAE reaction in the culture supernatant, followed by purification.

In a non-limiting embodiment, the present invention provides a method for producing a heteromultimer, comprising the following steps a) to c):
a) mixing a cell line producing the homo variant of the first polypeptides with a cell line producing the homo variant of the second polypeptides;
b) incubating the homo variant of the first polypeptides and the homo variant of the second polypeptides together so as to allow cysteines in hinge regions to cause disulfide bond isomerization in the culture supernatant; and
c) obtaining a heteromultimer comprising the first and second polypeptides.

In a non-limiting embodiment, the present invention provides a method for producing a heteromultimer, comprising the following steps a) to c):
a) separately culturing cell lines respectively producing the homo variants of the first and second polypeptides;
b) mixing the respective culture supernatants of the cell lines and incubating the homo variant of the first polypeptides and the homo variant of the second polypeptides together so as to allow cysteines in hinge regions to cause disulfide bond isomerization; and
c) obtaining a heteromultimer comprising the first and second polypeptides.

Method for Selecting Desired Heteromultimer

The present invention further provides a method for selecting a desired heteromultimer. In a preferred embodiment, the method is a method for selecting a heteromultimer having desired properties, comprising the following steps:
a) providing a first polypeptide set and a second polypeptide set, wherein each polypeptide constituting the first set has target specificity different from that of each polypeptide constituting the second set, and each polypeptide constituting the first and second sets contains the amino acid alteration related to interface control using charge repulsion and/or the amino acid alteration to destabilize the stability of a CH3 region;
b) incubating each polypeptide constituting the first set together with each polypeptide constituting the second set under a reducing condition, thereby preparing a mixture of plural types of heteromultimers;
c) assaying the resulting mixture of plural types of heteromultimers for the predetermined desired properties; and
d) selecting a heteromultimer having the desired properties.

Pharmaceutical Composition

The present invention also relates to a composition (drug) comprising the heteromultimer of the present invention and a pharmaceutically acceptable carrier.

In the present invention, the pharmaceutical composition usually refers to a drug for the treatment or prevention of a disease or for testing or diagnosis.

The pharmaceutical composition of the present invention can be formulated by a method generally known to those skilled in the art. For example, the pharmaceutical composition can be used in the form of a parenteral injection of an aseptic solution or suspension with water or any other pharmaceutically acceptable solution. For example, the pharmaceutical composition may be formulated with the heteromultimer mixed in a unit dosage form required for generally accepted pharmaceutical practice, in appropriate combination with pharmacologically acceptable carriers or media, specifically, sterilized water, physiological saline, plant oil, an emulsifier, a suspending agent, a surfactant, a stabilizer, a flavoring agent, an excipient, a vehicle, a preservative, a binder, etc. The amount of the active ingredient in these preparations is set so as to give an appropriate volume within a prescribed range.

An aseptic composition for injection can be formulated according to conventional pharmaceutical practice using a vehicle such as injectable distilled water.

Examples of aqueous solutions for injection include physiological saline, and isotonic solutions containing glucose and other adjuvants (e.g., D-sorbitol, D-mannose, D-mannitol, and sodium chloride). These solutions may be used in combination with an appropriate solubilizer, for example, an alcohol (ethanol, etc.) or a polyalcohol (propylene glycol, polyethylene glycol, etc.), or a nonionic surfactant (polysorbate 80™, HCO-50, etc.).

Examples of oily solutions include sesame oil and soybean oil. These solutions may be used in combination with benzyl benzoate and/or benzyl alcohol as a solubilizer. The solutions may be further mixed with a buffer (e.g., a phosphate buffer solution and a sodium acetate buffer solution), a soothing agent (e.g., procaine hydrochloride), a stabilizer (e.g., benzyl alcohol and phenol), and an antioxidant. The injection solutions thus prepared are usually charged into appropriate ampules.

The pharmaceutical composition of the present invention is preferably administered parenterally. The composition can be in the dosage form of, for example, an injection, a nasal administration agent, a transpulmonary administration agent, or a percutaneous administration agent. The pharmaceutical composition can be administered systemically or locally through, for example, intravenous injection, intramuscular injection, intraperitoneal injection, or subcutaneous injection.

The administration method can be appropriately selected depending on the age and symptoms of a patient. The dose of a pharmaceutical composition containing an antibody or a polynucleotide encoding the antibody can be set to within a range of, for example, 0.0001 to 1000 mg/kg of body weight per dose. Alternatively, the dose may be, for example, 0.001 to 100000 mg per patient, though the present invention is not necessarily limited by these numeric values. Although the dose and the administration method vary depending on the weight, age, symptoms, etc., of a patient, those skilled in the art can appropriately select an appropriate dose and administration method in consideration of their conditions.

In the present invention, the heteromultimer of the present invention is useful as an active ingredient for a therapeutic or preventive agent for a cancer. Examples of the cancer include, but are not limited to: lung cancer (including small-cell lung cancer, non-small-cell lung cancer, lung adenocarcinoma, and lung squamous cell carcinoma), large bowel cancer, rectal cancer, colon cancer, breast cancer, liver cancer, stomach cancer, pancreatic cancer, kidney cancer, prostate cancer, ovary cancer, thyroid gland cancer, bile duct cancer, peritoneal cancer, mesothelioma, squamous cell cancer, uterine cervix cancer, uterine body cancer, bladder cancer, esophagus cancer, head and neck cancer, nasopharyngeal cancer, salivary gland tumor, thymoma, skin cancer, basal cell tumor, malignant melanoma, anus cancer, penis cancer, testis cancer, Wilms's tumor, acute myeloid leukemia (including acute myeloleukemia, acute myeloblastic leukemia, acute promyelocytic leukemia, acute myelomonocytic leukemia, and acute monocytic leukemia), chronic myeloid leukemia, acute lymphoid leukemia, chronic lymphoid leukemia, Hodgkin's lymphoma, non-Hodgkin's lymphoma (Burkitt's lymphoma, chronic lymphocytic leukemia, mycosis fungoides, mantle cell lymphoma, follicular lymphoma, diffuse large-cell lymphoma, marginal zone lymphoma, hairy cell leukemia, plasmacytoma, peripheral T-cell lymphoma, and adult T-cell leukemia/lymphoma), Langerhans' cell histiocytosis, multiple myeloma, myelodysplastic syndrome, brain tumor (including glioma, astroglioma, glioblastoma, meningioma, and ependymoma), neuroblastoma, retinoblastoma, osteosarcoma, Kaposi's sarcoma, Ewing's sarcoma, angiosarcoma, and hemangiopericytoma.

If necessary, the polypeptide or the heteromultimer of the present invention can be made into preparations in combination with other pharmaceutical ingredients.

The present invention also provides a kit for use in the treatment method or prevention method of the present invention, comprising at least a heteromultimer produced by the production method of the present invention or the pharmaceutical composition of the present invention. In the kit, for example, a pharmaceutically acceptable carrier, a vehicle, or an instruction stating the usage can also be additionally packaged. The present invention also relates to use of the polypeptide of the present invention or a polypeptide produced by the production method of the present invention for producing a therapeutic or preventive agent for immunological and inflanmmatory diseases. The present invention further relates to the polypeptide of the present invention or a polypeptide produced by the production method of the present invention for use in the treatment method or the prevention method of the present invention.

The three-letter codes of the amino acids used herein and their corresponding one-letter codes are as follows:
Alanine: Ala: A
Arginine: Arg: R
Asparagine: Asn: N
Aspartic acid: Asp: D
Cysteine: Cys: C
Glutamine: Gin: Q
Glutamic acid: Glu: E
Glycine: Gly: G
Histidine: His: H
Isoleucine: Ile: I
Leucine: Leu: L
Lysine: Lys: K
Methionine: Met: M
Phenylalanine: Phe: F
Proline: Pro: P
Serine: Ser: S
Threonine: Thr: T
Tryptophan: Trp: W
Tyrosine: Tyr: Y
Valine: Val: V All prior technical literatures cited herein are incorporated herein by reference.

EXAMPLES

[Example 1] Study on Improvement in Fab Arm Exchange Efficiency by Introduction of Association Interface-Controlling Alteration to Antibody In Fab arm exchange, two types of homomeric antibodies are mixed in the presence of a reducing agent, and the resulting four H-L chain pairs of the antibody molecules (referred to as half-molecules or HL molecules, each of which is a molecule composed of one heavy chain and one light chain) reassociate by swapping to yield bispecific antibodies. Since the reassociation of HL molecules occurs at random, the bispecific antibody of interest is theoretically obtained at only 50% of the total amount of antibodies present in the system. Provided that different charges are introduced in advance to two types of homomeric antibodies, it is assumed that heterodimerization can occur preferentially over homodimerization during the reassociation of the resulting HL molecules to prepare a bispecific antibody with high efficiency. Accordingly, the alteration to control association interface between antibody CH3 regions (alteration to promotion of hetero-association of two types of H chains through the use of the charge interaction and repulsion between their CH3 regions) as reported in WO2006/106905 was used to test whether or not it can improve the reaction efficiency of Fab arm exchange (rate of bispecific antibody formation).

The antibody H chain variable regions used were H chain variable regions WT(H) (SEQ ID NO: 1; hereinafter, referred to as MRAH) and H54 (SEQ ID NO: 2) of the antibody against human interleukin 6 receptor disclosed in WO2009/125825. MRAH-G1d (SEQ ID NO: 3) and H54-G1d (SEQ ID NO: 4) having an antibody H chain constant region G1d derived from a human IgG1 H chain constant region by the removal of C-terminal Gly and Lys and MRAH-wtG4d (SEQ ID NO: 5) and H54-wtG4d (SEQ ID NO: 6) having an antibody H chain constant region wtG4d derived from a human IgG4 H chain constant region by the removal of C-terminal Gly and Lys were prepared using the H chain variable regions. Next, P228S and K409R alterations were introduced to MRAH-G1d and H54-G1d to prepare MRAH-G1dsr (SEQ ID NO: 7) and H54-G1dsr (SEQ ID NO: 8) having an IgG4-type hinge sequence and CH3 domain sequence. D356K was further introduced as association interface-controlling alteration to MRAH-G1dsr to prepare MRAH-G1dsrP1 (SEQ ID NO: 9). K439E was further introduced as association interface-controlling alteration to H54-G1dsr to prepare H54-G1dsrN1 (SEQ ID NO: 10). E356K was further introduced as association interface-controlling alteration to MRAH-wtG4d to prepare MRAH-wtG4dP1 (SEQ ID NO: 11). K439E was further introduced as association interface-controlling alteration to H54-wtG4d to prepare H54-wtG4dN1 (SEQ ID NO: 12). Antibody L chains MRAL-k0 (SEQ ID NO: 13) and L28-k0 (SEQ ID NO: 14) were used for the H chain variable regions MRAH and H54, respectively. MRAH-G1dsr/MRAL-k0, H54-G1dsr/L28-k0, MRAH-G1dsrP1/MRAL-k0, H54-G1dsrN1/L28-k0, MRAH-wtG4d/MIRAL-k0, H54-wtG4d/L28-k0, MRAH-wtG4dP1/MRAL-k0, and H54-wtG4dN1/L28-k0 were expressed and purified according to the method of Reference Example 1.

Next, two types of homo variants thus obtained were mixed in the combinations given below, and the reaction products were evaluated according to the method of Reference Example (1) MRAH-wtG4d/MRAL-k0 and H54-wtG4d/L28-k0
(2) MRAH-wtG4dP1/MRAL-k0 and H54-wtG4dN1/L28-k0
(3) MRAH-G1dsr/MRAL-k0 and H54-G1dsr/L28-k0
(4) MRAH-G1dsrP1/MRAL-k0 and H54-G1dsrN1/L28-k0

Reaction conditions: in PBS (Sigma-Aldrich Corp., pH 7.4), [each mAb]=0.2 mg/ml, [GSH (Sigma-Aldrich Corp.)] =0.5 mM, 0.05% Tween 20 (Junsei Chemical Co., Ltd.), 37° C., 24 hours.

The two types of antibody variable regions MRAH/MRAL and H54/L28 used in this study differ largely in p1. Therefore, peaks corresponding to their respective homo variants and the resulting bispecific antibodies can be easily separated by ion-exchange chromatography, and the reaction efficiency can be evaluated. FIG. 1 shows the results of evaluating the reaction products by ion-exchange chromatography. The reaction product wtG4d produced from MRAH-wtG4d/MRAL-k0 and H54-wtG4d/L28-k0 and the reaction product G1dsr produced from MRAH-G1dsr/ MRAL-k0 and H54-G1dsr/L28-k0 carrying no association interface-controlling alteration had 50.5% and 52.7% rates, respectively, of bispecific antibody formation.

By contrast, the reaction product wtG4dP1/N1 produced from MRAH-wtG4dP1/MRAL-k0 and H54-wtG4dN1/L28-k0 carrying the association interface-controlling alteration had 99.0% rate of bispecific antibody formation, and the reaction product G1dsrP1/N1 produced from MRAH-G1dsrP1/MRAL-k0 and H54-G1dsrN1/L28-k0 carrying the association interface-controlling alteration had 98.5% rate of bispecific antibody formation. Thus, the bispecific antibody was found to be formed with exceedingly high efficiency. These results demonstrated that the bispecific antibody can be prepared with exceedingly high efficiency by mixing two types of homo variants carrying the association interface-controlling alteration reported in WO2006/106905 in the presence of a reducing agent.

[Example 2] Fab Arm Exchange in Homo Variant Having Hinge Sequence of Human Naturally Occurring IgG1

In Example 1, Fab arm exchange was conducted by the introduction of P228S alteration to IgG1 in order to obtain a hinge region having a sequence of naturally occurring human IgG4 type. However, naturally occurring IgG4 administered into a living body reportedly causes half-molecule exchange with endogenous IgG4. This is due to Ser at EU numbering position 228 in the hinge region. The substitution of this amino acid by IgG1-type Pro has been reported to improve stability and to prevent the in vivo exchange (Labrijn A F et al., Nat. Biotechnol. 2009, 27, 767-771). Thus, in consideration of administration into a living body, the hinge sequence of the prepared bispecific antibody is desirably 226C-227P-228P-229C. Accordingly, this study was conducted to test whether or not to efficiently cause Fab arm exchange by the introduction of association interface-controlling alteration even using the hinge sequence of naturally occurring human IgG1.

First, K409R and D356K were introduced to MRAH-G1d to prepare MRAH-G1drP1 (SEQ ID NO: 15), and K409R and K439E were introduced to H54-G1d to prepare H54-G1drN1 (SEQ ID NO: 16). Antibody L chains MRAL-k0 and L28-k0 were used for the H chain variable regions MRAH and H54, respectively. MRAH-G1drP1/MRAL-k0 and H54-G1drN1/L28-k0 were expressed and purified according to the method of Reference Example 1. Next, two types of homo variants thus obtained were mixed under reaction conditions given below, and the reaction products were evaluated according to the method of Reference Example 2.

Reaction condition: in TBS (Takara Bio Inc., pH 7.6), [each mAb]=0.2 mg/ml. 0.05% Tween 20 (Junsei Chemical Co., Ltd.), 37° C., 24 hours. The study was conducted under 3 conditions of a reducing agent [GSH (Sigma-Aldrich Corp.)]=0.5 mM or 5 mM or [2-MEA (Sigma-Aldrich Corp.)]=25 mM.

FIG. 2 shows the results of analyzing the reaction products according to the method of Reference Example 2. The rate of bispecific antibody formation under the same condition as in Example 1 (GSH=0.5 mM) was 21.8%, which was drastically reduced compared with the efficiency of the case where the amino acid residue at EU numbering position 228 was Ser. By contrast, the rate of bispecific antibody formation under the reducing condition of 2-MEA (25 mM) or GSH (5 mM) was 99% or more. These results demonstrated that the bispecific antibody can be prepared with high efficiency by introducing association interface-controlling alteration and using an appropriate reducing condition even if the hinge sequence is the sequence of naturally occurring human IgG1.

[Example 3] Fab Arm Exchange Using CH3 of Human Naturally Occurring IgG1

The preceding studies showed that the bispecific antibody of interest is obtained with exceedingly high efficiency by Fab arm exchange by introducing K409R alteration (which gives IgG4-type CH3) to human IgG1 and association interface-controlling alteration (D356K and K439E).

Meanwhile, it is known that if an amino acid residue at position 409 is Arg, the stability of the antibody is reduced under an acidic condition (WO/2009/041613). Antibody drug production inevitably requires a virus inactivation step of exposing the antibody under an acidic condition. In this respect, the stability of the antibody under an acidic condition is desirably high for keeping the quality of the antibody. Accordingly, it is desirable that the amino acid residue at position 409 should not be Arg. On the other hand, the K409R alteration was used as alteration reported to be able to efficiently cause Fab arm exchange reaction. In this case, the amino acid residue at position 409 is Arg, probably leading to the stability problem under an acidic condition. Accordingly, this study was conducted to test whether or not to induce Fab arm exchange by introducing only association interface-controlling alteration reported in WO02006/106905 to a completely naturally occurring human IgG1 antibody without introducing K409R alteration.

The combinations of association interface-controlling alterations studied are shown in Table 1.

TABLE 1

| Antibody H chain gene name | SEQ ID NO | Alteration introduced to MRAH-G1d | Antibody H chain gene name | SEQ ID NO | Alteration introduced to H54-G1d |
|---|---|---|---|---|---|
| MRAH-G1dP1 | 17 | D356K | H54-G1dN1 | 22 | K439E |
| MRAH-G1dP3 | 18 | D399K | H54-G1dN3 | 23 | K409D |
| MRAH-G1dP4 | 19 | E357K | H54-G1dN4 | 24 | K370E |
| MRAH-G1dP5 | 20 | D356K/ D399K | H54-G1dN5 | 25 | K409D/ K439E |
| MRAH-G1dP6 | 21 | D356K/ E357K | H54-G1dN6 | 26 | K370E/ K439E |

Antibody L chains MRAL-k0 and L28-k0 were used for the H chain variable regions MRAH and H54, respectively. MRAH-GdP1/MIRAL-k0, H54-G1dN1/L28-k0, MRAH-G1dP3/MRAL-k0, H54-G1dN3/L28-k0, MRAH-G1dP4/MRAL-k0, H54-G1dN4/L28-k0, MRAH-G1dP5/MRAL-k0, H54-G1dN5/L28-k0, MRAH-G1dP6/MRAL-k0, and H54-G1dN6/L28-k0 were expressed and purified according to the method of Reference Example 1.

Next, two types of homo variants thus obtained were mixed in the combinations given below, and the reaction products were evaluated according to the method of Reference Example 2.

(1) MRAH-G1dP1/MRAL-k0 and H54-G1dN1/L28-k0
(2) MRAH-G1dP3/MRAL-k0 and H54-G1dN3/L28-k0
(3) MRAH-G1dP4/MRAL-k0 and H54-G1dN4/L28-k0
(4) MRAH-G1dP5/MRAL-k0 and H54-G1dN5/L28-k0
(5) MRAH-G1dP6/MRAL-k0 and H54-G1dN6/L28-k0

Reaction condition: in TBS (Takara Bio Inc., pH 7.6), [each mAb]=0.2 mg/ml, 0.05% Tween 20 (Junsei Chemical Co., Ltd.), [GSH (Sigma-Aldrich Corp.)]=5 mM, 37° C., 24 hours.

The obtained results are shown in Table 2.

TABLE 2

| Abbreviation | Name of H chain constant region of MoAb1 used | Introduced alteration | Name of H chain constant region of MoAb2 used | Introduced alteration | Rate of bispecific antibody formation (%) |
|---|---|---|---|---|---|
| G1dP1/N1 | G1dP1 | D356K | G1dN1 | K439E | 1.7 |
| G1dP3/N3 | G1dP3 | D399K | G1dN3 | K409D | 93.4 |
| G1dP4/N4 | G1dP4 | E357K | G1dN4 | K370E | 4.4 |
| G1dP5/N5 | G1dP5 | D356K/D399K | G1dN5 | K409D/K439E | 98.1 |
| G1dP6/N6 | G1dP6 | D356K/E357K | G1dN6 | K370E/K439E | 29.3 |

In the table. "Abbreviation" denotes the abbreviation of the homo variant combination used in the reaction. For example, the abbreviation G1dP1/N1 represents that MRAH-G1dP1/MRAL-k0 and H54-G1dN1/L28-k0 were reacted. "Name of H chain constant region of MoAb1 used" denotes the name of the constant region of the antibody having the variable region MRAH. "Name of H chain constant region of MoAb2 used" denotes the name of the constant region of the antibody having the variable region H54. "Introduced alteration" denotes the alteration introduced to MRAH-G1d or H54-G d.

G1dP1/N1 with D356K introduced to one homo variant and K439E introduced to another homo variant had 1.7% rate of bispecific antibody formation. In FIG. 2, G1drP1/N1 having K409R alteration and association interface-controlling alteration (D356K and K439E) had 99.3% rate of bispecific antibody formation under the same reaction conditions (5 mM GSH), showing that the reaction efficiency was drastically reduced in G1dP1/N1 instead containing Lys as the amino acid residue at EU numbering position 409. By contrast, G1dP3/N3 with association interface-controlling alteration D399K introduced to one homo variant and K409D introduced to another homo variant and G1dP5/N5 with D356K/D399K introduced to one homo variant and K409D/K439E introduced to another homo variant exhibited a rate of bispecific antibody formation as very high as 93.4% and 98.1%, respectively. These results demonstrated that Fab arm exchange can be induced with high efficiency by introducing only association interface-controlling alteration without the use of K409R alteration that gives an IgG4-type CH3 domain.

Next, reaction efficiency was compared under 3 types of reducing conditions as to G1dP3/N3 and G1dP5/N5 having high reaction efficiency. In this comparison, G1drP1/N1 used in Example 2 and an altered form having the combination of K409R introduced to one antibody and F405L introduced to another homo variant as reported by Labrijn et al. as alterations for efficient bispecific antibody preparation by Fab arm exchange were also tested as controls (Labrijn A F et al., Proc. Natl., Acad. Sci., 2013. 110. 5145-5150).

K409R was introduced to MRAH-G1d to prepare MRAH-G1dr (SEQ ID NO: 27), and F405L was introduced to H54-G1d to prepare H54-G1d1 (SEQ ID NO: 28). Antibody L chains MRAL-k0 and L28-k0 were used for the H chain variable regions MRAH and H54, respectively. MRAH-G1drP1/MRAL-k0, H54-G1drN1/L28-k0, MRAH-G1dP3/MRAL-k0, H54-G1dN3/L28-k0, MRAH-GdP5/MRAL-k0, H54-G1dN5/L28-k0, MRAH-G1dr/MRAL-k0, and H54-G1d1/L28-k0 were expressed and purified according to the method of Reference Example 1.

Next, two types of homo variants thus obtained were mixed in the combinations given below, and the reaction products were evaluated according to the method of Reference Example 2.

(1) MRAH-G1drP1/MRAL-k0 and H54-G1drN1/L28-k0
(2) MRAH-G1dP3/MRAL-k0 and H54-G1dN3/L28-k0
(3) MRAH-G1dP5/MRAL-k0 and H54-GLdN5/L28-k0
(4) MRAH-G1dr/MRAL-k0 and H54-G dl/L28-k0

Reaction condition: in TBS (Takara Bio Inc., pH 7.6), [each mAb]=0.2 mg/ml, 0.05% Tween 20 (Junsei Chemical Co., Ltd.), 37° C., 24 hours. The study was conducted under 3 conditions of a reducing agent [GSH (Sigma-Aldrich Corp.)]=0.5 mM or 5 mM or [2-MEA (Sigma-Aldrich Corp.)]=25 mM.

The obtained results are shown in Table 3.

TABLE 3

| Abbreviation | Name of H chain constant region of MoAb1 used | Introduced alteration | Name of H chain constant region of MoAb2 used | Introduced alteration | Rate of bispecific antibody formation (%) | Reductive condition |
|---|---|---|---|---|---|---|
| G1dr/1 | G1dr | K409R | G1d1 | F405L | 87.3 | GSH(5 mM) |
| G1dP3/N3 | G1dP3 | D399K | G1dN3 | K409D | 85.2 | GSH(5 mM) |
| G1dP5/N5 | G1dP5 | D356K/D399K | G1dN5 | K409D/K439E | 99.1 | GSH(5 mM) |
| G1drP1/N1 | G1drP1 | D356K/K409R | G1drN1 | K439E/K409R | 99.3 | GSH(5 mM) |
| G1dr/1 | G1dr | K409R | G1d1 | F405L | 95.6 | 2MEA(25 mM) |
| G1dP3/N3 | G1dP3 | D399K | G1dN3 | K409D | 92.8 | 2MEA(25 mM) |
| G1dP5/N5 | G1dP5 | D356K/D399K | G1dN5 | K409D/K439E | 100.0 | 2MEA(25 mM) |
| G1drP1/N1 | G1drP1 | D356K/K409R | G1drN1 | K439E/K409R | 99.7 | 2MEA(25 mM) |
| G1dr/1 | G1dr | K409R | G1d1 | F405L | 9.5 | GSH(0.5 mM) |
| G1dR3/N3 | G1dP3 | D399K | G1dN3 | K409D | 4.8 | GSH(0.5 mM) |
| G1dP5/N5 | G1dP5 | D356K/D399K | G1dN5 | K409D/K439E | 75.4 | GSH(0.5 mM) |
| G1drP1/N1 | G1drP1 | D356K/K409R | G1drN1 | K439E/K409R | 21.8 | GSH(0.5 mM) |

In the table, "Abbreviation" denotes the abbreviation of the homo variant combination used in the reaction. For example, the abbreviation G1dP1/N1 represents that MRAH-G1dP1/MRAL-k0 and H54-G1dN1/L28-k0 were reacted. "Name of H chain constant region of MoAb1 used" denotes the name of the constant region of the antibody having the variable region MRAH. "Name of H chain constant region of MoAb2 used" denotes the name of the constant region of the antibody having the variable region H54. "Introduced alteration" denotes the alteration introduced to MRAH-G1d or H54-G1d.

G1dr/1 carrying the existing alteration to improve Fab arm exchange efficiency as reported by Labrijn et al. had 87.3% rate of bispecific antibody formation under the reducing condition of 5 mM GSH. Under this condition. G1dP3/N3 with D399K introduced to one homo variant and K409D introduced to another homo variant had 85.2% rate of bispecific antibody formation, and G1dP5/N5 with D356K/D399K introduced to one homo variant and K409D/K439E introduced to another homo variant had 99.1% rate of bispecific antibody formation. Also, G1drP1/N having D356K in one homo variant and K439E in another homo variant in addition to IgG4-type K409R alteration had 99.3% rate of bispecific antibody formation.

G1dr/1 carrying the existing alteration to improve Fab arm exchange efficiency as reported by Labrijn et al. had 95.6% rate of bispecific antibody formation under the reducing condition of 25 mM 2MEA. Under this condition, G1dP3/N3 with D399K introduced to one homo variant and K409D introduced to another homo variant had 92.8% rate of bispecific antibody formation, and G1dP5/N5 with D356K/D399K introduced to one homo variant and K409D/K439E introduced to another homo variant had 100% rate of bispecific antibody formation. Also, G1drP1/N1 having D356K in one homo variant and K439E in another homo variant in addition to IgG4-type K409R alteration had 99.7% rate of bispecific antibody formation.

G1dr/i carrying the existing alteration to improve Fab arm exchange efficiency had 9.5% rate of bispecific antibody formation under the reducing condition of 0.5 mM GSH. Under this condition, G1dP3/N3 with D399K introduced to one homo variant and K409D introduced to another homo variant had 4.8% rate of bispecific antibody formation, and G1dP5/N5 with D356K/D399K introduced to one homo variant and K409D/X439E introduced to another homo variant had 75.4% rate of bispecific antibody formation. Also, G1drP1/N1 having D356K in one homo variant and K439E in another homo variant in addition to IgG4-type K409R alteration had 21.8% rate of bispecific antibody formation. This reducing condition drastically reduced the rate of bispecific antibody formation in all of the samples as compared with the other reducing conditions.

These results demonstrated that G1dP5/N5 with D356K/D399K introduced to one homo variant and K409D/K439E introduced to another homo variant exhibits a higher rate of bispecific antibody formation under all of the reaction conditions as compared with the existing alteration to improve Fab arm exchange efficiency as reported by Labrijn et al. The high rate of bispecific antibody formation is very important for the actual production of bispecific antibodies as drugs. Thus, this alteration is considered to be highly useful as compared with the existing alteration.

[Example 4] Development of Highly Efficient Fab Arm Exchange Using Alteration for CH3 Domain Destabilization The preceding Examples showed that provided that different charges are introduced to two types of homo variants by association interface-controlling alteration, a half-molecule formed from one homo variant in the presence of a reducing agent associates preferentially with a half-molecule derived from the other homo variant to form a bispecific antibody with high efficiency. Meanwhile, in the process of forming bispecific antibodies by Fab arm exchange, the dissociation of CH3 domains that forms half-molecules (HL molecules) after cleavage of two types of homo variants with a reducing agent reportedly becomes a rate-determining stage (Rispens T et al., J. Am. Chem. Soc., 2011. 133. 10302-10311). In short, if the dissociation of CH3 domains can be promoted by the moderate destabilization of the CH3 domains of each homo variant, Fab arm exchange can be expected to be induced more efficiently. Accordingly, the relationship between the rate of bispecific antibody formation and the stability of the CH3 domains of each homo variant was first evaluated in the presence of 5 mM GSH shown in Tables 2 and 3. The stability of the CH3 domains was determined with Tm (intermediate temperature of thermal denaturation) measured according to the method of Reference Example 3 as an index.

FIG. 3 shows the relationship between the rate of bispecific antibody formation and the value of higher Tm of CH3 in two types of homo variants used. G1dP1/N1 or G1dP4/N4 having a low rate of bispecific antibody formation had a CH3 Tm as high as 76° C. or higher, whereas G1dP5/N5, G1dP3/N3, and G1drP1/N1 having high reaction efficiency had a homo variant CH3 Tm of 65.1° C., 69.6° C., and 69.5° C., respectively. These results revealed that the rate of bispecific antibody formation correlates evidently with the CH3 stability of each homo variant in Fab arm exchange. For achieving high reaction efficiency, it was also found preferable to destabilize the stability of the CH3 regions of a homo variant having more stable CH3 between two types of homo variants used such that Tm of this CH3 falls below 70° C., etc. In this context, Tm of the CH3 regions (having the sequence of naturally occurring human IgG) of MRAH-G1d/MRAL-k0 measured under the same condition as above was 83.6° C., demonstrating that for achieving high reaction efficiency in Fab arm exchange, it is required to destabilize the stability of the CH3 regions so as to decrease the Tm of the CH3 regions by, for example, 13° C. or more from that of naturally occurring human IgG1.

Thus, this study was conducted to test whether or not to improve the rate of bispecific antibody formation by decreasing the Tm of the CH3 domains of the homo variants used. IgG2-type alteration V397M was used as alteration to reduce the stability of CH3. IgG2 contains Met as an amino acid residue at EU numbering position 397. The introduction of the alteration to substitute this amino acid by IgG1-type Val reportedly improves the stability (Tm) of the CH3 regions (WO2009/041613). Thus, it was expected that the introduction of the V397M alteration to IgG1-type CH3 domains would destabilize the CH3 domains and facilitate their dissociation.

Thus, V397M alteration was introduced to both homo variants of G1dP1/N1, G1dP4/N4, or G1dP6/N6 having a low rate of bispecific antibody formation in Table 2, and the resulting G1dP8/N8, G1dP9/N9, and G1dP10/N10 were studied. Specifically, V397M was introduced to MRAH-G1dP1, MRAH-G1dP4, MRAH-G1dP6, H54-G1dN1, H54-G1dN4, and H54-G1dN6 to prepare MRAH-G1dP8 (SEQ ID NO: 29), MRAH-G1dP9 (SEQ ID NO: 30), MRAH-G1dP10 (SEQ ID NO: 31), H54-G1dN8 (SEQ ID NO: 32), H54-G1dN9 (SEQ ID NO: 33), and H54-G1dN10 (SEQ ID NO: 34). Antibody L chains MRAL-k0 and L28-k0 were used for the H chain variable regions MRAH and H54. MRAH-G1dP8/MRAL-k0, H54-G1dN8/L28-k0, MRAH-G1dP9/MRAL-k0. H54-G1dN9/L28-k0, MRAH-G1dP10/MRAL-k0, and H54-G1dN10/L28-k0 were expressed and purified according to the method of Reference Example 1. The Tm of the obtained antibodies was measured according to the method of Reference Example 3.

Next, two types of homo variants thus obtained were mixed in the combinations given below, and the reaction products were evaluated according to the method of Reference Example 2.
(1) MRAH-G1dP8/MRAL-k0 and H54-G1dN8/L28-k0
(2) MRAH-G1dP9/MRAL-k0 and H54-G1dN9/L28-k0
(3) MRAH-G1dP10/MRAL-k0 and H54-G1dN10/L28-k0
(4) MRAH-G1dr/MRAL-k0 and H54-G1d1/L28-k0

Reaction condition: in TBS (Takara Bio Inc., pH 7.6), [each mAb]=0.2 mg/ml, 0.05% Tween 20 (Junsei Chemical Co., Ltd.), [GSH (Sigma-Aldrich Corp.)]=5 mM, 37° C., 24 hours.

The obtained results are shown in Table 4.

TABLE 4

| Abbreviation | Name of H chain constant region of MoAb1 used | Introduced alteration | Name of H chain constant region of MoAb2 used | Introduced alteration | Rate of bispecific antibody formation (%) | Tm of MoAb1 CH3 (° C.) | Tm of MoAb2 CH3 (° C.) |
|---|---|---|---|---|---|---|---|
| G1dr/1 | G1dr | K409R | G1d1 | F405L | 88.1 | 70.7 | 69.7 |
| G1dP8/N8 | G1dP8 | D356K/V397M | G1dN8 | V397M/K439E | 73.2 | 70.1 | 70.5 |
| G1dP9/N9 | G1dP9 | E357K/V397M | G1dN9 | K370E/V397M | 67.3 | 67 | 71 |
| G1dP10/N10 | G1dP10 | D356K/E357K/V397M | G1dN10 | K370E/V397M/K439E | 96.9 | 63.8 | 70.2 |
| G1dP1/N1 (extracted from Table 2) | G1dP1 | D356K | G1dN1 | K439E | 1.7 | 76.7 | 74.7 |
| G1dP4/N4 (extracted from Table 2) | G1dP4 | E357K | G1dN4 | K370E | 4.4 | 68.5 | 76.5 |
| G1dP6/N6 (extracted from Table 2) | G1dP6 | D356K/E357K | G1dN6 | K370E/K439E | 29.3 | 66 | 70.1 |

In the table, "Tm of MoAb1 CH3" denotes the Tm of CH3 of the homo variant having the variable region MRAH. "Tm of MoAb2 CH3" denotes the Tm of CH3 of the homo variant having the variable region H54.

In G1dP8/N8 with V397M alteration introduced to both homo variants of G1dP1/N1, the Tm of CH3 was decreased by 6.6° C. to 70.1° C. for MoAb1 and decreased by 4.2° C. to 70.5° C. for MoAb2, and the rate of bispecific antibody formation was improved from 1.7% to 73.2%. In G1dP9/N9 with V397M alteration introduced to both homo variants of G1dP4/N4, the Tm of CH3 was decreased by 1.5° C. to 67° C. for MoAb1 and decreased by 5.5° C. to 71° C. for MoAb2, and the rate of bispecific antibody formation was improved from 4.4% to 67.3%. In G1dP10/N10 with V397M alteration introduced to both homo variants of G1dP6/N6, the Tm of CH3 was decreased by 2.2° C. to 63.8° C. for MoAb1, albeit with no change in the Tm of MoAb2 CH3, and the rate of bispecific antibody formation was improved from 29.3% to 96.9%. These results demonstrated that the bispecific antibody formation efficiency in Fab arm exchange is improved by decreasing the Tm of homo variant CH3 through V397M alteration. In this test, G1dr/1 carrying the existing alteration to improve Fab arm exchange efficiency had 88.1% rate of bispecific antibody formation. Thus, G1dP10/N10 was found to be superior thereto in the rate of bispecific antibody formation.

Thus, this study was conducted to test whether or not to further improve the rate of bispecific antibody formation by introducing alteration expected to produce a larger CH3-destabilizing effect to the neighborhood of effective EU numbering position 397. FIG. 4 shows the EU numbering position 397 of the CH3 domains and its neighborhood using the reported X-ray crystallographic structural data (PDB: 3DO3) on IgG1.

First, D399 on the A chain is considered to interact electrostatically with K392 on the B chain. Therefore, it is possible that the substitution of K392 by Asp or Glu in addition to V397M alteration can cause the electrostatic repulsion between these chains to further destabilize the interaction between the chains. It is also expected that the substitution of K392 by an amino acid having a branched side chain can further destabilize the association between these chains through steric hindrance with M397. Furthermore, the possibility was also expected that the substitution of the amino acid residue at EU numbering position 397 by a more bulky amino acid could suppress CH3-CH3 association more than V397M alteration. From these viewpoints, 7 types of antibody H chain genes shown in Table 5 were newly prepared on the basis of MRAH-G1dP1 and H54-G1dN1.

TABLE 5

| Antibody H chain gene name | SEQ ID NO | Alteration introduced to MRAH-G1d | Antibody H chain gene name | SEQ ID NO | Alteration introduced to H54-G1d |
|---|---|---|---|---|---|
| MRAH-G1dP14 | 35 | D356K/K392D/V397M | H54-G1dN14 | 42 | K392D/V397M/K439E |
| KRAH-G1dP15 | 36 | D356K/K392E/V397M | H54-G1dN15 | 43 | K392E/V397M/K439E |

TABLE 5-continued

| Antibody H chain gene name | SEQ ID NO | Alteration introduced to MRAH-G1d | Antibody H chain gene name | SEQ ID NO | Alteration introduced to H54-G1d |
|---|---|---|---|---|---|
| MRAH-G1dP16 | 37 | D356K/V397F | H54-G1dN16 | 44 | V397F/K439E |
| MRAH-G1dP17 | 38 | D356K/V397Y | H54-G1dN17 | 45 | V397Y/K439E |
| MRAH-G1dP18 | 39 | D356K/K392T/V397M | H54-G1dN18 | 46 | K392T/V397M/K439E |
| MRAH-G1dP19 | 40 | D356K/K392V/V397M | H54-G1dN19 | 47 | K392V/V397M/K439E |
| MRAH-G1dP20 | 41 | D356K/K392I/V397M | H54-G1dN20 | 48 | K392I/V397M/K439E |

Antibody L chains MRAL-k0 and L28-k0 were used for the H chain variable regions MRAH and H54, respectively. MRAH-G1dP14/MRAL-k0, H54-G1dN14/L28-k0, MRAH-G1dP15/MRAL-k0, H54-G1dN15/L28-k0, MRAH-G1dP16/MRAL-k0, H54-G1dN16/L28-k0, MRAH-G1dP17/MRAL-k0, H54-G1dN17/L28-k0, MRAH-G1dP18/MRAL-k0, H54-G1dN18/L28-k0, MRAH-G1dP19/MRAL-k0, H54-GdN19/L28-k0, MRAH-G1dP20/MRAL-k0, and H54-G1dN20/L28-k0 were expressed and purified according to the method of Reference Example 1. The Tm of the obtained antibodies was measured according to the method of Reference Example 3.

Next, two types of homo variants thus obtained were mixed in the combinations given below, and the reaction products were evaluated according to the method of Reference Example 2.
(1) MRAH-G1dP14/MRAL-k0 and H54-G1dN14/L28-k0
(2) MRAH-G1dP15/MRAL-k0 and H54-G1dN15/L28-k0
(3) MRAH-G1dP16/MRAL-k0 and H54-G1dN16/L28-k0
(4) MRAH-G1dP17/MRAL-k0 and H54-G1dN17/L28-k0
(5) MRAH-G1dP18/MRAL-k0 and H54-G1dN18/L28-k0
(6) MRAH-G1dP19/MRAL-k0 and H54-G1dN19/L28-k0
(7) MRAH-G1dP20/MRAL-k0 and H54-G1dN20/L28-k0
(8) MRAH-G1dr/MRAL-k0 and H54-G1d1/L28-k0
(9) MRAH-G1dP1/MRAL-k0 and H54-G1dN1/L28-k0
(10) MRAH-G1dP8/MRAL-k0 and H54-G1dN8/L28-k0

Reaction condition: in TBS (Takara Bio Inc., pH 7.6). [each mAb]=0.2 mg/ml, 0.05% Tween 20 (Junsei Chemical Co., Ltd.), [2-MEA (Sigma-Aldrich Corp.)]=25 mM, 37° C., 24 hours.

The obtained results are shown in Table 6.

G1dP8/N8 with V397M alteration introduced to both homo variants of G1dP1/N1 had 73.2% rate of bispecific antibody formation. By contrast, the rate of bispecific antibody formation was largely improved to 96.5% for G1dP14/N14 with K392D introduced to both chains thereof, 96.9% for G1dP15/N15 with K392E introduced, and 98.9% for G1dP18/N18 with K392T introduced. Also, the rate of bispecific antibody formation was improved to 96.5% for G1dP16/N16 with V397F introduced instead of V397M to G1dP1N1 and 98% for G1dP17/N17 with V397Y introduced, as compared with V397M. This is probably because, as seen from the fact that the CH3 domains of MoAb1 and MoAb2 in G1dP8/N8 containing V397M had a Tm of 70.1° C. and 70.5° C., respectively, while the Tm of the CH3 domains of MoAb1 and MoAb2 was 69.1° C. and 69.7° C. for G1dP16/N16 and 69.2° C. and 69.8° C. for G1dP17N17, these alterations compared with the V397M alteration weakened the interaction between the CH3 domains of each homo variant and facilitated their dissociation as intended. In this test, G1dr/l carrying the existing alteration to improve Fab arm exchange efficiency had 91.7% rate of bispecific antibody formation. Thus, G1dP14/N14, G1dP15/N15. G1dP16/N16, G1dP17/N17, and G1dP18/N18 were found to be superior thereto in the rate of bispecific antibody formation.

In consideration of applicability to drug production, G1dP16/N16 (D356K1V397F and V397F/K439E) and G1dP17/N17 (D356K/V397Y and V397Y/K439E) are very useful because of their higher rates of bispecific antibody formation and smaller amounts of heterogeneous components as compared with the existing alteration to improve Fab arm exchange efficiency.

FIG. 5 shows the relationship between the CH3 stability of the altered forms studied in Tables 3 and 6 and the rate of bispecific antibody formation using 25 mM 2MEA as a reducing agent. As shown in FIG. 5, the CH3 stability of each homo variant used correlates evidently with Fab arm

TABLE 6

| Abbreviation | Name of H chain constant region of MoAb1 used | Introduced alteration | Name of H chain constant region of MoAb2 used | Introduced alteration | Rate of bispecific antibody formation (%) | Tm of MoAb1 CH3 (° C.) | Tm of MoAb2 CH3 (° C.) |
|---|---|---|---|---|---|---|---|
| G1dr/1 | G1dr | K409R | G1d1 | F405L | 91.7 | 70.7 | 69.7 |
| G1dP1/N1 | G1dP1 | D356K | G1dN1 | K439E | 0.1 | 76.7 | 74.7 |
| G1dP8/N8 | G1dP8 | D356K/V397M | G1dN8 | V397M/K439E | 73.2 | 70.1 | 70.5 |
| G1dP14/N14 | G1dP14 | D356K/K392D/V397M | G1dN14 | K392D/V397M/K439E | 96.5 | 68.3 | 69.2 |
| G1dP15/N15 | G1dP15 | D356K/K392E/V397M | G1dN15 | K392E/V397M/K439E | 96.9 | 69.3 | 70.2 |
| G1dP16/N16 | G1dP16 | D356K/V397F | G1dN16 | V397F/K439E | 96.5 | 69.1 | 69.7 |
| G1dP17/N17 | G1dP17 | D356K/V397Y | G1dN17 | V397Y/K439E | 98.0 | 69.2 | 69.8 |
| G1dP18/N18 | G1dP18 | D356K/K392T/V397M | G1dN18 | K392T/V397M/K439E | 98.9 | 70.1 | 70.8 |
| G1dP19/N19 | G1dP19 | D356K/K392V/V397M | G1dN19 | K392V/V397M/K439E | 70.8 | 70.7 | 71.1 |
| G1dP20/N20 | G1dP20 | D356K/K392I/V397M | G1dN20 | K392I/V397M/K439E | 54.3 | 70.5 | 71.2 | exchange efficiency. The high rate of bispecific antibody formation is achieved by destabilizing the stability of the CH3 regions of a homo variant having more stable CH3 between two types of homo variants used such that Tm of this CH3 falls below 70° C., etc.

[Example 5] Study on Reaction Time

The relationship between reaction time and reaction efficiency was studied using G1dP17/N17 found in Example 4.

Reaction condition: in TBS (Takara Bio Inc., pH 7.6), [each mAb]=1.0 mg/ml, [2-MEA (Sigma-Aldrich Corp.)]= 25 mM, 37° C., total amount=50 μl.

After 90 minutes, 3 hours, or 24 hours, 450 μl of a 25 mM MES buffer solution (pH 5.0) cooled to 4° C. was added to the reaction solution, which was further stored at 4° C. to terminate the reaction. Then, the reaction efficiency was evaluated according to the method of Reference Example 2 (FIG. 6).

As shown in FIG. 6, the rate of bispecific antibody formation of G1dP17/N17 was 94.6% in 90 minutes, 95.2% in 3 hours, and 97.4% in 24 hours in the presence of 25 mM 2-MEA. Thus, the reaction time of 90 minutes offered the rate of approximately 95%. These results demonstrated that this altered form exhibits sufficiently higher reaction efficiency than the rate of bispecific antibody formation (Table 6) of G1dr/1 with K409R alteration introduced to one chain and F405L alteration introduced to another chain.

[Example 6] Evaluation of Binding of Altered Form Exhibiting Highly Efficient Fab Arm Exchange to Human FcgR and Human FcRn The altered form G dP17/N17 that exhibited highly efficient FAE efficiency in Example 4 was evaluated for its binding to human FcgR and human FcRn. First, MRAH-G1d/MRAL-k0 having the sequence of naturally occurring IgG1 and the altered form MRAH-G1dP17/MRAL-k0//H54-G1dN17/L28-k0 after Fab arm exchange were tested for their binding to human FcRn according to the method of Reference Example 5. The results of analyzing binding to human FcRn are shown in Table 7.

TABLE 7

| Abbreviation | KD for human FcRn (M) |
|---|---|
| G1d | 2.1E−06 |
| G1dP17/N17 | 1.9E−06 |

The results shown in Table 7 demonstrated that the altered form MRAH-G1dP I7/MRAL-k0//H54-G1dN17/L28-k0 prepared by Fab arm exchange has human FcRn-binding activity equivalent to that of naturally occurring IgG1.

Next, the binding activity against human FcgR was evaluated according to the method of Reference Example 4. In this context, MRAH-G1 d/MRAL-k0 having the sequence of naturally occurring IgG1, the altered form MRAH-G1dP17/MRAL-k0//H54-G1dN17/L28-k0 after Fab arm exchange, two types of homo variants before Fab arm exchange reaction (MRAH-G1dP17/MRAL-k0 and H54-G1dN17/L28-k0), and two types of homo variants lacking the alteration V397Y to destabilize CH3 domains (MRAH-G1dP1/MRAL-k0 and H54-G1dN1/L28-k0) were evaluated together. In Table 8, KD fold hFcgRIa, KD fold hFcgRIIaR, KD fold hFcgRIIaH, KD fold hFcgRIIb, and KD fold hFcgRIIIaV are values that indicate the relative binding activity of each altered form when KD of G1d for each FcgR is defined as 1.

TABLE 8

| Abbreviation | Introduced alteration | KD for hFcgRIa (M) | KD for hFcgRIIaR (M) | KD for hFcgRIIaH (M) | KD for hFcgRIIb (M) | KD for hFcgRIIIaV (M) |
|---|---|---|---|---|---|---|
| G1d |  | 1.6E−10 | 1.6E−06 | 8.7E−07 | 6.2E−06 | 5.1E−07 |
| G1dP17 | D356K + V397Y | 2.6E−10 | 6.5E−07 | 4.1E−07 | 2.7E−06 | 2.5E−07 |
| G1dN17 | K439E + V397Y | 1.3E−10 | 5.9E−07 | 3.9E−07 | 2.4E−06 | 2.0E−07 |
| G1dP1 | D356K | 1.6E−10 | 1.7E−06 | 9.9E−07 | 7.0E−06 | 5.1E−07 |
| G1dN1 | K439E | 2.5E−10 | 1.5E−06 | 9.6E−07 | 7.1E−06 | 4.5E−07 |
| G1dP17/N17 | D356K + V397Y/ K439E + V397Y | 1.4E−10 | 5.8E−07 | 3.7E−07 | 2.5E−06 | 2.1E−07 |

| Abbreviation | KD fold hFcgRIa | KD fold hFcgRIIaR | KD fold hFcgRIIaH | KD fold hFcgRIIb | KD fold hFcgRIIIaV |
|---|---|---|---|---|---|
| G1d | 1 | 1 | 1 | 1 | 1 |
| G1dP17 | 0.6 | 2.4 | 2.1 | 2.3 | 2.0 |
| G1dN17 | 1.3 | 2.6 | 2.2 | 2.6 | 2.5 |
| G1dP1 | 1.0 | 0.9 | 0.9 | 0.9 | 1.0 |
| G1dN1 | 0.6 | 1.0 | 0.9 | 0.9 | 1.1 |
| G1dP17/N17 | 1.1 | 2.7 | 2.3 | 2.5 | 2.5 |

The binding of the altered form G1dP17/N17 after Fab arm exchange compared with the naturally occurring antibody was enhanced by 1.1 times for hFcgRIa, 2.7 times for hFcgRIIaR, 2.3 times for hFcgRIIaH, 2.5 times for hFcgRIIb, and 2.5 times for hFcgRIIIaV. In this context, the homo variants G1dP1 and G1dN1 before the introduction of CH3 domain-destabilizing V397Y bound to each FcgR with activity equivalent to that of the naturally occurring antibody. Also, the homo variants derived therefrom by the introduction of V397Y (G1dP17 and G1dN17) exhibited enhanced binding to each FcgR. Therefore, the V397Y alteration was found to enhance the binding to hFcgR.

These results demonstrated that G1dP17/N17 that achieves high Fab arm exchange efficiency does not impair the binding to human FcRn and human FcgR as compared with the naturally occurring antibody.

[Example 7] Study on Fab Arm Exchange in Culture Supernatant

For the production of bispecific antibodies by Fab arm exchange, it is assumed that two types of homo variants are separately cultured and purified, followed by the Fab arm exchange. If the reaction can occur in a culture supernatant, the homo variant purification step can be omitted. Therefore, this approach is highly advantageous. Accordingly, this study was conducted to test whether or not to cause Fab arm exchange with high efficiency by mixing two types of homo variants with a reducing agent in a culture supernatant.

First, an amino acid residue at position 356 in MRAH-G1d and H54-G1d was substituted by E, and an amino acid residue at position 358 therein was substituted by M to prepare MRAH-G1m (SEQ ID NO: 49), H54-G1m (SEQ ID NO: 50), respectively. Next, E356K and K409R were introduced to MRAH-G1m to prepare MRAH-G1mrP1 (SEQ ID NO: 51). K439E and K409R were introduced to H54-G1m to prepare H54-G1mrN1 (SEQ ID NO: 52). Antibody L chains MRAL-k0 and L28-k0 were used for the H chain variable regions MRAH and H54, respectively. MRAH-G1mrP1/MIRAL-k0 and H54-G1mrN1/L28-k0 were expressed and purified according to the method of Reference Example 1.

FreeStyle 293 cells (Invitrogen Corp.) were cultured in FreeStyle 293 Expression medium and then centrifuged to recover a supernatant, which was then filtered through a 0.22 m filtration membrane and used as Mock C M in Fab arm exchange.

Reaction condition: in Mock C M (pH 7.6), [each mAb]= 1.0 mg/ml, [2-MEA (Sigma-Aldrich Corp.)]=25 mM, 37° C., 90 minutes After the reaction, rProtein A Sepharose Fast Flow (GE Healthcare Japan Corp.) was added to the reaction solution for purification. Then, the reaction efficiency was evaluated according to the method of Reference Example 2 (FIG. 7).

As shown in FIG. 7, the bispecific antibody was shown to be formed with 98% or higher reaction efficiency through the reaction at 37° C. for 90 minutes in the presence of 25 mM 2-MEA even in the culture supernatant.

[Example 8] Development of Fab Arm Exchange in Mouse IgG1

The preceding Examples showed that Fab arm exchange is efficiently induced in human IgG1 or human IgG4. This study was conducted to test whether or not to similarly form a bispecific antibody by Fab arm exchange in mouse IgG1.

From the reported crystallographic structure (Harris L J et al., J. Mol. Biol., 1998. 275. 861-872), D at EU numbering position 399 and K at EU numbering position 409 were presumed to contribute to the inter-chain interaction between CH3 domains (FIG. 8). Accordingly, this study was conducted to test whether or not to induce Fab arm exchange by introducing charges for promoting heterodimerization to these sites, as in human IgG1.

The antibody H chain variable regions used were H chain variable regions WT(H) (SEQ ID NO: 1; hereinafter, referred to as MRAH) and H54 (SEQ ID NO: 2) of the antibody against human interleukin 6 receptor disclosed in WO2009/125825. MRAH-mIgG1 (SEQ ID NO: 53) and H54-mIgG1 (SEQ ID NO: 54) having a mouse IgG1 H chain constant region as an antibody H chain constant region were prepared using the H chain variable regions. In addition, D399K was introduced as association interface-controlling alteration to MRAH-mIgG1 to prepare MRAH-mIgG1mP3 (SEQ ID NO: 55). D399R was introduced as association interface-controlling alteration to MRA4H-mIgG1 to prepare MRAH-mIgG1mP4 (SEQ ID NO: 56). K409D was introduced as association interface-controlling alteration to H54-mIgG1 to prepare H54-mIgG1mN3 (SEQ ID NO: 57). K409E was introduced as association interface-controlling alteration to H54-mIgG1 to prepare H54-mIgG1mN4 (SEQ ID NO: 58). MRAL-mk1 (SEQ ID NO: 59) and L28-mk1 (SEQ ID NO: 60) having the sequence of a mouse K chain constant region were prepared as L chains. The antibody L chains MRAL-mk1 and L28-mk1 were used for the H chain variable regions MRAH and H54, respectively. MRAH-mIgG1mP3/MRAL-mk1, MRAH-mIgG1mP4/MRAL-mk11, H54-mIgG1mN3/L28-mk1, and H54-mIgG1mN4/L28-mk1 were expressed and purified according to the method of Reference Example 1.

Next, Fab arm exchange was carried out using the following combinations:

(1) MRAH-mIgG1mP3/MRAL-mk1 and H54-migG1mN3/L28-mk1

(2) MRAH-mIgG1mP4/MRAL-mk1 and H54-mIgG1mN4/L28-mk1

Reaction condition: in TBS (Takara Bio Inc., pH 7.6), [each mAb]=2 mg/ml, [2-MEA (Sigma-Aldrich Corp.)]=25 mM, 37° C., 19 hours.

After the reaction, the reaction efficiency was determined by CE-IEF according to the method of Reference Example 5 (FIG. 9).

As a result, the bispecific antibody was confirmed to be formed with efficiency as high as 89.2% by the reaction of MRAH-mIgG1mP3/MRAL-mk1 and H54-mIgG1mN3/L28-mk1 and 89.9% by the reaction of MRAH-mIgG1mP4/MRAL-mk1 and H54-mIgG1mN4/L28-mk1. This reaction efficiency was slightly lower than that of the Fab arm exchange using human IgG1 or human IgG4. This is presumably because mouse IgG1 has 3 disulfide bonds in the hinge regions, resulting in stronger binding between two heavy chains than that in the human IgG1 or human IgG4 hinges (Harris L J et al., J. Mol. Biol., 1998. 275. 861-872).

[Example 9] Evaluation of Binding Activity of Bispecific Antibody Prepared by Fab Arm Exchange of Mouse IgG1 Against Mouse FcgR and Mouse FcRn The two types of bispecific antibodies (MRAH-mIgG1mP3/MRAL-mk1//H54-mIgG1mN3/L28-mk1 and MRAH-mIgG1mP4/MRAL-mk1//H54-mIgG1mN4/L28-mk1) prepared by mouse IgG-type Fab arm exchange were tested for their binding to mouse FcgR and mouse FcRn according to Reference Example 4-3. Also, MRAH-mIgG1/MRAL-mk1 was prepared according to Reference Example 1 and assayed as a control. The assay results are shown in Table 9.

TABLE 9

| Abbreviation | KD for mFcgRI (M) | KD for mFcgRII (M) | KD for mFcgRIII (M) | KD for hFcgRIV (M) | KD fold mFcgRII | KD fold mFcgRIII |
|---|---|---|---|---|---|---|
| mIgG1 | N.D. | 8.2E−07 | 7.9E−07 | N.D. | 1.0 | 1.0 |
| mIgG1mP3/mN3 | N.D. | 6.7E−07 | 6.7E−07 | N.D. | 1.2 | 1.2 |
| mIgG1mP4/mN4 | N.D. | 6.7E−07 | 6.8E−07 | N.D. | 1.2 | 1.2 |

Both of the two types of bispecific antibodies prepared exhibited a binding profile similar to that of naturally occurring mIgG1. Specifically, these bispecific antibodies exhibited 1.2 times the binding activity of naturally occurring mIgG1 against mFcgRII and mFcgRIII, without binding to mFcgRI and mFcgRIV.

Next, the binding to mFcRn was evaluated according to Reference Example 4-4. The results are shown in Table 10.

TABLE 10

| Abbreviation | KD for mouse FcRn (M) | fold KD |
|---|---|---|
| mIgG1 | 2.5E−06 | 1.0 |
| mP3/mN3 | 2.1E−06 | 1.2 |
| mP4/mN4 | 1.9E−06 | 1.3 |

Both of the two types of bispecific antibodies prepared were found to maintain mFcRn binding equivalent to that of naturally occurring mIgG1.

[Example 10] Measurement of Cytotoxic Activity

Whether each human IgG-type bispecific antibody and mouse IgG-type bispecific antibody prepared by Fab arm exchange would maintain functions equivalent to those of a bispecific antibody prepared by an existing approach was evaluated by measuring the cytotoxic activity of an anti-human glypican 3 and anti-human CD3 bispecific antibody. First, an anti-human GPC3/anti-human CD3 bispecific antibody having human IgG4 constant regions was prepared as a control by the CrossMab technology reported by Schaefer et al. (Proc Natl Acad Sci, 2011, 108, 11187-11192). This molecule prepared by the CrossMab technology was a molecule in which the VH domain and the VL domain were exchanged within Fab against human GPC3 as described in WO2012/073985. The Knobs-into-Holes technology was used in an antibody H chain constant region in order to promote the hetero-association. The Knobs-into-Holes technology is a technique which involves substituting an amino acid side chain present in the CH3 region of one H chain with a larger side chain (knob), and substituting its counterpart amino acid side chain present in the CH3 region of another H chain with a smaller side chain (hole) so that the knob is inserted into the hole to promote the heterodimerization of the H chains, whereby the heterodimerized antibody of interest can be efficiently obtained (Nature, 1994, 372, 379-383). The alteration described in WO2011/108714 was used as alteration to attenuate binding to FcgR. Specifically, this alteration was introduced to substitute amino acid residues at EU numbering positions 234, 235, and 297 with Ala. Gly at EU numbering position 446 and Lys at EU numbering position 447 were removed from the C termini of the antibody H chains. In order to facilitate purification after antibody expression, a histidine tag was further added to the C terminus of the anti-human GPC3 H chain, and a FLAG tag was further added to the C terminus of the anti-human CD3 H chain. GC33(2)H-G4dKnHS (SEQ ID NO: 61) was prepared as the anti-human GPC3 H chain thus altered. Also, rCE115H-G4dH1FS (SEQ ID NO: 62) was prepared as the anti-human CD3 H chain. Antibody L chains GC33(2)L-k0 (SEQ ID NO: 63) and rCE115L-k0 (SEQ ID NO: 64) were used on the anti-human GPC3 side and the anti-human CD3 side, respectively. The resulting antibody was expressed by transient expression in FreeStyle 293 cells according to Reference Example 1. The obtained culture supernatant was added to MabSelect SuRe column (GE Healthcare Japan Corp.), and the column was washed, followed by elution with 50 mM acetic acid. The fraction containing the antibody was added to HisTrap HP column (GE Healthcare Japan Corp.) or Ni Sepharose FF column (GE Healthcare Japan Corp.), and the column was washed, followed by elution with imidazole. The fraction containing the antibody was concentrated through an ultrafiltration membrane. Then, the concentrate was added to Superdex 200 column (GE Healthcare Japan Corp.). Only a monomeric antibody in the eluate was recovered to obtain a purified antibody GPC3 ERY22-rCE115.

Next, each bispecific antibody having human IgG1-type, human IgG4-type, or mouse IgG1-type constant regions and anti-human GPC3/anti-human CD3 variable regions was prepared by Fab arm exchange. For the human IgG1-type and human IgG4-type H chain constant regions, the alteration to substitute an amino acid residue at EU numbering position 235 with Arg and an amino acid residue at EU numbering position 239 with Lys was introduced as FcgR binding-reducing alteration to G1dP17, G1dN17, G1drP1, G1drN1, G4dP1, and G4dN1 containing the alteration for Fab arm exchange to prepare F760P17, F760N17, F760G1drP1, F760G1drN1, F760G4dP1, and F760G4dN1, respectively. For the mouse IgG1-type H chain constant region, the alteration to substitute amino acid residues at EU numbering positions 235 and 239 with Lys was introduced as FcgR binding-reducing alteration to mIgG1mP4 and mIgG1mN4 used in Example 8 to prepare mF18mP4 and mF18mN4, respectively. The anti-human GPC3 sequence described in WO2012/073985 was used as a variable region to prepare H0000-F760N17 (SEQ ID NO: 65), H0000-F760G1drN1 (SEQ ID NO: 66), H0000-F760G4dN1 (SEQ ID NO: 67), and H0000-mF18mN4 (SEQ ID NO: 68). On the other hand, rCE115H-F760P17 (SEQ ID NO: 69), rCE115H-F760G1drP1 (SEQ ID NO: 70), rCE115H-F760G4dP1 (SEQ ID NO: 71), and rCE115H-mF18mP4 (SEQ ID NO: 72) were prepared as human CD3 side H chains. GL4-k0 (SEQ ID NO: 79) on the anti-human GPC3 side and rCE115L-k0 (SEQ ID NO: 64) on the anti-human CD3 side were commonly used as human IgG1-type and human IgG4-type antibody L chains. GL4-mk1 (SEQ ID NO: 80) on the anti-human GPC3 side and rCE115L-mk1 (SEQ ID NO: 81) on the anti-human CD3 side were used as mouse IgG1-type antibody L chains. These homo variants were expressed and purified according to the method of Reference Example 1 to obtain rCE115H-F760P17/rCE115L-k0, H0000-F760N17/GL4-k0, rCE115H-F760G1drP1/rCE115L-k0, H0000-F760G1drN1/GL4-k0, rCE115H-F760G4dP1/rCE115L-k0, H0000-F760G4dN1GL4-k0, rCE115H-mF18mP4/rCE115L-mk1, and H0000-mF18mP4/GL4-mk1.

Next, two types of homo variants thus obtained were mixed in the combinations given below to cause FAE reaction.

(1) rCE115H-F760P17/rCE115L-k0 and H0000-F760N17/GL4-k0
(2) rCE115H-F760G1drP1/rCE115L-k0 and H0000-F760G1drN1/GL4-k0
(3) rCE115H-F760G4dP1/rCE115L-k0 and H0000-F760G4dN1/GL4-k0
(4) rCE115H-mF18mP4/rCE115 L-mk1 and H0000-mF18mP4/GL4-mk1

Reaction condition: in TBS (Takara Bio Inc., pH 7.6), [each mAb]=0.36 mg/ml, [2-MEA (Sigma-Aldrich Corp.)] =25 mM, 37° C., 18 hours.

After the reaction, the products were dialyzed against PBS and used in the evaluation of cytotoxic activity.

The evaluation of cytotoxic activity was carried out by the method described in Reference Example 6. The results are shown in FIGS. 10-1 and 10-2.

As shown in FIG. 10-1, all of the bispecific antibodies prepared by human IgG1-type and human IgG4-type Fab arm exchange exhibited cytotoxic activity equivalent to that of the control antibody (GPC3 ERY22-rCE115) prepared by the existing bispecific antibody preparation technique. As shown in FIG. 10-2, the bispecific antibody prepared by mouse IgG-type Fab arm exchange also exhibited cytotoxic activity equivalent to that of the control antibody (GPC3 ERY22-rCE115) prepared by the existing bispecific antibody preparation technique.

[Example 11] Normal Mouse PK Test (11-1) In Vivo Test Using Normal Mouse

The in vivo test using a normal mouse was conducted to evaluate whether antibodies prepared by human IgG-type and mouse IgG-type Fab arm exchange would exhibit change in concentration in blood at the same level as in an antibody prepared by the existing approach.

Three types of anti-human glypican 3/anti-human CD3 bispecific antibodies TR-G1drP1/N1, TR-G1dP17/N17, and TR-G4dP1N1 were prepared as human IgG-type antibodies by human IgG-type Fab arm exchange. Also, bispecific antibodies TR-G1dKiH and TR-G4dKiH having the same anti-human glypican 3/anti-human CD3 variable regions as above were prepared using constant regions prepared by the introduction of Knobs-into-Holes alteration (Nature, 1994, 372, 379-383) to a constant region G1d starting at Ala at EU numbering position 118 in MRAH-G1d (SEQ ID NO: 3) or a constant region G4d (constant region wtG4d starting at Ala at EU numbering position 118 in MRAH-wtG4d (SEQ ID NO: 5) and further containing an IgG1-type hinge resulting from the substitution of an amino acid residue Ser at position 228 by Pro), and used as control antibodies. In this context, the constant region names G1dKiH and G4dKiH each denote constant regions expressed as a Knob chain and a Hole chain in combination using a Knob chain in which the knob alteration (alteration to substitute an amino acid residue at position 349 by Cys and an amino acid residue at position 366 by Trp) was introduced in the constant region G d or G4d and a Hole chain in which the Hole alteration (alteration to substitute an amino acid residue at position 356 by Cys, an amino acid residue at position 366 by Ser, an amino acid residue at position 368 by Ala, and an amino acid residue at position 407 by Val) was introduced in the constant region G1d or G4d.

On the other hand, H237-mIgG1mP3 (SEQ ID NO: 74), H237-mIgG1mN3 (SEQ ID NO: 75), H237-mIgG1mP4 (SEQ ID NO: 76), and H237-mIgG1mN4 (SEQ ID NO: 77) were prepared as mouse IgG-type antibodies by introducing alteration for Fab arm exchange to H237-mIgG1 (SEQ ID NO: 73) having the sequence of an H chain variable region H237 of the anti-human IL-6 receptor antibody described in WO02009/125825 and the sequence of a naturally occurring mIgG1 constant region. L104-mk1 (SEQ ID NO: 78) consisting of the sequence of an anti-human IL-6 receptor L chain variable region L104 and a mouse K chain constant region mk1 was used as an antibody L chain. These homo variants were expressed according to the method of Reference Example 1 to obtain H237-mIgG1mP3/L104-mk1, H237-mIgG1mN3/L104-mk1, H237-mIgG1mP4/L104-mk1, and H237-mIgG1mN4/L104-mk1. Fab arm exchange was carried out using the obtained homo variants to obtain SA-mIgG1mP3/mN3 (H237-mIgG1mP3/L104-mk1 and H237-mIgG1mN3/L104-mk1 in combination) and SA-mIgG1mP4/mN4 (H237-mIgG1mP4/L104-mk1 and H237-mIgG1mN4/L104-mk1 in combination). SA-mIgG1 expressed using H237-mIgG1 and L104-mk1 was used as a control antibody.

The Fab arm exchange was conducted under reaction conditions given below in all cases. After the reaction, the products were dialyzed against PBS and used in the in vivo test.

Reaction condition: in TBS (Takara Bio Inc., pH 7.6), [each mAb]=0.225 mg/ml, [2-MEA (Sigma-Aldrich Corp.)]= 25 mM, 37° C., 17 hours.

Each human IgG-type anti-human glypican 3/anti-human CD3 bispecific antibody (TR-G1dKiH, TR-G1drP1N1, TR-G1dP17/N17, TR-G4dKiH, and TR-G4dP1/N1) or each anti-human IL-6 receptor mouse antibody (SA-mIgG1, SA-mIgG1mP3/mN3, and SA-mIgG1mP4/mN4) was administered to a normal mouse (C57BL/6J mouse. Charles River Laboratories Japan, Inc.). Then, each antibody was evaluated for its in vivo kinetics. The antibody was adjusted to 0.1 mg/mL and administered at 10 mL/kg to the tail vein. After a lapse of 5 minutes, 2 hours, 1 day, 2 days, 3 days, 7 days, 14 days, 21 days, and 28 days after the antibody administration, blood was collected from the mouse. The collected blood was immediately centrifuged at 15,000 rpm at 4° C. for 15 minutes to obtain plasma. The separated plasma was stored in a freezer set to −20° C. or lower until the start of the assay.

(11-2) Measurement of Bispecific Antibody Concentration in Plasma by ECLLA

The bispecific antibody concentration in the mouse plasma was measured by ECLIA. First, soluble human glypican 3 was dispensed to wells of MULTI-ARRAY 96-well Plate (Meso Scale Discovery) and left standing overnight at 4° C. to prepare a soluble human glypican 3-immobilized plate. Calibration samples containing each bispecific antibody at 200, 100, 50, 25, 12.5, 6.25, or 3.125 ng/mL as a plasma concentration and mouse plasma assay samples diluted 100-fold or more were prepared. These calibration samples and plasma assay samples were dispensed at 100 µL/well to the soluble human glypican 3-immobilized plate and stirred at room temperature for 2 hours. Subsequently, a rabbit idiotype antibody against an anti-human CD3 antibody was stirred in the plate at room temperature for 1 hour. Then, Anti-Rabbit IgG-Sulfotag antibody (Meso Scale Discovery) was reacted therewith at room temperature for 1 hour. After addition of Read Buffer T (Meso Scale Discovery), light emission was measured using SECTOR Imager 2400 (Meso Scale Discovery). The antibody concentration in the mouse plasma was calculated from emission signals in the calibration curve using analysis software SOFTmax PRO (Molecular Devices). The results are shown in FIG. 11. PK parameters are shown in Table 11. The results shown in FIG. 11 and Table 11 demonstrated that all of the bispecific antibodies prepared by human IgG-type Fab arm exchange exhibit change in concentration in blood at the same level as in the control antibody prepared using the Knobs-into-Holes technology as the existing bispecific antibody preparation technique.

TABLE 11

| Abbreviation | t½ (days) | CL (mL/day/kg) | Vss (mL/kg) |
|---|---|---|---|
| TR-G1dKiH | 17 | 3.49 | 84.5 |
| TR-G1drP1/N1 | 15.3 | 3.98 | 83.5 |
| TR-G1dP17/N17 | 16.9 | 3.05 | 71.5 |
| TR-G4dKiH | 19.5 | 3.05 | 84.9 |
| TR-G4dP1/N1 | 23.7 | 2.22 | 73.5 |

(11-3) Measurement of Anti-Human IL-6 Receptor Mouse Antibody Concentration in Plasma by ELISA The anti-human IL-6 receptor mouse antibody concentration in the mouse plasma was measured by ELISA. First, soluble human IL-6 receptor was dispensed to wells of Nunc-Immuno Plate, MaxiSoup (Nalge Nunc International Corp.) and left standing overnight at 4° C. to prepare a soluble human IL-6 receptor-immobilized plate. Calibration samples containing each anti-human IL-6 receptor mouse antibody at 2.50, 1.25, 0.625, 0.313, 0.156, 0.078, or 0.039 µg/mL as a plasma concentration and mouse plasma assay samples diluted 100-fold or more were prepared. These calibration samples and plasma assay samples were dispensed at 100 L/well to the soluble human IL-6 receptor-immobilized plate and stirred at room temperature for 2 hours. Then, Anti-Mouse IgG-Peroxidase antibody (Sigma-Aldrich Corp.) was reacted therewith at room temperature for 2 hours, and the color reaction of the reaction solution was carried out using TMB One Component HRP Microwell Substrate (BioFX Laboratories, Inc.) as a substrate. The reaction was terminated by the addition of 1 N sulfuric acid (Showa Chemical Industry Co., Ltd.). The absorbance of the reaction solution in each well was measured at 450 nm using a microplate reader. The antibody concentration in the mouse plasma was calculated from the absorbance in the calibration curve using analysis software SOFTmax PRO (Molecular Devices). The results are shown in FIG. 12. The antibody parameters are shown in Table 12. The results shown in FIG. 12 and Table 12 demonstrated that the antibodies prepared by mouse IgG-type Fab arm exchange exhibit change in concentration in blood at the same level as in the control antibody having the sequence of naturally occurring mIgG1.

TABLE 12

| Abbreviation | t½ (days) | CL (mL/day/kg) | Vss (mL/kg) |
|---|---|---|---|
| SA-mIgG1 | 12.8 | 5.13 | 98.7 |
| SA-mIgG1mP3/mN3 | 16.6 | 3.7 | 86.7 |
| SA-mIgG1mP4/mN4 | 21.9 | 3.47 | 104 |

Reference Example 1

Preparation of Antibody Expression Vector and Expression and Purification of Antibody The full-length genes having nucleotide sequences encoding the H chain and the L chain of each antibody were synthesized using assembly PCR or the like and prepared by a method generally lknown to those skilled in the art. Amino acid substitution was introduced by a method generally known to those skilled in the art using PCR or the like. The obtained plasmid fragments were inserted to expression vectors for animal cells to prepare H chain expression vectors and L chain expression vectors. The nucleotide sequences of the obtained expression vectors were determined by a method generally known to those skilled in the art. The prepared plasmids were transiently transferred to a human embryonic kidney cancer cell-derived HEK293H line (Invitrogen Corp.) or FreeStyle 293 cells (Invitrogen Corp.) for antibody expression. The obtained culture supernatant was recovered and then passed through a 0.22 µm filter MILLEX(R)-GV (Millipore Corp.) or a 0.45 µm filter MILLEX(R)-GV (Millipore Corp.) to obtain a culture supernatant. The antibody was purified from the obtained culture supernatant by a method generally known to those skilled in the art using rProtein A Sepharose Fast Flow (GE Healthcare Japan Corp.) or Protein G Sepharose 4 Fast Flow (GE Healthcare Japan Corp.). As for the concentration of the purified antibody, the absorbance was measured at 280 nm using a spectrophotometer, and the antibody concentration was calculated by use of an extinction coefficient calculated from the obtained value by a method such as PACE (Protein Science 1995; 4: 2411-2423).

Reference Example 2

Evaluation of Rate of Bispecific Antibody Formation by Ion-Exchange Chromatography The separation of each specimen was evaluated by the ion-exchange chromatography purification method using Prominence UFLC (Shimadzu Corp.). The bispecific antibody was separated by the two-solution mixed gradient method using a 25 mM MES buffer solution (pH 5.0) and a 25 mM MES buffer solution (pH 5.0) containing 500 mM sodium chloride as mobile phases and ProPac WCX-10 (Thermo Fisher Scientific K.K.) as a column. The data was obtained at a wavelength of 215 nm. The elution results were evaluated using Empower 2 (Waters Corp.).

A value determined by dividing the area value of the bispecific antibody by the area value of all antibodies present in the system, followed by multiplication by 100 was used as the rate of bispecific antibody formation (%). If one of the homo variants had a poor rate of recovery, the area value of the other homo variant was doubled and summed with the area value of the bispecific antibody, and the resulting value was used as the area value of all antibodies for the calculation.

Reference Example 3

Measurement of Tm

The Tm of CH3 domains was measured by a method generally known to those skilled in the art using Rotor-gene Q (Qiagen N.V.). A sample containing a mixture of each antibody at a concentration of 0.1 mg/mL and SYPRO orange at a concentration of 10× concentrate was heated from 30° C. to 99° C. The fluorescence intensity (excitation wavelength: 470 nm, fluorescence wavelength: 555 nm) was measured on the basis of 0.4° C. This measurement was conducted in PBS (Sigma-Aldrich Corp., pH 7.4). The analysis was conducted using Rotor-gene Q series software. The point of inflection determined by the first derivation of the fluorescence intensity was defined as Tm. The Tm of the CH3 domains was calculated through the use of Tm of MRAH CH2 around 70° C., Tm of MRAH Fab around 95° C., Tm of H54 CH2 around 70° C., and Tm of H54 Fab around 90° C.

Reference Example 4

Analysis of Interaction by SPR (4-1) Method for Preparing FcγR and Method for Analyzing Interaction Between Altered Antibody and FcγR The extracellular domain of each FcγR was prepared by the following method: first, the gene of the FcγR extracellular domain was synthesized by a method generally known to those skilled in the art. For this synthesis, the sequence of each FcγR was prepared on the basis of the information registered in NCBI. Specifically, FcγRI was prepared on the basis of the sequence of NCBI accession No. NM_000566.3; FcγRIIa was prepared on the basis of the sequence of NCBI accession No. NM_001136219.1; FcγRIIb was prepared on the basis of the sequence of NCBI accession No. NM_004001.3; FcγRIIIa was prepared on the basis of the sequence of NCBI accession No. NM_001127593.1; and FcγRIIIb was prepared on the basis of the sequence of NCBI accession No. NM_000570.3. These sequences were C-terminally tagged with a His tag sequence. Also, polymorphism is known about FcγRIIa, FcγRIIIa, and FcγRIIIb. The polymorphic sites were prepared with reference to J. Exp. Med., 1990, 172: 19-25 for FcγRIIa. J. Clin. Invest., 1997, 100 (5): 1059-1070 for FcγRIIIa, and J. Clin. Invest., 1989, 84, 1688-1691 for FcγRIIIb.

Each obtained gene fragment was inserted to expression vectors for animal cells to prepare expression vectors. The prepared expression vectors were transiently transferred to human embryonic kidney cancer cell-derived FreeStyle 293 cells (Invitrogen Corp.) to express the protein of interest. After culture, the obtained culture supernatant was recovered and then passed through a 0.22 μm filter to obtain a culture supernatant. The obtained culture supernatant was purified, as a rule, by the following 4 steps: cation-exchange column chromatography (SP Sepharose FF) as step 1, affinity column chromatography for the His tag (HisTrap HP) as step 2, gel filtration column chromatography (Superdex 200) as step 3, and sterile filtration as step 4. However, for FcγRI, anion-exchange column chromatography was carried out in step 1 using Q Sepharose FF. The absorbance was measured for each purified protein at 280 nm using a spectrophotometer, and the concentration of the purified protein was calculated by use of an extinction coefficient calculated from the obtained value by a method such as PACE (Protein Science 1995; 4: 2411-2423).

Each altered antibody was analyzed for its interaction with each Fcγ receptor thus prepared using Biacore T100 (GE Healthcare Japan Corp.), Biacore T200 (GE Healthcare Japan Corp.), Biacore A100, or Biacore 4000. The running buffer used was HBS-EP+ (GE Healthcare Japan Corp.). The assay temperature was set to 25° C. The sensor chips used were chips prepared by immobilizing the antigenic peptide, Protein A (Thermo Fisher Scientific K.K.), Protein A/G (Thermo Fisher Scientific K.K.), or Protein L (ACTIGEN or BioVision) onto Series S Sensor Chip CM5 (GE Healthcare Japan Corp.) or Series S Sensor Chip CM4 (GE Healthcare Japan Corp.) by the amine coupling method, or by immobilizing the antigenic peptide biotinylated in advance onto Series S Sensor Chip SA (certified) (GE Healthcare Japan Corp.) through interaction.

The antibody of interest was captured onto these sensor chips and allowed to interact with the Fcγ receptor diluted with a running buffer. The binding amount to the antibody was measured and compared among antibodies. Since the binding amount of the Fcγ receptor depends on the amount of the captured antibody, a correction value determined by dividing the binding amount of the Fcγ receptor by the amount of each captured antibody was used in the comparison. The antibody captured on the sensor chip was washed off through the reaction of 10 mM glycine-HCl (pH 1.5) to regenerate the sensor chip, which was repetitively used.

In order to calculate the KD value of each altered antibody for FcγR, kinetic analysis was conducted according to the following method: first, the antibody of interest was captured onto these chips and allowed to interact with the Fcγ receptor diluted with a running buffer. For the obtained sensorgram, the assay results were globally fit into the 1:1 Langmuir binding model using Biacore Evaluation Software to calculate an association rate constant ka (L/mol/s) and a dissociation rate constant kd (1/s). From these values, the dissociation constant KD (mol/L) was calculated.

(4-2) Method for Preparing FcRn and Method for Analyzing Interaction Between Altered Antibody and FcRn FcRn is a complex of FcRn and β2-microglobulin. Oligo DNA primers were prepared on the basis of the published gene sequence of human FcRn (J Exp Med. 1994 Dec. 1; 180 (6): 2377-81). The DNA fragment containing the whole gene encoding the FcRn was prepared by PCR using the prepared primers and human cDNA (Human Placenta Marathon-Ready cDNA, Clontech Laboratories, Inc.) as a template. A DNA fragment encoding the extracellular domain containing a signal region (Met1 to Leu290) was amplified by PCR using the obtained DNA fragment as a template and inserted to expression vectors for mammalian cells. Likewise, oligo DNA primers were prepared on the basis of the published gene sequence of human 132-microglobulin (Proc. Natl. Acad. Sci. U.S.A. 99 (26): 16899-16903 (2002)). The DNA fragment containing the whole gene encoding the β2-microglobulin was prepared by PCR using the prepared primers and human cDNA (Human Placenta Marathon-Ready cDNA, Clontech Laboratories, Inc.) as a template. A DNA fragment encoding the whole protein containing a signal region (Met1 to Met119) was amplified by PCR using the obtained DNA fragment as a template and inserted to expression vectors for mammalian cells.

Soluble human FcRn was expressed by the following procedures: the plasmids constructed for expressing human FcRn (SEQ ID NO: 30) and 12-microglobulin (SEQ ID NO: 31) were transferred to cells of a human embryonic kidney cancer cell-derived cell line HEK293H (Invitrogen Corp.) by lipofection using PEI (Polysciences, Inc.). The obtained culture supernatant was recovered and purified using IgG Sepharose 6 Fast Flow (Amersham Biosciences Corp.). Then, FcRn was further purified using HiTrap Q HP (GE Healthcare Japan Corp.) (J Immunol. 2002 Nov. 1; 169 (9): 5171-80).

A system using an antibody immobilized on the sensor chip described in J Immunol. 2009; 182 (12): 7663-71 and human FcRn as an analyte has been reported as an assay system for evaluating the interaction between the antibody and FcRn using Biacore. For this purpose, human FcRn was prepared as described in Reference Example 4. This system was used to evaluate the binding activity (dissociation constant KD) of Fv4-IgG1, Fv4-IgG1-v1, and Fv4-IgG1-v2 against human FcRn at pH 6.0 and pH 7.4. Each antibody as a test substance was directly immobilized onto Series S Sensor Chip CM5 and subjected to the test. The immobilization of the antibody to the sensor chip was carried out using 50 mmol/L sodium phosphate, 150 mmol/L NaCl, and 0.05% (v/v %) Surfactant P20 (pH 6.0) as a running buffer and an amine coupling kit according to the manual of the manufacturer in order to attain 500 RU as the target amount of the antibody immobilized.

The assay was conducted by use of the prepared sensor chip using 50 mmol/L sodium phosphate/150 mmol/L NaCl, and 0.05% Surfactant P20 (pH 6.0) or 50 mmol/L sodium phosphate. 150 mmol/L NaCl, and 0.05% Surfactant P20 (pH 7.4) as a running buffer. The assay was conducted at 25° C. for all samples. The diluted solution of the human FcRn or a running buffer (as a control solution) was injected thereto at a flow rate of 5 µL/min for 10 minutes so that the human FcRn was allowed to interact with the antibody on the sensor chip. Then, a running buffer was injected thereto at a flow rate of 5 µL/min for 1 minute. After observation of the dissociation of FcRn, 20 mmol/L Tris-HCl/150 mmol/L NaCl (pH 8.1) were injected at a flow rate of 30 µL/min for 15 seconds, and this operation was repeated twice to regenerate the sensor chip.

In order to calculate the KD value of each altered antibody for FcRn, kinetic analysis was conducted according to the following method: first, the antibody of interest was captured onto these chips and allowed to interact with FcRn diluted with a running buffer. For the obtained sensorgram, the assay results were globally fit into the 1:1 Langmuir binding model using Biacore Evaluation Software to calculate an association rate constant ka (L/mol/s) and a dissociation rate constant kd (1/s). From these values, the dissociation constant KD (mol/L) was calculated.

(4-3) Method for Preparing mFcγR and Method for Analyzing Interaction Between Altered Antibody and mFcγR The extracellular domain of each mouse FcγR was prepared by the following method: first, the gene of the FcγR extracellular domain was synthesized by a method generally known to those skilled in the art. For this synthesis, the sequence of each FcγR was prepared on the basis of the information registered in NCBI. Specifically, mFcγRI was prepared on the basis of the sequence of NCBI Reference Sequence: NP_034316.1; mFcγRII was prepared on the basis of the sequence of NCBI Reference Sequence: NP_034317.1; mFcγRIII was prepared on the basis of the sequence of NCBI Reference Sequence: NP_034318.2; and mFcγRIV was prepared on the basis of the sequence of NCBI Reference Sequence: NP_653142.2. These sequences were C-terminally tagged with a His tag sequence.

Each obtained gene fragment was inserted to expression vectors for animal cells to prepare expression vectors. The prepared expression vectors were transiently transferred to human embryonic kidney cancer cell-derived FreeStyle 293 cells (Invitrogen Corp.) to express the protein of interest. The obtained culture supernatant was recovered and then passed through a 0.22 µm filter to obtain a culture supernatant. The obtained culture supernatant was purified, as a rule, by the following 4 steps: ion-exchange column chromatography as step 1, affinity column chromatography for the His tag (HisTrap HP) as step 2, gel filtration column chromatography (Superdex 200) as step 3, and sterile filtration as step 4. The ion-exchange column chromatography of step 1 was carried out using Q Sepharose HP for mFcγRI, SP Sepharose FF for mFcγRII and mFcγRIV, and SP Sepharose HP for mFcγRIII. D-PBS(−) was used as a solvent in step 3 or later, while D-PBS(−) containing 0.1 M arginine was used for mFcγRIII. The absorbance was measured for each purified protein at 280 nm using a spectrophotometer, and the concentration of the purified protein was calculated by use of an extinction coefficient calculated from the obtained value by a method such as PACE (Protein Science 1995; 4: 2411-2423).

Each altered antibody was analyzed for its interaction with each Fcγ receptor thus prepared using Biacore T100 (GE Healthcare Japan Corp.), Biacore T200 (GE Healthcare Japan Corp.), Biacore A100, or Biacore 4000. The running buffer used was HBS-EP+(GE Healthcare Japan Corp.). The assay temperature was set to 25° C. The sensor chips used were chips prepared by immobilizing the antigenic peptide, Protein A (Thermo Fisher Scientific K.K.), Protein A/G (Thermo Fisher Scientific K.K.), or Protein L (ACTIGEN or BioVision) onto Series S Sensor Chip CM5 (GE Healthcare Japan Corp.) or Series S Sensor Chip CM4 (GE Healthcare Japan Corp.) by the amine coupling method, or by inmmobilizing the antigenic peptide biotinylated in advance onto Series S Sensor Chip SA (certified) (GE Healthcare Japan Corp.) through interaction.

The antibody of interest was captured onto these sensor chips and allowed to interact with mFcγR diluted with a running buffer. The binding amount to the antibody was measured and compared among antibodies. Since the binding amount of mFcγR depends on the amount of the captured antibody, a correction value determined by dividing the binding amount of mFcγR by the amount of each captured antibody was used in the comparison. The antibody captured on the sensor chip was washed off through the reaction of 10 mM glycine-HCl (pH 1.5) to regenerate the sensor chip, which was repetitively used.

In order to calculate the KD value of each altered antibody for FcγR, kinetic analysis was conducted according to the following method: first, the antibody of interest was captured onto these chips and allowed to interact with mFcγR diluted with a running buffer. For the obtained sensorgram, the assay results were globally fit into the 1:1 Langmuir binding model using Biacore Evaluation Software to calculate an association rate constant ka (L/mol/s) and a dissociation rate constant kd (l/s). From these values, the dissociation constant KD (mol/L) was calculated.

(4-4) Method for Preparing mFcRn and Method for Analyzing Interaction Between Altered Antibody and mFcRn Kinetic analysis was conducted on mouse FcRn and each antibody using Biacore T100, Biacore T200, Biacore A100, and Biacore 4000 (GE Healthcare Japan Corp.). An appropriate amount of protein L (ACTIGEN) was immobilized on Sensor Chip CM4 (GE Healthcare Japan Corp.) by the amine coupling method. The antibody of interest was captured onto the chip. Next, a diluted FcRn solution or a running buffer (as a control solution) was injected thereto so that the mouse FcRn was allowed to interact with the antibody captured on the sensor chip. The running buffer used was 50 mmol/L sodium phosphate, 150 mmol/L NaCl, and 0.05% (w/v) Tween 20 (pH 6.0), and each buffer was also used for diluting FcRn. 10 mmol/L glycine-HCl (pH 1.5) was used to regenerate the chip. The assay was conducted at 25° C. for all samples. From the sensorgram obtained by the assay, an association rate constant ka (1/Ms) and a dissociation rate constant 1d (1/s) were calculated as kinetic parameters. The KD (M) of each antibody for mouse FcRn was calculated on the basis of the parameters. Biacore Evaluation Software (GE Healthcare Japan Corp.) was used in the calculation of each parameter.

Reference Example 5

CE-IEF

The CE-IEF measurement was carried out by a method generally known to those skilled in the art using PA800 Plus (Beckman Coulter Inc.). Pharmalyte having a broad range of 5 to 8 and Pharmalyte having a broad range of 8 to 10.5 were mixed in equal amounts and analyzed in a pI range of 5 to 10.5. The analysis was conducted using a 4 mg/mL antibody solution, and the results were analyzed using 32 karat software (Beckman Coulter Inc.). A value determined by dividing the area value of the bispecific antibody by the area value of all antibodies present in the system, followed by multiplication by 100 was used as the rate of bispecific antibody formation (%).

Reference Example 6

Measurement of Cytotoxic Activity (6-1) Preparation of Human Peripheral Blood Mononuclear Cell (PBMC) Solution 50 mL of peripheral blood was collected from each healthy volunteer (adult) using a syringe pre-filled with 100 µL of 1,000 units/mL of a heparin solution (Novo-Heparin 5,000 units for Injection, Novo Nordisk A/S). The peripheral blood was diluted 2-fold with PBS(−) and then divided into four equal parts, which were then added to Leucosep lymphocyte separation tubes (Cat. No. 227290, Greiner Bio-One GmbH) pre-filled with 15 mL of Ficoll-Paque PLUS and centrifuged in advance. After centrifugation (2,150 rpm, 10 minutes, room temperature) of the separation tubes, a mononuclear cell fraction layer was separated. The cells in the mononuclear cell fraction were washed once with Dulbecco's Modified Eagle's Medium containing 10% FBS (Sigma-Aldrich Corp.; hereinafter, referred to as 10% FBS/ D-MEM). Then, the cells were adjusted to a cell density of $4 \times 10^6$ cells/mL with 10% FBS/D-MEM. The cell solution thus prepared was used as a human PBMC solution in the subsequent test.

(6-2) Measurement of Cytotoxic Activity

The cytotoxic activity was evaluated on the basis of the rate of cell growth inhibition using xCELLigence real-time cell analyzer (Roche Diagnostics). The target cells used were an SK-pca13a cell line established by forcing an SK-HEP-1 cell line to express human GPC3. SK-pca13a was dissociated from the dish and inoculated at 100 µL/well ($1 \times 10^4$ cells/well) to an E-Plate 96 (Roche Diagnostics) plate to start the assay of live cells using the xCELLigence real-time cell analyzer. On the next day, the plate was taken out of the xCELLigence real-time cell analyzer, and 50 µL of each antibody adjusted to each concentration (0.004, 0.04, 0.4, and 4 µg/ml) was added to the plate. After reaction at room temperature for 15 minutes, 50 µL ($2 \times 10^4$ cells/well) of the human PBMC solution prepared in the preceding paragraph (6-1) was added thereto. This plate was reloaded to the xCELLigence real-time cell analyzer to start the assay of live cells. The reaction was carried out under conditions of 5% $CO_2$ and 37° C. 72 hours after the addition of human PBMC. The rate of cell growth inhibition (%) was determined from the cell index value according to the expression given below. A numeric value after normalization against the cell index value immediately before the addition of the antibody defined as 1 was used as the cell index value in this calculation.

Rate of cell growth inhibition (%)=$(A-B) \times 100/(A-1)$, wherein

A represents the average cell index value of wells non-supplemented with the antibody (only the target cells and human PBMC), and B represents the average cell index value of the wells supplemented with each antibody.

INDUSTRIAL APPLICABILITY

Bispecific antibodies can be prepared under a reducing condition with higher efficiency by use of the method of the present invention than that by the conventional techniques.

The invention claimed is:

1. A method for producing a polypeptide heteromultimer, the method comprising:
   a) providing a first multimer comprising a plurality of identical first polypeptides, wherein each first polypeptide comprises (i) a human IgG1-type or human IgG4-type CH3 domain, and (ii) a hinge region, and wherein the hinge region of each first polypeptide forms one or more disulfide bonds with the hinge region of another first polypeptide in the first multimer;
   b) providing a second multimer comprising a plurality of identical second polypeptides, wherein each second polypeptide comprises (i) a human IgG1-type or human IgG4-type CH3 domain, and (ii) a hinge region, and wherein the hinge region of each second polypeptide forms one or more disulfide bonds with the hinge region of another second polypeptide in the second multimer; and
   c) contacting the first multimer with the second multimer under a reducing condition that permits isomerization of hinge region disulfide bonds, thereby producing a polypeptide heteromultimer comprising at least one of the first polypeptides linked via disulfide bond(s) to at least one of the second polypeptides,
   wherein the polypeptide heteromultimer is a multispecific antibody or a hetero-Fc fusion protein,
   wherein the CH3 domain of each first polypeptide meets any one, two, or three of the following criteria (1) to (3):
      (1) amino acid residues at EU numbering positions 356 and 439 in the CH3 domain of each first polypeptide either both have a positive charge or both have a negative charge;
      (2) amino acid residues at EU numbering positions 357 and 370 in the CH3 domain of each first polypeptide either both have a positive charge or both have a negative charge;
      (3) amino acid residues at EU numbering positions 399 and 409 in the CH3 domain of each first polypeptide either both have a positive charge or both have a negative charge; wherein (x) is true or both of (x) and (y) are true:
      (x) each of the first polypeptides and each of the second polypeptides comprises an amino acid residue at EU numbering position 397 that is independently selected from methionine, phenylalanine, and tyrosine;
      (y) each of the first polypeptides and each of the second polypeptides comprises an amino acid residue at EU numbering position 392 that is independently selected from aspartic acid, glutamic acid, threonine, valine, and isoleucine; and
   wherein the CH3 domains of the first polypeptides or of the second polypeptides or of both the first polypeptides and the second polypeptides have a thermal denaturation temperature (Tm) equal to or lower than 72.5° C. at pH 7.4.

2. The method of claim 1, wherein the CH3 domain of each second polypeptide meets any one, two, or three of the following criteria (4) to (6):
   (4) amino acid residues at EU numbering positions 356 and 439 in the CH3 domain of each second polypeptide either both have a positive charge or both have a negative charge;

(5) amino acid residues at EU numbering positions 357 and 370 in the CH3 domain of each second polypeptide either both have a positive charge or both have a negative charge;

(6) amino acid residues at EU numbering positions 399 and 409 in the CH3 domain of each second polypeptide either both have a positive charge or both have a negative charge;

provided that:

(i) if the CH3 domain of each first polypeptide meets criterion (1) and the CH3 domain of each second polypeptide meets criterion (4), then the amino acid residues at EU numbering positions 356 and 439 of each first polypeptide have a charge opposite to that of the amino acid residues at EU numbering positions 356 and 439 of each second polypeptide;

(ii) if the CH3 domain of each first polypeptide meets criterion (2) and the CH3 domain of each second polypeptide meets criterion (5), then the amino acid residues at EU numbering positions 357 and 370 of each first polypeptide have a charge opposite to that of the amino acid residues at EU numbering positions 357 and 370 of each second polypeptide;

(iii) if the CH3 domain of each first polypeptide meets criterion (3) and the CH3 domain of each second polypeptide meets criterion (6), then the amino acid residues at EU numbering positions 399 and 409 of each first polypeptide have a charge opposite to that of the amino acid residues at EU numbering positions 399 and 409 of each second polypeptide.

3. The method of claim 1, wherein the first multimer further comprises a third polypeptide, and the second multimer further comprises a fourth polypeptide, wherein the first and second polypeptides are antibody heavy chains, and the third and fourth polypeptides are antibody light chains.

4. The method of claim 1, wherein the positively charged amino acid residues are selected from lysine, arginine, and histidine; and the negatively charged amino acid residues are selected from glutamic acid and aspartic acid.

5. The method of claim 2, wherein one of the following (A), (B), or (C) is true:
(A) the CH3 domain of each first polypeptide meets criterion (1) and the CH3 domain of each second polypeptide meets criterion (4), and the amino acid residues at EU numbering positions 356 and 439 of each first polypeptide have a charge opposite to that of the amino acid residues at EU numbering positions 356 and 439 of each second polypeptide;
(B) the CH3 domain of each first polypeptide meets criterion (2) and the CH3 domain of each second polypeptide meets criterion (5), and the amino acid residues at EU numbering positions 357 and 370 of each first polypeptide have a charge opposite to that of the amino acid residues at EU numbering positions 357 and 370 of each second polypeptide;
(C) the CH3 domain of each first polypeptide meets criterion (3) and the CH3 domain of each second polypeptide meets criterion (6), and the amino acid residues at EU numbering positions 399 and 409 of each first polypeptide have a charge opposite to that of the amino acid residues at EU numbering positions 399 and 409 of each second polypeptide.

6. The method of claim 2, wherein
the CH3 domain of each first polypeptide meets criteria (1) and (3),
the CH3 domain of each second polypeptide meets criteria (4) and (6),
the amino acid residues at EU numbering positions 356 and 439 of each first polypeptide have a charge opposite to that of the amino acid residues at EU numbering positions 356 and 439 of each second polypeptide, and
the amino acid residues at EU numbering positions 399 and 409 of each first polypeptide have a charge opposite to that of the amino acid residues at EU numbering positions 399 and 409 of each second polypeptide.

7. The method of claim 1, wherein the CH3 domain of each first polypeptide and each second polypeptide comprises an amino acid residue at EU numbering position 392 that is independently selected from aspartic acid, glutamic acid, threonine, valine, and isoleucine.

8. The method of claim 1, wherein the CH3 domains of the first polypeptides or of the second polypeptides or of both the first polypeptides and the second polypeptides are of IgG1 type.

9. A method for producing a polypeptide heteromultimer, the method comprising:
a) providing a first multimer comprising a plurality of identical first polypeptides, wherein each first polypeptide comprises (i) a mouse IgG-type CH3 domain, and (ii) a hinge region, and wherein the hinge region of each first polypeptide forms one or more disulfide bonds with the hinge region of another first polypeptide in the first multimer;
b) providing a second multimer comprising a plurality of identical second polypeptides, wherein each second polypeptide comprises (i) a mouse IgG-type CH3 domain, and (ii) a hinge region, and wherein the hinge region of each second polypeptide forms one or more disulfide bonds with the hinge region of another second polypeptide in the second multimer; and
c) contacting the first multimer with the second multimer under a reducing condition that permits isomerization of hinge region disulfide bonds, thereby producing a polypeptide heteromultimer comprising at least one of the first polypeptides linked via disulfide bond(s) to at least one of the second polypeptides,
wherein the polypeptide heteromultimer is a multispecific antibody or a hetero-Fc fusion protein,
wherein the CH3 domain of each first polypeptide meets any one, two, or three of the following criteria (1a) to (3):
(1) amino acid residues at EU numbering positions 356 and 439 in the CH3 domain of each first polypeptide either both have a positive charge or both have a negative charge;
(2) amino acid residues at EU numbering positions 360 and 371 in the CH3 domain of each first polypeptide either both have a positive charge or both have a negative charge;
(3) amino acid residues at EU numbering positions 399 and 409 in the CH3 domain of each first polypeptide either both have a positive charge or both have a negative charge;
wherein (x) is true or both of (x) and (y) are true:
(x) each of the first polypeptides and the second polypeptides comprises an amino acid residue at EU numbering position 397 independently selected from methionine, phenylalanine, and tyrosine;
(y) each of the first polypeptides and the second polypeptides comprises an amino acid residue at EU numbering position 392 that is independently selected from aspartic acid, glutamic acid, threonine, valine, and isoleucine; and
wherein the CH3 domains of the first polypeptides or of the second polypeptides or of both the first polypeptides and the second polypeptides have a thermal denaturation temperature (Tm) equal to or lower than 72.5° C. at pH 7.4.

10. The method of claim 9, wherein the CH3 domain of each second polypeptide meets any one, two, or three of the following criteria (4) to (6):
(4) amino acid residues at EU numbering positions 356 and 439 in the CH3 domain of each second polypeptide either both have a positive charge or both have a negative charge;
(5) amino acid residues at EU numbering positions 360 and 371 in the CH3 domain of each second polypeptide either both have a positive charge or both have a negative charge;
(6) amino acid residues at EU numbering positions 399 and 409 in the CH3 domain of each second polypeptide either both have a positive charge or both have a negative charge;
provided that:
(i) if the CH3 domain of each first polypeptide meets criterion (1) and the CH3 domain of each second polypeptide meets criterion (4), then the amino acid residues at EU numbering positions 356 and 439 of each first polypeptide have a charge opposite to that of the amino acid residues at EU numbering positions 356 and 439 of each second polypeptide;
(ii) if the CH3 domain of each first polypeptide meets criterion (2) and the CH3 domain of each second polypeptide meets criterion (5), then the amino acid residues at EU numbering positions 360 and 371 of each first polypeptide have a charge opposite to that of the amino acid residues at EU numbering positions 360 and 371 of each second polypeptide;
(iii) if the CH3 domain of each first polypeptide meets criterion (3) and the CH3 domain of each second polypeptide meets criterion (6), then the amino acid residues at EU numbering positions 399 and 409 of each first polypeptide have a charge opposite to that of the amino acid residues at EU numbering positions 399 and 409 of each second polypeptide.

11. The method of claim 1, wherein the method comprises mixing a first cell line expressing the first multimer and a second cell line expressing the second multimer to produce a culture supernatant comprising the first multimer and the second multimer, wherein step c) is carried out in the culture supernatant.

12. The method of claim 1, wherein the polypeptide heteromultimer is a multispecific antibody.

13. The method of claim 1, wherein the polypeptide heteromultimer is a bispecific antibody.

14. The method of claim 1, wherein step c) comprises contacting the first multimer and the second multimer with a reducing agent.

15. The method of claim 14, wherein the reducing agent is selected from the group consisting of glutathione, L-cysteine, dithiothreitol, β-mercapto-ethanol, tris(2-carboxyethyl)phosphine (TCEP), and 2-mercaptoethylamine (2-MEA).

16. The method of claim 14, wherein the reducing agent is glutathione or 2-MEA.

17. A method for producing a polypeptide heteromultimer, the method comprising:
a) providing a first multimer comprising a plurality of identical first polypeptides, wherein each first polypeptide comprises (i) an antigen binding site that binds to a first epitope, and (ii) an Fc region having a human IgG1-type or human IgG4-type CH3 domain and a hinge region, and wherein the hinge region of each first polypeptide forms one or more disulfide bonds with the hinge region of another first polypeptide in the first multimer;
b) providing a second multimer comprising a plurality of identical second polypeptides, wherein each second polypeptide comprises (i) an antigen binding site that binds to a second epitope that is different from the first epitope, and (ii) an Fc region having a human IgG1-type or human IgG4-type CH3 domain and a hinge region, and wherein the hinge region of each second polypeptide forms one or more disulfide bonds with the hinge region of another second polypeptide in the second multimer; and
c) contacting the first multimer with the second multimer under a reducing condition that permits isomerization of hinge region disulfide bonds, thereby producing a polypeptide heteromultimer comprising at least one of the first polypeptides linked via disulfide bond(s) to at least one of the second polypeptides,
wherein (x) is true, or both of (x) and (y) are true:
(x) each of the first polypeptides and the second polypeptides comprises an amino acid residue at EU numbering position 397 that is independently selected from methionine, phenylalanine, and tyrosine;
(y) each of the first polypeptides and the second polypeptides comprises an amino acid residue at EU numbering position 392 that is independently selected from aspartic acid, glutamic acid, threonine, valine, and isoleucine; and
wherein the CH3 domains of the first polypeptides or of the second polypeptides or of both the first polypeptides and the second polypeptides have a thermal denaturation temperature (Tm) equal to or lower than 72.5° C. at pH 7.4.

18. The method of claim 1, wherein the CH3 domain of each first polypeptide and each second polypeptide comprises both of the following:
(i) an amino acid residue at EU numbering position 397 that is independently selected from methionine, phenylalanine, and tyrosine;
(ii) an amino acid residue at EU numbering position 392 that is independently selected from aspartic acid, glutamic acid, threonine, valine, and isoleucine.

19. The method of claim 9, wherein the CH3 domain of each first polypeptide and each second polypeptide comprises an amino acid residue at EU numbering position 392 that is independently selected from aspartic acid, glutamic acid, threonine, valine, and isoleucine.

20. The method of claim 1, wherein the amino acid residue at EU numbering position 397 of the first polypeptide is phenylalanine or tyrosine.

21. The method of claim 20, wherein the amino acid residue at EU numbering position 397 of the second polypeptide is phenylalanine or tyrosine.

22. The method of claim 9, wherein the amino acid residue at EU numbering position 397 of the first polypeptide is phenylalanine or tyrosine.

23. The method of claim 22, wherein the amino acid residue at EU numbering position 397 of the second polypeptide is phenylalanine or tyrosine.

24. The method of claim 2, wherein the first multimer further comprises a third polypeptide, and the second multimer further comprises a fourth polypeptide, wherein the first and second polypeptides are antibody heavy chains, and the third and fourth polypeptides are antibody light chains.

25. The method of claim 2, wherein the CH3 domain of each of the first polypeptides and each of the second polypeptides is an IgG1 CH3 domain.

26. The method of claim 2, wherein the method comprises mixing a first cell line expressing the first multimer and a second cell line expressing the second multimer to produce a culture supernatant comprising the first multimer and the second multimer, wherein step c) is carried out in the culture supernatant.

27. The method of claim 2, wherein the polypeptide heteromultimer is a multispecific antibody.

28. The method of claim 2, wherein the polypeptide heteromultimer is a bispecific antibody.

29. The method of claim 2, wherein step c) comprises contacting the first multimer and the second multimer with a reducing agent.

30. The method of claim 29, wherein the reducing agent is selected from the group consisting of glutathione, L-cysteine, dithiothreitol, β-mercapto-ethanol, tris(2-carboxyethyl)phosphine (TCEP), and 2-mercaptoethylamine (2-MEA).

31. The method of claim 29, wherein the reducing agent is glutathione or 2-MEA.

32. The method of claim 2, wherein the CH3 domain of each first polypeptide comprises both of the following:
   (i) an amino acid residue at EU numbering position 397 that is methionine, phenylalanine, or tyrosine;
   (ii) an amino acid residue at EU numbering position 392 that is aspartic acid, glutamic acid, threonine, valine, or isoleucine.

33. The method of claim 2, wherein the CH3 domain of each first polypeptide and each second polypeptide comprises both of the following:
   (i) an amino acid residue at EU numbering position 397 that is independently selected from methionine, phenylalanine, and tyrosine;
   (ii) an amino acid residue at EU numbering position 392 that is independently selected from aspartic acid, glutamic acid, threonine, valine, and isoleucine.

34. The method of claim 2, wherein the amino acid residue at EU numbering position 397 of each first polypeptide is phenylalanine or tyrosine.

35. The method of claim 34, wherein the amino acid residue at EU numbering position 397 of each first polypeptide and each second polypeptide is independently selected from phenylalanine and tyrosine.

36. The method of claim 10, wherein the CH3 domain of each first polypeptide and each second polypeptide comprises an amino acid residue at EU numbering position 392 that is independently selected from aspartic acid, glutamic acid, threonine, valine, and isoleucine.

37. The method of claim 10, wherein the amino acid residue at EU numbering position 397 of each first polypeptide is phenylalanine or tyrosine.

38. The method of claim 37, wherein the amino acid residue at EU numbering position 397 of each second polypeptide is phenylalanine or tyrosine.

* * * * *